US012559545B2

(12) United States Patent
Crowe, Jr.

(10) Patent No.: US 12,559,545 B2
(45) Date of Patent: Feb. 24, 2026

(54) HUMAN HENDRA VIRUS AND NIPAH VIRUS ANTIBODIES AND METHODS OF USE THEREFOR

(71) Applicant: Vanderbilt University, Nashville, TN (US)

(72) Inventor: James E. Crowe, Jr., Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 932 days.

(21) Appl. No.: 17/776,337

(22) PCT Filed: Nov. 12, 2020

(86) PCT No.: PCT/US2020/060129
§ 371 (c)(1),
(2) Date: May 12, 2022

(87) PCT Pub. No.: WO2021/097024
PCT Pub. Date: May 20, 2021

(65) Prior Publication Data
US 2023/0073075 A1 Mar. 9, 2023

Related U.S. Application Data

(60) Provisional application No. 62/934,295, filed on Nov. 12, 2019.

(51) Int. Cl.
| | |
|---|---|
| *A61K 39/42* | (2006.01) |
| *A61P 31/14* | (2006.01) |
| *C07K 16/10* | (2006.01) |
| *G01N 33/569* | (2006.01) |
| *A61K 39/00* | (2006.01) |
| *C07K 14/115* | (2006.01) |

(52) U.S. Cl.
CPC .......... *C07K 16/1027* (2013.01); *A61K 39/42* (2013.01); *A61P 31/14* (2018.01); *G01N 33/56983* (2013.01); *A61K 2039/505* (2013.01); *C07K 14/115* (2013.01); *C07K 2317/21* (2013.01); *C07K 2317/30* (2013.01); *C07K 2317/33* (2013.01); *C07K 2317/76* (2013.01); *C07K 2317/92* (2013.01); *G01N 2333/115* (2013.01)

(58) Field of Classification Search
CPC .. C07K 14/115; C07K 16/1027; A61K 39/42; A61P 31/14; G01N 33/56983; G01N 2333/115
See application file for complete search history.

(56) References Cited

U.S. PATENT DOCUMENTS

| | | |
|---|---|---|
| 2006/0053501 A1 | 3/2006 | Courbet et al. |
| 2007/0150972 A1 | 6/2007 | Courbet et al. |
| 2012/0039978 A1 | 2/2012 | Moscona et al. |
| 2016/0272697 A2 | 9/2016 | Broder et al. |
| 2016/0347827 A1 | 12/2016 | Yee-Peng et al. |
| 2017/0175086 A1 | 6/2017 | Schmitt et al. |
| 2019/0276520 A1 | 9/2019 | Crowe |

OTHER PUBLICATIONS

Aguilar, Hector C., et al. "A novel receptor-induced activation site in the Nipah virus attachment glycoprotein (G) involved in triggering the fusion glycoprotein (F)." *Journal of Biological Chemistry* 284.3 (2009): 1628-1635.
Bossart, Katharine N., et al. "A neutralizing human monoclonal antibody protects against lethal disease in a new ferret model of acute nipah virus infection." *PLoS pathogens* 5.10 (2009): e1000642.
Bossart, Katharine N., et al. "A neutralizing human monoclonal antibody protects african green monkeys from hendra virus challenge." *Science translational medicine* 3.105 (2011): 105ra103-105ra103.
Burkovitz, Anat, and Yanay Ofran. "Understanding differences between synthetic and natural antibodies can help improve antibody engineering." *MAbs.* vol. 8. No. 2. Taylor & Francis, 2016.
Clayton, Bronwyn A., et al. "Transmission routes for Nipah virus from Malaysia and Bangladesh." *Emerging infectious diseases* 18.12 (2012): 1983.
Doyle et al., "Isolation of highly potent monoclonal antibodies with therapeutic potential to combat Hendra and Nipah viruses," Poster presentation dated 2019.
International Search Report and Written Opinion issued in International Application No. PCT/US2020/060129, dated Apr. 2, 2021.
Invitation to Pay Additional Fees issued in International Application No. PCT/US2020/060129, dated Feb. 8, 2021.
Li, Yaohui, et al. "Fc-based recombinant henipavirus vaccines elicit broad neutralizing antibody responses in mice." *Viruses* 12.4 (2020): 480.
Lo, Michael K., et al. "Characterization of Nipah virus from outbreaks in Bangladesh, 2008-2010." *Emerging infectious diseases* 18.2 (2012): 248.
Mire, Chad E., et al. "Pathogenic differences between Nipah virus Bangladesh and Malaysia strains in primates: implications for antibody therapy." *Scientific reports* 6.1 (2016): 30916.
Playford, Elliott Geoffrey, et al. "Safety, tolerability, pharmacokinetics, and immunogenicity of a human monoclonal antibody targeting the G glycoprotein of henipaviruses in healthy adults: a first-in-human, randomised, controlled, phase 1 study." *The Lancet Infectious Diseases* 20.4 (2020): 445-454.

(Continued)

Primary Examiner — Zachary C Howard
(74) Attorney, Agent, or Firm — pH IP Law

(57) ABSTRACT

The present disclosure is directed to antibodies binding to and neutralizing henipavirus and methods for use thereof. Thus, in accordance with the present disclosure, there is provided a method of detecting a henipavirus infection in a subject comprising (a) contacting a sample from said subject with an antibody or antibody fragment having clone-paired heavy and light chain CDR sequences from Tables 3 and 4, respectively; and (b) detecting henipavirus in said sample by binding of said antibody or antibody fragment to a henipavirus antigen in said sample.

18 Claims, 30 Drawing Sheets

Specification includes a Sequence Listing.

(56)  References Cited

OTHER PUBLICATIONS

Rockx, Barry, et al. "A novel model of lethal Hendra virus infection in African green monkeys and the effectiveness of ribavirin treatment." *Journal of virology* 84.19 (2010): 9831-9839.

Xu, Kai, et al. "Crystal structure of the Hendra virus attachment G glycoprotein bound to a potent cross-reactive neutralizing human monoclonal antibody." *PLoS pathogens* 9.10 (2013): e1003684.

Zhu, Zhongyu, et al. "Exceptionally potent cross-reactive neutralization of Nipah and Hendra viruses by a human monoclonal antibody." *The Journal of infectious diseases* 197.6 (2008): 846-853.

Zhu, Zhongyu, et al. "Potent neutralization of Hendra and Nipah viruses by human monoclonal antibodies." *Journal of virology* 80.2 (2006): 891-899.

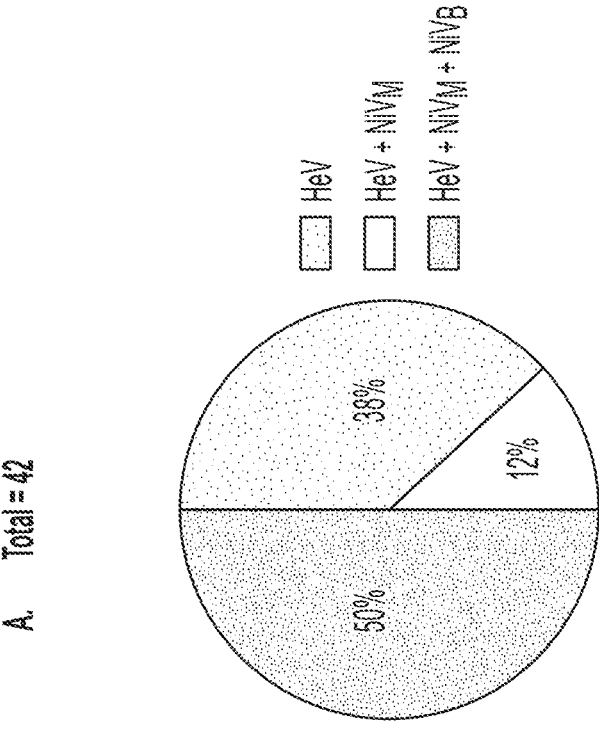
B.
| mAb | HeV-G | NIVM-G | NIVB-G |
|---|---|---|---|
| HENV-141 | 326 | 266 | 778 |
| HENV-150 | 328 | 270 | 332 |
| HENV-226 | 357 | 259 | 361 |
| HENV-122 | 387 | 407 | 382 |
| HENV-99 | 420 | 294 | 1,160 |
| HENV-188 | 423 | 287 | 1,260 |
| HENV-98 | 434 | 396 | 580 |
| HENV-113 | 440 | 251 | 16,400 |
| HENV-100 | 469 | 316 | 514 |
| HENV-137 | 515 | 332 | 840 |
| HENV-170 | 518 | 378 | 629 |
| HENV-83 | 560 | 260 | 2,790 |
| HENV-93 | 604 | 406 | 2,720 |
| HENV-103 | 806 | 611 | 1,340 |
| HENV-117 | 1,060 | 1,250 | 1,200 |
| HENV-58 | 1,140 | 739 | 1,440 |
| HENV-184 | 1,190 | 622 | 2,320 |
| HENV-142 | 1,860 | 1,030 | 13,040 |
| HENV-222 | 5,660 | 586 | 5,800 |
| HENV-242 | 6,600 | 716 | 7,670 |
EC50 (pM)
0-499
500-999
1,000-9,999
10,000-49,999
>50,000
A.    Total = 42
HeV
HeV + NIVM
HeV + NIVM + NIVB
50%
38%
12%
FIGS. 2A-B

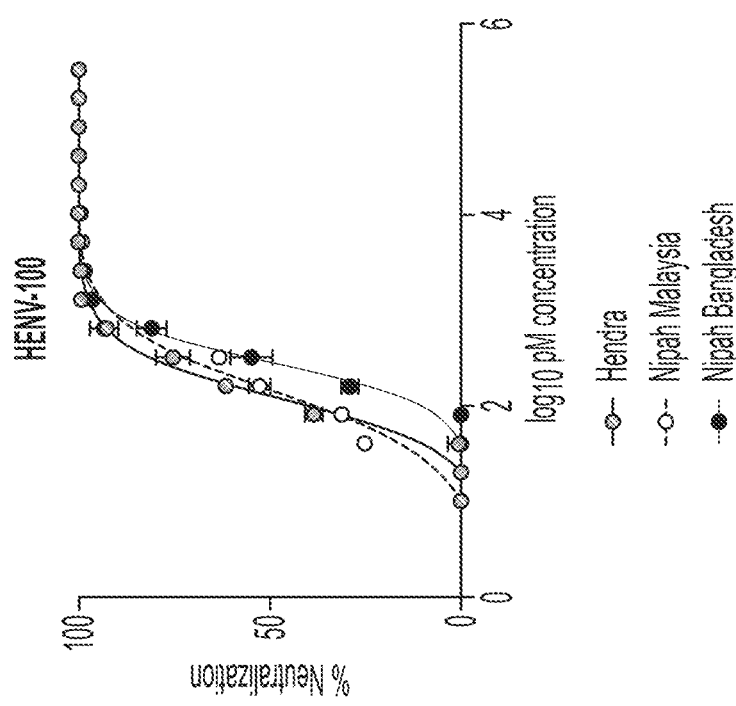
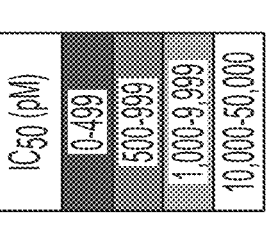
FIGS. 3A-B

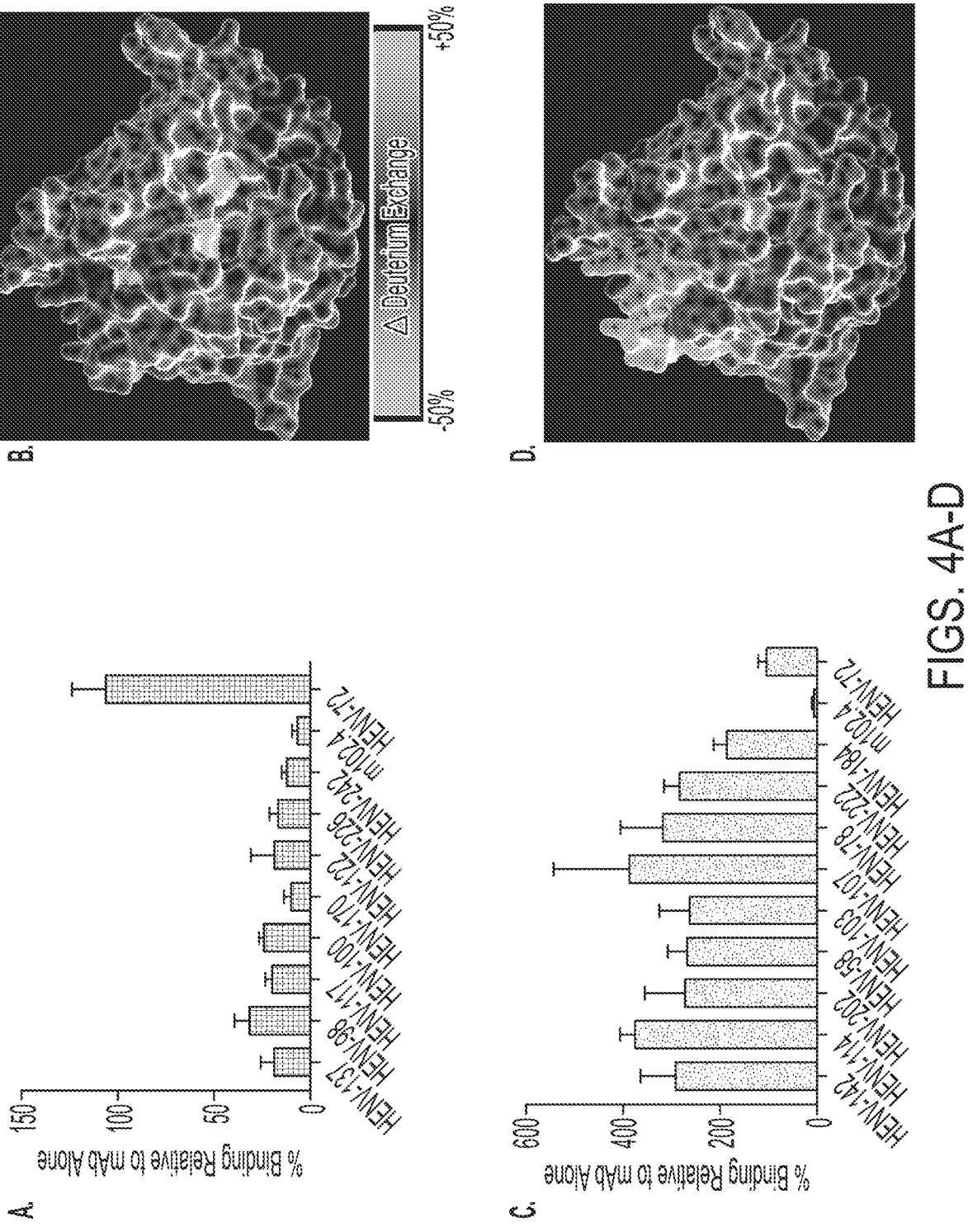
FIGS. 4A-D

| Second mAb applied | 26 | 97 | 100 | 99 | 100 | 97 | 97 | 109 | 91 | 91 | -5 |
| | 19 | 101 | 87 | 108 | 104 | 97 | 99 | 110 | 2 | 0 | 106 |
| | 18 | 70 | 86 | 104 | 106 | 102 | 101 | 106 | 3 | 0 | 112 |
| | 43 | 90 | 82 | 97 | 97 | 63 | 67 | 12 | 90 | 90 | 90 |
| | 9 | 100 | 103 | 105 | 100 | 3 | -4 | 62 | 99 | 98 | 104 |
| | 2 | -6 | -4 | -2 | -3 | -4 | 6 | 66 | 97 | 99 | 102 |
| | 10 | 88 | -5 | -4 | -1 | -6 | 84 | 105 | 94 | 94 | 97 |
| | 21 | 89 | -4 | -4 | -2 | -5 | 86 | 106 | 97 | 98 | 100 |
| | 32 | 53 | 6 | 47 | 49 | 19 | 87 | 91 | 91 | 94 | 98 |
| | 1 | -5 | 17 | 115 | 111 | 56 | 105 | 124 | 108 | 110 | 115 |
| MAb HENV- | 1 | 32 | 21 | 10 | 2 | 9 | 43 | 18 | 19 | 26 |

First mAb applied

FIG. 6

FIGS. 7A-C

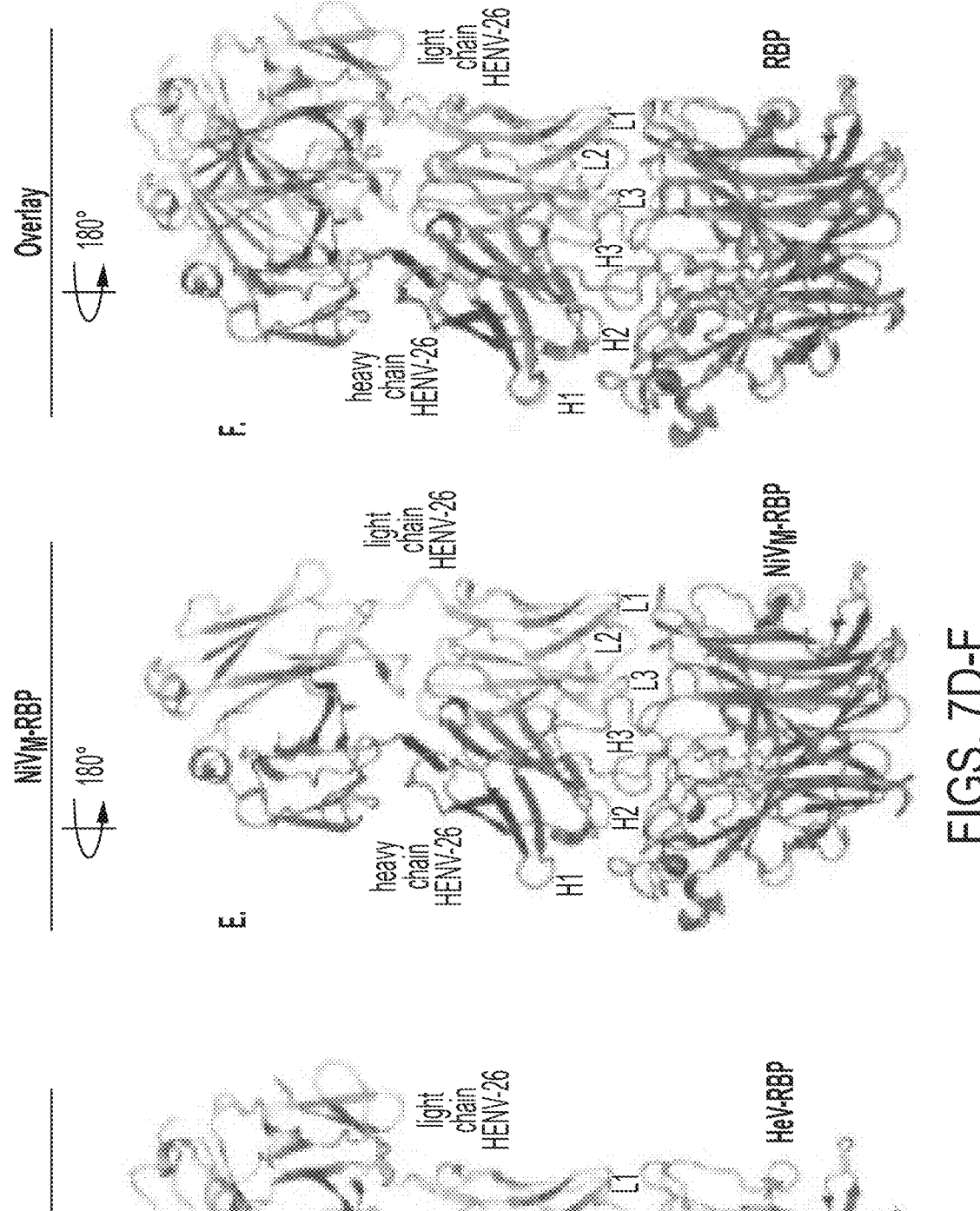
FIGS. 7D-F

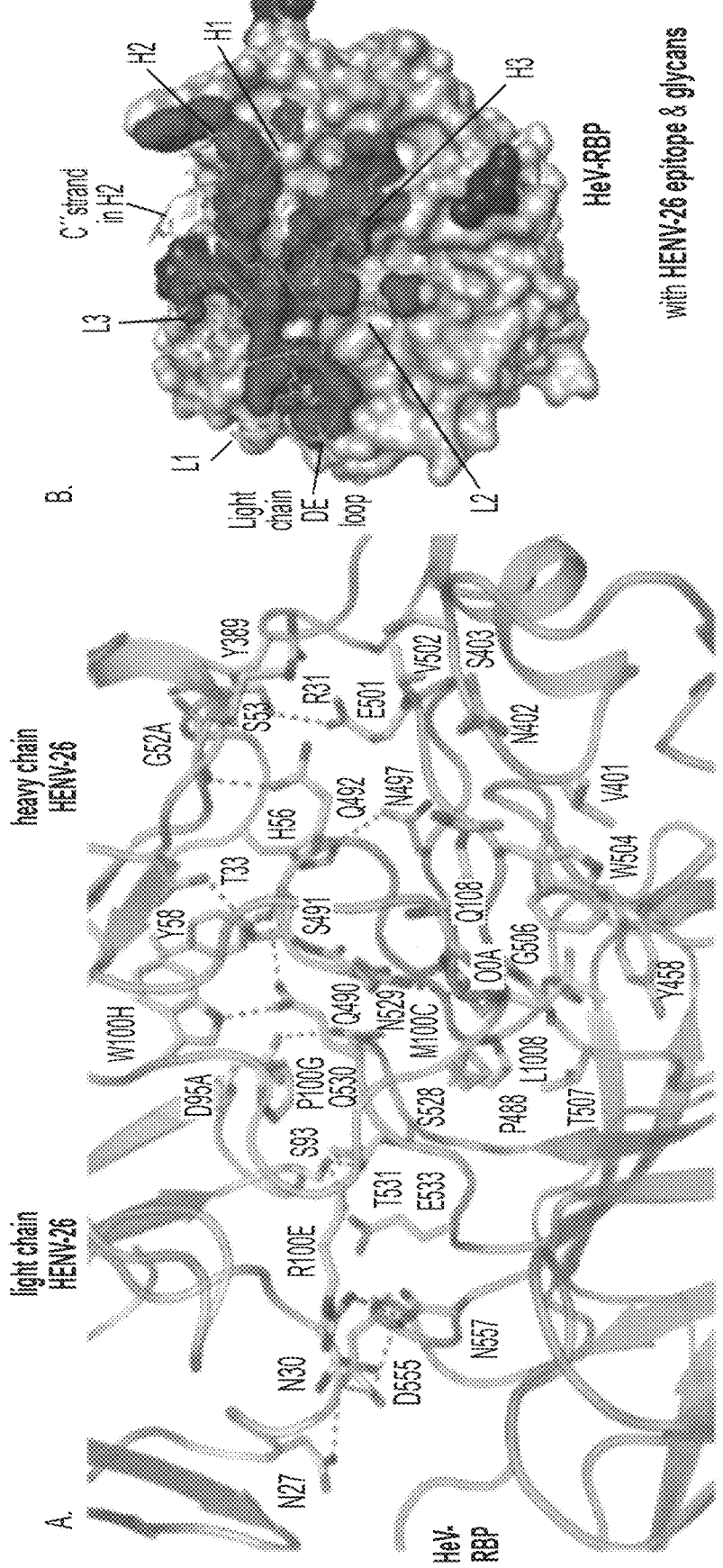
FIGS. 8A-B

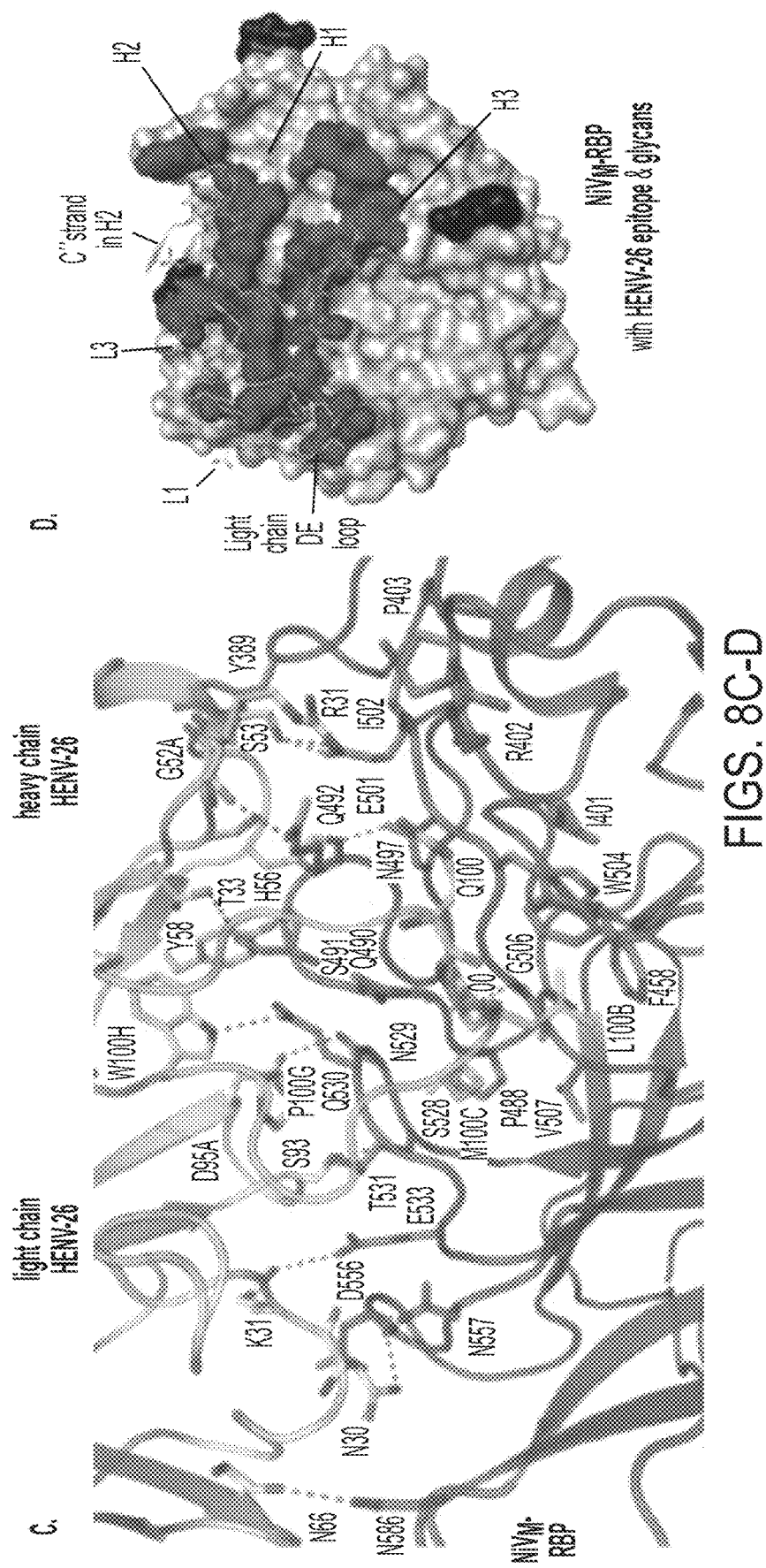
FIGS. 8C-D

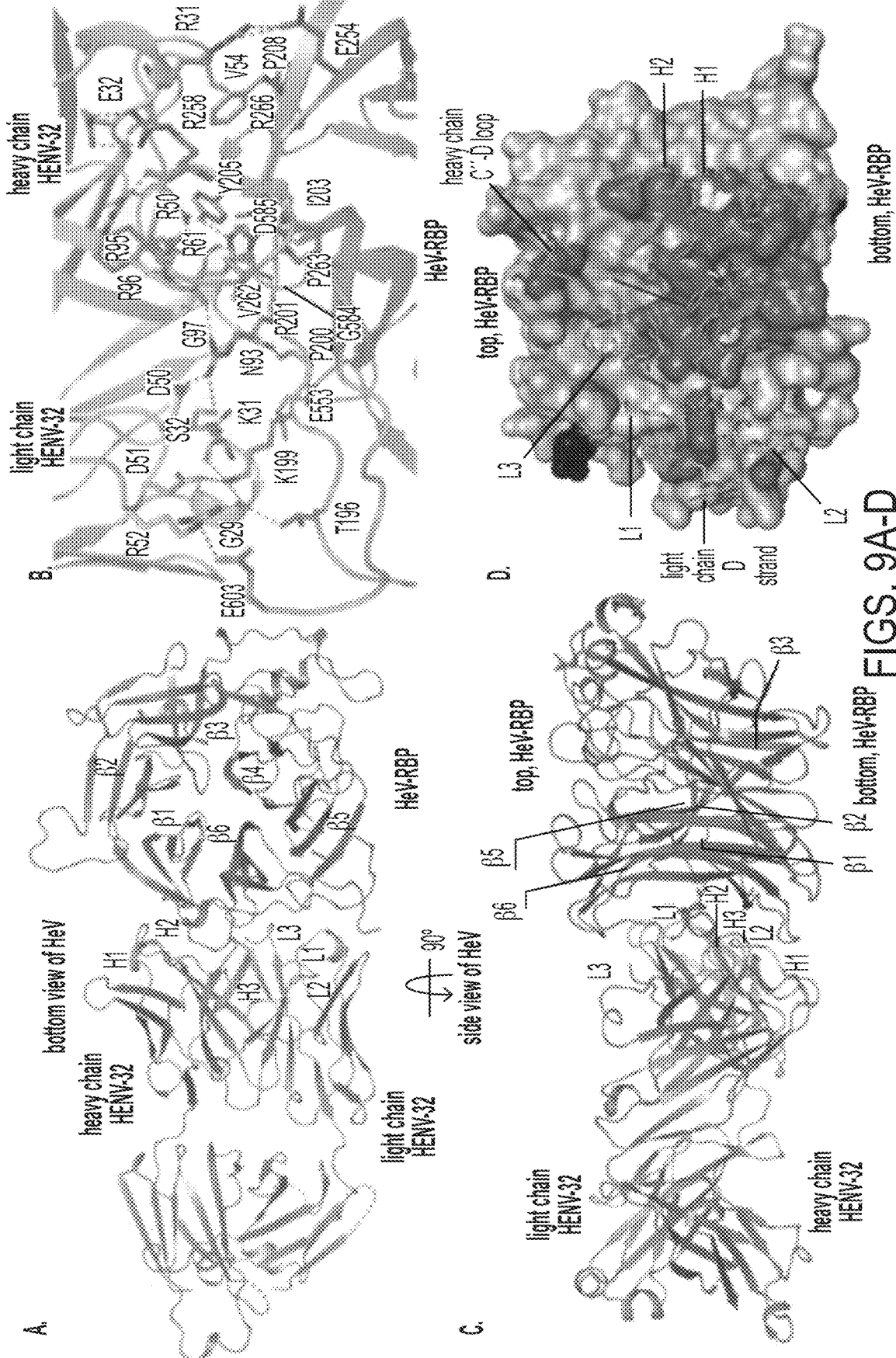
FIGS. 9A-D

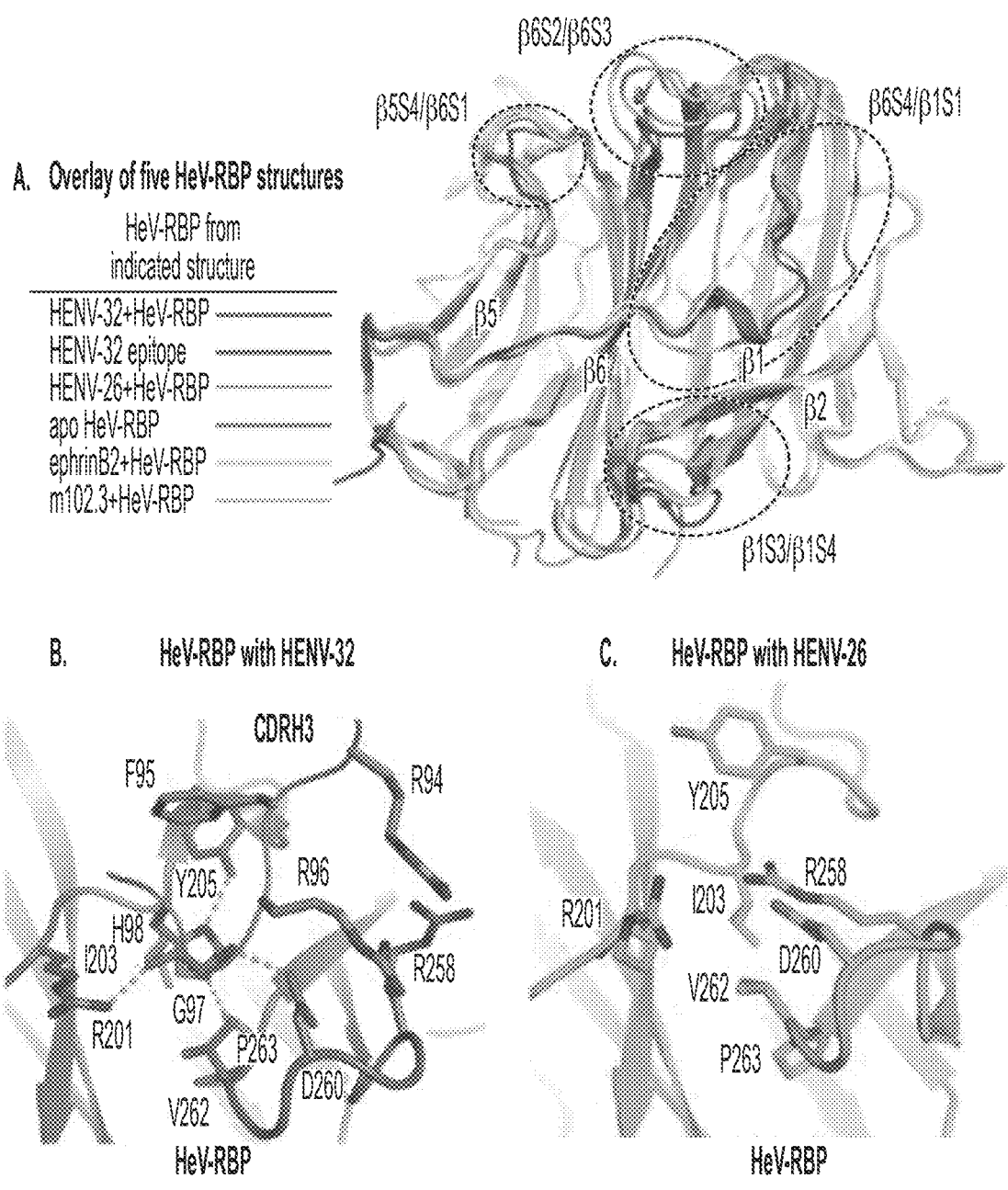
FIGS. 10A-C

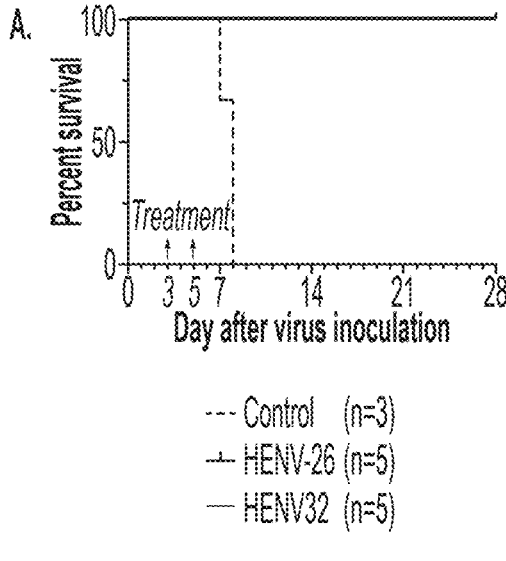
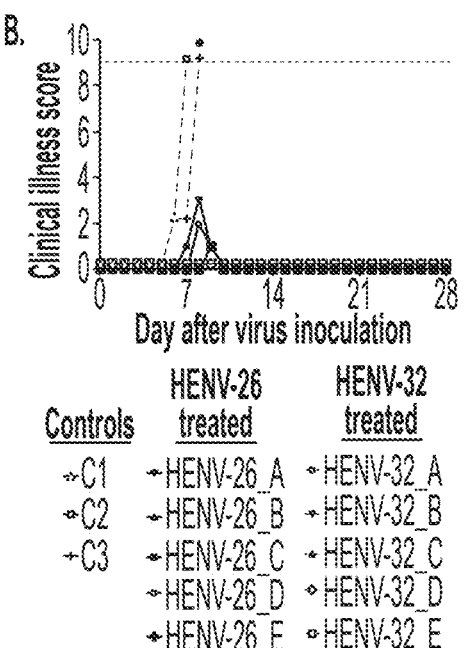
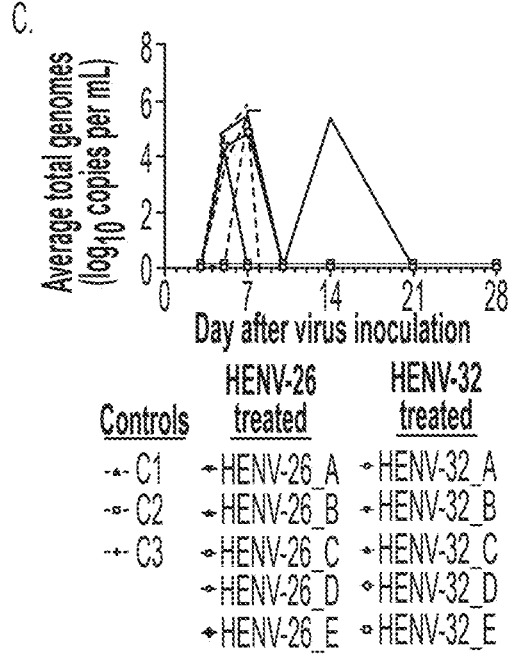
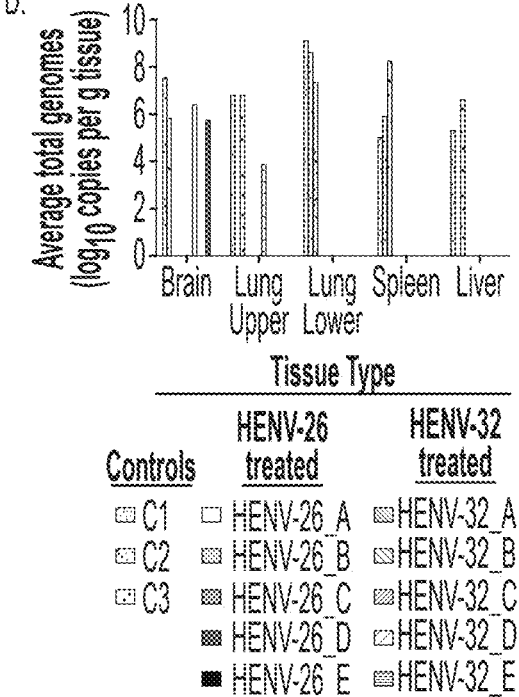
FIGS. 11A-D

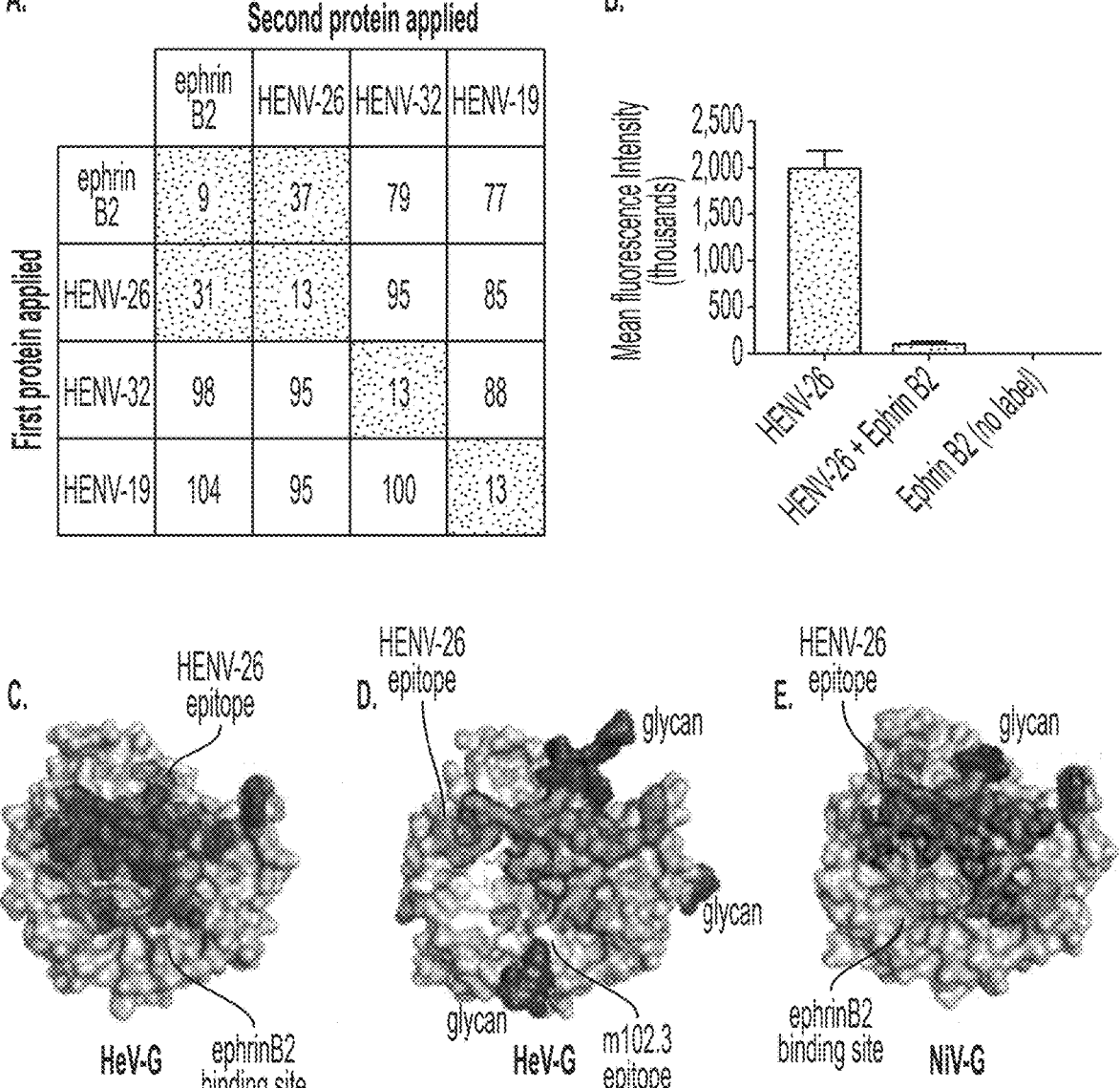
FIGS. 14A-E

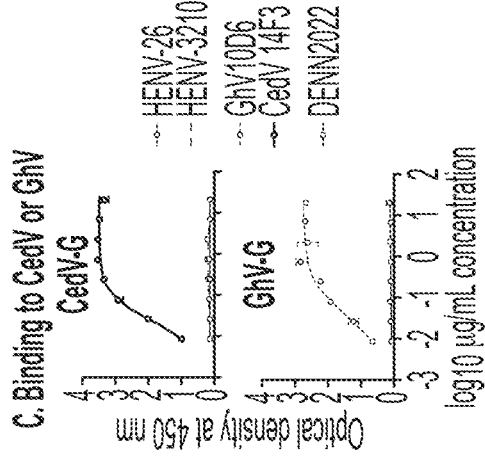
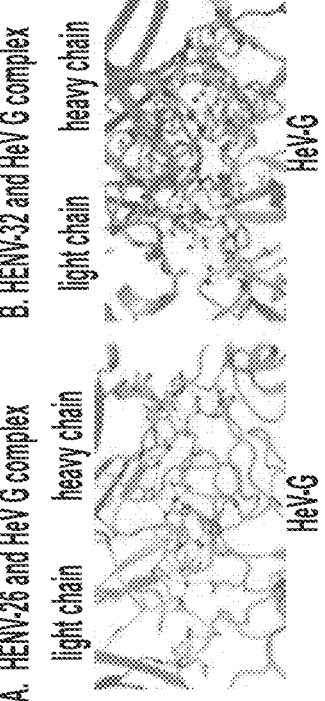
FIGS. 15A-C

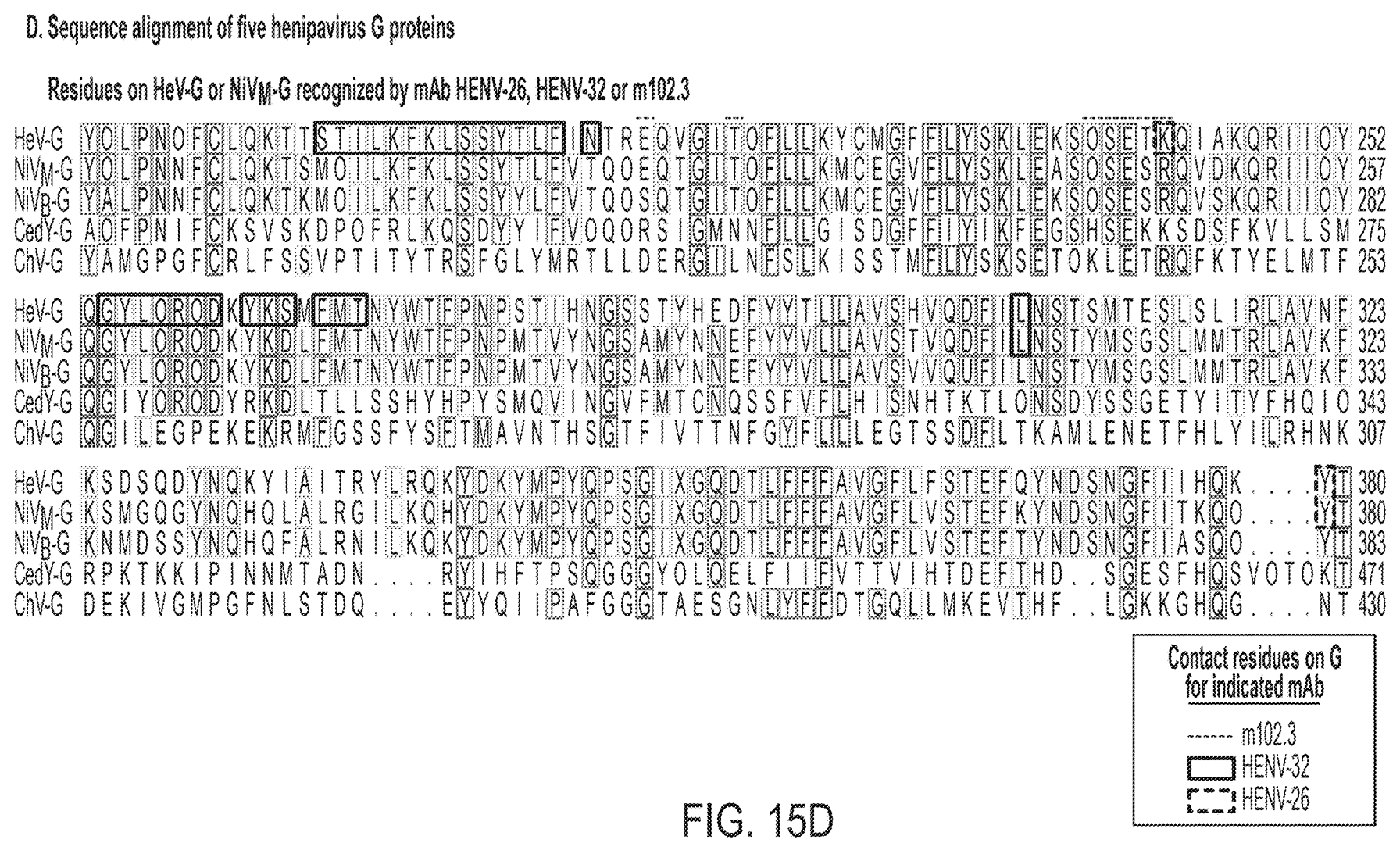

D. Sequence alignment of five henipavirus G proteins

Residues on HeV-G or NiVm-G recognized by mAb HENV-26, HENV-32 or m102.3

Contact residues on G for indicated mAb
- m102.3
- HENV-32
- HENV-26

FIG. 15D

A.  Contact site for the HENV-32 HCDR3
    in the apo (dimeric) form of HeV-G
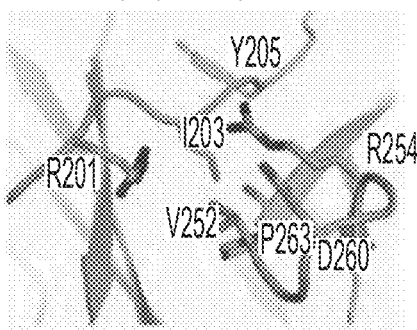
B.  Contact site for the HENV-32 HCDR3
    in the m102.3 HeV-G/complex
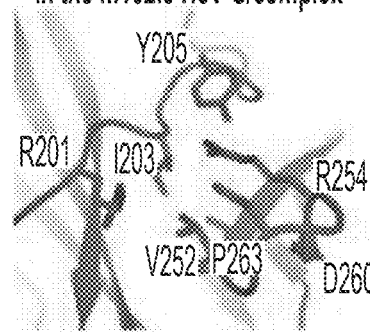
C.  HenV-32/HeV-G complex
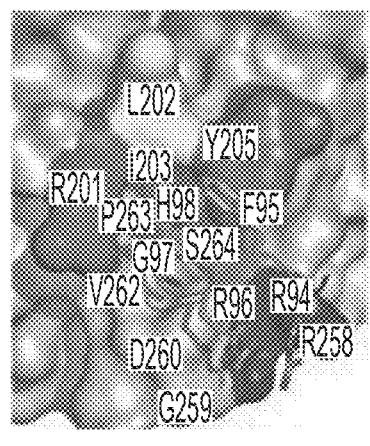
D.  HENV-26/HeV-G complex
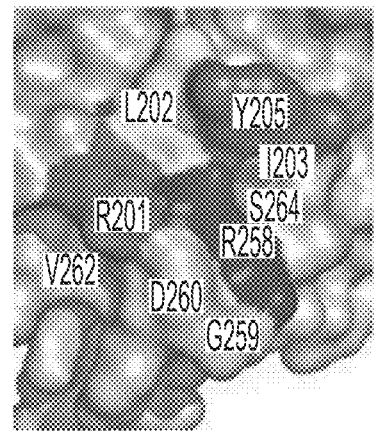
E.  m102.3/HeV-G complex
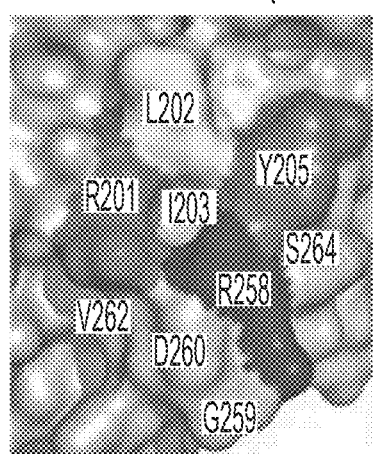
F.  HeV-G apo (dimeric form)
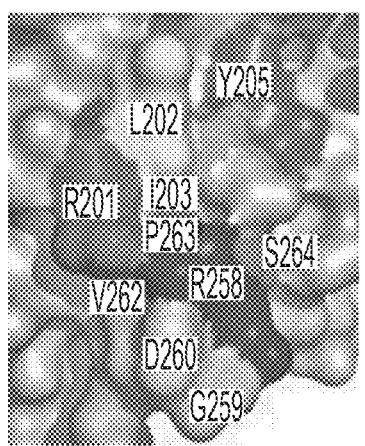
FIG. 17A-F

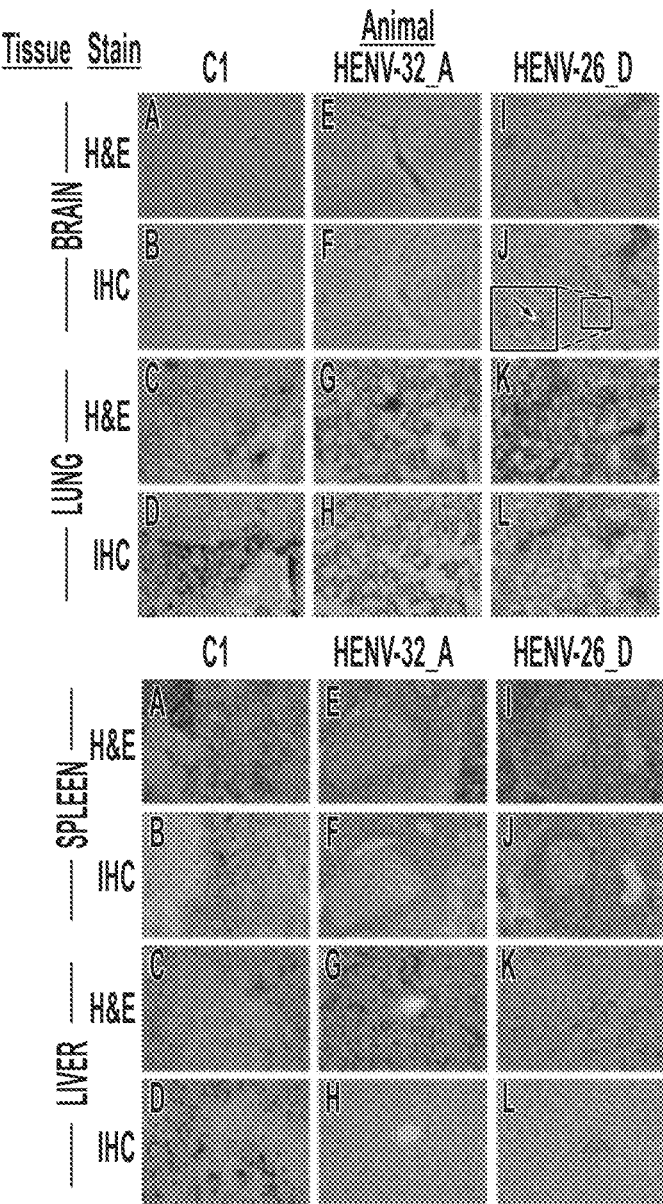
FIGS. 18A-L

SEQUENCE LISTING

<160> NUMBER OF SEQ ID NOS: 256

<210> SEQ ID NO 1

```
<211> LENGTH: 356
<212> TYPE: DNA
<213> ORGANISM: Artificial sequence
<220> FEATURE:
<223> OTHER INFORMATION: Synthetic oligonucleotide

<400> SEQUENCE: 1
ccaggtccag ctggtgcagt ctggggctga ggtgaagaag cctgggtcct cggtgaaggt      60
ctcctgcaaa gtttctggag gcatcttcaa cagggagacc atcaactggg tgcgacaggc     120
ccctggacaa gggcttgagt ggatgggaag gatcacccct attgttgacg tcccaaatta     180
ccctcggaag ttccgaggca gagtcaccat taccgcggac aaatccacga gtacagttta     240
catggagctg agcggcctga gatttgagga cacggccatc tatttctgtg cgcgttttcg     300
gggacacaac tacttcgacc cctggggcca gggaaccctg gtcaccgtct cctcag         356

<210> SEQ ID NO 2
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 2
tcctatgtgc tgactcagcc accctcggtg tcagtggccc caggacagac ggccaggatt      60
acctgtgggg gaaacaacat tgggggtaaa agtgtgcact ggtaccagca gaagccaggc     120
caggcccctg tcttggtcgt ctatgatgac cgcgaccggc cctcagggat ccctgagcga     180
ttctctggct ccaactctgg ggacacggcg tccctgacga tcagcagggt cgatgccggg     240
gatgaggccg actatttctg tcaggtgtgg gataatgcta gtgatgaagc ggtattcggc     300
ggagggacga agctgaccgt cctgg                                           325

<210> SEQ ID NO 3
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 3
caggtccagc tggtgcagtc tggggctgag gtgaagaagc ctgggtcctc ggtgaaggtc      60
tcctgtaagg cttctggagg caccttcagc aactatgtca tcagctgggt gcgacaggcc     120
cctggacaag ggtttgagtg gatgggaagg atcatcccta tgattggaat ctcaaactac     180
gcacagaagt tccaggacag agtcacgatt accgcggaca aggacgagtc cacgaccaca     240
gcctacatgg agttgcgcgg cctgagatct gaggacacgg ccatgtatta ttgtgcgagt     300
agtacggtga ctgaggtagg ggcctggggc cagggaaccc tggtcaccgt ctcctca        357

<210> SEQ ID NO 4
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 4
gccatccagt tgacccagtc cccatcctcc ctgtctgcat ctataggaga cagagtcacc      60
atcacttgcc gggcaagtca gggcattagc agtgctttag cctggtttca gcagaaacca     120
gggaaacctc ctatcctcct gatctatgat gcctccagtc tggaaagtgg ggtcccagca     180
```

-continued

```
aggttcagcg gcagtggatc tgggacagat ttcactctca ccatcagcag cctgcagcct      240
gaagattttg caacttacta ctgtcaacaa ttttataatc accctctcac tttcggccct      300
gggaccaaag tggatatcaa a                                                321
```

```
<210> SEQ ID NO 5
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 5
gaggtgcagc tggtggagtc tggggggaggc ctggtcaagc ctggggggtc cctgagactc      60
tcctgtgcag cctctggatt cacaatcatt aactatagtt tgagctgggt ccgccaggct      120
ccagggaagg ggctggagtg ggtctcatcc attagtggca gtagtgatta catatactac      180
ggagactcag tgaagggccg attcaccatc tccagagaca acgccaagaa ctcactgtat      240
ctgcaaatga acagcctgag agccgaggac gcggctgtat attactgtgc gagagaaaga      300
actggttttt tcagcccacc ctcatactta atggacgtct ggggccaagg gaccacggtc      360
accgtctcct ca                                                          372
```

```
<210> SEQ ID NO 6
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 6
gccatccaga tgacccagtc tccatcctcc ctgtctgcat ctgtaggaga cagagtcacc      60
atcacttgcc gggcaagtca gggcattaga aatgatttag ctggtatca acagaaacca      120 gggaaagccc ctaagctcct gatctatgct gcttccactt tacaaagtgg ggtcccatca      180
aggttcagcg gcagtggatc tggcacagat ttcactctca ccatcagcag cctgcagcct      240
gaagattttg caacttatta ctgtctacaa gattacaatt accctcggac gttcggccag      300
gggaccaagg tggaaatcaa a                                                321
```

```
<210> SEQ ID NO 7
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 7
caggttcagc tgctacagtc tggaggtgag gtgaagaagc ctggggcctc agtgaaggtc      60
tcctgcaagg ctactgataa caccttaacc acctatggtc tcagttgggt gcgacaggcc      120
cctggacaag ggcttgagtg gatgggatgg gtcagcgctt acaatggtca cccaaactat      180
gcacagaagt tccagggcag agtcaccatg accacagaca cgtccacgag cacagcctac      240
atggagctgc ggagcctgac ttctgacgac acggccgtct atttctgtgc gagaggtagc      300
agtgcctgga tccctgggg ccaagggaca ctggtcaccg tctcttca               348
```

```
<210> SEQ ID NO 8
<211> LENGTH: 321
<212> TYPE: DNA
```

```
<213> ORGANISM: Artificial sequence
<220> FEATURE:
<223> OTHER INFORMATION: Synthetic oligonucleotide

<400> SEQUENCE: 8
gacatccaga tgacccagtc tccttccacc ctgtctgcat ctgtaggaga cagagtcacc      60
atcacttgcc gggccagtca gagtattact agctggttgg cctggtatca gcagaaacca     120
gggaaagccc ctaacctcct gatctataag gcgtctagtt tagaaggtgg ggtcccatca     180
aggttcagcg gcagtggatc tgggacagaa ttcactctca ccatcagcag cctgcagcct     240
gatgatcttg caacttatta ctgccaacag tatagcagtt atccggtcac tttcggcgga     300
gggaccaagg tggagatcag a                                                321

<210> SEQ ID NO 9
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 9
caggtgcaat tggtggagtc ggggggaggc gtggtccagc ctggggggtc cctgagactc      60
tcctgtgcag cctctggatt caccttccgt agctattcta tgaactgggt ccgccaggct     120
ccaggcaagg ggccggagtg gatggcagtt atatcctatg atggaagtaa taaatactac     180
acagactccg tgaagggccg attcaccatc tccagagaca actccaagaa cacgctgaat     240
ctccaaatga acagcctgac atctgaggac acggctatat attactgcgc gagattccgg     300
ggggggggtc gaatagcagc tcgtccggac gactacggta tggacgtctg gggccagggg     360
accacggtca ccgtctccac a                                                381

<210> SEQ ID NO 10
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 10
gacatccaga tgacccagtc tccatcctcc ctgtctgcat ctgtaggaga cagagtcacc      60
atcacttgcc gggcaagtga gagcgtcatt acgtatttaa attggtatca gcagaaacca     120
gggaaagccc ctaagctcct gatctatggg gcatccactt tggaaagtgg ggtcccatcg     180
aggttcagtg gcagtggatc tgggacagtc ttcactctaa ccatcagcag tctgcaacct     240
gaagacattg caacttacta ctgtcaacag agttacaata tgtccccgta cacttttggc     300
caggggacca agctggagat caaa                                             324

<210> SEQ ID NO 11
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 11
caggtgcttc tggtgcagtc tggggctgag gtgaggaagc ctgggctc agtgaaggtc        60 tcctgcaggg cttctggata caccttcacc gactactata tgcactgggt gcgacaggcc     120
cctggacaag ggcttgagtg gatgggatgg atcaaccta acagtggtgc cacaaagtac      180
```

```
gcacagaagt tcagggcag ggtcaccttg accagggaca cgtccatcaa cacagcctac      240
atggagctca gcgggctgcg atctgtcgac acggccgtgt tttactgtgc gagtgttccc      300
cctagtggtt ttttctattg gggctctgac tactggggcc agggaaccct ggtcaccgtc      360
tcgtca                                                               366

<210> SEQ ID NO 12
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 12
gcggtccagc tggtggagtc tgggggaggc ctggtccagc ctggggggtc cctgagactc       60
tcctgtgaag cctctggatt caccttagt ggctattgga tgagctgggt ccgccaggct      120
ccagggaagg ggctggagtg ggtggccaac ataaagggag atggaagtga aaaatactat      180
gtggactctg tgaagggccg attcaccatc ttcagagaca cgccaagac ctcactgtat       240 ctgcaagtga acagcctgag agccgaggac acggctgtct attactgtgc gagagagagg      300
cacttcttag cagctcgtcc tggttactac atctacagcg gtctggacgt ctggggccca      360
gggaccacgg tcaccgtctc ctca                                           384

<210> SEQ ID NO 13
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 13
gacatccaga tgacccagtc tccatcctcc ctgtctgcat ctgtaggaga cagagtcacc       60
atcacttgcc gggcaagtca gagcattgac aactatttaa attggtatca gcagaaacca      120
gggaaggtcc ctaaactcct gatctatgct gcatccaatt tgcaaagtgg ggtcccatca      180
aagttcagtg gcggtggatc tgggacagat ttcactctca ccatcagcag tctgcaacct      240
gacgattttg caacctacta ctgtcaacag agtttcggta cccctcgaac gttcggccag      300
gggaccaggg tggaaatcaa a                                               321

<210> SEQ ID NO 14
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 14
caggtgcttc tggtgcagtc tggggctgag gtgaggaagc ctggggcctc agtgaaggtc       60
tcctgcaggg cttctggata caccttcacc gactactata tgcactgggt gcgacaggcc      120
cctggacaag ggcttgagtg gatgggatgg atcaacccta acagtggtgc cacaaagtac      180
gcacagaagt tcagggcag ggtcaccttg accagggaca cgtccatcaa cacagcctac      240
atggagctca gcgggctgcg atctgtcgac acggccgtgt tttactgtgc gagtgttccc      300
cctagtggtt ttttctattg gggctctgac tactggggcc agggaaccct ggtcaccgtc      360
tcgtca                                                               366
```

<210> SEQ ID NO 15
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 15
gatgttgtgt tgactcagtc tccgctctcc ctgcccgtca cccttggaca gccggcctcc        60
atctcctgta ggtctagtca aagcctcgta tacagtgatg ggaccaccta cttgaattgg       120
tttcagcaga ggccaggcca atctccaagg cgcctaattt ataaggtttc ttatcgggac       180
tctggggtcc cagacagatt cagtggcagt gggtcaggca ctgatttcac actggaaatc       240
agcagggtgg aggctgagga tgttgggatt tattactgca tgcacggtac acactgggaa       300
acgtggacgt tcggccaagg gaccaaggtg gaaatcaaa                               339

<210> SEQ ID NO 16
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 16
caggtgcagc tggtgcagtc tggggctgag gttaagaagc ctggggcctc agtgaaggtt        60
tcctgcaagg catcaggata caccttcacg agctactata ttaactgggt cgacaggcc        120 cctggacaag ggcttgagtg ggtaggaaca atcaaccta gtggaggtag cacaacctac       180
gcacagaagt tccagggcag agtcaccgtg accagggaca cgtccacgag cacagtctac       240
atggacctga gcggcctgag atcggggggac acggccgtgt attactgtgc gagagatcgt       300 aagggttag ctgctactcc cgtatattcc gactactact acggtatgga cgtctggggc        360
caggggacca cggtcaccgt ctcctca                                            387

<210> SEQ ID NO 17
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 17
gaaattgtgt tgacacagtc tccagccacc ctgtctttgt ctccagggga aagagccacc        60
ctctcctgca gggccagtca gagtgttagt agcttcttag cctggtacca acagaaacct       120
ggccaggctc ccaggctcct catctctgat gcatccaaaa gggccactgg catcccagcc       180
aggttcagtg gcagtgggtc tgggacggac ttctctctca ccatcagcag cctagaggct       240
gaagattttg cagtttatta ctgtcagcag agtaccaact ggcggatcac cttcggccaa       300
gggacacgac tggagcttaa a                                                  321

<210> SEQ ID NO 18
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 18
caggtgcagc tgcaggggtc gggcccagga ctggtgaagc cttcacagac cctgtccctc        60
acctgctctg tctctggtgg ctccgtcagc agaagtggct actactgggg ctggatccgg    120
cagcacccag ggaagggcct ggagtgtatt gggtacatct attacagtgg gatcacctac    180
tacaacccgt ccctcagcgg tcgacttacc atctcagtag acacgtctaa gaaccagttc    240
tccctggagc tgagctctgt gactgccgcg gacacggccg tgtattactg cgcgagagtt    300
tggttggggg gtggtgtctt tgacttctgg ggccagggat ccctggtcac cgtctcctca    360

<210> SEQ ID NO 19
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 19
gaaatagtga tgacgcagtc tccagccacc ctgtctgtgt ctccagggga aggagccacc     60
ctctcctgca gggccagtca gagtgttagc agcaacttag cctggtatca gcagaaacct    120
ggccaggctc ccaggctcct catctatgat gcatccacca gggccactgg tatcccagcc    180
aggttcagtg gcagtgggtc tgggacagag ttcactctca ccatcagcag cctgcagtct    240
gaagattttg cagtttatta ctgtcagcag tataatgact ggcggacgtt cggccgaggg    300
accaaggtgg aaatgaga                                                   318

<210> SEQ ID NO 20
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 20
caggtgcagc tgatggagtc tggggggaggc gtggtccagc ctgggaggtc cctgagactc     60
tcctgttcag cctctggatt caccttcagt aactatgctt tgcactgggt ccgccaggct    120
ccaggcaagg ggctggagtg gcttgcattt atttcatatg atggaagttt taaatattac    180
gcagactctg tgaagggccg attcaccgtc tcccgagacg attctaggaa tactctatat    240
ctccaaatga gcagcctgag acctgaggac acggctgtct attactgtac gagagatgat    300
gatccccccg ttgaaaactt ccagatctgg ggccagggta ccctggtcac cgtctcctca    360

<210> SEQ ID NO 21
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 21
caggtgcagc tgcaggagtc gggcccagga ctggtgaagc cttcacagac cctgtccctc     60
acctgttctg tctctggtga ctccatcagc agtggtactc actactggag ctggatccgg    120
cagcccgccg ggaagggact ggagtggatt gggcgtatct atgccactgg gaacagcaac    180
tacaacccct ccttcaggag tcgagtcacc atatcagtcg acacgtccaa gaaccaattc    240
tccctgaagc tgagctctgt gaccgccgca gacacggccg tctattactg tgtgagagat    300
gaagcagtgg ctgatatggc tgtcgaaaac tattacggta tggacgtctg gggccaaggg    360
acctcggtca ccgtctccgc a                                               381

<210> SEQ ID NO 22
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 22
gaaattgtgt tgacacagtc tccagccacc ctgtctttgt ctccagggga aagagccacc      60
ctctcctgca gggccagtca gacgattagc agctacttag tctggtacca acagaagcct     120
ggccaggctc ccaggcccct catctatgat gcatccatca gggccactgg catcccagcc     180
aggttcagtg gcagtgggtc tgggacagac ttcactctca ccatcagcag cctagagcct     240
gaagattttg cagtttatta ctgtcagcag cgttacaact ggcctcggac gttcggccaa     300
gggaccaagg tggaaatcaa a                                                321

<210> SEQ ID NO 23
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 23
caggtgcagc tacagcagtg gggcgcagga ctgttgaagc cttcggagac cctgtccctc      60
acctgcgatt tgtctggtgg gtccttcact aattactact ggacctggat acgccacctc     120
ccagggaagg ggctggagtg gcttggagaa atcaatcata gtggaagaac caactacagc     180
ccgtccctca agagtcgagt caccatatca gtagacacgt ccaagaacca gttctccctg     240
aggctgagtt ctgtgaccgc cgcggacacg gctgtatatt attgtgcgag agacatccgt     300
aagttggccc caaaacctca ttcttacgac ctctattacg gtatggacgt ctggggccaa     360
gggaccacgg tcaccgtctc ctca                                             384

<210> SEQ ID NO 24
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 24
gaaattgtgt tgacgcagtc tccaggcacc ctgtctttgt ctccagggga aagagccacc      60
ctctcctgca gggccagtca gagtgttggt agcaactatt aacctggta tcagcaaaaa      120 cctggccagc ctcccaggct cctcatctat ggtgcatcca accggggccgc tggcatccca     180 gacaggttca gtggcagtgg gtctgggaca gacttcactc tcaccatcag cagactggag     240
cctgaagatt ttgctgttta ttactgtcag caatatgaga cctcatcccg gacgttcggc     300
caagggacca aggtggacat caga                                             324

<210> SEQ ID NO 25
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 25
gaggtgcagc tgttggagtc tggggggaggc ctggtacagc ctggggggtc cctgagactc      60

-continued

```
tcctgtgcag cctctggatt cacctttagc accaatgcca tgagctgggt ccgccaggct      120
ccaggaaagg ggctggagtg ggtctctact gttagtggta gtggtgcaca cccaaattat      180
ggagactccg tgaagggccg gttcaccatc tccagagtca attccaagaa cacgctattt      240
ctacaaatga gcagcctgag agccgaggac acggccatat attactgtgc gagagtttcc      300
acggttacag ttgggggaca catacccggg ggctactact ttgactactg gggccaggga      360
accctggtca ccgtctcctc a                                               381
```

<210> SEQ ID NO 26
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 26

```
gaaattctgt tgacgcagtc tccaggcacc ctgtctttgt ctccagggga aagagccacc       60
ctctcctgca gggccagtca gagtgctagc agcagctact tagcctggta ccaacagaaa      120
cctggccagg ctcccaggct cctcatctat ggtgcatcca ccagggccac tggcatccca      180
gacaggttca gtggcagtgg gtctgggaca gagttcactc tcacaatcag cagactggag      240
tctgaagatt ttgcagtgta ttactgtcat cattatggta gttcacggac gttcggccaa      300
gggaccaagg tggaggtcaa a                                               321
```

<210> SEQ ID NO 27
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 27

```
gaggtgcagc tggtggagtc tgggggaggc ttggtccagc ctcgggggtc cctgagactc       60
tcctgtgcag cctctggatt cacctttagt ggctattgga tgagctgggt ccgccaggct      120
ccagggaagg ggctggagtg ggtggccaag ataaagaaag atggaagtga gaaaacctat      180
gtggactctg tgaagggccg attcaccatc tccagagaca acgccaagga ctcattgtat      240
ctgcaaatga acagcctgag agccgaggac acggctgtct attactgtgc gagagagcgg      300
ttgttagtac cagctgctat agttggattg gactactact acgctatgga cgtctggggc      360
caagggacca cggtcaccgt ctcctca                                         387
```

<210> SEQ ID NO 28
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 28

```
gacatccaga tgacccagtc tccatcctcc ctgtctgcat ctgtaggaga cagagtcacc       60
atcacttgcc gggcaagtca gaacatgagc acctatttaa attggtatca gcagaaacca      120
gggaaagccc ctaagttcct gatctatgga gcatccagat tacagaatgg ggtcccatca      180
aggttcagtg gcggtggatc tgggacagat ttcactctca ccatcagcag tctgcaacct      240
gaagattttg caacttacta ctgtcaacag agttacaata tcccgatcac cttcggccaa      300
```
gggacacgac tggagattaa a                                                     321

<210> SEQ ID NO 29
<211> LENGTH: 399
<212> TYPE: DNA
<213> ORGANISM: Artificial sequence
<220> FEATURE:
<223> OTHER INFORMATION: Synthetic oligonucleotide

<400> SEQUENCE: 29
caggtccaac tggtgcaatc tggggctgag gtgaagaagc ctgggtcctc ggtgaaggtc        60
tcctgtaagg cttctggagg caccttcagc agctatacta tcagctgggt acggcaggcc       120
cctggacaag ggcttgagtg gatgggaagg atcatcccta tttctggtat aacaaactac       180
gcacagaagt tccagggcag agtcacgatt accgcggaca atccacgag cacagcctac        240 atggagctga gcagcctgag atctgaggac acggccgtgt attactgtgc gaaagattgt       300
tactatggtt cagggactta ttatggttgc cgtgcggatt accagtggca ccacactatg       360
gacgtctggg gccagggac cacggtcacc gtctcctca                               399

<210> SEQ ID NO 30
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 30
gacatccaga tgacccagtc tccatcctcc ctgtctgcat ctgtaggaga cagagtcacc        60
atcacttgcc gggcaagtca gggcattaga aatgatttag ctggtttca gcagaaacca        120 gggaaagccc ctaagcgcct gatctatgct gcttccagtt tgcaaagtgg ggtcccatca       180
aggttcagcg gcagtggatc tgggacagaa ttcactctca caatcagcag cctgcagcct       240
gaagattttg caacttattt ctgtctacag cataatactt accctctgac gttcggccaa       300
gggaccaagg tggaaatcaa a                                                 321

<210> SEQ ID NO 31
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 31
caggtgcggc tgcaggagtc gggcccaaga ctggtgaagc cttcacagac cctgtccctc        60
acctgcactg tctctggtgg ctccatcagc agtcgggact actactggag ctggatccgc       120
cagcacccag ggaagggcct ggagtggatt ggctacatct attacagtgg gaccacctac       180
tacaacccgt ccctcgagag tcgagttacc ctctctctcg acacgtctaa gaaccagttc       240
tccctggacc tgacctctgt gactgccgcg gacacggccg tctatcactg cgcgagagtt       300
tggttggggg gtggtgtctt tgacttctgg ggccagggaa ccctggtcac cgtctccgca       360

<210> SEQ ID NO 32
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 32

-continued

```
gaaatagtga tgacgcagtc tccagacacc ctgtctgtgt ctccagggga aagagccacc        60
ctctcctgca gggccagtca cagtgttacc accaacttag cctggtacca gcagagacct       120
ggccaggctc ccaggctcct catttttgat gcatccacca gggccactgg tatcccagcc       180
aggttcagtg gcagtgggtc tgggacagag ttcactctca ccatcggcag cctacagtct       240
gaagattttg cagtttatta ctgtcaacaa tacaatgacg ggcggacgtt cggccaaggg       300
accaaggtgg aaatcaaa                                                     318

<210> SEQ ID NO 33
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 33
gaggtgcagc tgttggagtc tggggggaggc ttggtacagc ctggggggtc cctgagactc       60
tcctgtgcag cctctggatt cacctttagc agtagtgcca tgagctgggt ccgccagact       120
ccagggaagg ggctggagtg ggtctcaact attagtggta gtggtgctaa cacatactac       180
gcagcctccg tgaagggccg gttccccatc tccagagaca attccaagaa cacactcttt       240
ctgcaaatga acagcctgag agccgaggac acggccgtat attactgtgc gaaagtttcc       300
acggttacat ttgggggaca cgtaccccgg ggctcctact ttgactactg gggccaggga       360
acccaggtca ccgtctcctc a                                                 381

<210> SEQ ID NO 34
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 34
tcctatgtgc tgactcagcc accctcggtg tcagtggccc caggacagac ggccaggatt        60
ccctgtgggg gaaacaacat tggaagtaaa agtgtgcact ggtaccagca gaagccaggc       120
caggcccctg tgctggtcgt ctatgatgag aacgaccggc cctcagggat ccctgagcga       180
ttctctgctt ccaaatctgg gaacacggcc accctgacca tcagcaggt cgaagccggg        240 gatgaggccg actattactg tcaggtgtgg gatagtcgta gtgatcatta tgtcttcgga       300
actgggacca aggtcaccgt cctc                                              324

<210> SEQ ID NO 35
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 35
gaggtgcagc tgttggagtc tggggggaggc ttggtacagc ctggggggtc cctgagactc       60
tcctgtgcag cctctggatt cacctttagc agctatacca tgagctgggt ccgccaggct       120
ccagggaagg ggctggagtg ggtctccggt attagtggta gtggtggtaa cacatactac       180
gcaggctccg tgaagggccg gttccaccatc tccagagaca attccaagaa cacgctgtat      240
ctgcaaatga acagcctgag agccgaggac acggccgtat attactgtgc gaaagatggg       300
```

```
tatacaggtc aacagcttat gcgtcgagga ccctggtggt tcgacccctg gggccaggga      360
accctggtca ccgtctcctc a                                                381

<210> SEQ ID NO 36
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 36
tcctatgtgc tgactcagcc accctcggtg tcagtggccc caggacagac ggccaggatt       60
acctgtgggg gaaacaacat tggaagtaaa agtgtgcact ggtaccagca gaagccaggc      120
caggcccctg tgctggtcgt ctatgatgat agcgaccggc cctcagggat ccctgagcga      180
ttctctggct ccaagtctgg gaacacggcc accctgacca tcagcagggt cgaagccggg      240
gatgaggccg attattactg tcaggtgtgg gatagtagta gtgatcatgt agtattcggc      300
ggagggacca agctgaccgt ccta                                             324

<210> SEQ ID NO 37
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 37
caggtgcagc tggtacaatc tgggactgag gtgaagaacc ctgggtcctc ggtgaaggtc       60
tcctgcaagg cttctggagg cactttcagc ggctttggta tcagctgggt gcgacaggcc      120
cctggacaag gccttgagtg gatgggaggg gtcctcccta tttttggttc accaaactac      180
gcacagaagt tccagggcag agtcacgatt accgcggacg aatccacggg cacagcctac      240
atggatctga gcagcctgag atctgacgac acggccatgt attactgtgc gagagatcag      300
tcaggaggct cttttgacta ctgggggcag ggaaccctgg tcatcgtctc ctcc           354

<210> SEQ ID NO 38
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 38
gaaattgtgt tgacacagtc tccagccacc ctgtctttgt ctccagggga aagagccacc       60
ctctcctgca gggccagtca gagtgttagc agcaacttgg cctggtacca acaaaaacct      120
ggccaggctc ccaggctcct catctatgat gcatccgaca gggccactgg cgtcccagcc      180
aggttcagtg gcagtgggtc tgggacagac ttcactctca ccatcagcag cctagagcct      240
gaggattttg cactttatta ctgtcagcag cgttacaact ggcgggtcac cttcggccag      300
gggacacgac tggagattaa a                                                321

<210> SEQ ID NO 39
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 39
```

-continued

```
caggtgcagg tggtggagtc tggggggaggc gtggtccacc ctgggcggtc cctgcgactc        60
tcctgtgcag gctctggatt catcttcaat aactatgctt ttcactgggt ccgccaggct       120
ccaggcgggg ggctggagtg gatggcctat atttcatatg atgggaggta taaatactac       180
gcagcctccg tgaggggccg gttcaccatc tccagagacg attccaagaa caccctgtat       240
ctgcaaatgt ccagcctgag aactgaggac acggctctgt attactgtgc gatctcggac       300
tacgctgaac cccttgacaa ctggggccaa ggaaccctgg tcaccgtctc ctca            354

<210> SEQ ID NO 40
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 40
caaattgtgt tgacacagtc tccagccacc ctgtctttgt ctccagggga cagagccacc        60
ctctcctgcc gggccagtca gagtgttagc agcaacgtag cctggtacca acagaaacct       120
ggccaggctc ccaggctcct catctataat gtatccaaca gggccactgg catcccagcc       180
aggttcagtg gcagtgggtc tgggacagac ttcactctca ccatcagcag cctagagcct       240
gaagattttg cagtttatta ctgtcaccag cgtaccaact ggcccctcac tttcggcgga       300
gggaccaagg tggagatcaa a                                                321

<210> SEQ ID NO 41
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 41
caggggcagc tacagcagtg gggcgcagga ctgttgaagc cttcggagac cctgtccctc        60
acctgcggtg tctatagtgg gtccttcagt ggttactact ggagctggat ccgccagccc       120
ccagggaagg ggctggagtg gatcggggaa atcaatcata gtggaagaac agactacaac       180
ccgtccctca agagtcgagt caccatgtca gtggacacgt ccaagaacca gttctccctg       240
aggctgagct ctgtgaccgc cgcggacacg gctgtatatt tctgtgcgag agcgaccccc       300
ccgacactat gggtcaggga cttcttatgg ggctactttg actcctgggg ccagggaacc       360
ctggtctccg tctcctca                                                    378

<210> SEQ ID NO 42
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 42
gacatcgtga tgacccagtc tcctgactcc ctggctgtgt ctctgggcga gagggccacc        60
atcaactgca agtccagcca gagtgtctta tacacctcca acaataagaa ctacttagct       120
tggtaccagc agaaaccagg acagcctcct aaactactca ttttctgggc atctacccgg       180
gaatccgggg tccctgaccg attcagtggc agcgggtctg ggacagattt cactctcacc       240
atcagcagcc tgcaggctga agatgtggca gtttattact gtcagcaata ttatactact       300
```

-continued cctaagactt tcggccctgg gaccaaagtg gatctcaaa                              339

<210> SEQ ID NO 43
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 43
caggtgcagc tgcaggagtc gggcccagga ctggtgaagc cttcggagac cctgtccctc        60
acctgcactg tctctggtgg ctccatcgat agttactact ggagttggat ccggcagccc       120
gccgggaagg gactggagtg gattgggcgt atctatccca gtgggaccac caactacaac       180
ccctccctca agagtcgagt caccatgtca gtagacacgt ccaagaacca gttctccctg       240
aaggtgacct ctgtgaccgc cgcggacacg gccgtgtatt actgtgcgag gatgcaaacc       300
ggatttggca gcagcttgtt cttcgttcca tactttgaca actggggcca gggaaccctg       360
gtcaccgtct cctca                                                       375

<210> SEQ ID NO 44
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 44
gaaattgtgt tgacgcagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg cagtttatta ctgtcagcag cgtggcaact ggccgctcac tttcggcgga       300
gggaccaagg tggagatcaa a                                                 321

<210> SEQ ID NO 45
<211> LENGTH: 393
<212> TYPE: DNA
<213> ORGANISM: Artificial sequence
<220> FEATURE:
<223> OTHER INFORMATION: Synthetic oligonucleotide

<400> SEQUENCE: 45
gaagagcgac tggtgcagtc tggggggaggc ttggcacagc ctggacagtc tctgagactc        60
tcctgtgcag gctttggatt caccttcact agatacgaaa tgaattgggt ccgccaggct       120
ccagggaagg ggctggagtg gattgcgcac ataagtacta ggggcgatac cattagctac       180
gcggactctg tgaagggccg agccaccatc tccagagatg acaccaacaa ctcactggat       240
ctgcagatgg acagcctgag agccgaggac acggccattt attttgtgc gagagatagg        300 gggtctcttt caactcgacc tccagactca tatcactact actatcacgg tatggacgtc       360
tggggccaag ggaccacggt catcgtctcg tca                                    393

<210> SEQ ID NO 46
<211> LENGTH: 327
<212> TYPE: DNA
<213> ORGANISM: Artificial sequence
<220> FEATURE:
<223> OTHER INFORMATION: Synthetic oligonucleotide

<400> SEQUENCE: 46
gaaattgtgt tgacacagtc tcctgccacc ctgtctttgt ctccagggga aagagccacc          60
ctctcctgca gggccagtca gagcattgac acctacttag cctggtacca acaaaaacct         120
ggccaggctc ccaggctcct catctatgat gcatccaaca gggccactgg catcccagcc         180
aggttcagtg gcagtgggtc tgggacagac ttctctctca ccatcagcag cctcgagcct         240
gatgactttg cagtttatta ctgtcagcag cgttccaata ggcctcctag gtacactttt         300
ggcctgggga cgaggctgga gatcaaa                                            327

<210> SEQ ID NO 47
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 47
caggtccagc tggtgcagtc tggggctgag gtgaagaagc ctgggtcctc ggtgacagtc          60
tcctgcaaga cttctggggg caccttcagc ggctatgctg tcagttgggt gcgacaggcc         120
cctggacaag ggcttgagtg gatggggagg atcgtccctc agtttaatat tccaaactac         180
gcacagaagt tccaggacag agtcacgatt accgcggacg agtccacggg cacatcctac         240
atggagctga gcagcctgag atccgacgac acggccgtct tctactgtgc gagagaaaac         300
atccaaacga tttttggagt ggttgcgatg atgggcgggg gaggctactt tgactcctgg         360
ggccagggaa ccctggtcac cgtctcctca                                         390

<210> SEQ ID NO 48
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 48
gacatccaga tgacccagtc gccatcctcc ctgtctgcat ctgtaggaga cagagtcacc          60
atcacttgcc aggcgaatca ggacattaac acctatttaa attggtatct gcagaaacca         120
gggaaagccc ctcagctcct ggtcttcgat gcatccaatt tggtgacagg ggtcccatca         180
aggttcagtg gaggtggatc taggacagat tttactttga ccatcgacag cctgcagccc         240
gaagatattg aacatatta ctgtcaacag tatgatcatc tcccgaggcg tacattcact         300
ttcggccctg ggaccaaggt ggatctcaag                                         330

<210> SEQ ID NO 49
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Val Ser Gly Gly Ile Phe Asn Arg Glu
            20                  25                  30

Thr Ile Asn Trp Val Arg Gln Ala Pro Gly Gln Gly Leu Glu Trp Met
        35                  40                  45

Gly Arg Ile Thr Pro Ile Val Asp Val Pro Asn Tyr Pro Arg Lys Phe
    50                  55                  60

Arg Gly Arg Val Thr Ile Thr Ala Asp Lys Ser Thr Ser Thr Val Tyr
65                  70                  75                  80

Met Glu Leu Ser Gly Leu Arg Phe Glu Asp Thr Ala Ile Tyr Phe Cys
                85                  90                  95

Ala Arg Phe Arg Gly His Asn Tyr Phe Asp Pro Trp Gly Gln Gly Thr
            100                 105                 110

Leu Val Thr Val Ser Ser
        115

<210> SEQ ID NO 50
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 50

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Gly Lys Ser Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Glu Arg Phe Ser Gly Ser
    50                  55                  60

Asn Ser Gly Asp Thr Ala Ser Leu Thr Ile Ser Arg Val Asp Ala Gly
65                  70                  75                  80

Asp Glu Ala Asp Tyr Phe Cys Gln Val Trp Asp Asn Ala Ser Asp Glu
                85                  90                  95

Ala Val Phe Gly Gly Gly Thr Lys Leu Thr Val Leu
            100                 105

<210> SEQ ID NO 51
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Val Ile Ser Trp Val Arg Gln Ala Pro Gly Gln Gly Phe Glu Trp Met
        35                  40                  45

Gly Arg Ile Ile Pro Met Ile Gly Ile Ser Asn Tyr Ala Gln Lys Phe
    50                  55                  60

Gln Asp Arg Val Thr Ile Thr Ala Asp Lys Asp Glu Ser Thr Thr Thr
65                  70                  75                  80

Ala Tyr Met Glu Leu Arg Gly Leu Arg Ser Glu Asp Thr Ala Met Tyr
                85                  90                  95

Tyr Cys Ala Ser Ser Thr Val Thr Glu Val Gly Ala Trp Gly Gln Gly
            100                 105                 110

Thr Leu Val Thr Val Ser Ser

```
          115

<210> SEQ ID NO 52
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 52

Ala Ile Gln Leu Thr Gln Ser Pro Ser Ser Leu Ser Ala Ser Ile Gly
1               5                   10                  15

Asp Arg Val Thr Ile Thr Cys Arg Ala Ser Gln Gly Ile Ser Ser Ala
                20                  25                  30

Leu Ala Trp Phe Gln Gln Lys Pro Gly Lys Pro Pro Ile Leu Leu Ile
        35                  40                  45

Tyr Asp Ala Ser Ser Leu Glu Ser Gly Val Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Tyr Asn His Pro Leu
                85                  90                  95

Thr Phe Gly Pro Gly Thr Lys Val Asp Ile Lys
            100                 105

<210> SEQ ID NO 53
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 53

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Ile Ile Asn Tyr
                20                  25                  30

Ser Leu Ser Trp Val Arg Gln Ala Pro Gly Lys Gly Leu Glu Trp Val
        35                  40                  45

Ser Ser Ile Ser Gly Ser Ser Asp Tyr Ile Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Ala Ala Val Tyr Tyr Cys
                85                  90                  95

Ala Arg Glu Arg Thr Gly Phe Phe Ser Pro Pro Ser Tyr Leu Met Asp
            100                 105                 110

Val Trp Gly Gln Gly Thr Thr Val Thr Val Ser Ser
        115                 120

<210> SEQ ID NO 54
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 54

Ala Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105
```

<210> SEQ ID NO 55
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 55

```
Gln Val Gln Leu Leu Gln Ser Gly Gly Glu Val Lys Lys Pro Gly Ala
1               5                   10                  15

Ser Val Lys Val Ser Cys Lys Ala Thr Asp Asn Thr Leu Thr Thr Tyr
            20                  25                  30

Gly Leu Ser Trp Val Arg Gln Ala Pro Gly Gln Gly Leu Glu Trp Met
            35                  40                  45

Gly Trp Val Ser Ala Tyr Asn Gly His Pro Asn Tyr Ala Gln Lys Phe
        50                  55                  60

Gln Gly Arg Val Thr Met Thr Thr Asp Thr Ser Thr Ser Thr Ala Tyr
65                  70                  75                  80

Met Glu Leu Arg Ser Leu Thr Ser Asp Asp Thr Ala Val Tyr Phe Cys
                85                  90                  95

Ala Arg Gly Ser Ser Ala Trp Asn Pro Trp Gly Gln Gly Thr Leu Val
            100                 105                 110

Thr Val Ser Ser
        115
```

<210> SEQ ID NO 56
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 56

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Thr Ser Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Gly Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Leu Ala Thr Tyr Tyr Cys Gln Gln Tyr Ser Ser Tyr Pro Val
```

```
                        85                      90                      95

Thr Phe Gly Gly Gly Thr Lys Val Glu Ile Arg
                100                     105

<210> SEQ ID NO 57
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 57

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Pro Glu Trp Met
        35                  40                  45

Ala Val Ile Ser Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Asn
65                  70                  75                  80

Leu Gln Met Asn Ser Leu Thr Ser Glu Asp Thr Ala Ile Tyr Tyr Cys
                85                  90                  95

Ala Arg Phe Arg Gly Gly Gly Arg Ile Ala Ala Arg Pro Asp Asp Tyr
            100                 105                 110

Gly Met Asp Val Trp Gly Gln Gly Thr Thr Val Thr Val Ser Thr
        115                 120                 125

<210> SEQ ID NO 58
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Ile Thr Tyr
            20                  25                  30

Leu Asn Trp Tyr Gln Gln Lys Pro Gly Lys Ala Pro Lys Leu Leu Ile
        35                  40                  45

Tyr Gly Ala Ser Thr Leu Glu Ser Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Ile Ala Thr Tyr Tyr Cys Gln Gln Ser Tyr Asn Met Ser Pro
                85                  90                  95

Tyr Thr Phe Gly Gln Gly Thr Lys Leu Glu Ile Lys
            100                 105

<210> SEQ ID NO 59
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 59
```

```
Gln Val Leu Leu Val Gln Ser Gly Ala Glu Val Arg Lys Pro Gly Ala
1               5                   10                  15

Ser Val Lys Val Ser Cys Arg Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Ala Thr Lys Tyr Ala Gln Lys Phe
    50                  55                  60

Gln Gly Arg Val Thr Leu Thr Arg Asp Thr Ser Ile Asn Thr Ala Tyr
65              70                  75                  80

Met Glu Leu Ser Gly Leu Arg Ser Val Asp Thr Ala Val Phe Tyr Cys
            85                  90                  95

Ala Ser Val Pro Pro Ser Gly Phe Phe Tyr Trp Gly Ser Asp Tyr Trp
            100                 105                 110

Gly Gln Gly Thr Leu Val Thr Val Ser Ser
        115                 120
```

<210> SEQ ID NO 60
<211> LENGTH: 128
<212> TYPE: PRT
<213> ORGANISM: Artificial sequence
<220> FEATURE:
<223> OTHER INFORMATION: Synthetic polypeptide

<400> SEQUENCE: 60

```
Ala Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Ser Gly Tyr
            20                  25                  30

Trp Met Ser Trp Val Arg Gln Ala Pro Gly Lys Gly Leu Glu Trp Val
        35                  40                  45

Ala Asn Ile Lys Gly Asp Gly Ser Glu Lys Tyr Tyr Val Asp Ser Val
    50                  55                  60

Lys Gly Arg Phe Thr Ile Phe Arg Asp Asn Ala Lys Thr Ser Leu Tyr
65              70                  75                  80

Leu Gln Val Asn Ser Leu Arg Ala Glu Asp Thr Ala Val Tyr Tyr Cys
            85                  90                  95

Ala Arg Glu Arg His Phe Leu Ala Ala Arg Pro Gly Tyr Tyr Ile Tyr
            100                 105                 110

Ser Gly Leu Asp Val Trp Gly Pro Gly Thr Thr Val Thr Val Ser Ser
        115                 120                 125
```

<210> SEQ ID NO 61
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asn Tyr
            20                  25                  30

Leu Asn Trp Tyr Gln Gln Lys Pro Gly Lys Val Pro Lys Leu Leu Ile
        35                  40                  45

Tyr Ala Ala Ser Asn Leu Gln Ser Gly Val Pro Ser Lys Phe Ser Gly
```

-continued

```
            50                  55                  60

Gly Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Phe Gly Thr Pro Arg
                85                  90                  95

Thr Phe Gly Gln Gly Thr Arg Val Glu Ile Lys
            100                 105
```

```
<210> SEQ ID NO 62
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 62

Gln Val Leu Leu Val Gln Ser Gly Ala Glu Val Arg Lys Pro Gly Ala
1               5                   10                  15

Ser Val Lys Val Ser Cys Arg Ala Ser Gly Tyr Thr Phe Thr Asp Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Ala Thr Lys Tyr Ala Gln Lys Phe
        50                  55                  60

Gln Gly Arg Val Thr Leu Thr Arg Asp Thr Ser Ile Asn Thr Ala Tyr
65                  70                  75                  80

Met Glu Leu Ser Gly Leu Arg Ser Val Asp Thr Ala Val Phe Tyr Cys
                85                  90                  95

Ala Ser Val Pro Pro Ser Gly Phe Phe Tyr Trp Gly Ser Asp Tyr Trp
                100                 105                 110

Gly Gln Gly Thr Leu Val Thr Val Ser Ser
            115                 120
```

```
<210> SEQ ID NO 63
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 63

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Thr Thr Tyr Leu Asn Trp Phe Gln Gln Arg Pro Gly Gln Ser
            35                  40                  45

Pro Arg Arg Leu Ile Tyr Lys Val Ser Tyr Arg Asp Ser Gly Val Pro
        50                  55                  60

Asp Arg Phe Ser Gly Ser Gly Ser Gly Thr Asp Phe Thr Leu Glu Ile
65                  70                  75                  80

Ser Arg Val Glu Ala Glu Asp Val Gly Ile Tyr Tyr Cys Met His Gly
                85                  90                  95

Thr His Trp Glu Thr Trp Thr Phe Gly Gln Gly Thr Lys Val Glu Ile
                100                 105                 110

Lys
```

<210> SEQ ID NO 64
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile Asn Trp Val Arg Gln Ala Pro Gly Gln Gly Leu Glu Trp Val
            35                  40                  45

Gly Thr Ile Asn Pro Ser Gly Gly Ser Thr Thr Tyr Ala Gln Lys Phe
        50                  55                  60

Gln Gly Arg Val Thr Val Thr Arg Asp Thr Ser Thr Ser Thr Val Tyr
65                  70                  75                  80

Met Asp Leu Ser Gly Leu Arg Ser Gly Asp Thr Ala Val Tyr Tyr Cys
                85                  90                  95

Ala Arg Asp Arg Lys Gly Leu Ala Ala Thr Pro Val Tyr Ser Asp Tyr
                100                 105                 110

Tyr Tyr Gly Met Asp Val Trp Gly Gln Gly Thr Thr Val Thr Val Ser
        115                 120                 125

Ser

<210> SEQ ID NO 65
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
                20                  25                  30

Leu Ala Trp Tyr Gln Gln Lys Pro Gly Gln Ala Pro Arg Leu Leu Ile
            35                  40                  45

Ser Asp Ala Ser Lys Arg Ala Thr Gly Ile Pro Ala Arg Phe Ser Gly
        50                  55                  60

Ser Gly Ser Gly Thr Asp Phe Ser Leu Thr Ile Ser Ser Leu Glu Ala
65                  70                  75                  80

Glu Asp Phe Ala Val Tyr Tyr Cys Gln Gln Ser Thr Asn Trp Arg Ile
                85                  90                  95

Thr Phe Gly Gln Gly Thr Arg Leu Glu Leu Lys
                100                 105

<210> SEQ ID NO 66
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 66

Gln Val Gln Leu Gln Gly Ser Gly Pro Gly Leu Val Lys Pro Ser Gln
1               5                   10                  15

```
Thr Leu Ser Leu Thr Cys Ser Val Ser Gly Gly Ser Val Ser Arg Ser
            20                  25                  30

Gly Tyr Tyr Trp Gly Trp Ile Arg Gln His Pro Gly Lys Gly Leu Glu
        35                  40                  45

Cys Ile Gly Tyr Ile Tyr Tyr Ser Gly Ile Thr Tyr Tyr Asn Pro Ser
    50                  55                  60

Leu Ser Gly Arg Leu Thr Ile Ser Val Asp Thr Ser Lys Asn Gln Phe
65                  70                  75                  80

Ser Leu Glu Leu Ser Ser Val Thr Ala Ala Asp Thr Ala Val Tyr Tyr
            85                  90                  95

Cys Ala Arg Val Trp Leu Gly Gly Gly Val Phe Asp Phe Trp Gly Gln
            100                 105                 110

Gly Ser Leu Val Thr Val Ser Ser
        115                 120

<210> SEQ ID NO 67
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 67

Glu Ile Val Met Thr Gln Ser Pro Ala Thr Leu Ser Val Ser Pro Gly
1               5                   10                  15

Glu Gly Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Arg Thr
            85                  90                  95

Phe Gly Arg Gly Thr Lys Val Glu Met Arg
            100                 105

<210> SEQ ID NO 68
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 68

Gln Val Gln Leu Met Glu Ser Gly Gly Gly Val Val Gln Pro Gly Arg
1               5                   10                  15

Ser Leu Arg Leu Ser Cys Ser Ala Ser Gly Phe Thr Phe Ser Asn Tyr
            20                  25                  30

Ala Leu His Trp Val Arg Gln Ala Pro Gly Lys Gly Leu Glu Trp Leu
        35                  40                  45

Ala Phe Ile Ser Tyr Asp Gly Ser Phe Lys Tyr Tyr Ala Asp Ser Val
    50                  55                  60

Lys Gly Arg Phe Thr Val Ser Arg Asp Asp Ser Arg Asn Thr Leu Tyr
65                  70                  75                  80

Leu Gln Met Ser Ser Leu Arg Pro Glu Asp Thr Ala Val Tyr Tyr Cys
            85                  90                  95
```

```
Thr Arg Asp Asp Asp Pro Pro Val Glu Asn Phe Gln Ile Trp Gly Gln
        100                 105                 110

Gly Thr Leu Val Thr Val Ser Ser
    115                 120

<210> SEQ ID NO 69
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 69

Gln Val Gln Leu Gln Glu Ser Gly Pro Gly Leu Val Lys Pro Ser Gln
1               5                   10                  15

Thr Leu Ser Leu Thr Cys Ser Val Ser Gly Asp Ser Ile Ser Ser Gly
            20                  25                  30

Thr His Tyr Trp Ser Trp Ile Arg Gln Pro Ala Gly Lys Gly Leu Glu
        35                  40                  45

Trp Ile Gly Arg Ile Tyr Ala Thr Gly Asn Ser Asn Tyr Asn Pro Ser
    50                  55                  60

Phe Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Val Arg Asp Glu Ala Val Ala Asp Met Ala Val Glu Asn Tyr Tyr
            100                 105                 110

Gly Met Asp Val Trp Gly Gln Gly Thr Ser Val Thr Val Ser Ala
        115                 120                 125

<210> SEQ ID NO 70
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 70

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Ser Tyr
            20                  25                  30

Leu Val Trp Tyr Gln Gln Lys Pro Gly Gln Ala Pro Arg Pro Leu Ile
        35                  40                  45

Tyr Asp Ala Ser Ile Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Asn Trp Pro Arg
            85                  90                  95

Thr Phe Gly Gln Gly Thr Lys Val Glu Ile Lys
            100                 105

<210> SEQ ID NO 71
<211> LENGTH: 128
<212> TYPE: PRT
<213> ORGANISM: Artificial sequence
<220> FEATURE:
<223> OTHER INFORMATION: Synthetic polypeptide
```

<400> SEQUENCE: 71

```
Gln Val Gln Leu Gln Gln Trp Gly Ala Gly Leu Leu Lys Pro Ser Glu
1               5                   10                  15

Thr Leu Ser Leu Thr Cys Asp Leu Ser Gly Gly Ser Phe Thr Asn Tyr
            20                  25                  30

Tyr Trp Thr Trp Ile Arg His Leu Pro Gly Lys Gly Leu Glu Trp Leu
        35                  40                  45

Gly Glu Ile Asn His Ser Gly Arg Thr Asn Tyr Ser Pro Ser Leu Lys
    50                  55                  60

Ser Arg Val Thr Ile Ser Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Ile Arg Lys Leu Ala Pro Lys Pro His Ser Tyr Asp Leu Tyr
            100                 105                 110

Tyr Gly Met Asp Val Trp Gly Gln Gly Thr Thr Val Thr Val Ser Ser
        115                 120                 125
```

```
<210> SEQ ID NO 72
<211> LENGTH: 108
<212> TYPE: PRT
<213> ORGANISM: Artificial sequence
<220> FEATURE:
<223> OTHER INFORMATION: Synthetic polypeptide
```

<400> SEQUENCE: 72

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Asn
            20                  25                  30

Tyr Leu Thr Trp Tyr Gln Gln Lys Pro Gly Gln Pro Pro Arg Leu Leu
        35                  40                  45

Ile Tyr Gly Ala Ser Asn Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Thr Ser Ser
                85                  90                  95

Arg Thr Phe Gly Gln Gly Thr Lys Val Asp Ile Arg
            100                 105
```

```
<210> SEQ ID NO 73
<211> LENGTH: 127
<212> TYPE: PRT
<213> ORGANISM: Artificial sequence
<220> FEATURE:
<223> OTHER INFORMATION: Synthetic polypeptide
```

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Asn
            20                  25                  30

Ala Met Ser Trp Val Arg Gln Ala Pro Gly Lys Gly Leu Glu Trp Val
        35                  40                  45

Ser Thr Val Ser Gly Ser Gly Ala His Pro Asn Tyr Gly Asp Ser Val
    50                  55                  60
```

```
Lys Gly Arg Phe Thr Ile Ser Arg Val Asn Ser Lys Asn Thr Leu Phe
65                  70                  75                  80

Leu Gln Met Ser Ser Leu Arg Ala Glu Asp Thr Ala Ile Tyr Tyr Cys
                85                  90                  95

Ala Arg Val Ser Thr Val Thr Val Gly Gly His Ile Pro Arg Gly Tyr
            100                 105                 110

Tyr Phe Asp Tyr Trp Gly Gln Gly Thr Leu Val Thr Val Ser Ser
        115                 120                 125

<210> SEQ ID NO 74
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 74

Glu Ile Leu Leu Thr Gln Ser Pro Gly Thr Leu Ser Leu Ser Pro Gly
1               5                   10                  15

Glu Arg Ala Thr Leu Ser Cys Arg Ala Ser Gln Ser Ala Ser Ser Ser
                20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
        50                  55                  60

Gly Ser Gly Ser Gly Thr Glu Phe Thr Leu Thr Ile Ser Arg Leu Glu
65                  70                  75                  80

Ser Glu Asp Phe Ala Val Tyr Tyr Cys His His Tyr Gly Ser Ser Arg
                85                  90                  95

Thr Phe Gly Gln Gly Thr Lys Val Glu Val Lys
            100                 105

<210> SEQ ID NO 75
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 75

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Gly Tyr
                20                  25                  30

Trp Met Ser Trp Val Arg Gln Ala Pro Gly Lys Gly Leu Glu Trp Val
        35                  40                  45

Ala Lys Ile Lys Lys Asp Gly Ser Glu Lys Thr Tyr Val Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Leu Leu Val Pro Ala Ala Ile Val Gly Leu Asp Tyr
            100                 105                 110

Tyr Tyr Ala Met Asp Val Trp Gly Gln Gly Thr Thr Val Thr Val Ser
        115                 120                 125

Ser
```

<210> SEQ ID NO 76
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Met Ser Thr Tyr
            20                  25                  30

Leu Asn Trp Tyr Gln Gln Lys Pro Gly Lys Ala Pro Lys Phe Leu Ile
        35                  40                  45

Tyr Gly Ala Ser Arg Leu Gln Asn Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Ile Pro Ile
                85                  90                  95

Thr Phe Gly Gln Gly Thr Arg Leu Glu Ile Lys
            100                 105

<210> SEQ ID NO 77
<211> LENGTH: 133
<212> TYPE: PRT
<213> ORGANISM: Artificial sequence
<220> FEATURE:
<223> OTHER INFORMATION: Synthetic polypeptide

<400> SEQUENCE: 77

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Ser Gly Ile Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Asp Cys Tyr Tyr Gly Ser Gly Thr Tyr Tyr Gly Cys Arg Ala
            100                 105                 110

Asp Tyr Gln Trp His His Thr Met Asp Val Trp Gly Gln Gly Thr Thr
        115                 120                 125

Val Thr Val Ser Ser
    130

<210> SEQ ID NO 78
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Leu Gln His Asn Thr Tyr Pro Leu
            85                  90                  95

Thr Phe Gly Gln Gly Thr Lys Val Glu Ile Lys
            100                 105
```

```
<210> SEQ ID NO 79
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 79
```

```
Gln Val Arg Leu Gln Glu Ser Gly Pro Arg Leu Val Lys Pro Ser Gln
1               5                   10                  15

Thr Leu Ser Leu Thr Cys Thr Val Ser Gly Gly Ser Ile Ser Ser Arg
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Leu Glu Ser Arg Val Thr Leu Ser Leu Asp Thr Ser Lys Asn Gln Phe
65                  70                  75                  80

Ser Leu Asp Leu Thr Ser Val Thr Ala Ala Asp Thr Ala Val Tyr His
            85                  90                  95

Cys Ala Arg Val Trp Leu Gly Gly Gly Val Phe Asp Phe Trp Gly Gln
            100                 105                 110

Gly Thr Leu Val Thr Val Ser Ala
        115                 120
```

```
<210> SEQ ID NO 80
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 80
```

```
Glu Ile Val Met Thr Gln Ser Pro Asp Thr Leu Ser Val Ser Pro Gly
1               5                   10                  15

Glu Arg Ala Thr Leu Ser Cys Arg Ala Ser His Ser Val Thr Thr Asn
            20                  25                  30

Leu Ala Trp Tyr Gln Gln Arg Pro Gly Gln Ala Pro Arg Leu Leu Ile
        35                  40                  45

Phe Asp Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80
```

Glu Asp Phe Ala Val Tyr Tyr Cys Gln Gln Tyr Asn Asp Gly Arg Thr
                85                      90                      95

Phe Gly Gln Gly Thr Lys Val Glu Ile Lys
            100                 105

<210> SEQ ID NO 81
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 81

Glu Val Gln Leu Leu Glu Ser Gly Gly Gly Leu Val Gln Pro Gly Gly
1               5                       10                  15

Ser Leu Arg Leu Ser Cys Ala Ala Ser Gly Phe Thr Phe Ser Ser Ser
            20                      25                  30

Ala Met Ser Trp Val Arg Gln Thr Pro Gly Lys Gly Leu Glu Trp Val
        35                      40                  45

Ser Thr Ile Ser Gly Ser Gly Ala Asn Thr Tyr Tyr Ala Ala Ser Val
    50                      55                  60

Lys Gly Arg Phe Pro Ile Ser Arg Asp Asn Ser Lys Asn Thr Leu Phe
65                  70                      75                  80

Leu Gln Met Asn Ser Leu Arg Ala Glu Asp Thr Ala Val Tyr Tyr Cys
                85                      90                  95

Ala Lys Val Ser Thr Val Thr Phe Gly Gly His Val Pro Arg Gly Ser
            100                 105                 110

Tyr Phe Asp Tyr Trp Gly Gln Gly Thr Gln Val Thr Val Ser Ser
        115                 120                 125

<210> SEQ ID NO 82
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 82

Ser Tyr Val Leu Thr Gln Pro Pro Ser Val Ser Val Ala Pro Gly Gln
1               5                       10                  15

Thr Ala Arg Ile Pro Cys Gly Gly Asn Asn Ile Gly Ser Lys Ser Val
            20                      25                  30

His Trp Tyr Gln Gln Lys Pro Gly Gln Ala Pro Val Leu Val Val Tyr
        35                      40                  45

Asp Glu Asn Asp Arg Pro Ser Gly Ile Pro Glu Arg Phe Ser Ala Ser
    50                      55                  60

Lys Ser Gly Asn Thr Ala Thr Leu Thr Ile Ser Arg Val Glu Ala Gly
65                  70                      75                  80

Asp Glu Ala Asp Tyr Tyr Cys Gln Val Trp Asp Ser Arg Ser Asp His
                85                      90                  95

Tyr Val Phe Gly Thr Gly Thr Lys Val Thr Val Leu
            100                 105

<210> SEQ ID NO 83
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ser Gly Ile Ser Gly Ser Gly Gly Asn Thr Tyr Tyr Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Tyr Thr Gly Gln Gln Leu Met Arg Arg Gly Pro Trp
            100                 105                 110

Trp Phe Asp Pro Trp Gly Gln Gly Thr Leu Val Thr Val Ser Ser
            115                 120                 125

<210> SEQ ID NO 84
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 84

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
        50                  55                  60

Lys Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 85
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 85

Gln Val Gln Leu Val Gln Ser Gly Thr Glu Val Lys Asn Pro Gly Ser
1               5                   10                  15

Ser Val Lys Val Ser Cys Lys Ala Ser Gly Gly Thr Phe Ser Gly Phe
            20                  25                  30

Gly Ile Ser Trp Val Arg Gln Ala Pro Gly Gln Gly Leu Glu Trp Met
        35                  40                  45

Gly Gly Val Leu Pro Ile Phe Gly Ser Pro Asn Tyr Ala Gln Lys Phe
        50                  55                  60

```
Gln Gly Arg Val Thr Ile Thr Ala Asp Glu Ser Thr Gly Thr Ala Tyr
65                  70                  75                  80

Met Asp Leu Ser Ser Leu Arg Ser Asp Asp Thr Ala Met Tyr Tyr Cys
                85                  90                  95

Ala Arg Asp Gln Ser Gly Gly Phe Phe Asp Tyr Trp Gly Gln Gly Thr
            100                 105                 110

Leu Val Ile Val Ser Ser
        115
```

```
<210> SEQ ID NO 86
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 86
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
        35                  40                  45

Tyr Asp Ala Ser Asp Arg Ala Thr Gly Val Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Leu Tyr Tyr Cys Gln Gln Arg Tyr Asn Trp Arg Val
                85                  90                  95

Thr Phe Gly Gln Gly Thr Arg Leu Glu Ile Lys
            100                 105
```

```
<210> SEQ ID NO 87
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 87
```

```
Gln Val Gln Val Val Glu Ser Gly Gly Gly Val Val His Pro Gly Arg
1               5                   10                  15

Ser Leu Arg Leu Ser Cys Ala Gly Ser Gly Phe Ile Phe Asn Asn Tyr
                20                  25                  30

Ala Phe His Trp Val Arg Gln Ala Pro Gly Gly Gly Leu Glu Trp Met
        35                  40                  45

Ala Tyr Ile Ser Tyr Asp Gly Arg Tyr Lys Tyr Tyr Ala Ala Ser Val
    50                  55                  60

Arg Gly Arg Phe Thr Ile Ser Arg Asp Asp Ser Lys Asn Thr Leu Tyr
65                  70                  75                  80

Leu Gln Met Ser Ser Leu Arg Thr Glu Asp Thr Ala Leu Tyr Tyr Cys
                85                  90                  95

Ala Ile Ser Asp Tyr Ala Glu Pro Leu Asp Asn Trp Gly Gln Gly Thr
            100                 105                 110

Leu Val Thr Val Ser Ser
        115
```

```
<210> SEQ ID NO 88
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 88

Gln Ile Val Leu Thr Gln Ser Pro Ala Thr Leu Ser Leu Ser Pro Gly
1               5                   10                  15

Asp Arg Ala Thr Leu Ser Cys Arg Ala Ser Gln Ser Val Ser Ser Asn
            20                  25                  30

Val Ala Trp Tyr Gln Gln Lys Pro Gly Gln Ala Pro Arg Leu Leu Ile
        35                  40                  45

Tyr Asn Val Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Arg Thr Asn Trp Pro Leu
                85                  90                  95

Thr Phe Gly Gly Gly Thr Lys Val Glu Ile Lys
            100                 105

<210> SEQ ID NO 89
<211> LENGTH: 126
<212> TYPE: PRT
<213> ORGANISM: Artificial sequence
<220> FEATURE:
<223> OTHER INFORMATION: Synthetic polypeptide

<400> SEQUENCE: 89

Gln Gly Gln Leu Gln Gln Trp Gly Ala Gly Leu Leu Lys Pro Ser Glu
1               5                   10                  15

Thr Leu Ser Leu Thr Cys Gly Val Tyr Ser Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Arg Thr Asp Tyr Asn Pro Ser Leu Lys
    50                  55                  60

Ser Arg Val Thr Met Ser Val Asp Thr Ser Lys Asn Gln Phe Ser Leu
65                  70                  75                  80

Arg Leu Ser Ser Val Thr Ala Ala Asp Thr Ala Val Tyr Phe Cys Ala
                85                  90                  95

Arg Ala Thr Pro Pro Thr Leu Trp Val Arg Asp Phe Leu Trp Gly Tyr
            100                 105                 110

Phe Asp Ser Trp Gly Gln Gly Thr Leu Val Ser Val Ser Ser
        115                 120                 125

<210> SEQ ID NO 90
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
            20                  25                  30
```

```
Ser Asn Asn Lys Asn Tyr Leu Ala Trp Tyr Gln Gln Lys Pro Gly Gln
        35              40              45

Pro Pro Lys Leu Leu Ile Phe Trp Ala Ser Thr Arg Glu Ser Gly Val
    50              55              60

Pro Asp Arg Phe Ser Gly Ser Gly Ser Gly Thr Asp Phe Thr Leu Thr
65              70              75              80

Ile Ser Ser Leu Gln Ala Glu Asp Val Ala Val Tyr Tyr Cys Gln Gln
            85              90              95

Tyr Tyr Thr Thr Pro Lys Thr Phe Gly Pro Gly Thr Lys Val Asp Leu
            100             105             110

Lys
```

```
<210> SEQ ID NO 91
<211> LENGTH: 125
<212> TYPE: PRT
<213> ORGANISM: Artificial sequence
<220> FEATURE:
<223> OTHER INFORMATION: Synthetic polypeptide

<400> SEQUENCE: 91

Gln Val Gln Leu Gln Glu Ser Gly Pro Gly Leu Val Lys Pro Ser Glu
1               5               10              15

Thr Leu Ser Leu Thr Cys Thr Val Ser Gly Gly Ser Ile Asp Ser Tyr
            20              25              30

Tyr Trp Ser Trp Ile Arg Gln Pro Ala Gly Lys Gly Leu Glu Trp Ile
        35              40              45

Gly Arg Ile Tyr Pro Ser Gly Thr Thr Asn Tyr Asn Pro Ser Leu Lys
    50              55              60

Ser Arg Val Thr Met Ser Val Asp Thr Ser Lys Asn Gln Phe Ser Leu
65              70              75              80

Lys Val Thr Ser Val Thr Ala Ala Asp Thr Ala Val Tyr Tyr Cys Ala
            85              90              95

Arg Met Gln Thr Gly Phe Gly Ser Ser Leu Phe Phe Val Pro Tyr Phe
            100             105             110

Asp Asn Trp Gly Gln Gly Thr Leu Val Thr Val Ser Ser
        115             120             125
```

```
<210> SEQ ID NO 92
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 92

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
            20              25              30

Leu Ala Trp Tyr Gln Gln Lys Pro Gly Gln Ala Pro Arg Leu Leu Ile
        35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Arg Gly Asn Trp Pro Leu
            85              90              95
```

Thr Phe Gly Gly Gly Thr Lys Val Glu Ile Lys
            100                 105

<210> SEQ ID NO 93
<211> LENGTH: 131
<212> TYPE: PRT
<213> ORGANISM: Artificial sequence
<220> FEATURE:
<223> OTHER INFORMATION: Synthetic polypeptide

<400> SEQUENCE: 93

Glu Glu Arg Leu Val Gln Ser Gly Gly Leu Ala Gln Pro Gly Gln
1               5                   10                  15

Ser Leu Arg Leu Ser Cys Ala Gly Phe Gly Phe Thr Phe Thr Arg Tyr
            20                  25                  30

Glu Met Asn Trp Val Arg Gln Ala Pro Gly Lys Gly Leu Glu Trp Ile
            35                  40                  45

Ala His Ile Ser Thr Arg Gly Asp Thr Ile Ser Tyr Ala Asp Ser Val
            50                  55                  60

Lys Gly Arg Ala Thr Ile Ser Arg Asp Asp Thr Asn Asn Ser Leu Asp
65                  70                  75                  80

Leu Gln Met Asp Ser Leu Arg Ala Glu Asp Thr Ala Ile Tyr Phe Cys
                85                  90                  95

Ala Arg Asp Arg Gly Ser Leu Ser Thr Arg Pro Pro Asp Ser Tyr His
            100                 105                 110

Tyr Tyr Tyr His Gly Met Asp Val Trp Gly Gln Gly Thr Thr Val Ile
            115                 120                 125

Val Ser Ser
    130

<210> SEQ ID NO 94
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 94

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Asp Thr Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
            50                  55                  60

Ser Gly Ser Gly Thr Asp Phe Ser Leu Thr Ile Ser Ser Leu Glu Pro
65                  70                  75                  80

Asp Asp Phe Ala Val Tyr Tyr Cys Gln Gln Arg Ser Asn Arg Pro Pro
                85                  90                  95

Arg Tyr Thr Phe Gly Leu Gly Thr Arg Leu Glu Ile Lys
            100                 105

<210> SEQ ID NO 95
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 95

```
Gln Val Gln Leu Val Gln Ser Gly Ala Glu Val Lys Lys Pro Gly Ser
1               5                   10                  15

Ser Val Thr Val Ser Cys Lys Thr Ser Gly Gly Thr Phe Ser Gly Tyr
            20                  25                  30

Ala Val Ser Trp Val Arg Gln Ala Pro Gly Gln Gly Leu Glu Trp Met
        35                  40                  45

Gly Arg Ile Val Pro Gln Phe Asn Ile Pro Asn Tyr Ala Gln Lys Phe
    50                  55                  60

Gln Asp Arg Val Thr Ile Thr Ala Asp Glu Ser Thr Gly Thr Ser Tyr
65                  70                  75                  80

Met Glu Leu Ser Ser Leu Arg Ser Asp Asp Thr Ala Val Phe Tyr Cys
                85                  90                  95

Ala Arg Glu Asn Ile Gln Thr Ile Phe Gly Val Val Ala Met Met Gly
            100                 105                 110

Gly Gly Gly Tyr Phe Asp Ser Trp Gly Gln Gly Thr Leu Val Thr Val
        115                 120                 125

Ser Ser
    130
```

<210> SEQ ID NO 96
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Gln Ala Asn Gln Asp Ile Asn Thr Tyr
            20                  25                  30

Leu Asn Trp Tyr Leu Gln Lys Pro Gly Lys Ala Pro Gln Leu Leu Val
        35                  40                  45

Phe Asp Ala Ser Asn Leu Val Thr Gly Val Pro Ser Arg Phe Ser Gly
    50                  55                  60

Gly Gly Ser Arg Thr Asp Phe Thr Leu Thr Ile Asp Ser Leu Gln Pro
65                  70                  75                  80

Glu Asp Ile Gly Thr Tyr Tyr Cys Gln Gln Tyr Asp His Leu Pro Arg
                85                  90                  95

Arg Thr Phe Thr Phe Gly Pro Gly Thr Lys Val Asp Leu Lys
            100                 105                 110
```

<210> SEQ ID NO 97
<211> LENGTH: 8
<212> TYPE: PRT
<213> ORGANISM: Artificial sequence
<220> FEATURE:
<223> OTHER INFORMATION: Synthetic peptide

<400> SEQUENCE: 97

```
Gly Gly Ile Phe Asn Arg Glu Thr
1               5
```

<210> SEQ ID NO 98
<211> LENGTH: 8
<212> TYPE: PRT
<213> ORGANISM: Artificial sequence
<220> FEATURE:
<223> OTHER INFORMATION: Synthetic peptide

<400> SEQUENCE: 98

Ile Thr Pro Ile Val Asp Val Pro
1               5

<210> SEQ ID NO 99
<211> LENGTH: 11
<212> TYPE: PRT
<213> ORGANISM: Artificial sequence
<220> FEATURE:
<223> OTHER INFORMATION: Synthetic peptide

<400> SEQUENCE: 99

Ala Arg Phe Arg Gly His Asn Tyr Phe Asp Pro
1               5                   10

<210> SEQ ID NO 100
<211> LENGTH: 8
<212> TYPE: PRT
<213> ORGANISM: Artificial sequence
<220> FEATURE:
<223> OTHER INFORMATION: Synthetic peptide

<400> SEQUENCE: 100

Gly Gly Thr Phe Ser Asn Tyr Val
1               5

<210> SEQ ID NO 101
<211> LENGTH: 8
<212> TYPE: PRT
<213> ORGANISM: Artificial sequence
<220> FEATURE:
<223> OTHER INFORMATION: Synthetic peptide

<400> SEQUENCE: 101

Ile Ile Pro Met Ile Gly Ile Ser
1               5

<210> SEQ ID NO 102
<211> LENGTH: 10
<212> TYPE: PRT
<213> ORGANISM: Artificial sequence
<220> FEATURE:
<223> OTHER INFORMATION: Synthetic peptide

<400> SEQUENCE: 102

Ala Ser Ser Thr Val Thr Glu Val Gly Ala
1               5                   10

<210> SEQ ID NO 103
<211> LENGTH: 8
<212> TYPE: PRT
<213> ORGANISM: Artificial sequence
<220> FEATURE:
<223> OTHER INFORMATION: Synthetic peptide

<400> SEQUENCE: 103

Gly Phe Thr Ile Ile Asn Tyr Ser
1               5

<210> SEQ ID NO 104
<211> LENGTH: 8
<212> TYPE: PRT
<213> ORGANISM: Artificial sequence
<220> FEATURE:

```
<223> OTHER INFORMATION: Synthetic peptide

<400> SEQUENCE: 104

Ile Ser Gly Ser Ser Asp Tyr Ile
1               5

<210> SEQ ID NO 105
<211> LENGTH: 17
<212> TYPE: PRT
<213> ORGANISM: Artificial sequence
<220> FEATURE:
<223> OTHER INFORMATION: Synthetic peptide

<400> SEQUENCE: 105

Ala Arg Glu Arg Thr Gly Phe Phe Ser Pro Pro Ser Tyr Leu Met Asp
1               5                   10                  15

Val

<210> SEQ ID NO 106
<211> LENGTH: 8
<212> TYPE: PRT
<213> ORGANISM: Artificial sequence
<220> FEATURE:
<223> OTHER INFORMATION: Synthetic peptide

<400> SEQUENCE: 106

Asp Asn Thr Leu Thr Thr Tyr Gly
1               5

<210> SEQ ID NO 107
<211> LENGTH: 8
<212> TYPE: PRT
<213> ORGANISM: Artificial sequence
<220> FEATURE:
<223> OTHER INFORMATION: Synthetic peptide

<400> SEQUENCE: 107

Val Ser Ala Tyr Asn Gly His Pro
1               5

<210> SEQ ID NO 108
<211> LENGTH: 9
<212> TYPE: PRT
<213> ORGANISM: Artificial sequence
<220> FEATURE:
<223> OTHER INFORMATION: Synthetic peptide

<400> SEQUENCE: 108

Ala Arg Gly Ser Ser Ala Trp Asn Pro
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

<400> SEQUENCE: 109

Gly Phe Thr Phe Arg Ser Tyr Ser
1               5

<210> SEQ ID NO 110
<211> LENGTH: 8
<212> TYPE: PRT
<213> ORGANISM: Artificial sequence
```

```
<220> FEATURE:
<223> OTHER INFORMATION: Synthetic peptide

<400> SEQUENCE: 110

Ile Ser Tyr Asp Gly Ser Asn Lys
1               5

<210> SEQ ID NO 111
<211> LENGTH: 20
<212> TYPE: PRT
<213> ORGANISM: Artificial sequence
<220> FEATURE:
<223> OTHER INFORMATION: Synthetic peptide

<400> SEQUENCE: 111

Ala Arg Phe Arg Gly Gly Gly Arg Ile Ala Ala Arg Pro Asp Asp Tyr
1               5                   10                  15

Gly Met Asp Val
            20

<210> SEQ ID NO 112
<211> LENGTH: 8
<212> TYPE: PRT
<213> ORGANISM: Artificial sequence
<220> FEATURE:
<223> OTHER INFORMATION: Synthetic peptide

<400> SEQUENCE: 112

Gly Tyr Thr Phe Thr Asp Tyr Tyr
1               5

<210> SEQ ID NO 113
<211> LENGTH: 8
<212> TYPE: PRT
<213> ORGANISM: Artificial sequence
<220> FEATURE:
<223> OTHER INFORMATION: Synthetic peptide

<400> SEQUENCE: 113

Ile Asn Pro Asn Ser Gly Ala Thr
1               5

<210> SEQ ID NO 114
<211> LENGTH: 15
<212> TYPE: PRT
<213> ORGANISM: Artificial sequence
<220> FEATURE:
<223> OTHER INFORMATION: Synthetic peptide

<400> SEQUENCE: 114

Ala Ser Val Pro Pro Ser Gly Phe Phe Tyr Trp Gly Ser Asp Tyr
1               5                   10                  15

<210> SEQ ID NO 115
<211> LENGTH: 8
<212> TYPE: PRT
<213> ORGANISM: Artificial sequence
<220> FEATURE:
<223> OTHER INFORMATION: Synthetic peptide

<400> SEQUENCE: 115

Gly Phe Thr Phe Ser Gly Tyr Trp
1               5

<210> SEQ ID NO 116
<211> LENGTH: 8
```

```
<212> TYPE: PRT
<213> ORGANISM: Artificial sequence
<220> FEATURE:
<223> OTHER INFORMATION: Synthetic peptide

<400> SEQUENCE: 116

Ile Lys Gly Asp Gly Ser Glu Lys
1               5

<210> SEQ ID NO 117
<211> LENGTH: 21
<212> TYPE: PRT
<213> ORGANISM: Artificial sequence
<220> FEATURE:
<223> OTHER INFORMATION: Synthetic peptide

<400> SEQUENCE: 117

Ala Arg Glu Arg His Phe Leu Ala Ala Arg Pro Gly Tyr Tyr Ile Tyr
1               5                   10                  15

Ser Gly Leu Asp Val
            20

<210> SEQ ID NO 118
<211> LENGTH: 8
<212> TYPE: PRT
<213> ORGANISM: Artificial sequence
<220> FEATURE:
<223> OTHER INFORMATION: Synthetic peptide

<400> SEQUENCE: 118

Gly Tyr Thr Phe Thr Asp Tyr Tyr
1               5

<210> SEQ ID NO 119
<211> LENGTH: 8
<212> TYPE: PRT
<213> ORGANISM: Artificial sequence
<220> FEATURE:
<223> OTHER INFORMATION: Synthetic peptide

<400> SEQUENCE: 119

Ile Asn Pro Asn Ser Gly Ala Thr
1               5

<210> SEQ ID NO 120
<211> LENGTH: 15
<212> TYPE: PRT
<213> ORGANISM: Artificial sequence
<220> FEATURE:
<223> OTHER INFORMATION: Synthetic peptide

<400> SEQUENCE: 120

Ala Ser Val Pro Pro Ser Gly Phe Phe Tyr Trp Gly Ser Asp Tyr
1               5                   10                  15

<210> SEQ ID NO 121
<211> LENGTH: 8
<212> TYPE: PRT
<213> ORGANISM: Artificial sequence
<220> FEATURE:
<223> OTHER INFORMATION: Synthetic peptide

<400> SEQUENCE: 121

Gly Tyr Thr Phe Thr Ser Tyr Tyr
1               5
```

```
<210> SEQ ID NO 122
<211> LENGTH: 8
<212> TYPE: PRT
<213> ORGANISM: Artificial sequence
<220> FEATURE:
<223> OTHER INFORMATION: Synthetic peptide

<400> SEQUENCE: 122

Ile Asn Pro Ser Gly Gly Ser Thr
1               5

<210> SEQ ID NO 123
<211> LENGTH: 22
<212> TYPE: PRT
<213> ORGANISM: Artificial sequence
<220> FEATURE:
<223> OTHER INFORMATION: Synthetic peptide

<400> SEQUENCE: 123

Ala Arg Asp Arg Lys Gly Leu Ala Ala Thr Pro Val Tyr Ser Asp Tyr
1               5                   10                  15

Tyr Tyr Gly Met Asp Val
            20

<210> SEQ ID NO 124
<211> LENGTH: 10
<212> TYPE: PRT
<213> ORGANISM: Artificial sequence
<220> FEATURE:
<223> OTHER INFORMATION: Synthetic peptide

<400> SEQUENCE: 124

Gly Gly Ser Val Ser Arg Ser Gly Tyr Tyr
1               5                   10

<210> SEQ ID NO 125
<211> LENGTH: 7
<212> TYPE: PRT
<213> ORGANISM: Artificial sequence
<220> FEATURE:
<223> OTHER INFORMATION: Synthetic peptide

<400> SEQUENCE: 125

Ile Tyr Tyr Ser Gly Ile Thr
1               5

<210> SEQ ID NO 126
<211> LENGTH: 12
<212> TYPE: PRT
<213> ORGANISM: Artificial sequence
<220> FEATURE:
<223> OTHER INFORMATION: Synthetic peptide

<400> SEQUENCE: 126

Ala Arg Val Trp Leu Gly Gly Gly Val Phe Asp Phe
1               5                   10

<210> SEQ ID NO 127
<211> LENGTH: 8
<212> TYPE: PRT
<213> ORGANISM: Artificial sequence
<220> FEATURE:
<223> OTHER INFORMATION: Synthetic peptide

<400> SEQUENCE: 127

Gly Phe Thr Phe Ser Asn Tyr Ala
1               5
```

<210> SEQ ID NO 128
<211> LENGTH: 8
<212> TYPE: PRT
<213> ORGANISM: Artificial sequence
<220> FEATURE:
<223> OTHER INFORMATION: Synthetic peptide

<400> SEQUENCE: 128

Ile Ser Tyr Asp Gly Ser Phe Lys
1               5

<210> SEQ ID NO 129
<211> LENGTH: 13
<212> TYPE: PRT
<213> ORGANISM: Artificial sequence
<220> FEATURE:
<223> OTHER INFORMATION: Synthetic peptide

<400> SEQUENCE: 129

Thr Arg Asp Asp Asp Pro Pro Val Glu Asn Phe Gln Ile
1               5                   10

<210> SEQ ID NO 130
<211> LENGTH: 10
<212> TYPE: PRT
<213> ORGANISM: Artificial sequence
<220> FEATURE:
<223> OTHER INFORMATION: Synthetic peptide

<400> SEQUENCE: 130

Gly Asp Ser Ile Ser Ser Gly Thr His Tyr
1               5                   10

<210> SEQ ID NO 131
<211> LENGTH: 7
<212> TYPE: PRT
<213> ORGANISM: Artificial sequence
<220> FEATURE:
<223> OTHER INFORMATION: Synthetic peptide

<400> SEQUENCE: 131

Ile Tyr Ala Thr Gly Asn Ser
1               5

<210> SEQ ID NO 132
<211> LENGTH: 19
<212> TYPE: PRT
<213> ORGANISM: Artificial sequence
<220> FEATURE:
<223> OTHER INFORMATION: Synthetic peptide

<400> SEQUENCE: 132

Val Arg Asp Glu Ala Val Ala Asp Met Ala Val Glu Asn Tyr Tyr Gly
1               5                   10                  15

Met Asp Val

<210> SEQ ID NO 133
<211> LENGTH: 8
<212> TYPE: PRT
<213> ORGANISM: Artificial sequence
<220> FEATURE:
<223> OTHER INFORMATION: Synthetic peptide

<400> SEQUENCE: 133

Gly Gly Ser Phe Thr Asn Tyr Tyr

-continued

```
1               5

<210> SEQ ID NO 134
<211> LENGTH: 7
<212> TYPE: PRT
<213> ORGANISM: Artificial sequence
<220> FEATURE:
<223> OTHER INFORMATION: Synthetic peptide

<400> SEQUENCE: 134

Ile Asn His Ser Gly Arg Thr
1               5

<210> SEQ ID NO 135
<211> LENGTH: 22
<212> TYPE: PRT
<213> ORGANISM: Artificial sequence
<220> FEATURE:
<223> OTHER INFORMATION: Synthetic peptide

<400> SEQUENCE: 135

Ala Arg Asp Ile Arg Lys Leu Ala Pro Lys Pro His Ser Tyr Asp Leu
1               5                   10                  15

Tyr Tyr Gly Met Asp Val
            20

<210> SEQ ID NO 136
<211> LENGTH: 8
<212> TYPE: PRT
<213> ORGANISM: Artificial sequence
<220> FEATURE:
<223> OTHER INFORMATION: Synthetic peptide

<400> SEQUENCE: 136

Gly Phe Thr Phe Ser Thr Asn Ala
1               5

<210> SEQ ID NO 137
<211> LENGTH: 8
<212> TYPE: PRT
<213> ORGANISM: Artificial sequence
<220> FEATURE:
<223> OTHER INFORMATION: Synthetic peptide

<400> SEQUENCE: 137

Val Ser Gly Ser Gly Ala His Pro
1               5

<210> SEQ ID NO 138
<211> LENGTH: 20
<212> TYPE: PRT
<213> ORGANISM: Artificial sequence
<220> FEATURE:
<223> OTHER INFORMATION: Synthetic peptide

<400> SEQUENCE: 138

Ala Arg Val Ser Thr Val Thr Val Gly Gly His Ile Pro Arg Gly Tyr
1               5                   10                  15

Tyr Phe Asp Tyr
            20

<210> SEQ ID NO 139
<211> LENGTH: 8
<212> TYPE: PRT
<213> ORGANISM: Artificial sequence
<220> FEATURE:
```

<223> OTHER INFORMATION: Synthetic peptide

<400> SEQUENCE: 139

Gly Phe Thr Phe Ser Gly Tyr Trp
1               5

<210> SEQ ID NO 140
<211> LENGTH: 8
<212> TYPE: PRT
<213> ORGANISM: Artificial sequence
<220> FEATURE:
<223> OTHER INFORMATION: Synthetic peptide

<400> SEQUENCE: 140

Ile Lys Lys Asp Gly Ser Glu Lys
1               5

<210> SEQ ID NO 141
<211> LENGTH: 22
<212> TYPE: PRT
<213> ORGANISM: Artificial sequence
<220> FEATURE:
<223> OTHER INFORMATION: Synthetic peptide

<400> SEQUENCE: 141

Ala Arg Glu Arg Leu Leu Val Pro Ala Ala Ile Val Gly Leu Asp Tyr
1               5                   10                  15

Tyr Tyr Ala Met Asp Val
            20

<210> SEQ ID NO 142
<211> LENGTH: 8
<212> TYPE: PRT
<213> ORGANISM: Artificial sequence
<220> FEATURE:
<223> OTHER INFORMATION: Synthetic peptide

<400> SEQUENCE: 142

Gly Gly Thr Phe Ser Ser Tyr Thr
1               5

<210> SEQ ID NO 143
<211> LENGTH: 8
<212> TYPE: PRT
<213> ORGANISM: Artificial sequence
<220> FEATURE:
<223> OTHER INFORMATION: Synthetic peptide

<400> SEQUENCE: 143

Ile Ile Pro Ile Ser Gly Ile Thr
1               5

<210> SEQ ID NO 144
<211> LENGTH: 26
<212> TYPE: PRT
<213> ORGANISM: Artificial sequence
<220> FEATURE:
<223> OTHER INFORMATION: Synthetic peptide

<400> SEQUENCE: 144

Ala Lys Asp Cys Tyr Tyr Gly Ser Gly Thr Tyr Tyr Gly Cys Arg Ala
1               5                   10                  15

Asp Tyr Gln Trp His His Thr Met Asp Val
            20                  25

```
<210> SEQ ID NO 145
<211> LENGTH: 10
<212> TYPE: PRT
<213> ORGANISM: Artificial sequence
<220> FEATURE:
<223> OTHER INFORMATION: Synthetic peptide

<400> SEQUENCE: 145

Gly Gly Ser Ile Ser Ser Arg Asp Tyr Tyr
1               5                   10

<210> SEQ ID NO 146
<211> LENGTH: 7
<212> TYPE: PRT
<213> ORGANISM: Artificial sequence
<220> FEATURE:
<223> OTHER INFORMATION: Synthetic peptide

<400> SEQUENCE: 146

Ile Tyr Tyr Ser Gly Thr Thr
1               5

<210> SEQ ID NO 147
<211> LENGTH: 12
<212> TYPE: PRT
<213> ORGANISM: Artificial sequence
<220> FEATURE:
<223> OTHER INFORMATION: Synthetic peptide

<400> SEQUENCE: 147

Ala Arg Val Trp Leu Gly Gly Gly Val Phe Asp Phe
1               5                   10

<210> SEQ ID NO 148
<211> LENGTH: 8
<212> TYPE: PRT
<213> ORGANISM: Artificial sequence
<220> FEATURE:
<223> OTHER INFORMATION: Synthetic peptide

<400> SEQUENCE: 148

Gly Phe Thr Phe Ser Ser Ser Ala
1               5

<210> SEQ ID NO 149
<211> LENGTH: 8
<212> TYPE: PRT
<213> ORGANISM: Artificial sequence
<220> FEATURE:
<223> OTHER INFORMATION: Synthetic peptide

<400> SEQUENCE: 149

Ile Ser Gly Ser Gly Ala Asn Thr
1               5

<210> SEQ ID NO 150
<211> LENGTH: 20
<212> TYPE: PRT
<213> ORGANISM: Artificial sequence
<220> FEATURE:
<223> OTHER INFORMATION: Synthetic peptide

<400> SEQUENCE: 150

Ala Lys Val Ser Thr Val Thr Phe Gly Gly His Val Pro Arg Gly Ser
1               5                   10                  15

Tyr Phe Asp Tyr
            20
```

```
<210> SEQ ID NO 151
<211> LENGTH: 8
<212> TYPE: PRT
<213> ORGANISM: Artificial sequence
<220> FEATURE:
<223> OTHER INFORMATION: Synthetic peptide

<400> SEQUENCE: 151

Gly Phe Thr Phe Ser Ser Tyr Thr
1               5

<210> SEQ ID NO 152
<211> LENGTH: 8
<212> TYPE: PRT
<213> ORGANISM: Artificial sequence
<220> FEATURE:
<223> OTHER INFORMATION: Synthetic peptide

<400> SEQUENCE: 152

Ile Ser Gly Ser Gly Gly Asn Thr
1               5

<210> SEQ ID NO 153
<211> LENGTH: 20
<212> TYPE: PRT
<213> ORGANISM: Artificial sequence
<220> FEATURE:
<223> OTHER INFORMATION: Synthetic peptide

<400> SEQUENCE: 153

Ala Lys Asp Gly Tyr Thr Gly Gln Gln Leu Met Arg Arg Gly Pro Trp
1               5                   10                  15

Trp Phe Asp Pro
            20

<210> SEQ ID NO 154
<211> LENGTH: 8
<212> TYPE: PRT
<213> ORGANISM: Artificial sequence
<220> FEATURE:
<223> OTHER INFORMATION: Synthetic peptide

<400> SEQUENCE: 154

Gly Gly Thr Phe Ser Gly Phe Gly
1               5

<210> SEQ ID NO 155
<211> LENGTH: 8
<212> TYPE: PRT
<213> ORGANISM: Artificial sequence
<220> FEATURE:
<223> OTHER INFORMATION: Synthetic peptide

<400> SEQUENCE: 155

Val Leu Pro Ile Phe Gly Ser Pro
1               5

<210> SEQ ID NO 156
<211> LENGTH: 11
<212> TYPE: PRT
<213> ORGANISM: Artificial sequence
<220> FEATURE:
<223> OTHER INFORMATION: Synthetic peptide

<400> SEQUENCE: 156
```

Ala Arg Asp Gln Ser Gly Gly Phe Phe Asp Tyr
1               5                   10

<210> SEQ ID NO 157
<211> LENGTH: 8
<212> TYPE: PRT
<213> ORGANISM: Artificial sequence
<220> FEATURE:
<223> OTHER INFORMATION: Synthetic peptide

<400> SEQUENCE: 157

Gly Phe Ile Phe Asn Asn Tyr Ala
1               5

<210> SEQ ID NO 158
<211> LENGTH: 8
<212> TYPE: PRT
<213> ORGANISM: Artificial sequence
<220> FEATURE:
<223> OTHER INFORMATION: Synthetic peptide

<400> SEQUENCE: 158

Ile Ser Tyr Asp Gly Arg Tyr Lys
1               5

<210> SEQ ID NO 159
<211> LENGTH: 11
<212> TYPE: PRT
<213> ORGANISM: Artificial sequence
<220> FEATURE:
<223> OTHER INFORMATION: Synthetic peptide

<400> SEQUENCE: 159

Ala Ile Ser Asp Tyr Ala Glu Pro Leu Asp Asn
1               5                   10

<210> SEQ ID NO 160
<211> LENGTH: 8
<212> TYPE: PRT
<213> ORGANISM: Artificial sequence
<220> FEATURE:
<223> OTHER INFORMATION: Synthetic peptide

<400> SEQUENCE: 160

Ser Gly Ser Phe Ser Gly Tyr Tyr
1               5

<210> SEQ ID NO 161
<211> LENGTH: 7
<212> TYPE: PRT
<213> ORGANISM: Artificial sequence
<220> FEATURE:
<223> OTHER INFORMATION: Synthetic peptide

<400> SEQUENCE: 161

Ile Asn His Ser Gly Arg Thr
1               5

<210> SEQ ID NO 162
<211> LENGTH: 20
<212> TYPE: PRT
<213> ORGANISM: Artificial sequence
<220> FEATURE:
<223> OTHER INFORMATION: Synthetic peptide

<400> SEQUENCE: 162

Ala Arg Ala Thr Pro Pro Thr Leu Trp Val Arg Asp Phe Leu Trp Gly

-continued

```
1               5               10              15

Tyr Phe Asp Ser
            20

<210> SEQ ID NO 163
<211> LENGTH: 8
<212> TYPE: PRT
<213> ORGANISM: Artificial sequence
<220> FEATURE:
<223> OTHER INFORMATION: Synthetic peptide

<400> SEQUENCE: 163

Gly Gly Ser Ile Asp Ser Tyr Tyr
1               5

<210> SEQ ID NO 164
<211> LENGTH: 7
<212> TYPE: PRT
<213> ORGANISM: Artificial sequence
<220> FEATURE:
<223> OTHER INFORMATION: Synthetic peptide

<400> SEQUENCE: 164

Ile Tyr Pro Ser Gly Thr Thr
1               5

<210> SEQ ID NO 165
<211> LENGTH: 19
<212> TYPE: PRT
<213> ORGANISM: Artificial sequence
<220> FEATURE:
<223> OTHER INFORMATION: Synthetic peptide

<400> SEQUENCE: 165

Ala Arg Met Gln Thr Gly Phe Gly Ser Ser Leu Phe Phe Val Pro Tyr
1               5                   10                  15

Phe Asp Asn

<210> SEQ ID NO 166
<211> LENGTH: 8
<212> TYPE: PRT
<213> ORGANISM: Artificial sequence
<220> FEATURE:
<223> OTHER INFORMATION: Synthetic peptide

<400> SEQUENCE: 166

Gly Phe Thr Phe Thr Arg Tyr Glu
1               5

<210> SEQ ID NO 167
<211> LENGTH: 8
<212> TYPE: PRT
<213> ORGANISM: Artificial sequence
<220> FEATURE:
<223> OTHER INFORMATION: Synthetic peptide

<400> SEQUENCE: 167

Ile Ser Thr Arg Gly Asp Thr Ile
1               5

<210> SEQ ID NO 168
<211> LENGTH: 24
<212> TYPE: PRT
<213> ORGANISM: Artificial sequence
<220> FEATURE:
<223> OTHER INFORMATION: Synthetic peptide
```

<400> SEQUENCE: 168

Ala Arg Asp Arg Gly Ser Leu Ser Thr Arg Pro Pro Asp Ser Tyr His
1               5                   10                  15

Tyr Tyr Tyr His Gly Met Asp Val
            20

<210> SEQ ID NO 169
<211> LENGTH: 8
<212> TYPE: PRT
<213> ORGANISM: Artificial sequence
<220> FEATURE:
<223> OTHER INFORMATION: Synthetic peptide

<400> SEQUENCE: 169

Gly Gly Thr Phe Ser Gly Tyr Ala
1               5

<210> SEQ ID NO 170
<211> LENGTH: 8
<212> TYPE: PRT
<213> ORGANISM: Artificial sequence
<220> FEATURE:
<223> OTHER INFORMATION: Synthetic peptide

<400> SEQUENCE: 170

Ile Val Pro Gln Phe Asn Ile Pro
1               5

<210> SEQ ID NO 171
<211> LENGTH: 23
<212> TYPE: PRT
<213> ORGANISM: Artificial sequence
<220> FEATURE:
<223> OTHER INFORMATION: Synthetic peptide

<400> SEQUENCE: 171

Ala Arg Glu Asn Ile Gln Thr Ile Phe Gly Val Val Ala Met Met Gly
1               5                   10                  15

Gly Gly Gly Tyr Phe Asp Ser
            20

<210> SEQ ID NO 172
<211> LENGTH: 6
<212> TYPE: PRT
<213> ORGANISM: Artificial sequence
<220> FEATURE:
<223> OTHER INFORMATION: Synthetic peptide

<400> SEQUENCE: 172

Asn Ile Gly Gly Lys Ser
1               5

<210> SEQ ID NO 173
<211> LENGTH: 3
<212> TYPE: PRT
<213> ORGANISM: Artificial sequence
<220> FEATURE:
<223> OTHER INFORMATION: Synthetic peptide

<400> SEQUENCE: 173

Asp Asp Arg
1

<210> SEQ ID NO 174

-continued

```
<211> LENGTH: 11
<212> TYPE: PRT
<213> ORGANISM: Artificial sequence
<220> FEATURE:
<223> OTHER INFORMATION: Synthetic peptide

<400> SEQUENCE: 174

Gln Val Trp Asp Asn Ala Ser Asp Glu Ala Val
1               5                   10

<210> SEQ ID NO 175
<211> LENGTH: 6
<212> TYPE: PRT
<213> ORGANISM: Artificial sequence
<220> FEATURE:
<223> OTHER INFORMATION: Synthetic peptide

<400> SEQUENCE: 175

Gln Gly Ile Ser Ser Ala
1               5

<210> SEQ ID NO 176
<211> LENGTH: 3
<212> TYPE: PRT
<213> ORGANISM: Artificial sequence
<220> FEATURE:
<223> OTHER INFORMATION: Synthetic peptide

<400> SEQUENCE: 176

Asp Ala Ser
1

<210> SEQ ID NO 177
<211> LENGTH: 9
<212> TYPE: PRT
<213> ORGANISM: Artificial sequence
<220> FEATURE:
<223> OTHER INFORMATION: Synthetic peptide

<400> SEQUENCE: 177

Gln Gln Phe Tyr Asn His Pro Leu Thr
1               5

<210> SEQ ID NO 178
<211> LENGTH: 6
<212> TYPE: PRT
<213> ORGANISM: Artificial sequence
<220> FEATURE:
<223> OTHER INFORMATION: Synthetic peptide

<400> SEQUENCE: 178

Gln Gly Ile Arg Asn Asp
1               5

<210> SEQ ID NO 179
<211> LENGTH: 3
<212> TYPE: PRT
<213> ORGANISM: Artificial sequence
<220> FEATURE:
<223> OTHER INFORMATION: Synthetic peptide

<400> SEQUENCE: 179

Ala Ala Ser
1

<210> SEQ ID NO 180
<211> LENGTH: 9
```

```
<212> TYPE: PRT
<213> ORGANISM: Artificial sequence
<220> FEATURE:
<223> OTHER INFORMATION: Synthetic peptide

<400> SEQUENCE: 180

Leu Gln Asp Tyr Asn Tyr Pro Arg Thr
1               5

<210> SEQ ID NO 181
<211> LENGTH: 6
<212> TYPE: PRT
<213> ORGANISM: Artificial sequence
<220> FEATURE:
<223> OTHER INFORMATION: Synthetic peptide

<400> SEQUENCE: 181

Gln Ser Ile Thr Ser Trp
1               5

<210> SEQ ID NO 182
<211> LENGTH: 3
<212> TYPE: PRT
<213> ORGANISM: Artificial sequence
<220> FEATURE:
<223> OTHER INFORMATION: Synthetic peptide

<400> SEQUENCE: 182

Lys Ala Ser
1

<210> SEQ ID NO 183
<211> LENGTH: 9
<212> TYPE: PRT
<213> ORGANISM: Artificial sequence
<220> FEATURE:
<223> OTHER INFORMATION: Synthetic peptide

<400> SEQUENCE: 183

Gln Gln Tyr Ser Ser Tyr Pro Val Thr
1               5

<210> SEQ ID NO 184
<211> LENGTH: 6
<212> TYPE: PRT
<213> ORGANISM: Artificial sequence
<220> FEATURE:
<223> OTHER INFORMATION: Synthetic peptide

<400> SEQUENCE: 184

Glu Ser Val Ile Thr Tyr
1               5

<210> SEQ ID NO 185
<211> LENGTH: 3
<212> TYPE: PRT
<213> ORGANISM: Artificial sequence
<220> FEATURE:
<223> OTHER INFORMATION: Synthetic peptide

<400> SEQUENCE: 185

Gly Ala Ser
1

<210> SEQ ID NO 186
<211> LENGTH: 10
<212> TYPE: PRT
```

-continued

```
<213> ORGANISM: Artificial sequence
<220> FEATURE:
<223> OTHER INFORMATION: Synthetic peptide

<400> SEQUENCE: 186

Gln Gln Ser Tyr Asn Met Ser Pro Tyr Thr
1               5                   10

<210> SEQ ID NO 187
<211> LENGTH: 6
<212> TYPE: PRT
<213> ORGANISM: Artificial sequence
<220> FEATURE:
<223> OTHER INFORMATION: Synthetic peptide

<400> SEQUENCE: 187

Gln Ser Ile Asp Asn Tyr
1               5

<210> SEQ ID NO 188
<211> LENGTH: 3
<212> TYPE: PRT
<213> ORGANISM: Artificial sequence
<220> FEATURE:
<223> OTHER INFORMATION: Synthetic peptide

<400> SEQUENCE: 188

Ala Ala Ser
1

<210> SEQ ID NO 189
<211> LENGTH: 9
<212> TYPE: PRT
<213> ORGANISM: Artificial sequence
<220> FEATURE:
<223> OTHER INFORMATION: Synthetic peptide

<400> SEQUENCE: 189

Gln Gln Ser Phe Gly Thr Pro Arg Thr
1               5

<210> SEQ ID NO 190
<211> LENGTH: 11
<212> TYPE: PRT
<213> ORGANISM: Artificial sequence
<220> FEATURE:
<223> OTHER INFORMATION: Synthetic peptide

<400> SEQUENCE: 190

Gln Ser Leu Val Tyr Ser Asp Gly Thr Thr Tyr
1               5                   10

<210> SEQ ID NO 191
<211> LENGTH: 3
<212> TYPE: PRT
<213> ORGANISM: Artificial sequence
<220> FEATURE:
<223> OTHER INFORMATION: Synthetic peptide

<400> SEQUENCE: 191

Lys Val Ser
1

<210> SEQ ID NO 192
<211> LENGTH: 10
<212> TYPE: PRT
<213> ORGANISM: Artificial sequence
```

-continued

```
<220> FEATURE:
<223> OTHER INFORMATION: Synthetic peptide

<400> SEQUENCE: 192

Met His Gly Thr His Trp Glu Thr Trp Thr
1               5                   10

<210> SEQ ID NO 193
<211> LENGTH: 6
<212> TYPE: PRT
<213> ORGANISM: Artificial sequence
<220> FEATURE:
<223> OTHER INFORMATION: Synthetic peptide

<400> SEQUENCE: 193

Gln Ser Val Ser Ser Phe
1               5

<210> SEQ ID NO 194
<211> LENGTH: 3
<212> TYPE: PRT
<213> ORGANISM: Artificial sequence
<220> FEATURE:
<223> OTHER INFORMATION: Synthetic peptide

<400> SEQUENCE: 194

Asp Ala Ser
1

<210> SEQ ID NO 195
<211> LENGTH: 9
<212> TYPE: PRT
<213> ORGANISM: Artificial sequence
<220> FEATURE:
<223> OTHER INFORMATION: Synthetic peptide

<400> SEQUENCE: 195

Gln Gln Ser Thr Asn Trp Arg Ile Thr
1               5

<210> SEQ ID NO 196
<211> LENGTH: 6
<212> TYPE: PRT
<213> ORGANISM: Artificial sequence
<220> FEATURE:
<223> OTHER INFORMATION: Synthetic peptide

<400> SEQUENCE: 196

Gln Ser Val Ser Ser Asn
1               5

<210> SEQ ID NO 197
<211> LENGTH: 3
<212> TYPE: PRT
<213> ORGANISM: Artificial sequence
<220> FEATURE:
<223> OTHER INFORMATION: Synthetic peptide

<400> SEQUENCE: 197

Asp Ala Ser
1

<210> SEQ ID NO 198
<211> LENGTH: 8
<212> TYPE: PRT
<213> ORGANISM: Artificial sequence
<220> FEATURE:
```

```
<223> OTHER INFORMATION: Synthetic peptide

<400> SEQUENCE: 198

Gln Gln Tyr Asn Asp Trp Arg Thr
1               5

<210> SEQ ID NO 199
<211> LENGTH: 6
<212> TYPE: PRT
<213> ORGANISM: Artificial sequence
<220> FEATURE:
<223> OTHER INFORMATION: Synthetic peptide

<400> SEQUENCE: 199

Gln Thr Ile Ser Ser Tyr
1               5

<210> SEQ ID NO 200
<211> LENGTH: 3
<212> TYPE: PRT
<213> ORGANISM: Artificial sequence
<220> FEATURE:
<223> OTHER INFORMATION: Synthetic peptide

<400> SEQUENCE: 200

Asp Ala Ser
1

<210> SEQ ID NO 201
<211> LENGTH: 9
<212> TYPE: PRT
<213> ORGANISM: Artificial sequence
<220> FEATURE:
<223> OTHER INFORMATION: Synthetic peptide

<400> SEQUENCE: 201

Gln Gln Arg Tyr Asn Trp Pro Arg Thr
1               5

<210> SEQ ID NO 202
<211> LENGTH: 7
<212> TYPE: PRT
<213> ORGANISM: Artificial sequence
<220> FEATURE:
<223> OTHER INFORMATION: Synthetic peptide

<400> SEQUENCE: 202

Gln Ser Val Gly Ser Asn Tyr
1               5

<210> SEQ ID NO 203
<211> LENGTH: 3
<212> TYPE: PRT
<213> ORGANISM: Artificial sequence
<220> FEATURE:
<223> OTHER INFORMATION: Synthetic peptide

<400> SEQUENCE: 203

Gly Ala Ser
1

<210> SEQ ID NO 204
<211> LENGTH: 9
<212> TYPE: PRT
<213> ORGANISM: Artificial sequence
<220> FEATURE:
<223> OTHER INFORMATION: Synthetic peptide
```

<400> SEQUENCE: 204

Gln Gln Tyr Glu Thr Ser Ser Arg Thr
1               5

<210> SEQ ID NO 205
<211> LENGTH: 7
<212> TYPE: PRT
<213> ORGANISM: Artificial sequence
<220> FEATURE:
<223> OTHER INFORMATION: Synthetic peptide

<400> SEQUENCE: 205

Gln Ser Ala Ser Ser Ser Tyr
1               5

<210> SEQ ID NO 206
<211> LENGTH: 3
<212> TYPE: PRT
<213> ORGANISM: Artificial sequence
<220> FEATURE:
<223> OTHER INFORMATION: Synthetic peptide

<400> SEQUENCE: 206

Gly Ala Ser
1

<210> SEQ ID NO 207
<211> LENGTH: 8
<212> TYPE: PRT
<213> ORGANISM: Artificial sequence
<220> FEATURE:
<223> OTHER INFORMATION: Synthetic peptide

<400> SEQUENCE: 207

His His Tyr Gly Ser Ser Arg Thr
1               5

<210> SEQ ID NO 208
<211> LENGTH: 6
<212> TYPE: PRT
<213> ORGANISM: Artificial sequence
<220> FEATURE:
<223> OTHER INFORMATION: Synthetic peptide

<400> SEQUENCE: 208

Gln Asn Met Ser Thr Tyr
1               5

<210> SEQ ID NO 209
<211> LENGTH: 3
<212> TYPE: PRT
<213> ORGANISM: Artificial sequence
<220> FEATURE:
<223> OTHER INFORMATION: Synthetic peptide

<400> SEQUENCE: 209

Gly Ala Ser
1

<210> SEQ ID NO 210
<211> LENGTH: 9
<212> TYPE: PRT
<213> ORGANISM: Artificial sequence
<220> FEATURE:
<223> OTHER INFORMATION: Synthetic peptide -continued

```
<400> SEQUENCE: 210

Gln Gln Ser Tyr Asn Ile Pro Ile Thr
1               5

<210> SEQ ID NO 211
<211> LENGTH: 6
<212> TYPE: PRT
<213> ORGANISM: Artificial sequence
<220> FEATURE:
<223> OTHER INFORMATION: Synthetic peptide

<400> SEQUENCE: 211

Gln Gly Ile Arg Asn Asp
1               5

<210> SEQ ID NO 212
<211> LENGTH: 3
<212> TYPE: PRT
<213> ORGANISM: Artificial sequence
<220> FEATURE:
<223> OTHER INFORMATION: Synthetic peptide

<400> SEQUENCE: 212

Ala Ala Ser
1

<210> SEQ ID NO 213
<211> LENGTH: 9
<212> TYPE: PRT
<213> ORGANISM: Artificial sequence
<220> FEATURE:
<223> OTHER INFORMATION: Synthetic peptide

<400> SEQUENCE: 213

Leu Gln His Asn Thr Tyr Pro Leu Thr
1               5

<210> SEQ ID NO 214
<211> LENGTH: 6
<212> TYPE: PRT
<213> ORGANISM: Artificial sequence
<220> FEATURE:
<223> OTHER INFORMATION: Synthetic peptide

<400> SEQUENCE: 214

His Ser Val Thr Thr Asn
1               5

<210> SEQ ID NO 215
<211> LENGTH: 3
<212> TYPE: PRT
<213> ORGANISM: Artificial sequence
<220> FEATURE:
<223> OTHER INFORMATION: Synthetic peptide

<400> SEQUENCE: 215

Asp Ala Ser
1

<210> SEQ ID NO 216
<211> LENGTH: 8
<212> TYPE: PRT
<213> ORGANISM: Artificial sequence
<220> FEATURE:
<223> OTHER INFORMATION: Synthetic peptide

<400> SEQUENCE: 216
```

```
Gln Gln Tyr Asn Asp Gly Arg Thr
1               5

<210> SEQ ID NO 217
<211> LENGTH: 6
<212> TYPE: PRT
<213> ORGANISM: Artificial sequence
<220> FEATURE:
<223> OTHER INFORMATION: Synthetic peptide

<400> SEQUENCE: 217

Asn Ile Gly Ser Lys Ser
1               5

<210> SEQ ID NO 218
<211> LENGTH: 3
<212> TYPE: PRT
<213> ORGANISM: Artificial sequence
<220> FEATURE:
<223> OTHER INFORMATION: Synthetic peptide

<400> SEQUENCE: 218

Asp Glu Asn
1

<210> SEQ ID NO 219
<211> LENGTH: 11
<212> TYPE: PRT
<213> ORGANISM: Artificial sequence
<220> FEATURE:
<223> OTHER INFORMATION: Synthetic peptide

<400> SEQUENCE: 219

Gln Val Trp Asp Ser Arg Ser Asp His Tyr Val
1               5                   10

<210> SEQ ID NO 220
<211> LENGTH: 6
<212> TYPE: PRT
<213> ORGANISM: Artificial sequence
<220> FEATURE:
<223> OTHER INFORMATION: Synthetic peptide

<400> SEQUENCE: 220

Asn Ile Gly Ser Lys Ser
1               5

<210> SEQ ID NO 221
<211> LENGTH: 3
<212> TYPE: PRT
<213> ORGANISM: Artificial sequence
<220> FEATURE:
<223> OTHER INFORMATION: Synthetic peptide

<400> SEQUENCE: 221

Asp Asp Ser
1

<210> SEQ ID NO 222
<211> LENGTH: 11
<212> TYPE: PRT
<213> ORGANISM: Artificial sequence
<220> FEATURE:
<223> OTHER INFORMATION: Synthetic peptide

<400> SEQUENCE: 222
```

-continued

```
Gln Val Trp Asp Ser Ser Ser Asp His Val Val
1               5                   10

<210> SEQ ID NO 223
<211> LENGTH: 6
<212> TYPE: PRT
<213> ORGANISM: Artificial sequence
<220> FEATURE:
<223> OTHER INFORMATION: Synthetic peptide

<400> SEQUENCE: 223

Gln Ser Val Ser Ser Asn
1               5

<210> SEQ ID NO 224
<211> LENGTH: 3
<212> TYPE: PRT
<213> ORGANISM: Artificial sequence
<220> FEATURE:
<223> OTHER INFORMATION: Synthetic peptide

<400> SEQUENCE: 224

Asp Ala Ser
1

<210> SEQ ID NO 225
<211> LENGTH: 9
<212> TYPE: PRT
<213> ORGANISM: Artificial sequence
<220> FEATURE:
<223> OTHER INFORMATION: Synthetic peptide

<400> SEQUENCE: 225

Gln Gln Arg Tyr Asn Trp Arg Val Thr
1               5

<210> SEQ ID NO 226
<211> LENGTH: 6
<212> TYPE: PRT
<213> ORGANISM: Artificial sequence
<220> FEATURE:
<223> OTHER INFORMATION: Synthetic peptide

<400> SEQUENCE: 226

Gln Ser Val Ser Ser Asn
1               5

<210> SEQ ID NO 227
<211> LENGTH: 3
<212> TYPE: PRT
<213> ORGANISM: Artificial sequence
<220> FEATURE:
<223> OTHER INFORMATION: Synthetic peptide

<400> SEQUENCE: 227

Asn Val Ser
1

<210> SEQ ID NO 228
<211> LENGTH: 9
<212> TYPE: PRT
<213> ORGANISM: Artificial sequence
<220> FEATURE:
<223> OTHER INFORMATION: Synthetic peptide

<400> SEQUENCE: 228

His Gln Arg Thr Asn Trp Pro Leu Thr
```

-continued

```
1               5

<210> SEQ ID NO 229
<211> LENGTH: 12
<212> TYPE: PRT
<213> ORGANISM: Artificial sequence
<220> FEATURE:
<223> OTHER INFORMATION: Synthetic peptide

<400> SEQUENCE: 229

Gln Ser Val Leu Tyr Thr Ser Asn Asn Lys Asn Tyr
1               5                   10

<210> SEQ ID NO 230
<211> LENGTH: 3
<212> TYPE: PRT
<213> ORGANISM: Artificial sequence
<220> FEATURE:
<223> OTHER INFORMATION: Synthetic peptide

<400> SEQUENCE: 230

Trp Ala Ser
1

<210> SEQ ID NO 231
<211> LENGTH: 9
<212> TYPE: PRT
<213> ORGANISM: Artificial sequence
<220> FEATURE:
<223> OTHER INFORMATION: Synthetic peptide

<400> SEQUENCE: 231

Gln Gln Tyr Tyr Thr Thr Pro Lys Thr
1               5

<210> SEQ ID NO 232
<211> LENGTH: 6
<212> TYPE: PRT
<213> ORGANISM: Artificial sequence
<220> FEATURE:
<223> OTHER INFORMATION: Synthetic peptide

<400> SEQUENCE: 232

Gln Ser Val Ser Ser Tyr
1               5

<210> SEQ ID NO 233
<211> LENGTH: 3
<212> TYPE: PRT
<213> ORGANISM: Artificial sequence
<220> FEATURE:
<223> OTHER INFORMATION: Synthetic peptide

<400> SEQUENCE: 233

Asp Ala Ser
1

<210> SEQ ID NO 234
<211> LENGTH: 9
<212> TYPE: PRT
<213> ORGANISM: Artificial sequence
<220> FEATURE:
<223> OTHER INFORMATION: Synthetic peptide

<400> SEQUENCE: 234

Gln Gln Arg Gly Asn Trp Pro Leu Thr
1               5
```

```
<210> SEQ ID NO 235
<211> LENGTH: 6
<212> TYPE: PRT
<213> ORGANISM: Artificial sequence
<220> FEATURE:
<223> OTHER INFORMATION: Synthetic peptide

<400> SEQUENCE: 235

Gln Ser Ile Asp Thr Tyr
1               5

<210> SEQ ID NO 236
<211> LENGTH: 3
<212> TYPE: PRT
<213> ORGANISM: Artificial sequence
<220> FEATURE:
<223> OTHER INFORMATION: Synthetic peptide

<400> SEQUENCE: 236

Asp Ala Ser
1

<210> SEQ ID NO 237
<211> LENGTH: 11
<212> TYPE: PRT
<213> ORGANISM: Artificial sequence
<220> FEATURE:
<223> OTHER INFORMATION: Synthetic peptide

<400> SEQUENCE: 237

Gln Gln Arg Ser Asn Arg Pro Pro Arg Tyr Thr
1               5                   10

<210> SEQ ID NO 238
<211> LENGTH: 6
<212> TYPE: PRT
<213> ORGANISM: Artificial sequence
<220> FEATURE:
<223> OTHER INFORMATION: Synthetic peptide

<400> SEQUENCE: 238

Gln Asp Ile Asn Thr Tyr
1               5

<210> SEQ ID NO 239
<211> LENGTH: 3
<212> TYPE: PRT
<213> ORGANISM: Artificial sequence
<220> FEATURE:
<223> OTHER INFORMATION: Synthetic peptide

<400> SEQUENCE: 239

Asp Ala Ser
1

<210> SEQ ID NO 240
<211> LENGTH: 12
<212> TYPE: PRT
<213> ORGANISM: Artificial sequence
<220> FEATURE:
<223> OTHER INFORMATION: Synthetic peptide

<400> SEQUENCE: 240

Gln Gln Tyr Asp His Leu Pro Arg Arg Thr Phe Thr
1               5                   10
```

<210> SEQ ID NO 241
<211> LENGTH: 28
<212> TYPE: PRT
<213> ORGANISM: Artificial sequence
<220> FEATURE:
<223> OTHER INFORMATION: Synthetic polypeptide

<400> SEQUENCE: 241

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala
            20                  25

<210> SEQ ID NO 242
<211> LENGTH: 17
<212> TYPE: PRT
<213> ORGANISM: Artificial sequence
<220> FEATURE:
<223> OTHER INFORMATION: Synthetic peptide

<400> SEQUENCE: 242

Met Arg Ala Trp Ile Phe Phe Leu Leu Cys Leu Ala Gly Arg Ala Leu
1               5                   10                  15

Ala

<210> SEQ ID NO 243
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 243
cgtcacacat cagctctgac aa                                                   22

<210> SEQ ID NO 244
<211> LENGTH: 20
<212> TYPE: PRT
<213> ORGANISM: Artificial sequence
<220> FEATURE:
<223> OTHER INFORMATION: Synthetic peptide

<400> SEQUENCE: 244

Ala Arg Leu Lys Trp Leu Leu Ser Arg Gly Leu Arg Gly His Tyr Tyr
1               5                   10                  15

Gly Met Asp Val
            20

<210> SEQ ID NO 245
<211> LENGTH: 15
<212> TYPE: PRT
<213> ORGANISM: Artificial sequence
<220> FEATURE:
<223> OTHER INFORMATION: Synthetic peptide

<400> SEQUENCE: 245

Ala Arg Arg Gly Ala Trp Ser Gly Tyr Arg Asn Trp Phe Asp Pro
1               5                   10                  15

<210> SEQ ID NO 246
<211> LENGTH: 12
<212> TYPE: PRT
<213> ORGANISM: Artificial sequence
<220> FEATURE:
<223> OTHER INFORMATION: Synthetic peptide

<400> SEQUENCE: 246

Ala Lys Asp Gly Gln Ser Leu Glu Trp Leu Val Tyr
1               5                   10

<210> SEQ ID NO 247
<211> LENGTH: 12
<212> TYPE: PRT
<213> ORGANISM: Artificial sequence
<220> FEATURE:
<223> OTHER INFORMATION: Synthetic peptide

<400> SEQUENCE: 247

Ala Gly Ser Tyr Gly Glu Tyr Val Ser Phe Gly His
1               5                   10

<210> SEQ ID NO 248
<211> LENGTH: 20
<212> TYPE: PRT
<213> ORGANISM: Artificial sequence
<220> FEATURE:
<223> OTHER INFORMATION: Synthetic peptide

<400> SEQUENCE: 248

Ala Arg Glu Pro Pro Gln Tyr Ser Ser Gly Trp Arg Gln Ser Leu Tyr
1               5                   10                  15

Tyr Phe Asp Tyr
            20

<210> SEQ ID NO 249
<211> LENGTH: 11
<212> TYPE: PRT
<213> ORGANISM: Artificial sequence
<220> FEATURE:
<223> OTHER INFORMATION: Synthetic peptide

<400> SEQUENCE: 249

Ala Arg Ala Asn Ser Gly Ser Phe Leu Asp Tyr
1               5                   10

<210> SEQ ID NO 250
<211> LENGTH: 20
<212> TYPE: PRT
<213> ORGANISM: Artificial sequence
<220> FEATURE:
<223> OTHER INFORMATION: Synthetic peptide

<400> SEQUENCE: 250

Ala Lys Asp Gly Phe Val Gly Gln Gln Leu Met Arg Arg Gly Pro Trp
1               5                   10                  15

Trp Phe Asp Pro
            20

<210> SEQ ID NO 251
<211> LENGTH: 21
<212> TYPE: PRT
<213> ORGANISM: Artificial sequence
<220> FEATURE:
<223> OTHER INFORMATION: Synthetic peptide

<400> SEQUENCE: 251

Ala Arg Asp Pro Pro Tyr Cys Ser Gly Asn Ile Cys Tyr Leu Tyr His
1               5                   10                  15

Tyr Ala Leu Asp Val
            20

```
<210> SEQ ID NO 252
<211> LENGTH: 422
<212> TYPE: PRT
<213> ORGANISM: Henipavirus hendraense

<400> SEQUENCE: 252

Val Gly Leu Pro Asn Gln Ile Cys Leu Gln Lys Thr Thr Ser Thr Ile
1               5                   10                  15

Leu Lys Pro Arg Leu Ile Ser Tyr Thr Leu Pro Ile Asn Thr Arg Glu
            20                  25                  30

Gly Val Cys Ile Thr Asp Pro Leu Leu Ala Val Asp Asn Gly Phe Phe
            35                  40                  45

Ala Tyr Ser His Leu Glu Lys Ile Gly Ser Cys Thr Arg Gly Ile Ala
        50                  55                  60

Lys Gln Arg Ile Ile Gly Val Gly Glu Val Leu Asp Arg Gly Asp Lys
65                  70                  75                  80

Val Pro Ser Met Phe Met Thr Asn Val Trp Thr Pro Pro Asn Pro Ser
                85                  90                  95

Thr Ile His His Cys Ser Ser Thr Tyr His Glu Asp Phe Tyr Tyr Thr
                100                 105                 110

Leu Cys Ala Val Ser His Val Gly Asp Pro Ile Leu Asn Ser Thr Ser
            115                 120                 125

Trp Thr Glu Ser Leu Ser Leu Ile Arg Leu Ala Val Arg Pro Lys Ser
            130                 135                 140

Asp Ser Gly Asp Tyr Asn Gln Lys Tyr Ile Ala Ile Thr Lys Val Glu
145                 150                 155                 160

Arg Gly Lys Tyr Asp Lys Val Met Pro Tyr Gly Pro Ser Gly Ile Lys
                165                 170                 175

Gln Gly Asp Thr Leu Tyr Phe Pro Ala Val Gly Phe Leu Pro Arg Thr
                180                 185                 190

Glu Phe Gln Tyr Asn Asp Ser Asn Cys Pro Ile Ile His Cys Lys Tyr
                195                 200                 205

Ser Lys Ala Glu Asn Cys Arg Leu Ser Met Gly Val Asn Ser Lys Ser
            210                 215                 220

His Tyr Ile Leu Arg Ser Gly Leu Leu Lys Tyr Asn Leu Ser Leu Gly
225                 230                 235                 240

Gly Asp Ile Ile Leu Gln Phe Ile Glu Ile Ala Asp Asn Arg Leu Thr
                245                 250                 255

Ile Gly Ser Pro Ser Lys Ile Tyr Asn Ser Leu Gly Gln Pro Val Phe
            260                 265                 270

Tyr Gln Ala Ser Tyr Ser Trp Asp Thr Met Ile Lys Leu Gly Asp Val
            275                 280                 285

Asp Thr Val Asp Pro Leu Arg Val Gln Trp Arg Asn Asn Ser Val Ile
        290                 295                 300

Ser Arg Pro Gly Gln Ser Gln Cys Pro Arg Phe Asn Val Cys Pro Glu
305                 310                 315                 320

Val Cys Trp Glu Gly Thr Tyr Asn Asp Ala Phe Leu Ile Asp Arg Leu
                325                 330                 335

Asn Trp Val Ser Ala Gly Val Tyr Leu Asn Ser Asn Gln Thr Ala Glu
                340                 345                 350

Asn Pro Val Phe Ala Val Phe Lys Asp Asn Glu Ile Leu Tyr Gln Val
                355                 360                 365

Pro Leu Ala Glu Asp Asp Thr Asn Ala Gln Lys Thr Ile Thr Asp Cys
```

-continued

```
       370               375               380

Phe Leu Leu Glu Asn Val Ile Trp Cys Ile Ser Leu Val Glu Ile Tyr
385               390               395               400

Asp Thr Gly Asp Ser Val Ile Arg Pro Lys Leu Phe Ala Val Lys Ile
                405               410               415

Pro Ala Gln Cys Ser Glu
            420

<210> SEQ ID NO 253
<211> LENGTH: 421
<212> TYPE: PRT
<213> ORGANISM: Nipah virus

<400> SEQUENCE: 253

Val Gly Leu Pro Asn Asn Ile Cys Leu Gln Lys Thr Ser Asn Gln Ile
1               5               10               15

Leu Lys Pro Lys Leu Ile Ser Tyr Thr Leu Pro Val Val Gly Gln Ser
                20               25               30

Gly Thr Cys Ile Thr Asp Pro Leu Leu Ala Met Asp Glu Gly Tyr Phe
            35               40               45

Ala Tyr Ser His Leu Glu Arg Ile Gly Ser Cys Ser Arg Gly Val Ser
        50               55               60

Lys Gln Arg Ile Ile Gly Val Gly Glu Val Leu Asp Arg Gly Asp Glu
65               70               75               80

Val Pro Ser Leu Phe Met Thr Asn Val Trp Thr Pro Pro Asn Pro Asn
                85               90               95

Thr Val Tyr His Cys Ser Ala Val Tyr Asn Asn Glu Phe Tyr Tyr Val
            100               105               110

Leu Cys Ala Val Ser Thr Val Gly Asp Pro Ile Leu Asn Ser Thr Tyr
            115               120               125

Trp Ser Gly Ser Leu Met Met Thr Arg Leu Ala Val Lys Pro Lys Ser
        130               135               140

Asn Gly Gly Gly Tyr Asn Gln His Gln Leu Ala Leu Arg Ser Ile Glu
145               150               155               160

Lys Gly Arg Tyr Asp Lys Val Met Pro Tyr Gly Pro Ser Gly Ile Lys
                165               170               175

Gln Gly Asp Thr Leu Tyr Phe Pro Ala Val Gly Phe Leu Val Arg Thr
            180               185               190

Glu Phe Lys Tyr Asn Asp Ser Asn Cys Pro Ile Thr Lys Cys Gln Tyr
            195               200               205

Ser Lys Pro Glu Asn Cys Arg Leu Ser Met Gly Ile Arg Pro Asn Ser
        210               215               220

His Tyr Ile Leu Arg Ser Gly Leu Leu Lys Tyr Asn Leu Ser Asp Gly
225               230               235               240

Glu Asn Pro Lys Val Val Phe Ile Glu Ile Ser Asp Gln Arg Leu Ser
                245               250               255

Ile Gly Ser Pro Ser Lys Ile Tyr Asp Ser Leu Gly Gln Pro Val Phe
            260               265               270

Tyr Gln Ala Ser Phe Ser Trp Asp Thr Met Ile Lys Phe Gly Asp Val
            275               280               285

Leu Thr Val Asn Pro Leu Val Val Asn Trp Arg Asn Asn Thr Val Ile
        290               295               300

Ser Arg Pro Gly Gln Ser Gln Cys Pro Arg Phe Asn Thr Cys Pro Glu
305               310               315               320
```

-continued

```
Ile Cys Trp Glu Gly Val Tyr Asn Asp Ala Phe Leu Ile Asp Arg Ile
            325                 330                 335

Asn Trp Ile Ser Ala Gly Val Phe Leu Asp Ser Asn Gln Thr Ala Glu
            340                 345                 350

Asn Pro Val Phe Thr Val Phe Lys Asp Asn Glu Ile Leu Tyr Arg Ala
            355                 360                 365

Gln Leu Ala Ser Glu Asp Thr Asn Ala Gln Lys Thr Ile Thr Asn Cys
        370                 375                 380

Phe Leu Leu Lys Asn Lys Ile Trp Cys Ile Ser Leu Val Glu Ile Tyr
385                 390                 395                 400

Asp Thr Gly Asp Asn Val Ile Arg Pro Lys Leu Phe Ala Val Lys Ile
                405                 410                 415

Pro Glu Gln Cys Thr
                420

<210> SEQ ID NO 254
<211> LENGTH: 421
<212> TYPE: PRT
<213> ORGANISM: Nipah virus

<400> SEQUENCE: 254

Val Gly Leu Pro Asn Asn Ile Cys Leu Gln Lys Thr Ser Asn Gln Ile
1               5                   10                  15

Leu Lys Pro Lys Leu Ile Ser Tyr Thr Leu Pro Val Val Gly Gln Ser
            20                  25                  30

Gly Thr Cys Ile Thr Asp Pro Leu Leu Ala Met Asp Glu Gly Tyr Phe
            35                  40                  45

Ala Tyr Ser His Leu Glu Arg Ile Gly Ser Cys Ser Arg Gly Val Ser
        50                  55                  60

Lys Gln Arg Ile Ile Gly Val Gly Glu Val Leu Asp Arg Gly Asp Glu
65                  70                  75                  80

Val Pro Ser Leu Phe Met Thr Asn Val Trp Thr Pro Ser Asn Pro Asn
                85                  90                  95

Thr Val Tyr His Cys Ser Ala Val Tyr Asn Asn Glu Phe Tyr Tyr Val
            100                 105                 110

Leu Cys Ala Val Ser Val Val Gly Asp Pro Ile Leu Asn Ser Thr Tyr
            115                 120                 125

Trp Ser Gly Ser Leu Met Met Thr Arg Leu Ala Val Lys Pro Lys Asn
        130                 135                 140

Asn Gly Glu Ser Tyr Asn Gln His Gln Phe Ala Leu Arg Asn Ile Glu
145                 150                 155                 160

Lys Gly Lys Tyr Asp Lys Val Met Pro Tyr Gly Pro Ser Gly Ile Lys
                165                 170                 175

Gln Gly Asp Thr Leu Tyr Phe Pro Ala Val Gly Phe Leu Val Arg Thr
            180                 185                 190

Glu Phe Thr Tyr Asn Asp Ser Asn Cys Pro Ile Ala Glu Cys Gln Tyr
            195                 200                 205

Ser Lys Pro Glu Asn Cys Arg Leu Ser Met Gly Ile Arg Pro Asn Ser
        210                 215                 220

His Tyr Ile Leu Arg Ser Gly Leu Leu Lys Tyr Asn Leu Ser Asp Glu
225                 230                 235                 240

Glu Asn Ser Lys Ile Val Phe Ile Glu Ile Ser Asp Gln Arg Leu Ser
                245                 250                 255

Ile Gly Ser Pro Ser Lys Ile Tyr Asp Ser Leu Gly Gln Pro Val Phe
            260                 265                 270
```

```
Tyr Gln Ala Ser Phe Ser Trp Asp Thr Met Ile Lys Phe Gly Asp Val
        275             280             285

Gln Thr Val Asn Pro Leu Val Val Asn Trp Arg Asp Asn Thr Val Ile
    290             295             300

Ser Arg Pro Gly Gln Ser Gln Cys Pro Arg Phe Asn Lys Cys Pro Glu
305             310             315             320

Val Cys Trp Glu Gly Val Tyr Asn Asp Ala Phe Leu Ile Asp Arg Ile
            325             330             335

Asn Trp Ile Ser Ala Gly Val Phe Leu Asp Ser Asn Gln Thr Ala Glu
            340             345             350

Asn Pro Val Phe Thr Val Phe Lys Asp Asn Glu Val Leu Tyr Arg Ala
            355             360             365

Gln Leu Ala Ser Glu Asp Thr Asn Ala Gln Lys Thr Ile Thr Asn Cys
    370             375             380

Phe Leu Leu Lys Asn Lys Ile Trp Cys Ile Ser Leu Val Glu Ile Tyr
385             390             395             400

Asp Thr Gly Asp Asn Val Ile Arg Pro Lys Leu Phe Ala Val Lys Ile
            405             410             415

Pro Glu Gln Cys Thr
            420

<210> SEQ ID NO 255
<211> LENGTH: 418
<212> TYPE: PRT
<213> ORGANISM: Cedar virus

<400> SEQUENCE: 255

Ala Gly Pro Pro Lys Ile Phe Cys Lys Ser Val Ser Lys Asp Pro Asp
1               5               10              15

Phe Arg Leu Lys Gln Ile Asp Tyr Val Ile Pro Val Gln Gln Asp Arg
            20              25              30

Ser Ile Cys Met Asn Asn Pro Leu Leu Asp Ile Ser Asp Gly Phe Phe
            35              40              45

Thr Tyr Ile His Tyr Glu Gly Ile Asn Ser Cys Lys Lys Ser Asp Ser
    50              55              60

Phe Lys Val Leu Leu Ser His Gly Glu Ile Val Asp Arg Gly Asp Tyr
65              70              75              80

Arg Pro Ser Leu Tyr Leu Leu Ser Ser His Tyr His Pro Tyr Ser Met
            85              90              95

Gln Val Ile Asn Cys Val Pro Val Thr Cys Asn Gln Ser Ser Phe Val
            100             105             110

Phe Cys His Ile Ser Asn Asn Thr Lys Thr Leu Asp Asn Ser Asp Tyr
            115             120             125

Ser Ser Asp Glu Tyr Tyr Ile Thr Tyr Phe Asn Gly Ile Asp Arg Pro
    130             135             140

Lys Thr Lys Lys Ile Pro Ile Asn Asn Met Thr Ala Asp Asn Arg Tyr
145             150             155             160

Ile His Phe Thr Phe Ser Gly Gly Gly Gly Val Cys Leu Gly Glu Glu
            165             170             175

Phe Ile Ile Pro Val Thr Thr Val Ile Asn Thr Asp Val Phe Thr His
            180             185             190

Asp Tyr Cys Glu Ser Phe Asn Cys Ser Val Gln Thr Gly Lys Ser Leu
            195             200             205

Lys Glu Ile Cys Ser Glu Ser Leu Arg Ser Pro Thr Asn Ser Ser Arg
```

```
         210              215              220
Tyr Asn Leu Asn Gly Ile Met Ile Ser Gln Asn Asn Met Thr Asp
225              230              235              240

Phe Lys Ile Gln Leu Asn Gly Ile Thr Tyr Asn Lys Leu Ser Phe Gly
             245              250              255

Ser Pro Gly Arg Leu Ser Lys Thr Leu Gly Gln Val Leu Tyr Tyr Gln
             260              265              270

Ser Ser Met Ser Trp Asp Thr Tyr Leu Lys Ala Gly Phe Val Glu Lys
         275              280              285

Trp Lys Pro Phe Thr Pro Asn Trp Met Asn Asn Thr Val Ile Ser Arg
         290              295              300

Pro Asn Gln Gly Asn Cys Pro Arg Tyr His Lys Cys Pro Glu Ile Cys
305              310              315              320

Tyr Gly Gly Thr Tyr Asn Asp Ile Ala Pro Leu Asp Leu Gly Lys Asp
             325              330              335

Met Tyr Val Ser Val Ile Leu Asp Ser Asp Gln Leu Ala Glu Asn Pro
         340              345              350

Glu Ile Thr Val Phe Asn Ser Thr Thr Ile Leu Tyr Lys Glu Arg Val
         355              360              365

Ser Lys Asp Glu Leu Asn Thr Arg Ser Thr Thr Thr Ser Cys Phe Leu
     370              375              380

Phe Leu Asp Glu Pro Trp Cys Ile Ser Val Leu Glu Thr Asn Arg Phe
385              390              395              400

Asn Gly Lys Ser Ile Arg Pro Glu Ile Tyr Ser Tyr Lys Ile Pro Lys
             405              410              415

Tyr Cys
```

```
<210> SEQ ID NO 256
<211> LENGTH: 416
<212> TYPE: PRT
<213> ORGANISM: Ghana virus

<400> SEQUENCE: 256

Val Ala His Gly Pro Ser Pro Cys Arg Asn Phe Ser Ser Val Pro Thr
1               5               10              15

Ile Tyr Tyr Tyr Arg Ile Pro Gly Leu Tyr Asn Arg Thr Ala Leu Asp
             20              25              30

Glu Arg Cys Ile Leu Asn Pro Arg Leu Thr Ile Ser Ser Thr Lys Phe
         35              40              45

Ala Tyr Val His Ser Glu Tyr Asp Lys Asn Cys Thr Arg Gly Phe Lys
     50              55              60

Tyr Tyr Glu Leu Met Thr Phe Gly Glu Ile Leu Glu Gly Pro Glu Lys
65              70              75              80

Glu Pro Arg Met Phe Ser Arg Ser Phe Tyr Ser Pro Thr Asn Ala Val
             85              90              95

Asn Tyr His Ser Cys Thr Pro Ile Val Thr Val Asn Glu Gly Tyr Phe
         100             105             110

Leu Cys Leu Glu Cys Thr Ser Ser Asp Pro Leu Tyr Lys Ala Asn Leu
     115             120             125

Ser Asn Ser Thr Phe His Leu Val Ile Leu Arg His Asn Lys Asp Glu
     130             135             140

Lys Ile Val Ser Met Pro Ser Phe Asn Leu Ser Thr Asp Gln Glu Tyr
145             150             155             160

Val Gln Ile Ile Pro Ala Glu Gly Gly Gly Thr Ala Glu Ser Gly Asn
```

-continued

```
             165                    170                    175

Leu Tyr Phe Pro Cys Ile Gly Arg Leu Leu His Lys Arg Val Thr His
             180                    185                    190

Pro Leu Cys Lys Lys Ser Asn Cys Ser Arg Thr Asp Asp Glu Ser Cys
             195                    200                    205

Leu Lys Ser Tyr Tyr Asn Gln Gly Ser Pro Gln His Gln Val Val Asn
         210                    215                    220

Cys Leu Ile Arg Ile Arg Asn Ala Gln Arg Asp Asn Pro Thr Trp Asp
225                    230                    235                    240

Val Ile Thr Val Asp Leu Thr Asn Thr Tyr Pro Gly Ser Arg Ser Arg
                 245                    250                    255

Ile Phe Gly Ser Phe Ser Lys Pro Met Leu Tyr Gln Ser Ser Val Ser
                 260                    265                    270

Trp His Thr Leu Leu Gln Val Ala Glu Ile Thr Asp Leu Asp Lys Tyr
             275                    280                    285

Gln Leu Asp Trp Leu Asp Thr Pro Tyr Ile Ser Arg Pro Gly Gly Ser
     290                    295                    300

Glu Cys Pro Phe Gly Asn Tyr Cys Pro Thr Val Cys Trp Glu Gly Thr
305                    310                    315                    320

Tyr Asn Asp Val Tyr Ser Leu Thr Pro Asn Asn Asp Leu Phe Val Thr
                 325                    330                    335

Val Tyr Leu Lys Ser Glu Gln Val Ala Glu Asn Pro Tyr Phe Ala Ile
             340                    345                    350

Phe Ser Arg Asp Gln Ile Leu Lys Glu Phe Pro Leu Asp Ala Trp Ile
             355                    360                    365

Ser Ser Ala Arg Thr Thr Thr Ile Ser Cys Phe Met Phe Asn Asn Glu
     370                    375                    380

Ile Trp Cys Ile Ala Ala Leu Glu Ile Thr Arg Leu Asn Asp Asp Ile
385                    390                    395                    400

Ile Arg Pro Ile Tyr Tyr Ser Phe Trp Leu Pro Thr Asp Cys Arg Thr
                 405                    410                    415
```

HUMAN HENDRA VIRUS AND NIPAH VIRUS ANTIBODIES AND METHODS OF USE THEREFOR

PRIORITY CLAIM

This application is a national phase application under 35 U.S.C. § 371 of International Application No. PCT/US2020/060129, filed Nov. 12, 2020, which claims benefit of priority to U.S. Provisional Application Ser. No. 62/934,295, filed Nov. 12, 2019, the entire contents of which are hereby incorporated by reference.

REFERENCE TO A SEQUENCE LISTING

A Sequence Listing is submitted concurrently with the specification as an ASCII formatted text file, with a file name of VBLT.P0301US_updated_ST25.txt, a creation date of Aug. 20, 2025, and a size of 132,103 bytes. The information in the electronic format of the Sequence Listing is part of the specification and is hereby incorporated herein by reference in its entirety.

BACKGROUND

1. Field of the Disclosure

The present disclosure relates generally to the fields of medicine, infectious disease, and immunology. More particular, the disclosure relates to human antibodies binding to Hendra virus and Nipah virus.

2. Background

Hendra virus (HeV) and Nipah virus (NiV), belonging to the Henipavirus genus in the Paramyxoviridae family, are zoonotic pathogens that cause severe viral disease in humans characterized by serious respiratory illness and encephalitis with high mortality (Weatherman et al., 2018). Fruit bats of the *Pteropus* genus are natural reservoirs of both HeV and NiV, and the viruses are understood to have co-evolved with these bats (Halpin et al., 2011; Vidgen et al., 2015). Transmission of HeV to humans can occur indirectly from fruit bats following direct human contact with infected horses (Field, 2016; Murray et al., 1995; Selvey et al., 1995). Transmission of NiV to humans may occur directly from fruit bats, infected pigs, or from infected humans (Clayton et al., 2012; Weatherman et al., 2018). There are two distinct major strains of NiV, designated NiV Malaysia (NiV$_M$) and NiV Bangladesh (NiV$_B$) (Lo et al., 2012). NiV$_B$ may be more pathogenic than NiV$_M$, as suggested by differences in mortality rates and transmission patterns (Gurley et al., 2007; Homaira et al., 2010; Mire et al., 2016). Recently, 20 new species of viruses in the Henipavirus genus, including Ghana virus (GH-M74a henipavirus) and Cedar virus, were identified in bats in Africa (Drexler et al., 2012) or Australia (Marsh et al., 2012). In 2014, a novel henipavirus-like virus, designated Mòjiāng virus, whose genes have high nucleotide sequence identities to those of the known henipaviruses, was found in yellow-breasted rats (*Rattus flavipectus*) in China after miners in the region succumbed to irregular pneumonia with unknown etiology (Wu et al., 2014). These viruses have high potential to cause significant human epidemics following their spillover from wildlife reservoirs to humans and domestic animals due to their wide host tropism and high pathogenicity (Smith and Wang, 2013). Henipavirus spillovers are appreciated to be increasing in frequency and distribution due to changes in wild reservoir species distribution and food sources (such as due to changing climate and human related habitat losses) resulting in increased contact with human populations and agriculture (Kessler et al., 2018; Martin et al., 2018; Plowright et al., 2015; Walsh et al., 2017). Furthermore, human-to-human transmission of NiV in India and Bangladesh shows that a large human outbreak is possible (Chadha et al., 2006; Gurley et al., 2007). There is also concern about the potential to weaponize henipaviruses (Luby, 2013). There are no licensed human vaccines or antiviral treatments for HeV or NiV infections (Broder et al., 2013).

The two henipavirus surface proteins, RBP and F, mediate viral entry by viral attachment to cells and fusion between the viral envelope and host cell membrane (Aguilar and Iorio, 2012). HeV or NiV first attach to host cells by binding to the receptors ephrinB2 or ephrinB3 using the viral receptor binding proteins HeV-RBP or NiV-RBP (Bonaparte et al., 2005; Negrete et al., 2005; Negrete et al., 2006). Like other members in the Orthoparamyxovirinae subfamily, henipavirus attachment proteins are required to enable fusion proteins to function in fusion, and conformational changes of the attachment proteins caused by receptor binding activate F proteins to undergo the transition from the pre-fusion to the post-fusion form in order to complete the fusion process (Bossart et al., 2013; Jardetzky and Lamb, 2014; Wong et al., 2017).

HeV-RBP and NiV-RBP proteins consist of an N-terminal cytoplasmic tail, a single transmembrane helix, a stalk region, and a globular C-terminal receptor binding domain (RBD) with a 6-bladed propeller fold. The two RBPs have about 80% amino acid sequence identity to each other, but <30% amino acid sequence identity to the other henipaviruses. In paramyxoviruses, the ectodomains of the RBPs typically assemble into homotetramers (Bose et al., 2015). The RBP stalk regions form a parallel four helix bundle, while the head domains are organized into a tetramer of two separate dimers (Bose et al., 2011; Welch et al., 2013; Yuan et al., 2008; Yuan et al., 2011; Yuan et al., 2005). In contrast, although isolated head domains of paramyxovirus RBPs can be expressed as monomers in solution, these proteins can dimerize in crystalline phase with the same or similar dimeric interfaces as seen in the naturally occurring ectodomains (Crennell et al., 2000; Lawrence et al., 2004; Santiago et al., 2010). Similarly, the RBP ectodomain or the full-length HeV-RBP and NiV-RBP form tetramers in solution by forming disulfide bonds in the stem region, and head domains are monomers in solution (Bowden et al., 2010; Maar et al., 2012). A negative-stain EM study of NiV-RBP ectodomain showed that the protein assembles into an asymmetric tetramer, with a dimer of head domains at its apex and two monomeric head domains on sides of a central stalk (Wong et al., 2017). In the crystalline state, isolated HeV-RBP head domains can form dimers with a conserved dimeric interface, as occurs with other paramyxovirus RBPs (Bowden et al., 2010). In summary, henipaviruses possess quaternary structures of RBPs in which the stem regions form a major homo-tetrameric interface, while the head domains can associate as dimers or tetramers with a very dynamic quaternary arrangement.

To date, naturally occurring human monoclonal antibodies (mAbs) for HeV or NiV isolated from immune individuals have not been described. MAbs binding to HeV/NiV have been isolated by phage display from a henipavirus-naïve human Fab library (Zhu et al., 2006). An affinity-matured variant of one of those clones, designated m102.4, was converted to a recombinant IgG1 form in which it exhibited neutralization of HeV and NiV (Zhu et al., 2008) and protected animals after lethal NiV Malaysia challenge (Bossart et al., 2011; Bossart et al., 2009; Rockx et al., 2010). Crystal structures of the HeV-RBP head domain in complex with a derivative of the Fab m102.4 (designated m102.3) revealed that binding of the mAb heavy chain complementarity determining region 3 (CDRH3) loop binds to the receptor binding site on RBP for ephrinB2/ephrinB3 (Xu et al., 2013). m102.4 was well tolerated and exhibited linear pharmacokinetics in a recent Phase 1 human trail and has been used on compassionate grounds in the postexposure therapy of 14 humans following high-risk HeV exposures since 2010, highlighting the benefit and practicality of mAb postexposure therapy (Playford et al., 2020).

The demonstrated activity of the m102.4 antibody represents an important conceptual advance. However, the treatment failure of m102.4 in a day 5 and 7 treatment regimen of $NiV_B$ in African green monkeys (Mire et al., 2016) suggests a more potent antibody regimen may be of benefit. Second, cocktails of human mAbs that recognize diverse sites on viral glycoproteins and neutralize by differing mechanisms may be desirable for therapeutic development for RNA viruses that easily escape virus neutralization. Third, it is preferable in human therapeutic antibody development to use naturally occurring human mAbs from immune donors that possess naturally paired heavy and light chains and naturally occurring somatic mutations.

Improved methods to diagnose, prevent and treat henipavirus infections are urgently needed.

SUMMARY

Thus, in accordance with the present disclosure, there is provided a method of detecting a henipavirus infection in a subject comprising (a) contacting a sample from said subject with an antibody or antibody fragment having clone-paired heavy and light chain CDR sequences from Tables 3 and 4, respectively; and (b) detecting henipavirus in said sample by binding of said antibody or antibody fragment to a henipavirus antigen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in henipavirus antigen levels as compared to the first assay. The antibody or antibody fragment may be encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')₂ fragment, or Fv fragment.

In another embodiment, there is provided a method of treating a subject infected with henipavirus, or reducing the likelihood of infection of a subject at risk of contracting henipavirus, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')₂ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')₂ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

Also provided is a vaccine formulation comprising one or more antibodies or antibody fragments characterized by clone-paired heavy and light chain CDR sequences from Tables 3 and 4, respectively. At least of said antibody or antibody fragment may be encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. At least one of said antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. At least one antibody fragment may be a recombinant scFv (single chain fragment variable) antibody, Fab fragment, F(ab')$_2$ fragment, or Fv fragment. At least one antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. At least one antibody may be a chimeric antibody or a bispecific antibody. At least one antibody or antibody fragment may further comprise a cell penetrating peptide and/or is an intrabody.

In a further embodiment, there is provided a vaccine formulation comprising one or more expression vectors encoding a first antibody or antibody fragment as described herein. The expression vector(s) may be Sindbis virus or VEE vector(s). The vaccine formulation may be formulated for delivery by needle injection, jet injection, or electroporation. The vaccine formulation may further comprise one or more expression vectors encoding for a second antibody or antibody fragment, such as a distinct antibody or antibody fragment as described herein.

In yet a further embodiment, there is provided a method of protecting the health of a placenta and/or fetus of a pregnant a subject infected with or at risk of infection with henipavirus comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increases the size of the placenta as compared to an untreated control, or may reduce viral load and/or pathology of the fetus as compared to an untreated control.

In still yet a further embodiment, there is provide a method of determining the antigenic integrity, correct conformation and/or correct sequence of a henipavirus antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen or a vaccine formulation or vaccine production batch. Detection may comprise ELISA, RIA, western blot, a biosensor using surface plasmon resonance or biolayer interferometry, or flow cytometric staining.

The first antibody or antibody fragment is encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2; or may comprise light and heavy chain variable sequences having 95% identity to clone-paired sequences from Table 2. The first antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment is encoded by clone-paired variable sequences as set forth in Table 1, encoded by light and heavy chain variable sequences having 70%, 80%, or 90% identity to clone-paired variable sequences as set forth in Table 1, or encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2; or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the antigen over time.

Further provided is a human monoclonal antibody or antibody fragment, or hybridoma or engineered cell producing the same, wherein said antibody binds to henipavirus attachment glycoprotein and neutralizes both Hendra virus and diverse Nipah viruses.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

Figure 2C:
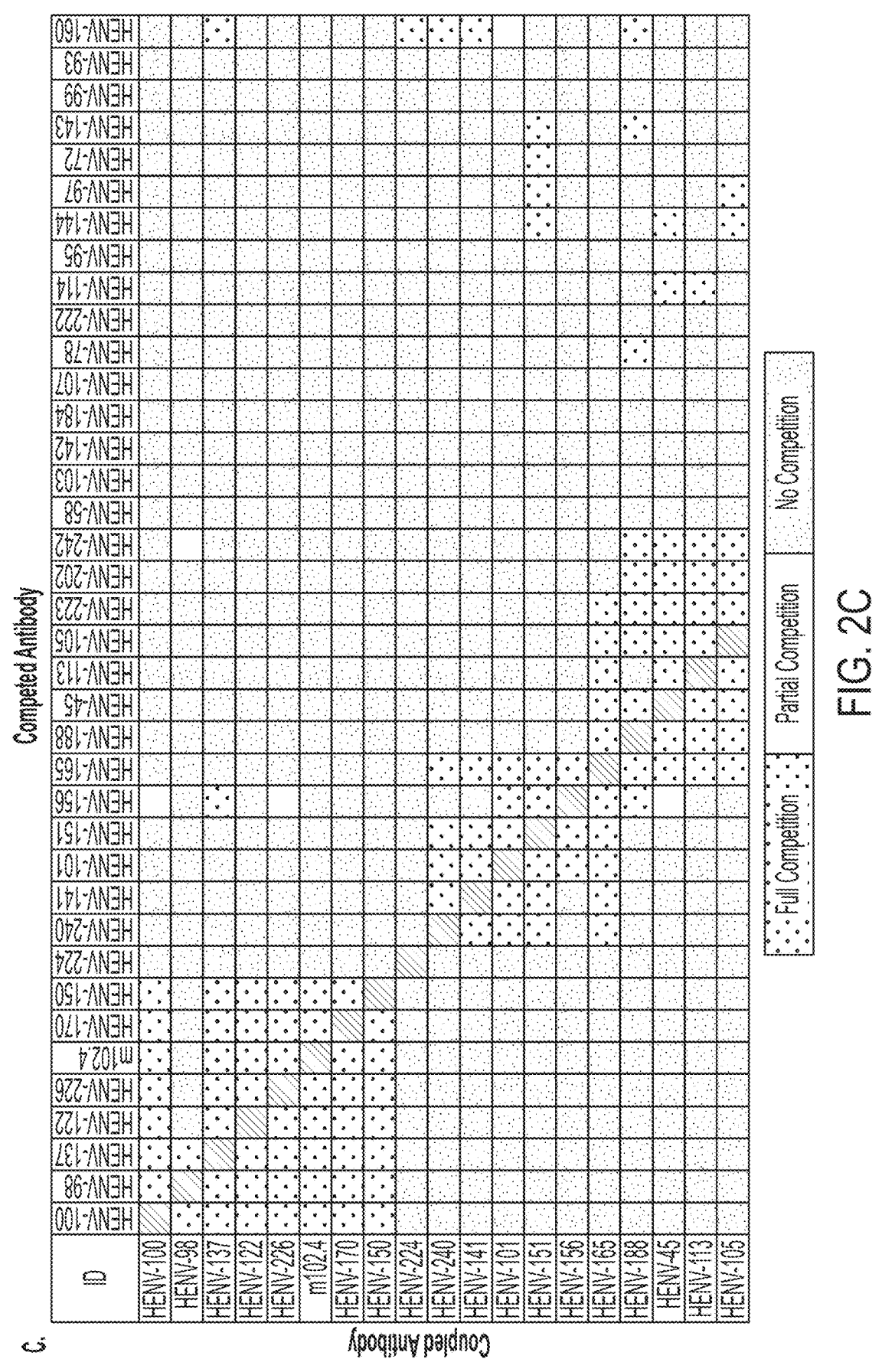
Figure 2D:
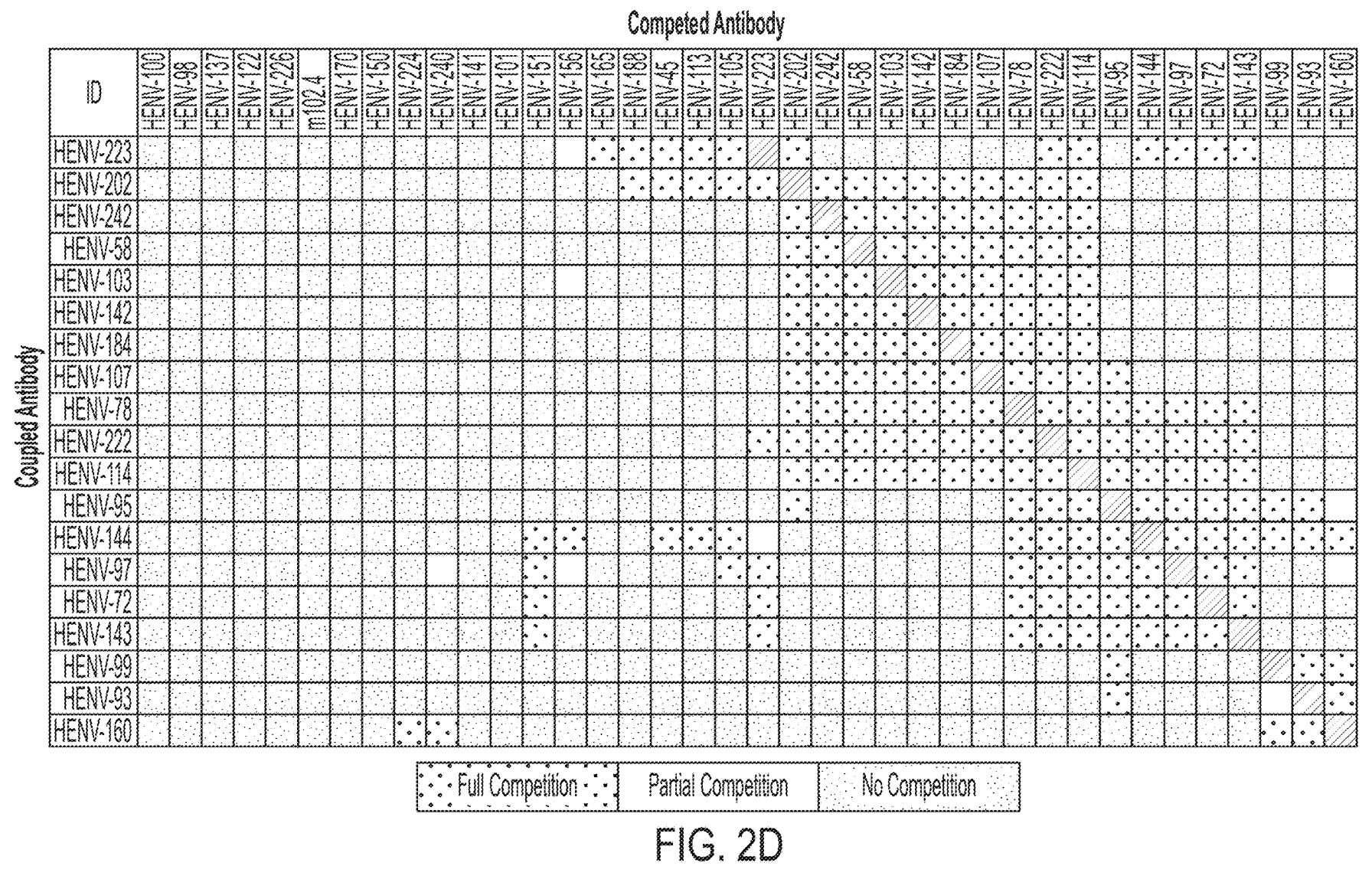

FIGS. 2A-D. Binding characteristics of henipavirus-specific antibodies. (FIG. 2A) Breakdown of antigen specificities (Hendra (HeV), Nipah Malaysia (NiV$_M$), Nipah Bangladesh (NiV$_B$)) of 42 mAbs isolated from a human subject. (FIG. 2B) Half maximal binding concentrations (EC$_{50}$) of mAbs that cross-react to attachment glycoproteins of HeV and both NiV strains as determined by ELISA. (FIGS. 2C-D) Competition binding of antibodies using Carterra's surface plasmon resonance (SPR) platform. Data represent at least six distinct antigenic sites.

FIGS. 3A-B. Neutralization of Hendra and Nipah viruses by cross-reactive antibodies. Antibodies were tested for neutralization of Hendra, Nipah Malaysia, and Nipah Bangladesh viruses in BSL-4 facilities. (FIG. 3A) Half maximal inhibitory concentrations (IC$_{50}$) of cross-reactive antibodies as determined by a plaque reduction neutralization test. (FIG. 3BA) Representative neutralization curve of a potently neutralizing, cross-reactive antibody HENV-100.

FIGS. 4A-D. Interactions of mAbs with HeV-G in the presence of ephrin-B2. (FIG. 4A) Antibodies blocked by receptor ephrin-B2 as analyzed via flow cytometry. 293F cells expressing HeV-G on cell surface were incubated with saturating concentrations of soluble ephrin-B2, followed by incubation with antibody. Cells were analyzed by flow cytometry. Values are expressed as a percentage of binding relative to antibody binding in the absence of ephrin-B2. (FIG. 4B) HDX-MS analysis of receptor blocking antibody HENV-98 in complex with HeV-G. (FIG. 4C) Antibodies that show enhanced binding to HeV-G in the presence of ephrin-B2 as analyzed via flow cytometry (analyzed as in FIG. 4A). (FIG. 4D) HDX-MS analysis of a receptor-enhanced antibody HENV-103 in complex with HeV-G.

(FIG. 5A) Binding curves of receptor-enhanced mAbs to cell surface-displayed HeV-G after cells were pre-incubated with either receptor-blocking mAb or buffer only. (FIG. 5B)-Fold increase in HeV-G binding by receptor-enhanced antibody at 5 g/mL after pre-incubation of select receptor-blocking mAbs.

FIG. 6. Competition-binding assay data enabling binning into groups of mAbs recognizing common antigenic sites. Ten human IgG mAbs were competed for binding to HeV RBP head domain using biolayer interferometry. Numbers in boxes are the percentage binding signal of the second mAb applied after binding of the first mAb, compared with binding signal of the second mAb alone. The antibodies were defined as competing antibodies if the first antibody reduced binding of the second antibody by more than 70 percent. The antibodies were defined as non-competing antibodies if the first antibody reduced binding of the second antibody by less than 40 percent. Binding signals 40 to 70% were considered intermediate competition (grey boxes with black numbers). Inferred competition-binding groups A to E (designated in order left to right and top to bottom).

FIGS. 7A-F. Crystal structures of Fab HENV-26 in complex with HeV-RBP or NiV-RBP head domains. Heavy chain CDRs are labeled as H1, H2, and H3, and light chain CDRs labeled as L1, L2, and L3. (FIG. 7A) The structure of HENV-26 in complex with HeV-RBP head domain. (FIG. 7B) The structure of HENV-26 in complex with NiV-RBP head domain. (FIG. 7C) The superimposition of the two structures. (FIG. 7D), (FIG. 7E), or (FIG. 7F) are 180° rotation views along the designated axis of FIGS. 7A-C, respectively.

FIGS. 8A-D. Interface of mAb HENV-26 in complex with HeV-RBP or NiV-RBP. Residues in the crystal structures of protein complexes with an interatomic distance between antigen (RBP) and antibody of less than 5 Å were designated as participating in the interface. (FIG. 8A) Side view of the interface between mAb HENV-26 and the HeV-RBP head domain. The interface residues are shown in stick representation. Polar interactions between HeV-RBP and HENV-26 are represented as broken lines. (FIG. 8B) Top view of the interface between HENV-26 and HeV-RBP head domain. HeV-RBP head domain is shown in grey as surface representation, glycans on HeV-RBP are colored in black. Interface residues and neighboring residues of HENV-26 are shown as cartoon representation, and interface residues as stick representation. CDRs, the light chain DE loop, and heavy chain C'' strand of the mAb are labeled. (FIG. 8C) Side view of the interface between HENV-26 and NiV-RBP head domain. The interface residues are shown in stick representation. Polar interactions between NiV-RBP and HENV-26 are represented as broken lines. (FIG. 8D) Top view of the interface between HENV-26 and NiV-RBP head domain. NiV-RBP head domain is shown in grey as surface representation, glycans on NiV-RBP are colored in black. Interface residues and neighboring residues of HENV-26 are shown as cartoon representation, and interface residues as stick representation. CDRs, the light chain DE loop, and heavy chain C'' strand of the mAb are labeled.

FIGS. 9A-D. Crystal structure of HENV-32 in complex with HeV-RBP head domain. FIG. 9A and FIG. 9C show cartoon representations of the crystal structures. Individual CDRs are labeled. The six blades of HeV-RBP head domain are labeled ($\beta$1 to $\beta$6). FIG. 9A is the bottom view of HeV-RBP head domain, and FIG. 9C is side view. FIG. 9B and FIG. 9D show the interface of the complex (residues with an interatomic distance between antigen and mAb of less than 5 Å). In FIG. 9B, interface residues are shown as cartoon representation. The polar interactions are shown as broken lines. In FIG. 9D, HeV-RBP head domain is shown as surface representation and colored in grey. Again, the paratope residues are shown as sticks. CDRs, loop between the heavy chain C'' strands and D loop, and light chain D strand of the mAb are labeled.

FIGS. 10A-C. Functional significance of conformational changes of HeV-RBP head domain upon HENV-32 binding. (FIG. 10A) Overlay of five HeV-RBP head domain crystal structures. All structures are shown as cartoon representation. (FIG. 10B) Structural details of the binding interface of HENV-32 CDRH3 and HeV-RBP head domain. Interacting residues are shown as stick representation, and the hydrogen bonds between CDRH3 and HeV-RBP are shown as broken lines. (FIG. 10C) Structural details of HENV-32 CDRH3 binding site in the crystal structure of the HeV-RBP/HENV-26 complex are shown for comparison. Residues interacting with the HENV-32 CDRH3 are shown as sticks. Comparison of the two structures of HeV-RBP head domain reveals extensive conformational changes at the site caused by CDRH3 binding. In the crystal structure of HENV-32/HeV-RBP complex, HENV-32 CDRH3 residue H98 is surrounded by a pocket on HeV-RBP formed by residues I203, Y205, V262, and P263, while in the crystal structure of HENV-26/HeV-RBP complex, there is no pocket at this site. The strong ionic bonding between HeV-RBP residues R258 and D260 forms a lid covering the site. HENV-32 HCDR3 remodels the site by inducing an outward flipping of the main chain of the $\beta$1/S3-S4 loop, residues L256-S264, and corresponding side chain rearrangements (especially the outward flipping of R258 side chain). The major driving force for this induced fit might be the interactions between HENV-32 R94/R96 and HeV-RBP R258/D260, and interaction of HENV-32 H98 with the surrounding cavity residues of HeV-RBP.

FIGS. 11A-D. Ferret protection studies. (FIG. 11A) Kaplan-Meier survival curve of ferrets infected with NiV-Bangladesh. (FIG. 11B) Clinical scores of ferrets infected with NiV-Bangladesh. Dotted line represents the threshold for euthanasia criteria. (FIG. 11C) Circulating viral genomes from ferrets infected with NiV-Bangladesh. (FIG. 11D) Viral genomes present in select tissues at study endpoints.

(FIG. 12A) Neutralization was tested with live viruses; percent neutralization is shown over a varying antibody concentration range. m102.4 is shown for comparative purposes. (FIG. 12B) Binding in ELISA to recombinant RBPs. Optical density at 405 nm is shown over a varying antibody concentration range.

(FIG. 13A) Binding assays of HENV-26 or HENV-32 to full-length HeV-RBP or NiV-RBP proteins detected by flow cytometric analysis. Binding to cells transfected with HeV-RBP (red), $NiV_M$-RBP (blue), $NiV_B$-RBP (green), or un-transfected (black) cells was analyzed using an Intellicyt iQue instrument. Values are expressed as mean fluorescence intensity (MFI) of PE-conjugated secondary antibody signal and were plotted in GraphPad to interpolate $EC_{50}$ values by non-linear regression analysis. Serial dilutions of HENV-26 or HENV-32 were performed in triplicate, with data representative of three independent assays shown. Error bars indicate SEM. (FIG. 13B) Kinetics of binding of HENV-26 or HENV-32 to full-length HeV-RBP or NiV-RBP proteins in biolayer interferometry to determine affinity of binding. Binding kinetics of Fab fragments corresponding to HENV-26 and HENV-32 were performed on an Octet RED instrument (FortéBio). Recombinant histidine-tagged RBP head domain was immobilized to HIS1K biosensor tips (FortéBio) at 10 µg/mL in kinetics buffer. After a brief baseline step, serial dilutions of HENV-26 or HENV-32 Fab starting at 200 nM then were associated to coated biosensor tips, followed by a dissociation step in 1× kinetics buffer. Curve-fitting was performed to extrapolate equilibrium dissociation constant values.

FIGS. 14A-E, Related to FIGS. 2A-F and FIG. 3A-D. Comparison of the eprhinB2 binding site on HeV-RBP with the epitope for binding of HENV-26. (FIG. 14A) Competition-binding assay of three human mAbs with ephrinB2 for binding to HeV-RBP head domain using biolayer interferometry. Numbers in boxes are the percentage binding signal of the second protein applied after binding of the first protein, compared with binding signal of the second protein alone. The proteins were defined as competing if the first protein reduced binding of the second protein by more than 70 percent. The proteins were defined as non-competing if the first protein reduced binding of the second protein by less than 40 percent. (FIG. 14B) Cell surface display flow cytometric assay to test for mAb blocking of HeV-RBP protein binding to the host receptor ephrinB2. 293F cells were transfected to display the full-length HeV-RBP protein on the cell surface. Cells were incubated with soluble ephrinB2 protein or FACS buffer, then HENV-26 labeled with AlexaFluor-647 was added to cells and incubated. Cells then were washed and analyzed using an Intellicyt iQue flow cytometry instrument. Binding of HENV-26 in the presence or absence of ephrinB2 was expressed as mean fluorescence intensity (MFI). (FIGS. 14C-E) Binding site mapping of ephrinB2 and m102.3 onto the HeV-RBP or NiV-RBP head domain surface. The surfaces of HeV-RBP or NiV-RBP head domains are colored in grey, with glycans colored in black. (FIG. 14C) The ephrinB2 binding site is mapped onto HeV-RBP head domain surface. The surface envelope (shown as mesh) of the epitope of HeV-RBP head domain recognized by HENV-26 is overlaid onto the HeV-RBP head domain. (FIG. 14D) The mAb m102.3 binding site is mapped onto the HeV-RBP head domain surface. The surface envelope (shown as mesh) of the epitope on HeV-RBP head domain recognized by HENV-26 is overlaid onto the HeV-RBP head domain. (FIG. 14E) The ephrinB2 binding site is mapped onto the NiV-RBP head domain surface. The surface envelope (shown as mesh) of the epitope on NiV-RBP head domain recognized by HENV-26 is overlaid on to the NiV-RBP head domain.

FIGS. 15A-G, Related to FIGS. 3A-D and FIGS. 4A-D. Molecular recognition of HeV-RBP head domain by mAbs. (FIG. 15A) Water-mediated interactions between HeV-RBP head domain and mAb HENV-26. Involved residues are shown as sticks and labeled. Hydrogen bonds are represented as broken lines. (FIG. 15B) Water-mediated interactions between HeV-RBP head domain and mAb HENV-32. Involved residues are shown as sticks, and labeled. Hydrogen bonds are represented as broken lines. (FIG. 15C) CedV-RBP or GhV-RBP ELISA. Binding of HENV-26 or HENV-32 was tested in ELISA using recombinant CedV-RBP head domain or GhV-RBP full ectodomain. MAbs to CedV-RBP (14F3) or GhV-RBP (10D5) were used as controls. (FIGS. 15D-G) Epitope mapping of RBP head domains of HeV, NiV$_M$, and NiV$_B$. The RBP amino acid sequences of the three viruses were aligned with MUSCLE (1), and the figure was made with sequence alignment editor, ALINE (2). For comparison, the sequences of Cedar virus RBP (CedV-RBP) and Ghana virus RBP (GhV-RBP) also are shown. (FIGS. 15D-E) The epitope residues recognized by HENV-26 (in complex with HeV-RBP [PDB ID 6VY6] or NiV-RBP Malaysia [NiV-RBPm; PDB ID 6VY5] are highlighted with boxes, the epitope residues recognized by HENV-32 (in complex with HeV-RBP [PDB ID 6VY4]) with boxes, and epitope resides recognized by m102.3 [PDB ID 6CMG] are indicated with lines over the alignment. (FIGS. 15F-G) The ephrinB2 binding residues from complexes with HeV-RBP [PDB ID 6PDL] or NiV-RBPm [PDB ID 2VSM] are highlighted with boxes, and the ephrinB3 binding residues from a complex with NiV-RBPm [PDB ID 3D12] with boxes. [HeV-G=SEQ ID NO:252; NIV$_M$-G=SEQ ID NO:253; NIV$_B$-G=SEQ ID NO:254; CedV-G=SEQ ID NO:255; GhV-G=SEQ ID NO:256]

(FIG. 16A) Superimposition of the crystal structures of HeV-RBP head domain in complex with HENV-26 or HENV-32. The CDRs of both mAbs and the individual blades of the HeV-RBP head domain are labeled. Regions in the HeV-RBP head domain with large structural differences between structures are indicated within broken lines. (FIG. 16B) Superimposition of the crystal structures of the dimeric HeV-RBP head domain and HeV-RBP head domain in complex with HENV-32. Individual blades of the superimposed HeV-RBP head domains are labeled ($\beta$1 to $\beta$6). (FIG. 16C) Superimposition of HeV-RBP structures in the HENV-32/HeV-RBP complex and ephrinB2/HeV-RBP complex. The overlay suggests that the conformation of HeV-RBP $\beta$6/S2-S3 and $\beta$5/S4-$\beta$6/S1 loops in the HENV-32/HeV-RBP complex causes potential steric clashes between the loops and the ephrinB2 G-H loop. The potential steric clashes between the HENV-32 bound HeV-RBP structure and ephrinB2 G-H loop are represented with broken red lines, and the residues with potential steric clashes are shown in stick, and corresponding residues of the ephrinB2 bound HeV-RBP structure are shown as line representation.

FIGS. 17A-F, Related to FIGS. 5A-C. Structural details of the HENV-32 CDRH3 binding site in the crystal structures of HeV-RBP-apo (dimeric form) (FIG. 17A) or the HeV-RBP/m102.3 complex (FIG. 17B). Residues interacting with HENV-32 CDRH3 are shown as sticks. Consistent with the structure in the HeV-RBP/HENV-26 complex, the HENV-32 CDRH3 binding pocket is hidden underneath salt bridges between residue R258 and D260 in both structures. (FIGS. 17C-F) Surface representation of the HENV-32 CDRH3 binding site in four different crystal structure forms of HeV-RBP. The residues interacting with the HENV-32 CDRH3 are indicated. (FIG. 17C) HENV-32/HeV-RBP complex; the HENV-32 CDRH3 paratope is shown as both ribbon and stick representations. (FIG. 17D) HENV-26/HeV-RBP complex. (FIG. 17E) m102.3/HeV-RBP complex. (FIG. 17F) HeV-RBP apo (dimeric form). Residue P263 in the HeV-RBP/HENV-26 complex and HeV-RBP/m102.3 complex is not solvent accessible.

FIGS. 18A-L/top (brain and lung) and FIGS. 18A-L/bottom (spleen and liver), Related to FIGS. 6A-D. Representative histopathology of brain and liver tissues from ferrets infected with NiV$_B$ and treated with recombinant anti-HENV mAbs, compared with untreated control animals. (FIGS. 18A-D/top and bottom) Tissues from tissue from subject C1. (FIG. 18A/top and bottom) H&E staining of brain tissue did not show significant histological lesions. (FIG. 18B/top and bottom) Immunolabeling of brain tissue showed the endothelium of small caliber vessels within the neuronal parenchyma multifocally had diffuse cytoplasmic immunolabeling. (FIG. 18C/top and bottom) H&E staining of lung tissue showed mild interstitial pneumonia with multifocal nodular formation composed of necrotic debris, hemorrhage and mixed inflammatory infiltrates of neutrophils and macrophages. (FIG. 18D/top and bottom) Immunolabeling of lung tissue showed diffuse cytoplasmic immunolabeling of segmental regions of the alveolar septa largely centered on the necrotic nodules, mononuclear cells within alveolar septa, mononuclear cells free within alveolar spaces (alveolar macrophages), endothelium of small to medium caliber vessels, and rarely lower airway epithelium (FIG. 18D/top and bottom). (FIGS. 18E-H/top and bottom) Tissues from subject HENV-32_A did not show significant histological lesions or immunolabeling. (FIG. 18E/top and bottom) H&E staining of brain. (FIG. 18F/top and bottom)

Immunolabeling of brain. (FIG. 18G/top and bottom) H&E staining of lung. (FIG. 18H/top and bottom) Immunolabeling of lung. (FIGS. 18I-L/top and bottom) Tissues from subject HENV-26_D. (FIG. 18I/top and bottom) H&E staining of brain showed moderate cuffing of small caliber vessels with lymphocytes in the brainstem and in vessels surrounding the ventricular system. (FIG. 18J/top and bottom) Immunolabeling of brain showed diffuse cytoplasmic immunolabeling of neurons in association with the lymphocytic infiltrates (inset and arrow). (FIG. 18K/top and bottom) H&E staining of lung showed rare cuffing of small caliber vessels of the lung with lymphocytes and plasma cells present. (FIG. 18L/top and bottom) Immunolabeling of lung was not detected. For FIG. 18I (top and bottom), all images represent 20× magnification of the representative tissues. For FIG. 18J (top and bottom), a small window was enlarged to show neuronal staining in detail (inset).

DESCRIPTION OF ILLUSTRATIVE EMBODIMENTS

Figure 1:
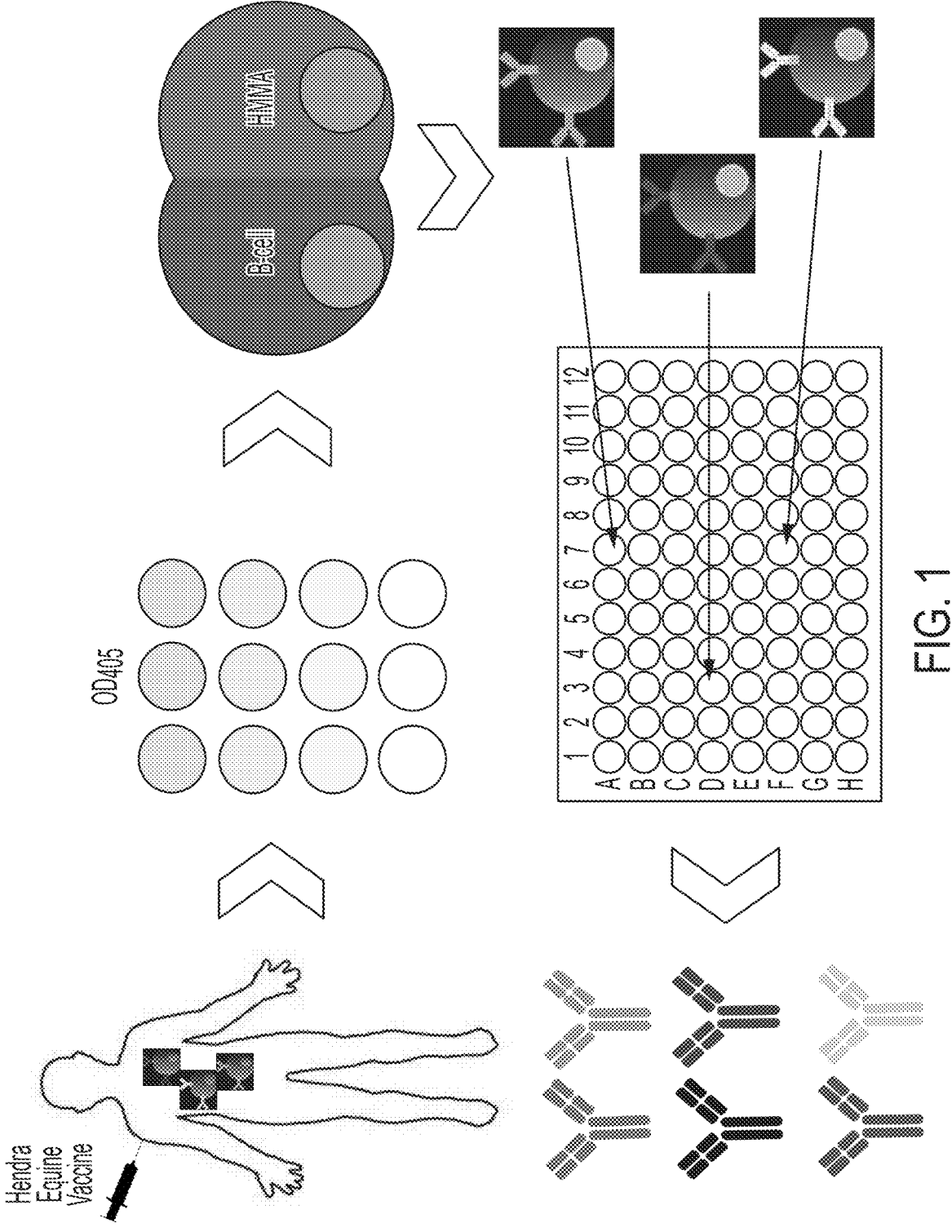
FIG. 1. Scheme for isolation of monoclonal antibodies. Peripheral blood mononuclear cells (PBMCs) from a human subject are transformed using Epstein-Barr Virus, followed by expansion on feeder layers. Resulting lymphoblastoid cell line (LCL) supernatants are screened via ELISA against for binding to immobilized henipavirus antigens. LCLs from positive wells are fused to a myeloma partner using an electrofusion protocol to yield immortalized, fully human hybridomas. These hybridomas are then cloned by fluorescence activated cell sorting and expanded into serum free medium. Monoclonal antibodies are purified from serum-free medium using MabSelect SuRe affinity chromatography.

As discussed above, Hendra virus and Nipah virus are emerging zoonotic pathogens in the henipavirus genus causing outbreaks of viral disease with very high mortality rates. Here, the inventors report the first naturally occurring human monoclonal antibodies against HeV glycoproteins. All mAbs isolated neutralized HeV and some also neutralized NiV. Epitope binning experiments identified five major antigenic sites on HeV-G. Animal studies demonstrated that the most potent cross-reactive neutralizing mAbs, HENV-26 and HENV-32, protected ferrets in lethal models of infection with HeV or NiV infections. The inventors solved the crystal structures of mAb HENV-26 in complex with both HeV-G and NiV-G and of the mAb HENV-32 in complex with HeV-G. These studies reveal the diverse sites of vulnerability on henipavirus G recognized by potent human mAbs that inhibit virus by multiple mechanisms. These studies identify promising prophylactic antibodies and define protective epitopes that can be used in rational henipavirus vaccine design.

These and other aspects of the disclosure are described in detail below.

I. Henipaviruses

Henipavirus is a genus of RNA viruses in the family Paramyxoviridae, order Mononegavirales containing five established species. Henipaviruses are naturally harboured by pteropid fruit bats (flying foxes) and microbats of several species. Henipaviruses are characterized by long genomes and a wide host range. Their recent emergence as zoonotic pathogens capable of causing illness and death in domestic animals and humans is a cause of concern.

In 2009, RNA sequences of three novel viruses in phylogenetic relationship to known henipaviruses were detected in African straw-colored fruit bats (*Eidolon helvum*) in Ghana. The finding of these novel henipaviruses outside Australia and Asia indicates that the region of potential endemicity of henipaviruses may be worldwide. These African henipaviruses are slowly being characterized.

Henipavirions are pleomorphic (variably shaped), ranging in size from 40 to 600 nm in diameter. They possess a lipid membrane overlying a shell of viral matrix protein. At the core is a single helical strand of genomic RNA tightly bound to N (nucleocapsid) protein and associated with the L (large) and P (phosphoprotein) proteins, which provide RNA polymerase activity during replication.

Embedded within the lipid membrane are spikes of F (fusion) protein trimers and G (attachment) protein tetramers. The function of the G protein is to attach the virus to the surface of a host cell via EFNB2, a highly conserved protein present in many mammals. The structure of the attachment glycoprotein has been determined by X-ray crystallography. The F protein fuses the viral membrane with the host cell membrane, releasing the virion contents into the cell. It also causes infected cells to fuse with neighboring cells to form large, multinucleated syncytia.

As all mononegaviral genomes, Hendra virus and Nipah virus genomes are non-segmented, single-stranded negative-sense RNA. Both genomes are 18.2 kb in length and contain six genes corresponding to six structural proteins.

In common with other members of the Paramyxoviridae family, the number of nucleotides in the henipavirus genome is a multiple of six, consistent with what is known as the 'rule of six'.[14] Deviation from the rule of six, through mutation or incomplete genome synthesis, leads to inefficient viral replication, probably due to structural constraints imposed by the binding between the RNA and the N protein.

Henipaviruses employ an unusual process called RNA editing to generate multiple proteins from a single gene. The specific process in henipaviruses involves the insertion of extra guanosine residues into the P gene mRNA prior to translation. The number of residues added determines whether the P, V or W proteins are synthesized. The functions of the V and W proteins are unknown, but they may be involved in disrupting host antiviral mechanisms.

Nipah virus and Hendra virus are closely related paramyxoviruses that emerged from bats during the 1990s to cause deadly outbreaks in humans and domesticated animals. National Institute of Allergy and Infectious Diseases (NIAID)-supported investigators developed vaccines for Nipah and Hendra virus based on the soluble G-glycoproteins of the viruses formulated with adjuvants. Both vaccines have been shown to induce strong neutralizing antibodies in different laboratory animals. Trials began in 2015 to evaluate a monoclonal antibody to be used as a possible complementary treatment for humans exposed to Hendra virus infected horses.

When considering any zoonosis, one must understand the social, ecological, and biological contributions that may be facilitating this spillover. Hendra virus is believed to be partially seasonally related. For, there is a suggested correlation between breeding time and an increase in incidences of Hendra virus in flying fox bats.

Ephrin B2 has been identified as the main receptor for the henipaviruses.

A. Hendra Virus

Hendra virus (originally called "Equine morbillivirus") was discovered in September 1994 when it caused the deaths of thirteen horses, and a trainer at a training complex at 10 Williams Avenue, Hendra, a suburb of Brisbane in Queensland, Australia.

The index case, a mare called Drama Series, brought in from a paddock in Cannon Hill, was housed with 19 other horses after falling ill, and died two days later. Subsequently, all of the horses became ill, with 13 dying. The remaining six animals were subsequently euthanized as a way of preventing relapsing infection and possible further transmission. The trainer, Victory ('Vic') Rail, and the stable foreman, Ray Unwin, were involved in nursing the index case, and both fell ill with an influenza-like illness within one week of the first horse's death. The stable hand recovered but Rail died of respiratory and renal failure. The source of the virus was most likely frothy nasal discharge from the index case.

A second outbreak occurred in August 1994 (chronologically preceding the first outbreak) in Mackay 1,000 km north of Brisbane resulting in the deaths of two horses and their owner. The owner, Mark Preston, assisted in necropsies of the horses and within three weeks was admitted to hospital suffering from meningitis. Mr. Preston recovered, but 14 months later developed neurologic signs and died. This outbreak was diagnosed retrospectively by the presence of Hendra virus in the brain of the patient.

Flying foxes have been identified as the reservoir host of Hendra Virus. A seroprevalence of 47% is found in the flying foxes, suggesting an endemic infection of the bat population throughout Australia. Horses become infected with Hendra after exposure to bodily fluid from an infected flying fox. This often happens in the form of urine, feces, or masticated fruit covered in the flying fox's saliva when horses are allowed to graze below roosting sites. The seven human cases have all been infected only after contact with sick horses. As a result, veterinarians are particularly at risk for contracting the disease. Three main approaches are currently followed to reduce the risk to humans.

In November 2012, a vaccine became available for horses. The vaccine is to be used in horses only, since, according to CSIRO veterinary pathologist Dr Deborah Middleton, breaking the transmission cycle from flying foxes to horses prevents it from passing to humans, as well as, "a vaccine for people would take many more years."

The vaccine is a subunit vaccine that neutralizes Hendra virus and is composed of a soluble version of the G surface antigen on Hendra virus and has been successful in ferret models.

By December 2014, about 300,000 doses had been administered to more than 100,000 horses. About 3 in 1000 had reported incidents; the majority being localized swelling at the injection site. There had been no reported deaths.

In August 2015, the Australian Pesticides and Veterinary Medicines Authority (APVMA) registered the vaccine. In its statement the Australian government agency released all its data on reported side effects. In January 2016, APVMA approved its use in pregnant mares. Stall-side test to assist in diagnosing the disease in horses rapidly.

Although the research on the Hendra virus detection is ongoing, a promising result has found using antibody-conjugated magnetic particles and quantum dots.

Flying foxes experimentally infected with the Hendra virus develop a viremia and shed the virus in their urine, feces and saliva for approximately one week. There is no other indication of an illness in them. Symptoms of Hendra virus infection of humans may be respiratory, including hemorrhage and edema of the lungs, or in some cases viral meningitis. In horses, infection usually causes pulmonary oedema, congestion and/or neurological signs.

Additionally, recent research suggests that the upsurge in deforestation within Australia may be leading to an increase in incidences of Hendra virus. Flying fox bats tend to feed in trees during a large part of the year. However, due to the lack of specific fruit trees within the area, these bats are having to relocate and thereby are coming into contact with horses more often. The two most recent outbreaks of Hendra virus in 2011 and 2013 appear to be related to an increased level of nutritional stress among the bats as well as relocation of bat populations. Work is currently being done to increase vaccination among horses as well as replant these important forests as feeding grounds for the flying fox bats.

Through these measures, the goal is to decrease the incidences of the highly fatal Hendra virus.

B. Nipah Virus

The first cases of Nipah virus infection were identified in 1998, when an outbreak of neurological and respiratory disease on pig farms in peninsular Malaysia resulted in 265 human cases, including 105 human deaths. The virus itself was isolated the following year in 1999. This outbreak resulted in the culling of one million pigs. In Singapore, 11 cases, including one death, occurred in abattoir workers exposed to pigs imported from the affected Malaysian farms. The Nipah virus has been classified by the Centers for Disease Control and Prevention as a Category C agent. The name "Nipah" refers to the place, Sungai Nipah in Port Dickson, Negeri Sembilan, the source of the human case from which Nipah virus was first isolated. Nipah virus is one of several viruses identified by WHO as a likely cause of a future epidemic in a new plan developed after the Ebola epidemic for urgent research and development before and during an epidemic toward new diagnostic tests, vaccines and medicines.

The outbreak was originally mistaken for Japanese encephalitis, but physicians in the area noted that persons who had been vaccinated against Japanese encephalitis were not protected in the epidemic, and the number of cases among adults was unusual. Despite the fact that these observations were recorded in the first month of the outbreak, the Ministry of Health failed to react accordingly, and instead launched a nationwide campaign to educate people on the dangers of Japanese encephalitis and its vector, *Culex* mosquitoes.

Symptoms of infection from the Malaysian outbreak were primarily encephalitic in humans and respiratory in pigs. Later outbreaks have caused respiratory illness in humans, increasing the likelihood of human-to-human transmission and indicating the existence of more dangerous strains of the virus.

Based on seroprevalence data and virus isolations, the primary reservoir for Nipah virus was identified as Pteropid fruit bats, including *Pteropus vampyrus* (large flying fox), and *Pteropus hypomelanus* (small flying fox), both of which occur in Malaysia.

The transmission of Nipah virus from flying foxes to pigs is thought to be due to an increasing overlap between bat habitats and piggeries in peninsular Malaysia. At the index farm, fruit orchards were in close proximity to the piggery, allowing the spillage of urine, faeces and partially eaten fruit onto the pigs. Retrospective studies demonstrate that viral spillover into pigs may have been occurring in Malaysia since 1996 without detection. During 1998, viral spread was aided by the transfer of infected pigs to other farms, where new outbreaks occurred.

The most likely origin Nipah this virus was in 1947 (95% credible interval: 1888-1988). There are two clades of this virus—one with its origin in 1995 (95% credible interval: 1985-2002) and a second with its origin in 1985 (95% credible interval: 1971-1996). The mutation rate was estimated to be $6.5 \times 10^{-4}$ substitution/site/year (95% credible interval: $2.3 \times 10^{-4}$-$1.18 \times 10^{-3}$), similar to other RNA viruses.

Eight more outbreaks of Nipah virus have occurred since 1998, all within Bangladesh and neighbouring parts of India. The outbreak sites lie within the range of *Pteropus* species (*Pteropus giganteus*). As with Hendra virus, the timing of the outbreaks indicates a seasonal effect. Cases occurring in Bangladesh during the winters of 2001, 2003, and 2004 were determined to have been caused by the Nipah virus. In February 2011, a Nipah outbreak began at Hatibandha Upazila in the Lalmonirhat District of northern Bangladesh. As of 7 Feb. 2011, there had been 24 cases and 17 deaths in this outbreak.

II. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to henipavirus will have several applications. These include the production of diagnostic kits for use in detecting and diagnosing henipavirus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuber-*

*culosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce henipavirus-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g. a conformational epitope).

Various techniques known to persons of ordinary skill in the art can be used to determine whether an antibody "interacts with one or more amino acids" within a polypeptide or protein, Exemplary techniques include, for example, routine cross-blocking assays, such as that described in Antibodies, Harlow and Lane (Cold Spring Harbor Press. Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See. e.g., Ehring (1999) Analytical Biochemistry 267: 252-259; Engen and Smith (2001) Anal. Chem. 73: 256A-265A. When the antibody neutralizes henipavirus, antibody escape mutant variant organisms can be isolated by propagating henipavirus in vitro or in animal models in the presence of high concentrations of the antibody. Sequence analysis of the henipavirus gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP nay be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-henipavirus antibody, the above-described binding methodology is performed in two orientations: In a first orientation, the reference antibody is allowed to bind to the henipavirus antigen under saturating conditions followed by assessment of binding of the test antibody to the henipavirus molecule. In a second orientation, the test antibody is allowed to bind to the henipavirus antigen molecule under saturating conditions followed by assessment of binding of the reference antibody to the henipavirus molecule. If, in both orientations, only the first (saturating) antibody is capable of binding to the henipavirus, then it is concluded that the test antibody and the reference antibody compete for binding to the henipavirus. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res 1990 50:1495-1502) Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using EISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example, with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example, antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002), J. Biol. Chem. 277(30): 26733-26740; Davies J. et al. (2001), Biotechnology & Bioengineering 74(4): 288-294). Methods of altering carbohydrate contents are known to those skilled in the art, see, e.g., Wallick, S. C. et al. (1988), J. Exp. Med. 168(3): 1099-1109; Tao, M. H. et al. (1989), J. Immunol. 143(8): 2595-2601; Routledge, E. G. et al. (1995), Transplantation 60(8):847-53; Elliott, S. et al. (2003), Nature Biotechnol. 21:414-21; Shields, R. L. et al. (2002), J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM®-T Easy vector (system for cloning PCT products), then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as E. coli, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401, 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fe glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., Nature Biotech., 22 (10), 1302-1306, 2004; Chennamsetty et al., PNAS, 106 (29), 11937-11942, 2009; Voynov et al., Biocon. Chem., 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning Calorimetry (DSC) measures the heat capacity, Cp, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, Biochem. Biophys. Res. Commun. 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

Solubility. One can determine the intrinsic solubility score of antibody sequences. The intrinsic solubility scores can be calculated using CamSol Intrinsic (Sormanni et al., J Mol Biol 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., $F(ab')_2$ bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from _E. coli_, which can be chemically coupled to form bispecific antibodies. Shalaby et al., J. Exp. Med., 175: 217-225 (1992) describe the production of a humanized bispecific antibody F(ab')$_2$ molecule. Each Fab' fragment was separately secreted from _E. coli_ and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., _Nat. Biotechnol._ 16, 677-681 (1998), doi:10.1038/nbt798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a dock-and-lock (DNL) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., _FEBS Letters._ 2005; 579: 3264; Wong and Scott, _Nat. Rev. Mol. Cell Biol._ 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., _Science,_ 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1)$_n$-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H)

(numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 ζ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/antiviral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a noncleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics.

Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/anti-viral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intra-cellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/

PAGE (Capaldi et al., 1977). It will therefore be appreciated that under differing electrophoresis conditions, the apparent molecular weights of purified or partially purified expression products may vary.

III. Active/Passive Immunization and Treatment/Prevention of Henipavirus Virus Infection A. Formulation and Administration The present disclosure provides pharmaceutical compositions comprising anti-henipavirus virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of henipavirus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example, by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine[211], [14]carbon, [51]chromium, [36]chlorine, [57]cobalt, [58]cobalt, copper[67], [152]Eu, gallium[67], [3]hydrogen, iodine[123], iodine[125], iodine[131], indium[111], [59]iron, [32]phosphorus, rhenium[186], rhenium[188], [75]selenium, [35]sulphur, technicium[99m] and/or yttrium[90]. [125]I is often being preferred for use in certain embodiments, and technicium[99m] and/or indium[111] are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium[99m] by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939, 350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphe-nyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting henipavirus and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of henipavirus in a subject. A wide variety of assay formats are contemplated, but specifically those that would be used to detect henipavirus in a fluid obtained from a subject, such as saliva, blood, plasma, sputum, semen or urine. In particular, semen has been demonstrated as a viable sample for detecting henipavirus (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of henipavirus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing henipavirus, and contacting the sample with a first antibody in accordance with the present disclosure, as the case may be, under conditions effective to allow the formation of immunocomplexes.

These methods include methods for purifying henipavirus or related antigens from a sample. The antibody will preferably be linked to a solid support, such as in the form of a column matrix, and the sample suspected of containing the henipavirus or antigenic component will be applied to the immobilized antibody. The unwanted components will be washed from the column, leaving the henipavirus antigen immunocomplexed to the immobilized antibody, which is then collected by removing the organism or antigen from the column.

The immunobinding methods also include methods for detecting and quantifying the amount of henipavirus or related components in a sample and the detection and quantification of any immune complexes formed during the binding process. Here, one would obtain a sample suspected of containing henipavirus or its antigens and contact the sample with an antibody that binds henipavirus or components thereof, followed by detecting and quantifying the amount of immune complexes formed under the specific conditions. In terms of antigen detection, the biological sample analyzed may be any sample that is suspected of containing henipavirus or henipavirus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to henipavirus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, for example, with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the henipavirus or henipavirus antigen is added to the wells. After binding and washing to remove non-specifically bound immune complexes, the bound antigen may be detected. Detection may be achieved by the addition of another anti-henipavirus virus antibody that is linked to a detectable label. This type of ELISA is a simple "sandwich ELISA." Detection may also be achieved by the addition of a second anti-henipavirus virus antibody, followed by the addition of a third antibody that has binding affinity for the second antibody, with the third antibody being linked to a detectable label.

In another exemplary ELISA, the samples suspected of containing the henipavirus or henipavirus antigen are immobilized onto the well surface and then contacted with the anti-henipavirus antibodies of the disclosure. After binding and washing to remove non-specifically bound immune complexes, the bound anti-henipavirus antibodies are detected. Where the initial anti-henipavirus antibodies are linked to a detectable label, the immune complexes may be detected directly. Again, the immune complexes may be detected using a second antibody that has binding affinity for the first anti-henipavirus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of henipavirus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled henipavirus monoclonal antibodies to determine the amount of henipavirus antibodies in a sample. The basic format would include contacting a known amount of henipavirus monoclonal antibody (linked to a detectable label) with henipavirus antigen or particle. The henipavirus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect henipavirus or henipavirus antigens, the antibodies may be included in the kit. The immunodetection kits will thus comprise, in suitable container means, a first antibody that binds to henipavirus or henipavirus antigen, and optionally an immunodetection reagent.

In certain embodiments, the henipavirus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the henipavirus or henipavirus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective henipavirus antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Hendra and Nipah viruses, the prototypic viruses of the Henipavirus genus, are emerging, zoonotic paramyxoviruses known to cause severe disease across six mammalian orders, including humans.[1] Because these viral agents can result in mortality rates as high as 90%, and due to the threat of use as bioterror agents, the WHO has classified henipaviruses as priority pathogens with urgent needs for accelerated research and development of antiviral therapeutics. While select research groups have made strides in developing candidate vaccines and therapeutics against henipaviruses, no licensed pharmaceuticals are available for human use, and significant gaps in knowledge about the human immune response to these viruses exist.

To address these gaps, the inventors used a highly efficient human B cell hybridoma technique to isolate a large panel of monoclonal antibodies (mAbs) from a subject with occupation-related exposure to the Hendra veterinary horse vaccine. These human antibodies bind the henipavirus attachment (G) glycoprotein, and display a wide variety of binding characteristics, from strain-specific to cross-reactive. These mAbs recognize at least six distinct antigenic sites on the G glycoprotein surface. Antibodies corresponding to multiple antigenic sites are capable of potent neutralization of Nipah and/or Hendra virus isolates in vitro. Flow cytometric studies suggest that the most potent and cross-reactive mAbs neutralize by blocking viral attachment to host receptors ephrin-B2 and ephrin-B3. These studies show that the henipavirus attachment glycoprotein elicits a humoral response to diverse antigenic sites and provide best-in-class lead candidates for further development as therapeutic biologics targeting Hendra and Nipah viruses.

Example 2—Materials and Methods

Data and Code availability. The crystal structures are deposited at the Protein Data Bank (PDB). The ID numbers of Fab bound structures are: 1) HENV-32 with HeV RBP: 6VY4, 2) HENV-26 with NiV RBP: 6VY5, HENV-26 with HeV RBP: 6VY6. All other data needed to evaluate the conclusions in the paper are present in the paper or the Supplemental Information. The antibodies in this study are available by Material Transfer Agreement with Vanderbilt University Medical Center.

Source of Human B Cells. The study was approved by the Vanderbilt University Medical Center Institutional Review Board. Peripheral blood was collected at Vanderbilt after written informed consent from a healthy donor with prior history of inadvertent inoculation with recombinant HeV-G in an equine HeV vaccine.

Ferret Model. The animal studies were performed at the Galveston National Laboratory, University of Texas Medical Branch at Galveston (UTMB) and were approved by the UTMB Institutional Animal Care and Use Committee (IACUC). This facility is fully accredited by the Association for Assessment and Accreditation of Laboratory Animal Care International.

Expression and purification of HeV and NiV attachment glycoproteins. The DNA segments correspondent to the head domain of HeV-RBP (residues 185-604), head domain of $NiV_M$-RBP (residues 183-602) (Bowden et al., 2008), and head domain of $NiV_B$-RBP (residues 185-602) were sequenced optimized for expression, synthesized, and cloned into the pcDNA3.1 (+) (HeV and $NiV_M$) or pcDNA3.1 (+)-C-6His ($NiV_B$) expression DNA plasmid downstream of the signal peptide from the pHLsec vector (MGILPSPGMPALLSLVSLLSVLLMGCVA (SEQ ID NO:241)) or osteonectin (MRAWIFFLLCLAGRALA (SEQ ID NO:242)) (GenScript). A TEV protease cleavage site and a His-tag also were incorporated at the C-terminus of HeV and $NiV_M$ constructs to facilitate protein purification. Expi293F cells were transfected transiently with plasmids encoding HeV-RBP, $NiV_M$-RBP, or $NiV_B$-RBP head domains, and culture supernatants were harvested after 6 to 7 days. The head domains were purified from the supernatants by nickel affinity chromatography with HISTRAP™ Excel columns (protein purification columns; GE Healthcare Life Sciences). For protein production used in crystallization trials, 5 µM kifunensine was included in the culture medium to produce the head domains with high mannose glycans. The high mannose glycoproteins subsequently were treated with endoglycosidase F1 (Millipore) to obtain homogeneously deglycosylated HeV-RBP or $NiV_M$-RBP head domains (Bowden et al., 2008).

PBMC isolation and hybridoma generation. Peripheral blood was collected at Vanderbilt after written informed consent from a healthy donor with prior history of inadvertent inoculation with recombinant HeV-RBP in an equine HeV vaccine. PBMCs from the donor were isolated by density gradient separation on Ficoll, cryopreserved and stored in the vapor phase of liquid nitrogen until use. Generation of human hybridoma cell lines secreting human mAbs was performed as described previously (Smith et al., 2012). Briefly, human B cells in the PBMC suspension were immortalized by transformation with EBV in the presence of CpG10103, cyclosporin A, and a Chk2 inhibitor and plated in 384-well culture plates. On day 7 to 10 after EBV transformation, the supernatants from transformed B cells were used to screen for the presence of antibodies binding to recombinant HeV-RBP head domain in ELISA. Cells from the wells containing B cells secreting HeV-RBP-reactive antibodies were fused with HMMA2.5 myeloma cells using a BTX ECM 2001 electro cell manipulator by an electrofusion method (Yu et al., 2008). After fusion, human hybridomas were selected in medium with HAT solution containing ouabain. The hybridomas were cloned by flow cytometric sorting of single cells into 384-well plates and then expanded in culture. Particular clones for downstream studies were selected by choosing the clone for each independently derived hybridoma line that exhibited the highest level of IgG secretion.

Production of IgG for mAbs from hybridoma cells. The selected cloned cell lines secreting mAbs were grown initially in hybridoma growth medium (ClonaCell-HY medium E from STEMCELL Technologies, 03805) and then switched to serum-free medium (GIBCO Hybridoma-SFM, Invitrogen, 12045084) for antibody expression and purification. Cloned hybridoma cells were expanded sequentially to 225 cm$^2$ flasks for mAb production. The supernatants from hybridoma cultures were filtered with 0.45 m pore diameter filter flasks, and then the IgG from the hybridoma cell line supernatants was purified by affinity chromatography using protein G columns (GE Life Sciences, Protein G HP Columns). Purified IgG generated from hybridomas was used for all EC$_{50}$ and IC$_{50}$ studies, competition-binding studies, HDX-MS studies, and animal studies. To generate the corresponding fragment antigen-binding (Fab) fragments for crystallization trials, papain digestion of purified mAb IgG was performed using the Pierce Fab Preparation Kit (Thermo Fisher Scientific). The resulting Fabs were purified from the digestions by affinity chromatography by coupling a protein G affinity column and an anti-human CH1 column (GE Healthcare Life Sciences).

Characterization of antibody isotype, subclass, and variable genes. The isotype and subclass of secreted antibodies were determined by ELISA. Antibody heavy and light chain variable region genes were sequenced from antigen-specific hybridoma lines that had been cloned biologically using flow cytometric single cell sorting. Briefly, total RNA was extracted using the RNEASY® Mini kit (RNA extraction kit; Qiagen, 74106) and reverse-transcriptase PCR (RT-PCR) amplification of the antibody gene cDNAs was performed using the PrimeScript One Step RT-PCR kit (Clontech, RR055A) according to the manufacturer's protocols with gene-specific primers as shown in Supplemental Table 3 of a previous report (Thornburg et al., 2016). PCR products were purified using Agencourt AMPure XP magnetic beads (Beckman Coulter) and sequenced directly using an ABI3700 automated DNA sequencer without cloning. The identities of gene segments and mutations from germlines were determined by alignment using ImMunoGeneTics database (Brochet et al., 2008; Giudicelli and Lefranc, 2011).

Determination of half maximal effective concentration (EC$_{50}$) for binding. To determine EC$_{50}$ concentrations for binding, the inventor performed ELISA using 384-well plates that were coated overnight at 4° C. with 2 µg/mL of a recombinant form of soluble head domain of HeV-RBP or NiV-RBP protein. The plates were blocked for 1 hour with 2% non-fat dry milk and 2% goat serum in PBS-T. After washing the plates 4 times with PBS-T, primary mAbs or hybridoma cell culture supernatants were applied to wells, and the plates were incubated at room temperature for 1 hour. Alkaline phosphatase-conjugated secondary antibodies (goat anti-human IgG Fc, Meridian Life Science), with a dilution of 1:4,000 in blocking solution, were placed into each well following plate wash with PBS-T. After 1-hour incubation, the plates were washed 4 times with PBS-T, and substrate solution (1 mg/mL pNPP disodium salt hexahydrate, Sigma) was added to each well. The plates were incubated at room temperature for approximately 30 min before reading the optical density at 405 nm with a Biotek plate reader. To obtain half maximal effective concentration (EC$_{50}$) values of human mAbs binding to HeV-RBP or NiV-RBP, ELISA experiments were performed with purified antibodies in three-fold serial dilutions, starting at 20 g/mL for HeV, and 50 µg/mL for NiV$_M$-RBP or NiV$_B$-RBP, and EC$_{50}$ values were estimated by a sigmoidal dose-response nonlinear curve fitting procedure with Prism software (GraphPad). Each dilution was performed in quadruplicate, and the experiment was conducted twice independently.

K$_D$ determination by bio-layer interferometry (BLI). Kinetic assays with BLI were performed on an Octet RED biosensor instrument (Pall FortéBio, Menlo Park). Recombinant histidine-tagged RBP (head domain) was immobilized to HIS1K biosensor tips (FortéBio) at 10 µg/mL in proprietary kinetics buffer (FortéBio). After a brief baseline step, serial dilutions of HENV-26 or HENV-32 Fab starting at 200 nM then were associated to coated biosensor tips for 300 seconds, followed by a 900 second dissociation step in 10× kinetics buffer. Data Analysis HT 11.0.2 software was used for curve-fitting to extrapolate equilibrium dissociation constant values. Association and dissociation steps were aligned to reference wells to account for dissociation of antigen from the biosensor tip. Global fitting using a 1:1 model with Savitzky-Golay filtering was used to fit curves.

Biolayer interferometry (BLI) to determine competition-binding groups. Competition-binding experiments were performed on the Octet RED biosensor, as described previously (Flyak et al., 2015). In brief, HeV-RBP or NiV-RBP with a C-terminal His-tag at 20 µg/mL was loaded onto Ni-NTA coated biosensor tips for 2 min. After 1 min wash in a kinetic buffer (1% BSA, 0.002% TWEEN® 20 (non-ionic detergent) in PBS), the biosensor tips were dipped into the first antibody solution at a concentration of 50 µg/mL for 5 min, and then biosensors were switched into a second antibody solution at a concentration of 50 µg/mL for 5 min. The ratio of the maximal signal from the seconding antibody after the first antibody binding to the maximal signal of the second antibody tested alone was calculated and expressed as a percentage.

Biolayer interferometry to test for mAb blocking of HeV-RBP protein binding to the host receptor ephrinB2. The human antibodies also were used in competition binding with a recombinant form of the host receptor ephrinB2 to determine if the mechanism of neutralization was blockade of receptor binding. The studies were performed using BLI on an Octet RED instrument. Streptavidin (SA) sensor tips were coated in 5 µg/mL biotinylated, recombinant HeV-RBP head domain protein diluted in proprietary Kinetics Buffer 10× (Pall FortéBio) for 30 seconds. Following a brief baseline step, 25 µg/mL HENV-26, HENV-32, or soluble ephrinB2 in buffer was associated to the coated sensor tips for 100 seconds. Tips then were dipped into wells containing a second antibody or ephrinB2. The data were analyzed using FortéBio software, with percentage binding determined by comparing the maximal binding signal of the second protein associated to that of the same protein associated alone.

Cell-surface display flow cytometric assay to test for mAb blocking of HeV-RBP protein binding to the host receptor ephrinB2. A suspension of 293F cells was transfected with cDNA encoding the full length HeV-RBP protein using PEI for 72 hours. Transfected cells were harvested and plated in V-bottom 96-well plates at 50,000 cells/well. After a wash step, cells were incubated with 50 µg/mL soluble ephrinB2 protein or FACS buffer for 30 minutes. Without washing, 2 µg/mL HENV-26 labeled with AlexaFluor-647 (Invitrogen) was added to cells and incubated for 30 minutes. Cells then were washed and analyzed using an Intellicyt iQue flow cytometry instrument. Binding of HENV-26 in the presence or absence of ephrinB2 was expressed as mean fluorescence intensity (MFI).

Crystallization and structural determination of antibody-antigen complexes. Purified Fabs were mixed with deglycosylated HeV-RBP or NiV-RBP head domain in a molar ratio of 1:1, and the mixtures were purified further by size-exclusion chromatography with a Superdex-200 HiLoad column (GE Healthcare Life Sciences) to obtain antibody-antigen complexes. The complexes were concentrated to about 10 mg/mL and subjected to crystallization trials. HeV-RBP head domain in complex with the Fab HENV-26 was crystallized in 30% MPD, 0.1 imidazole pH 6.5, 0.2 M ammonium sulfate, and 10% PEG 3350, and NiV-RBP head domain in complex with the Fab HENV-26 was in 1.0 M sodium malonate pH 7.0, 0.1 M Bis-Tris propane pH 7.0. Protein crystals were flash-frozen in liquid nitrogen after a quick soaking in the corresponding cryoprotection solutions (same as the crystallization solution for HeV-RBP/HENV26 complex, the solution of 25% sodium malonate pH 7.0 and 0.1 M Bis-Tris propane pH 7.0 for NiV-RBP/HENV-26 complex). Diffraction data were collected at the beamline 21-ID-G at the Advanced Photon Source. The diffraction data were processed with XDS (Kabsch, 2010) and CCP4 suite (Winn et al., 2011), The crystal structures were solved by molecular replacement using the structure of the head domain of HeV-RBP or NiV-RBP in human ephrinB2-HeV-RBP or ephrinB2-NiV-RBP complex (PDB ID 2VSK and 2VSM) and Fab structure of MR78 (PDB ID 5JRP) with the program Phaser (McCoy et al., 2007). The structure was refined and rebuilt manually with Phenix (Adams et al., 2010) and Coot (Emsley and Cowtan, 2004), respectively. The models have been deposited into the Protein Data Bank. PyMOL software (Schrodinger, 2015) was used to make all of the structural figures.

CedV-RBP and GhV-RBP ELISA. Constructs for CedV-RBP head domain and GhV-RBP full ectodomain were transfected transiently into Expi293F cells using Expifectamine transfection reagents (Thermo Fisher). Cell supernatants were harvested 7 days post-transfection. CedV-RBP head domain was purified using HISTRAP™ (protein purification columns) affinity chromatography as described above for HeV-RBP and NiV-RBP head domains (SigmaAldrich). Full-length ectodomain GhV-RBP containing a GCN tetramerization domain was purified using S-protein agarose (EMD Millipore). To test HENV-26 and HENV-32 for binding to CedV-RBP and GhV-RBP, 384-well plates were coated with 5 µg/mL CedV-RBP head domain or cell supernatant from GhV-RBP transfected cells and incubated overnight at 4° C. The following day, plates were blocked with DPBS-T containing 2% milk and 1% goat serum at room temperature for 1 hour. After a wash step, 3-fold serial dilutions of HENV-26, HENV-32, or control mAbs for CedV (14F3) or GhV (10D5) kindly provided by Christopher Broder were added to plates and incubated for 1 hour at room temperature. Secondary antibody (goat anti-human IgG-HRP for HENV-26 and HENV-32, goat anti-mouse human adsorbed Ig-HRP for controls) diluted 1:1,000 in DBPS-T containing 1% milk and 1% goat serum were added to plates. TMB substrate was used to develop plates, and the reaction was quenched using 1N HCl 10-15 minutes later. Absorbance at 450 nm was read using a Biotek plate reader, and binding curves were generated using non-linear regression analysis in GraphPad Prism software.

HeV and NiV viruses. Nipah virus number 1999011924 was obtained from a patient from the 1999 outbreak in Malaysia. The passage 3 (P3) virus stock of NiVM the inventor used for used for neutralization assays is known to have an N277K polymorphism in the RBP (Mire et al., 2016). The isolate of $NiV_B$ was 200401066 and was obtained from a fatal human case during the outbreak in Rajbari, Bangladesh in 2004 and passaged on Vero E6 cell monolayer cultures twice, making this a passage 2 virus. Hendra virus was obtained from a patient from the 1994 outbreak in Australia. All viruses were kindly provided by Dr. Thomas Ksiazek, UTMB. Each virus was propagated on Vero E6 cells in Eagle's minimal essential medium supplemented with 10% fetal calf serum. The $NiV_M$, $NiV_B$ and HeV challenge virus stocks were assessed for the presence of endotoxin using The Endosafe-Portable Test System (PTS) (Charles River Laboratories, Wilmington, MA). Each virus preparation was diluted 1:10 in Limulus Amebocyte Lysate (LAL) Reagent Water per the manufacturer's instructions, and endotoxin levels were tested in LAL Endosafe-PTS cartridges as directed by the manufacturer. Each preparation was found to be below detectable limits, whereas positive controls showed that the tests were valid. All experiments involving infectious henipaviruses were carried out at the UTMB Galveston National Laboratory under biosafety level 4 conditions.

Neutralization assays. The virus neutralizing activity concentrations were determined for $NiV_M$, $NiV_B$, and HeV using a plaque reduction assay. Briefly, antibodies were diluted serially two-fold from 50 µg/mL to extinction and incubated with a target of ~100 plaque-forming units (pfu) of $NiV_M$, $NiV_B$, or HeV for 45 min at 37° C. Virus and antibody mixtures then were added to individual wells of six-well plates of Vero76 cells. Plates were stained with neutral red two days after infection, and plaques were counted 24 h after staining. Neutralization potency was calculated based on pfu for each virus in the well without antibody. The neutralization experiments were performed in triplicate, with independent virus preparations and duplicate readings for each replicate. Mean half-maximal inhibitory concentrations were calculated from the plaque counts using GraphPad Prism software following the step-by-step protocol outlined explicitly in a previous report (Ferrara and Temperton, 2018).

Protection study in ferrets. Thirteen female ferrets weighing 0.75-1 kg were housed socially and placed into cohorts for treatment or no treatment (Table S4). For virus challenge and procedures, animals were anesthetized by isoflurane inhalation. Animals were inoculated intranasally (i.n.) with ~5×10³ plaque-forming units (pfu) of $NiV_B$ in 0.5 mL Dulbecco's minimal essential medium (Sigma-Aldrich, St. Louis, MO) on day 0. After challenge, ferrets in the treated cohorts were given mAb HENV-26 or HENV-32 by intraperitoneal (i.p.) injection on day 3 and 5 after challenge at a 15 mg/kg dose, a dosage lower than that used in prior studies in ferrets and nonhuman primates with an antiviral mAb (Bossart et al., 2011; Bossart et al., 2009; Geisbert et al., 2014; Mire et al., 2019; Mire et al., 2016). Animals were anesthetized for clinical examination including body weight, temperature, respiration quality, and blood collection on days 0, 3, 5, 7, 10, 14, and 28 after challenge. Before and after challenge, animals were assessed daily for clinical score on a scale of 0 of 12 for clinical observations based on coat appearance, body weight loss, social behavior, and provoked behavior; animals scoring 9 or greater were euthanized per the established UTMB IACUC protocol. The remaining subjects were euthanized at the study endpoint on day 28 after challenge.

Specimen collection and processing in NiV- and HeV-infected ferrets. On sampling days, blood was collected and placed in MiniCollect EDTA tubes (Greiner Bio-One, Monroe, NC) for virus load and hematology analysis or MiniCollect serum tubes (Greiner Bio-One) for clinical chemistry analysis. Necropsy was performed on all ferrets, and tissues sampled included lungs, liver, spleen, kidney, adrenal gland, pancreas, and brain (frontal cortex). Ten percent tissue homogenates of liver, spleen, kidney, adrenal gland, and brain were used for virus load analysis.

Measurement of infectious virus load in ferret tissues. Virus titration was performed by plaque assay with Vero cells from all tissue homogenates (10% w/v). In brief, increasing 10-fold dilutions of the samples were adsorbed to Vero cell monolayers in duplicate wells (200 μL); the limit of detection was 25 pfu/mL for whole blood and 250 pfu/gram for tissue.

RNA isolation from ferret tissues. Immediately following sampling, 100 μL of blood was added to 600 μL of AVL viral lysis buffer (Qiagen) for RNA extraction. For tissues, approximately 100 mg was stored in 1 ml RNAlater (Qiagen) for 7 days to stabilize RNA. RNAlater was completely removed, and tissues were homogenized in 600 μL RLT buffer (Qiagen) in a 2-mL cryovial using a tissue lyser (Qiagen) and ceramic beads. The tissues sampled included cerebral spinal cord, brain stem, brain (frontal cortex), lung (left upper and left lower), spleen, and liver. All blood samples were inactivated in AVL viral lysis buffer, and tissue samples were homogenized and inactivated in RLT buffer prior to removal from the BSL-4 laboratory. Subsequently, RNA was isolated from blood using the QIAamp viral RNA kit (Qiagen), and from tissues using the RNEASY® Mini kit (RNA extraction kit; Qiagen) according to the manufacturer's instructions supplied with each kit.

Detection of viral genomes in ferret samples. RNA was isolated from blood or tissues and analyzed using primers/probe targeting the nucleoprotein (N) gene and intergenic region between N and phosphoprotein (P) of NiV for quantitative real-time PCR (qRT-PCR), with the probe used here being 6-carboxyfluorescein (6FAM)-5' CGT CAC ACA TCA GCT CTG ACA A 3'-(SEQ ID NO:243)6 carboxytetramethylrhodamine (TAMRA) (Life Technologies, Carlsbad, CA). NiV RNA was detected using the CFX96 detection system (Bio-Rad) in One-step probe qRT-PCR kits (Qiagen) with the following cycle conditions: 50° C. for 10 minutes, 95° C. for 10 seconds, and 40 cycles of 95° C. for 10 seconds and 57° C. for 30 seconds. Threshold cycle (CT) values representing NiV genomes were analyzed with CFX Manager Software, and data are shown as genome equivalents (GEq). To create the GEq standard, RNA from NiV challenge stocks was extracted and the number of NiV genomes was calculated using Avogadro's number and the molecular weight of the NiV genome.

Hematology and serum biochemistry. Blood and sera were collected via the anterior vena cava from all 11 ferrets on days 0, 3, 5, 7, 10, 14, 21, and 28 after challenge or at euthanasia. Complete blood counts of total white blood cells, white blood cell differentials, red blood cells, platelets, hematocrit values, total hemoglobin concentrations, mean cell volumes, mean corpuscular volumes, and mean corpuscular hemoglobin concentrations were analyzed from blood collected in EDTA tubes (Greiner Bio One) using a VetScan HM5 hematology instrument per the manufacturer's instructions (Abaxis). Serum analysis of blood chemistries was completed using a Piccolo point-of-care analyzer and Biochemistry Panel Plus analyzer discs (Abaxis), which measured concentrations of albumin, amylase, alanine aminotransferase (ALT) aspartate aminotransferase (AST), alkaline phosphatase (ALP), gamma-glutamyltransferase (GGT), glucose, cholesterol, total protein, total bilirubin (TBIL), blood urea nitrogen (BUN), creatine (CRE), and C-reactive protein (CRP). All blood and serum samples were processed and analyzed immediately after collection.

Histopathology and immunohistochemistry. Necropsy was performed on all subjects. Tissue samples of all major organs were collected for histopathologic and immunohistochemical examination and were immersion-fixed in 10% neutral buffered formalin for at least 21 days in BSL-4. Subsequently, formalin was changed; specimens were removed from BSL-4, processed in BSL-2 by conventional methods and embedded in paraffin and sectioned at 5 m thickness. For immunohistochemistry, specific anti-NiV immunoreactivity was detected using an anti-NiV N protein rabbit primary antibody (kindly provided by Dr. Christopher Broder) at a 1:5,000 dilution for 30 minutes. The tissue sections were processed for immunohistochemistry using the Dako Autostainer (Dako, Carpinteria, CA). The secondary antibody used was biotinylated goat anti-rabbit IgG (Vector Laboratories, Burlingame, CA) at 1:200 for 30 minutes followed by Dako LSAB2 streptavidin-HRP (Dako) for 15 minutes. Slides were developed with Dako DAB chromagen (Dako) for 5 minutes and counterstained with hematoxylin for one minute. Non-immune rabbit IgG was used as a negative staining control.

Quantification and statistical analysis. In ELISA experiments, binding curves were generated using non-linear regression analysis in GraphPad Prism software. In the ferret studies, the constraints of high-containment work using animal studies in biosafety level 4 restrict the number of animal subjects and the volume of biological samples, which affects the ability to repeat assays independently and thus limit statistical analysis. Data are presented as the mean calculated from replicate samples, not from replicate assays, and error bars represent the standard deviation (s.d.) between replicates.

Example 3—Results

Isolation of human mAbs. To generate human cell lines secreting human mAbs to HeV, the inventor obtained peripheral blood mononuclear cells from an individual in Australia with occupation-related exposure to the equine HeV-RBP subunit vaccine (Equivac®). At the time of study, the individual had a serum 50% virus neutralization titer of 1:40, 1:16 or ≤1:4 for HeV, $NiV_M$ or $NiV_B$, respectively. The inventor transformed B cells in the blood sample with Epstein-Barr virus, as described in the Experimental Procedures section. He screened supernatants from EBV-transformed B cell lines for binding to HeV-RBP and NiV-RBP head domain proteins and fused the resulting B cell lines to make hybridomas secreting fully human naturally occurring mAbs. A total of 32 transformed cell lines secreting RBP-reactive antibodies were fused, and 12 independent hybridoma cell lines were recovered after selection that were still secreting RBP-reactive antibodies. After flow cytometric sorting at a single-cell level for biological cloning, clones for 11 of those 12 lines were recovered. One of the clones recovered (designated HENV-13) produced IgG poorly and was not studied further. Thus, 10 cloned hybridomas secreting RBP-reactive mAbs were carried forward; after all functional studies were completed, antibody variable gene sequencing revealed the independently-derived hybridoma clones HENV-18 and HENV-19 shared identical antibody variable gene sequences (Table S1).

Binding activity of human mAbs to HeV-RBP head domain in ELISA. In order to determine the breadth of mAb binding, the inventor screened the mAbs in ELISA for binding to recombinant RBP head domain proteins from multiple henipaviruses: HeV, NiV$_M$ [strain Malaysia], or NiV$_B$ [strain Bangladesh](Bowden et al., 2008). Determination of half maximal effective concentration (EC$_{50}$) for binding of each mAb against the autologous HeV-RBP or heterologous NiV-RBP head domain proteins revealed that the clones bound at low concentrations; all bound HeV RBP at ≤0.86 μg/mL and 6 of 10 bound at ≤0.25 μg/mL (Table A and FIG. 12A). Four of the HeV-reactive clones also cross-reacted with NiV$_B$-RBP head domain.

Figure 12A:
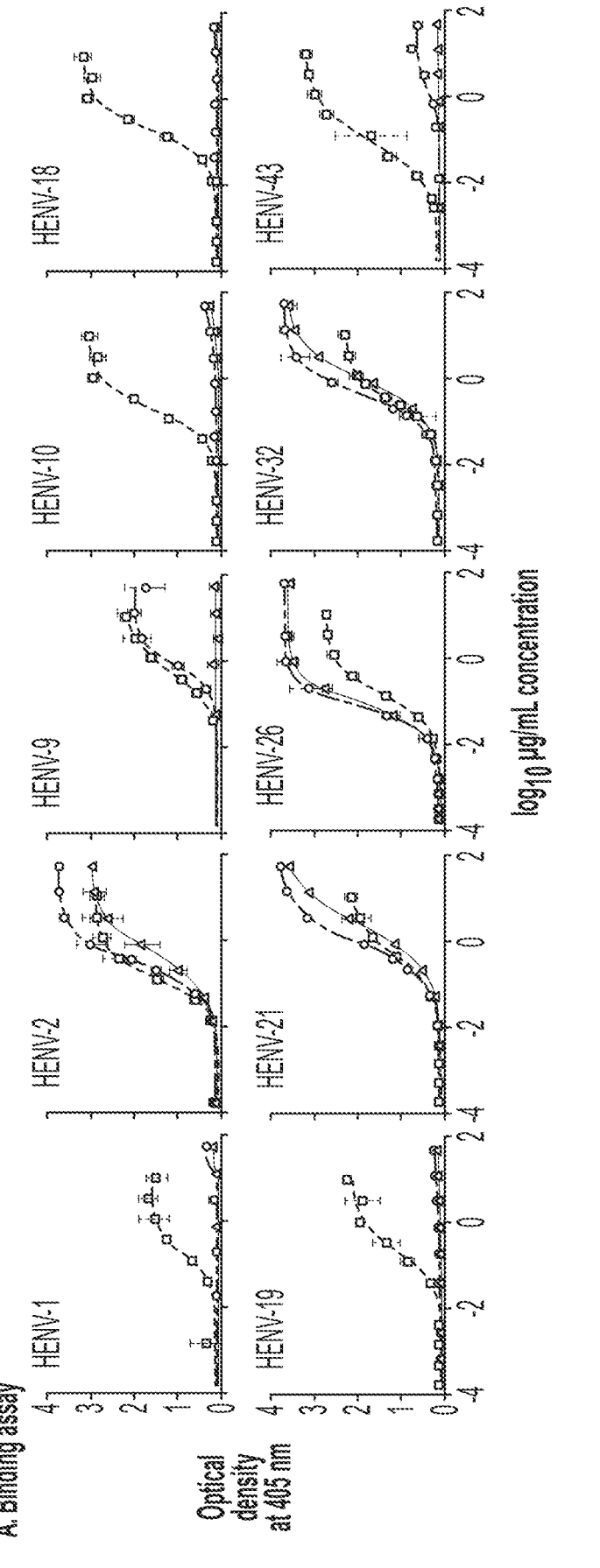
FIGS. 12A-B, Related to Table A. Full dilution curve data for neutralization or binding of 10 human monoclonal antibodies to HeV, $NiV_M$, or $NiV_B$.
Figure 12B:
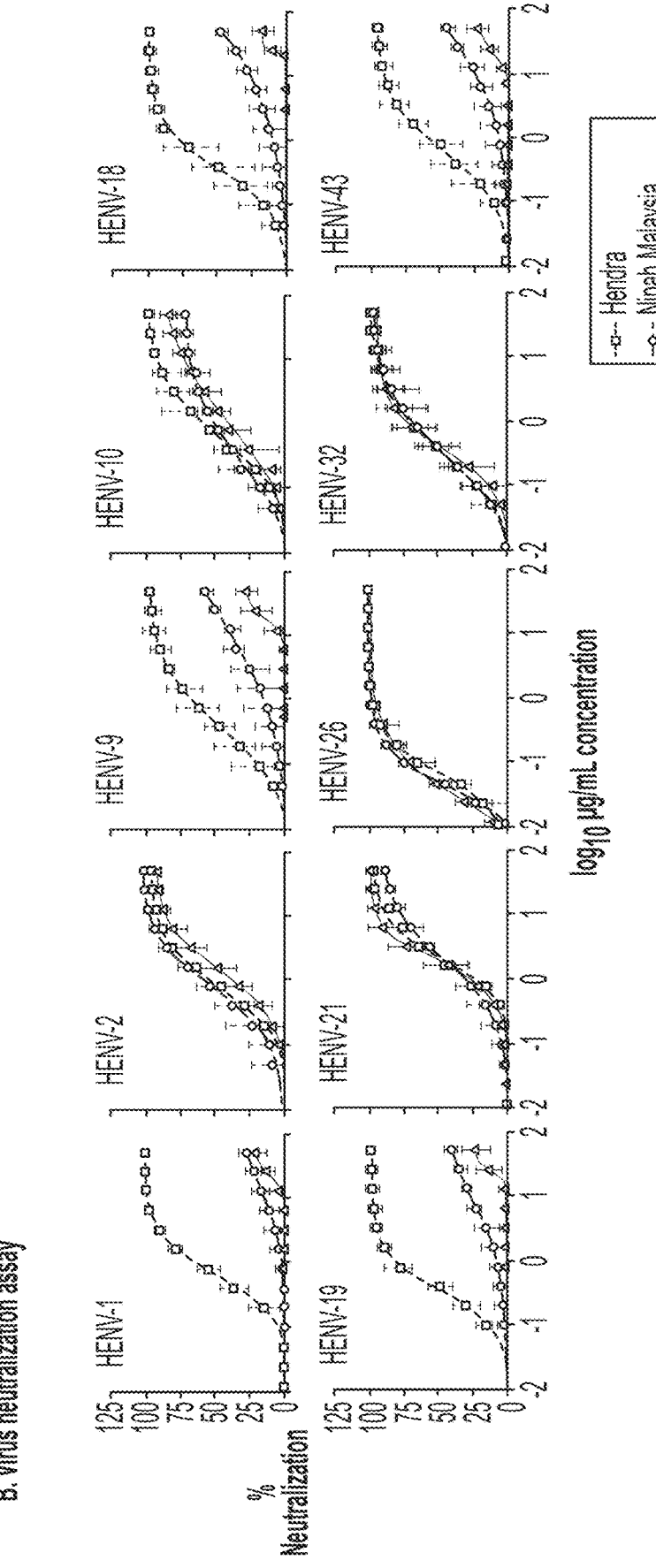

Neutralizing activity of human mAbs. To evaluate the inhibitory activity of the isolated mAbs, the inventor tested the mAbs in an in vitro neutralization assay using HeV. All 10 of the HeV-RBP-reactive mAbs neutralized HeV, with half-maximal inhibitory concentration (IC$_{50}$) values for 9 of 10 mAbs<0.78 μg/mL (Table a and FIG. 12B). The ELISA binding results discussed above suggested that cross-reactive mAbs in this panel might possess neutralizing activity to multiple henipaviruses. To test this hypothesis, the inventor screened the mAbs in NiV$_B$ and NiV$_M$ neutralization assays and found that 5 of the 10 mAbs also neutralized the heterologous NiV$_B$ strain, while 7 of 10 neutralized the NiV$_M$ strain (Table A). Five of the 6 remaining mAbs neutralized HeV well but neutralized NiV only incompletely, and one mAb (HENV-43) did not neutralize NiV (Table A). In parallel, the inventor tested the m102.4 antibody for comparative purposes and found the IC$_{50}$ values to be 0.26 (HeV), 0.02 ng/mL (NiV$_M$) or 0.049 μg/mL (NiV$_B$) (FIGS. 12A-B).

Figure 13A:
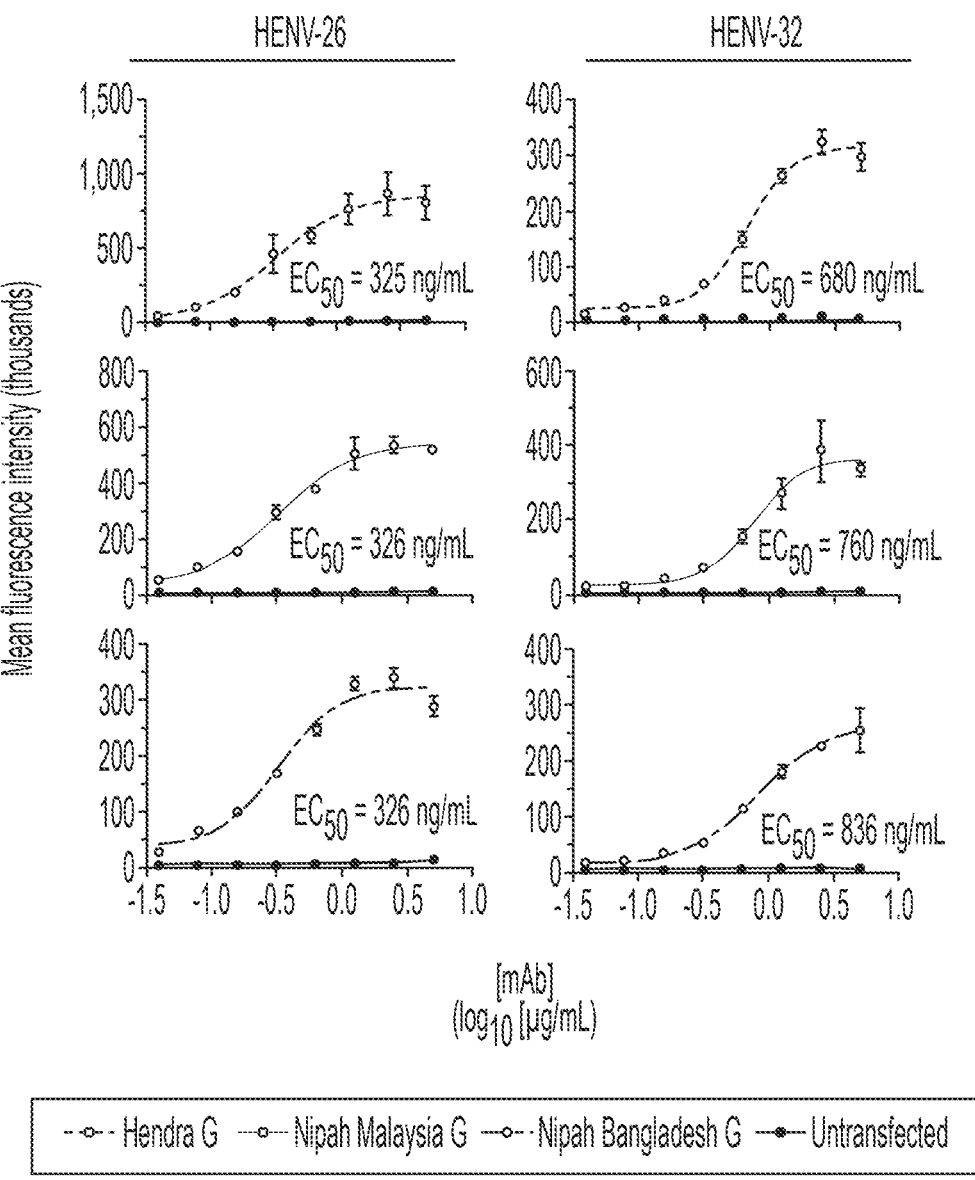
FIGS. 13A-B, Related to Table A.
Figure 13B:
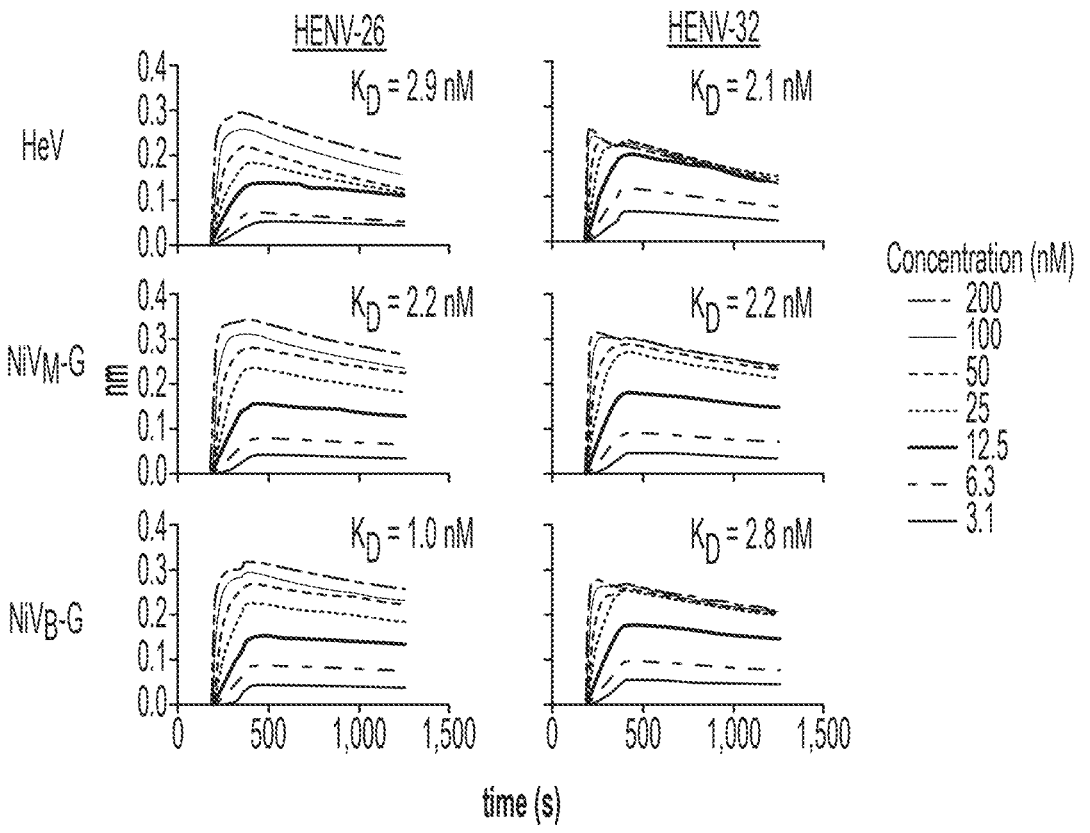

Binding activity of human mAbs to HeV, NiV$_M$, or NiV$_B$ RBPs on the surface of mammalian cells. The antibody discovery experiments and the ELISAs above were conducted with recombinant soluble forms of henipavirus RBP head domains. The inventor next sought to determine the binding capacity of the most potent mAbs, HENV-26 and HENV-32, to full-length RBPs expressed on the surface of mammalian cells. He transfected 3×10$^7$ cells with cDNAs encoding the full-length HeV, NiV$_M$, or NiV$_B$ RBP, allowed the cells to express the proteins, and then incubated the transfected cells with mAbs and tested for cell surface binding by flow cytometric detection. The results showed that these antibodies bound to the authentic full-length RBPs at low concentrations (FIGS. 13A-B). The EC$_{50}$ values for binding of HENV-26 or HENV-32 ranged from 325 to 343 ng/mL or 680 to 836 ng/mL respectively for binding to HeV, NiV$_M$, or NiV$_B$. The inventor tested kinetics of binding of these antibodies to RBPs on a biosensor to determine affinity (FIG. 13B). The K$_D$ for HENV-26 was 2.9, 2.2 or 1.0 nM and for HENV-32 was 2.1, 2.2, or 2.8 nM for HeV, NiV$_M$, or NiV$_B$, respectively.

Major antigenic sites recognized by human mAbs. To determine whether Abs from distinct binding groups targeted different antigenic regions on the HeV-RBP surface, the inventor performed a quantitative competition-binding assay using a real-time biosensor. He tested all mAbs in a tandem blocking assay in which HeV-RBP was attached to the biosensor. The data suggest that mAbs in this panel form at least 5 major competition-binding groups, consistent with recognition of 5 different antigenic regions on the HeV-RBP head domain (FIG. 1). The potently neutralizing mAbs HENV-26 and HENV-32 segregated into different competition-binding groups. Interestingly, mAb HENV-2 competed with 5 other mAbs, suggesting that it may bind to overlapping regions from 2 or 3 antigenic sites.

Competition-binding studies with the ephrinB2 receptor. Henipaviruses use the human ephrinB2 protein as a receptor for attachment and entry (Bonaparte et al., 2005; Negrete et al., 2005). The inventor sought to determine if anti-HeV-RBP mAbs neutralized virus by blocking virus attachment to ephrinB2 by studying three mAbs (HENV-19, -26 and -32) representing each of three main competition-binding groups. The inventor competed recombinant ephrinB2 protein with mAbs or buffer for binding to biosensor tips coated with HeV-RBP head domain. MAb HENV-26 reciprocally competed with ephrinB2 for binding to HeV-RBP, while mAbs HENV-19 and HENV-32 did not (FIG. 14A), suggesting that HENV-26 neutralizes by binding to the receptor binding site on HeV-RBP. MAb HENV-26 also competed with ephrinB2 for binding to full-length HeV-RBP expressed on the surface of 293F cells (FIG. 14B).

Crystal structures of HENV-26 in complex with HeV-RBP or NiV-RBP proteins. Next, the inventor determined the structure of antigen-antibody complexes for two mAbs using crystallography. The inventor selected the two most potent and cross-reactive mAbs from the panel, HENV-26 and HENV-32, for crystallographic studies and first determined their heavy and light chain variable gene sequences (Table S1). HENV-26 Fab complexes with HeV-RBP or NiV$_M$-RBP head domains were crystallized in spacegroups P22$_1$2$_1$ or P3$_2$2, and the crystal structures were solved at 2.60 Å or 3.40 Å, respectively (Table S2). Electron density for both structures was well defined except for several loop regions, e.g., S128-T131 of the HENV-26 heavy chain in the HENV-26/HeV-RBP complex, S127-A136 of the HENV-26 heavy chain in the HENV-26/HeV-RBP complex, P126-A137 of HENV-26 heavy chain, K156-V159 of HENV-26, A157-G158 of HENV-26 light chain, and I237-V244 of NiV-RBP in the HENV-26/NiV-RBP complex. The buried surface areas for the HENV-26/HeV-RBP complex or the HENV-26/NiV-RBP complex are 1,282.2 Å$^2$ or 1,323.1 Å$^2$, respectively. The overall structures of the two complexes are superimposable for the RBPs and the antibody variable domains, with an RMSD of 0.97 Å for 643 Cα atoms (FIGS. 2A-F). The relative orientations of Fab constant domains differed significantly because of the flexibility of the antibody elbow region and differing crystal contacts in the two crystals. HENV-26 has a relatively long CDRH3 loop (19 residues) and it adopts a spoon-shaped conformation that targets the central cavity of the HeV-RBP or NiV-RBP proteins (FIGS. 2A-F). In this engagement, HENV-26 shares some structural features with the antibody m102.3. (FIGS. 2A-F). In the m102.3/HeV-RBP complex (PDB 6CMG; PDB 6CMI), the paratope residues interacting with HeV- RBP are located mostly in the CDRH3 with an additional 3 interacting residues in CDRH2, 1 in CDRH1, and 1 in CDRL1 (Xu et al., 2013). In contrast, all CDRs of HENV-26 (except CDRL2 in the HENV-26/NiV-RBP complex), the light chain DE loop, and the heavy chain β strand C" of HENV-26 participate in antigen binding. The CDRH3 contributes more to antigen binding than the other structural elements (FIGS. 2A-F and FIGS. 3A-D). The HENV-26 CDRH3 and CDRH2/CDRH1/CDRL3 form a saddle-shaped conformation, straddling the RBP rim region formed by the β4S4-β5S1 loop and the β5S2-β5S3 loop, with CDRL1 and/or CDRL2 interacting with the β5S4-β6S1 loop, β6S2-β6S3 loop, and β1S2-β1S3 loops. Although the CDRH3s of both HENV-26 and m102.3 target the receptor-binding site of the RBPs, the two antibodies exhibit significantly different binding modes. This difference in binding modes between m102.3 and HENV-26 may be due to different conformations of their CDRH3s, since m102.3 has a relatively long, protruding CDRH3 with a β-hairpin conformation (Xu et al., 2013). The binding mode difference between the naturally occurring HENV-26 and the phage library-derived m102.3 is consistent with previous studies showing that naturally occurring human mAbs typically recognize their antigens using multiple CDRs to form an integrated interface, while phage library-derived mAbs often rely dominantly or even exclusively on their CDRH3 loops (Burkovitz and Ofran, 2016).

Overlays of the epitopes on the surface of HeV-RBP or NiV-RBP recognized by HENV-26 with that of the ephrinB2 receptor binding sites show that the antibody epitopes overlap greatly with the receptor binding sites (FIG. 14C), consistent with the competition-binding experiments (FIGS. 14A-B). Therefore, HENV-26 neutralizes HeV or NiV by competitive inhibition of viral attachment to the viral receptor.

In the HENV-26/HeV-RBP complex, 30 residues of HENV-26 (including 9 residues from CDRH3) and 31 residues plus the N-acetylglucosamine of the glycan at N529 of HeV-RBP from the Ab-Ag interface. The interaction contains a total of 19 hydrogen bonds (H-bonds) and 1 ionic interaction between Ab and Ag, and the H-bonds distribute relatively evenly among the CDRs, i.e., 5 H-bonds for CDRH3, 3 for CDRH2, 1 for CDRH1, 4 for CDRL3, 4 for CDRL1, and 2 for the heavy chain framework C" strand (FIG. 3A). Hydrophobic effects drive a portion of the Ab-Ag binding, as seen mainly between the tip of CDRH3 and the HeV-RBP cavity. CDRH3 residue M100C of HENV-26 is surrounded by residues P488, G489, T507, A532, residue L100B is surrounded by Y458, W504, and G506 mainchain atoms, and the Cβ and Cγ residues of Q100 stack on hydrophobic residues V401 and W504 (FIGS. 3A-B). In the ephrinB2/HeV-RBP complex, residues F111, P119, L121, and W122 of the ephrinB2 G-H loop occupy 4 hydrophobic pockets of the central cavity of HeV-RBP (here the inventor designated them as pocket F111, P119, L121, or W122, respectively), while L105, P107, and P109 on the m102.3 CDRH3 interact with the first three pockets (Bowden et al., 2008; Xu et al., 2013). HENV-26 CDRH3 residues M100C, L100B, or Q100 occupy similar positions to that of the ephrinB2 residues P119, L121, or W122, respectively, mimicking their interactions with HeV-RBP. In addition, atom Sδ of the M100C sidechain has relatively weak S—O polar interactions with the mainchain oxygen atoms of P488 and G489 on HeV-RBP, further strengthening the interaction between the HENV-26 CDRH3 and HeV-RBP. Importantly, the mainchain O atoms of L100B and Q100A make three H-bonds with the HeV-RBP Q490 Nε2 and G506 mainchain N atoms (FIG. 3A). It is most likely that the HENV-26 CDRH3 tip is a critical region for the Ab-Ag interaction. There are extensive van der Waals interactions between CDRH3/CDRH2/CDRL3/CDRL1 and HeV-RBP because of the high shape complementarity between these CDRs and the antigen (FIGS. 3A-B). Interestingly, 14 water molecules with well-defined electron density can be found at the Ab-Ag interface, forming H-bonds with antibody CDRs and HeV-RBP loops, and they distribute evenly at the interface (FIG. 15A). Given the high affinity of binding between HENV-26 and HeV-RBP, the H-bond network mediated by these water molecules must contribute positively to the binding free energy, i.e., the enthalpy gain from these H-bonds overcomes the entropy loss due to the loss of translational freedom of the water molecules.

As discussed above, the HENV-26/NiV-RBP complex shows very similar structure features to those of the HENV-26/HeV-RBP complex. The HeV and NiV RBPs have very high sequence identity (>80%). Mapping the epitopes on HeV-RBP or NiV-RBP recognized by HENV-26 onto their amino sequences at points of contact explains why HENV-26 cross-reacts with both RBPs (FIGS. 15D-G). Most Ab-Ag interface interactions in the HENV-26/HeV-RBP complex described above are conserved in the HENV-26/NiVHeV-RBP complex due to sequence conservation of RBPs at these regions. This observation is noted especially for the heavy chain CDRs and/CDRL3, and 3 regions of the RBPs (P488-E501, W504-T/V507 with F/Y459, and S528-E533), indicating that these CDRs (except heavy chain R31) likely contribute most to the binding energy (FIGS. 3A-D, FIGS. 15D-G). In contrast, for CDRL1 and RBP region D555-Q559, there are significant rearrangements of polar interactions between the two structures, which most likely relate to conformational differences at the β6S2-β6S3 and β6S4-β1S1 loops between HeV-RBP and NiV-RBP, suggesting a lesser contribution to the binding. Other minor interactions, such as a salt bridge formed between light chain D53 and HeV-RBP R242 in the HENV-26/HeV-RBP complex and an H-bond between light chain N66 mainchain oxygen and NiV-RBP N586 N62 in the HENV-26/NiV-RBP complex, are not conserved, but are located at the periphery of the interface, suggesting that they do not contribute significantly to the binding energy. N402 in HeV-RBP and R402 in NiV-RBP make non-specific van der Waals interactions with CDRH3 Q100, and sequence conservation at this site should affect binding affinity only minimally.

Figure 15E:
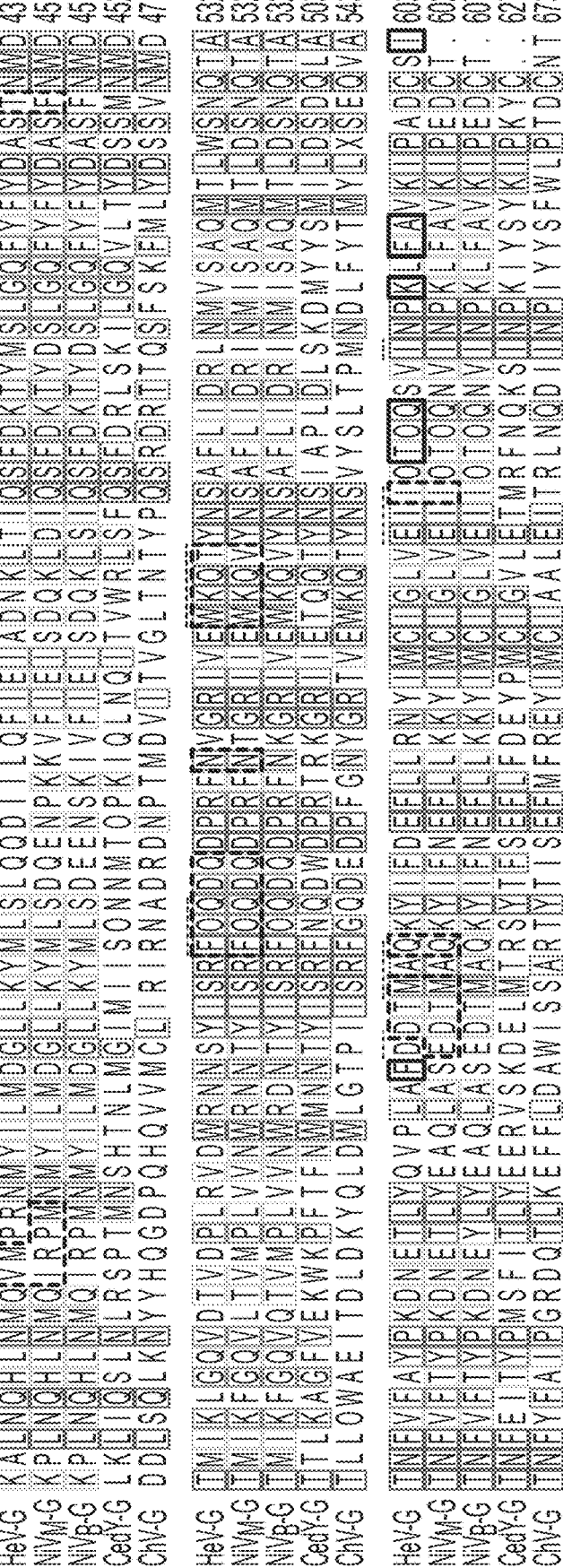
Figure 15F:
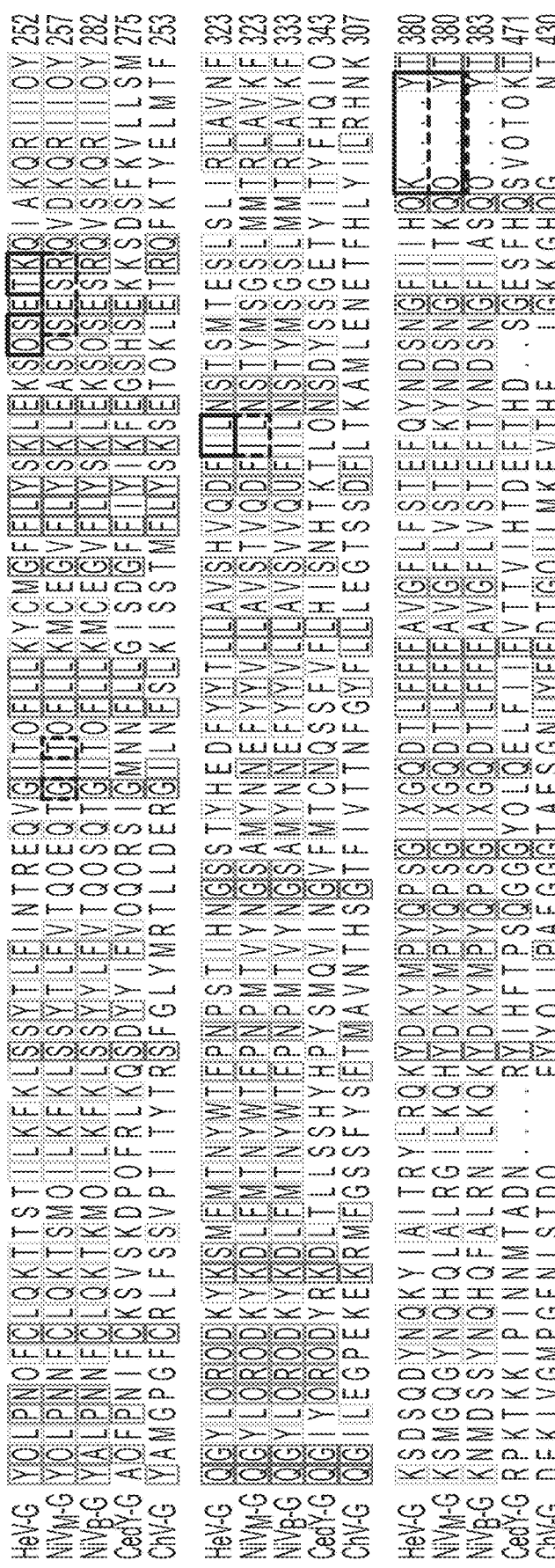
Figure 15G:
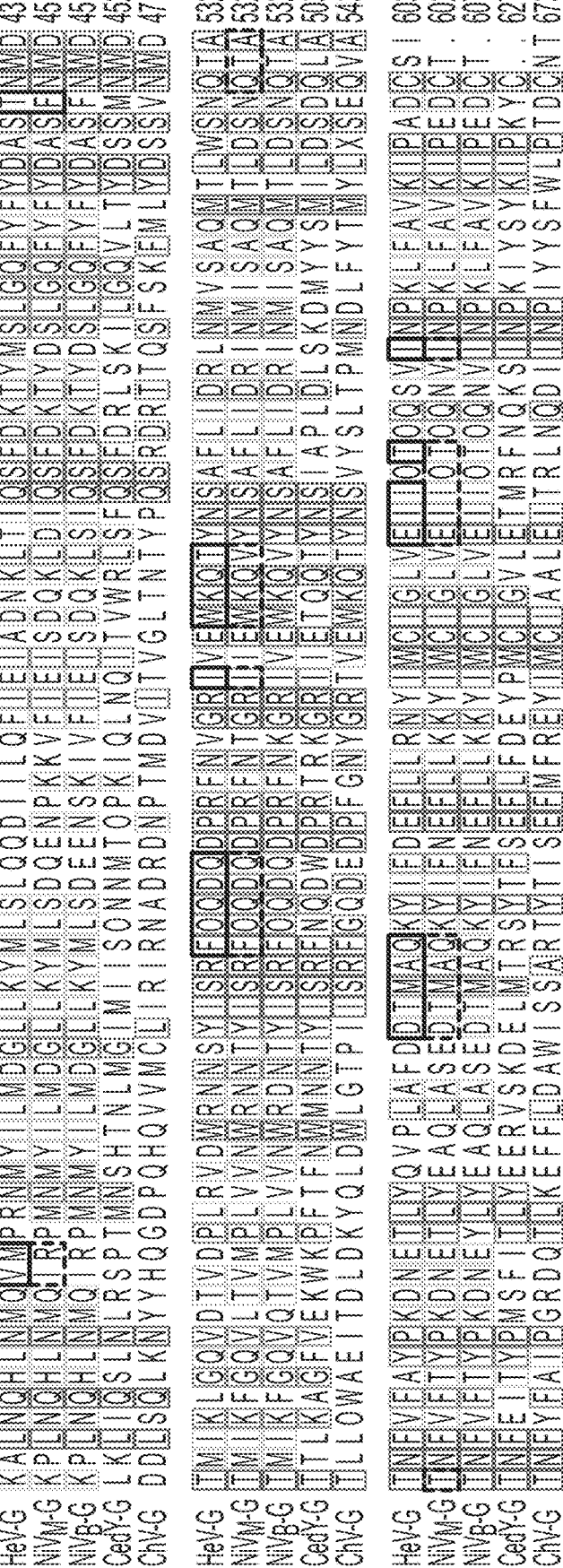
Figure 16A:
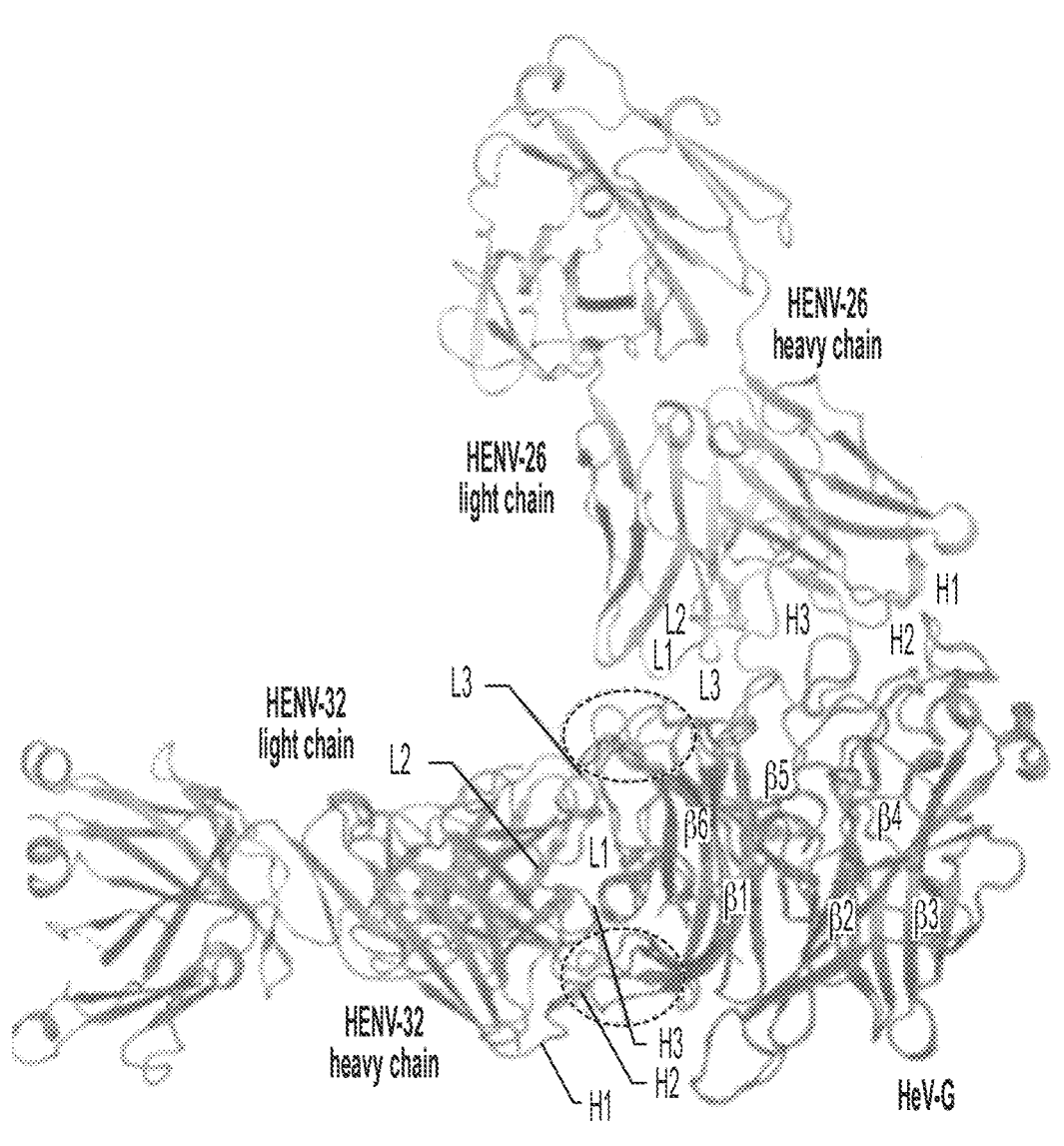
FIGS. 16A-C, Related to FIGS. 2A-F, FIGS. 4A-D and FIGS. 5A-C. Overlays of HENV-26 or 32 for comparative purposes.
Figure 16B:
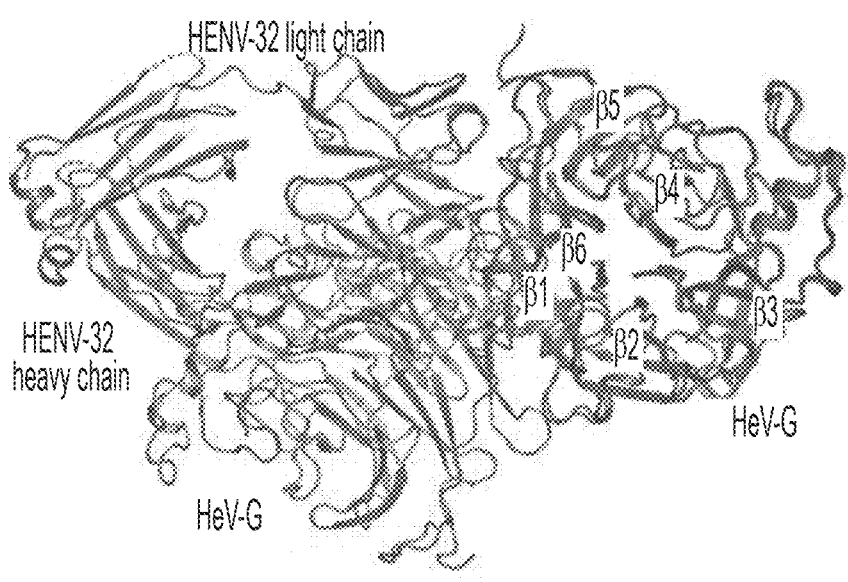

Crystal structures of HENV-32 in complex with HeV-RBP protein. It was apparent from the competition-binding studies with HENV-26 or with ephrinB2 shown above that the potent neutralizing mAb HENV-32 bound to an antigenic site distinct from the receptor-binding domain epitope recognized by HENV-26. Therefore, the inventor next determined the structure of antigen-antibody complexes for HENV-32 with HeV-RBP using crystallography. The structure revealed the molecular details of HENV-32 binding to an epitope distinct from that of HENV-26. HENV-32 in complex with HeV-RBP head domain crystallized in space-group C2 with a resolution of 2.0 Å (Table S2). There are two copies of HENV-32/HeV-RBP complex in one asymmetric unit (ASU). The structures of the two copies of the complex are very similar, with an RMSD of 1.05 Å for 640 Cα atoms of HeV-RBP and variable domains. The relatively high RMSD for the two copies in an ASU is likely due to motion of the HeV-RBP head domain and/or the difference of crystal contacts of the two copies. When the inventor overlaid antibody CDRs and interface regions of the HeV-RBP head domain, the RMSD for 264 mainchain atoms was only 0.36 Å. The constant domains adopt very different relative orientation to the variable domains in the two copies due to the high flexibility of the antibody elbow region and the crystal lattice packing. The buried surface areas for the two copies of the complex are 1,157 or 1,092 Å², respectively. HENV-32 mainly interacts with the highly flexible N-terminal segment T196-I209 and the (β1S3/(β1S4 β-turn on the bottom side of the head domain (FIGS. 4A-D, FIG. 15B, and FIG. 16A). All CDRs of HENV-32 contribute to antigen binding, with CDRH3 contributing the most among them. The N-terminal segment consists of the β6S4 strand and part of β6S4/β1S4 loop of HeV-RBP. The epitope overlaps the putative dimeric interface of HeV-RBP head domain (Bowden et al., 2010), especially at the N-terminal segment (FIG. 16B). HeV-RBP or NiV-RBP head domain alone exists as a monomeric form in solution but can self-associate as dimers in the crystalline state (Bowden et al., 2010), suggesting that the capacity of HeV-RBP or NiV-RBP head domain proteins to self-associate is weak.

The interface between Ab and Ag in the HENV-32/HeV-RBP complex comprises 29 or 30 residues from HENV-32 and 27 residues from the HeV-RBP head domain (depending on the copy in the ASU). There is a minor difference in the interface between the two copies in one ASU, for example, the heavy chain residues R61 and R64 form a polar interaction and salt bridge with G584 mainchain O atom and D585 side chain respectively in one copy, while the interactions are missing in the other copy. The interactions are highly exposed to solvent, and they do not contribute significantly to the binding free energy. 17 or 13 electrostatic interactions (including H-bonds, salt bridges, interactions between positively charged sidechain and mainchain O atoms) can be found between Ab and Ag, with 13 interactions shared by the two copies. Among these interactions, 12 of them most likely are important for binding. There are three focal interface locations for electrostatic interactions. The HENV-32 CDRH3 residue H98 sidechain forms two H-bonds with the mainchain O atoms of Y205 and P263 of the Ag, and the G97 mainchain N interacts with the HeV-RBP D260 sidechain via an H-bond (FIG. 4B). The positive charge on residue K199 of HeV-RBP is neutralized by the mainchain O atoms of residues G29 and K31 and the D51 sidechain of the light chain, and R201 is neutralized by the light chain D50 and mainchain O atom from the heavy chain CDRH3 G97. The R201 side chain also makes an H-bond with the light chain S32 Oγ atom. In addition to these three focal sites of contact, there are three more electrostatic interaction pairs: salt bridges between CDRH1 residue E32 and Ag residue R258, CDRH1 residue R31 and Ag residue E254, and H-bond between CDRL3 residue N93 sidechain and Ag residue P200 main chain O atom. Other important interactions include π-π stacking between CDRH3 F95 and Ag Y205, cation-π interactions between heavy chain residue R50 and HeV-RBP Y205, and CDRH1 R31 and Ag F266 (FIG. 4B). A hydrophobic effect can be seen between the CDRH2 I54 and Ag F266 residues, CDRH2 V55 and Ag P208 residues, CDRH3 F95 and Ag Y205 residues.

Figure 5A:
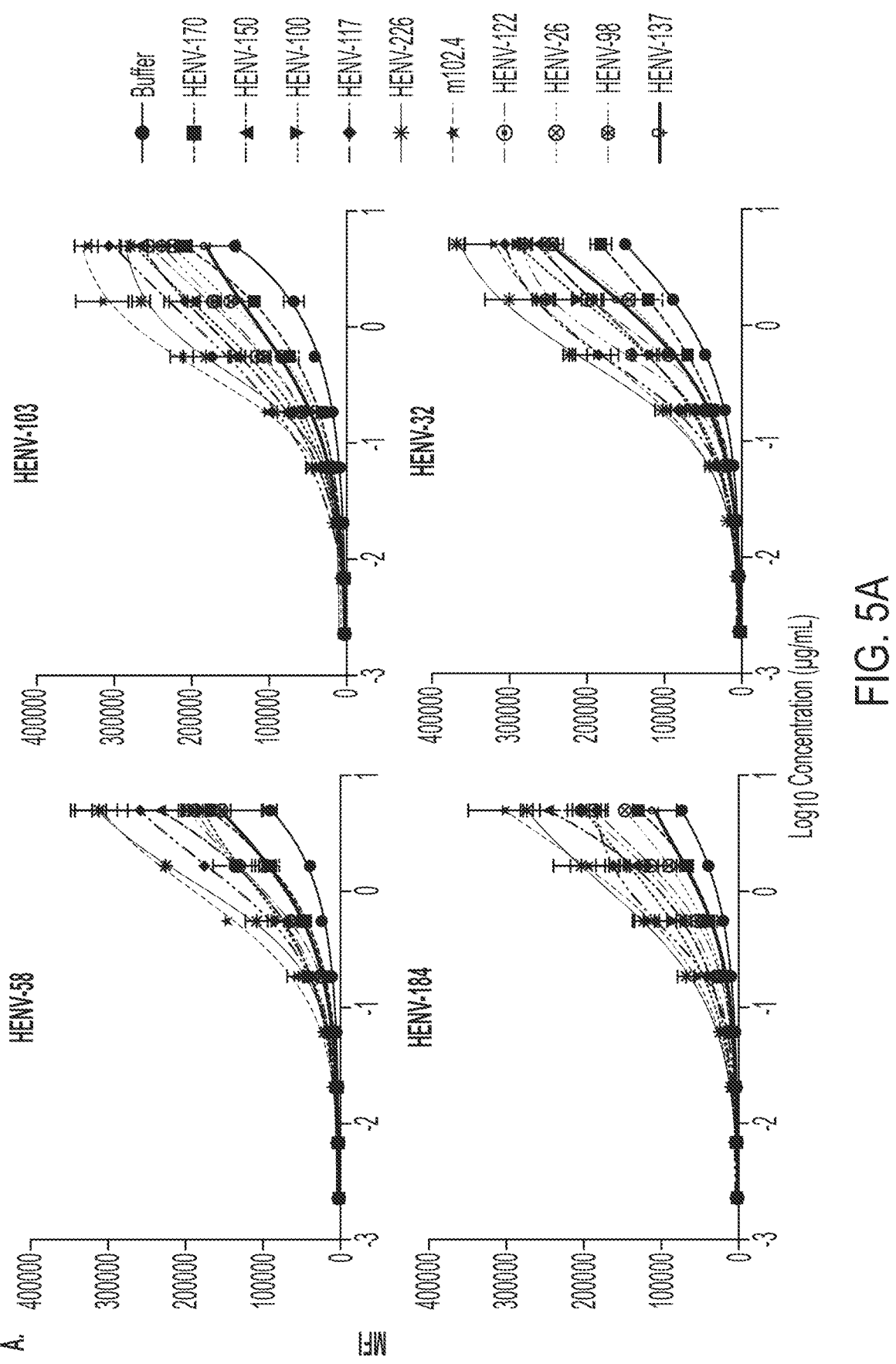
FIGS. 5A-B. Cooperative binding to HeV-G by neutralizing, cross-reactive mAbs with distinct neutralization mechanisms.
Figure 5B:
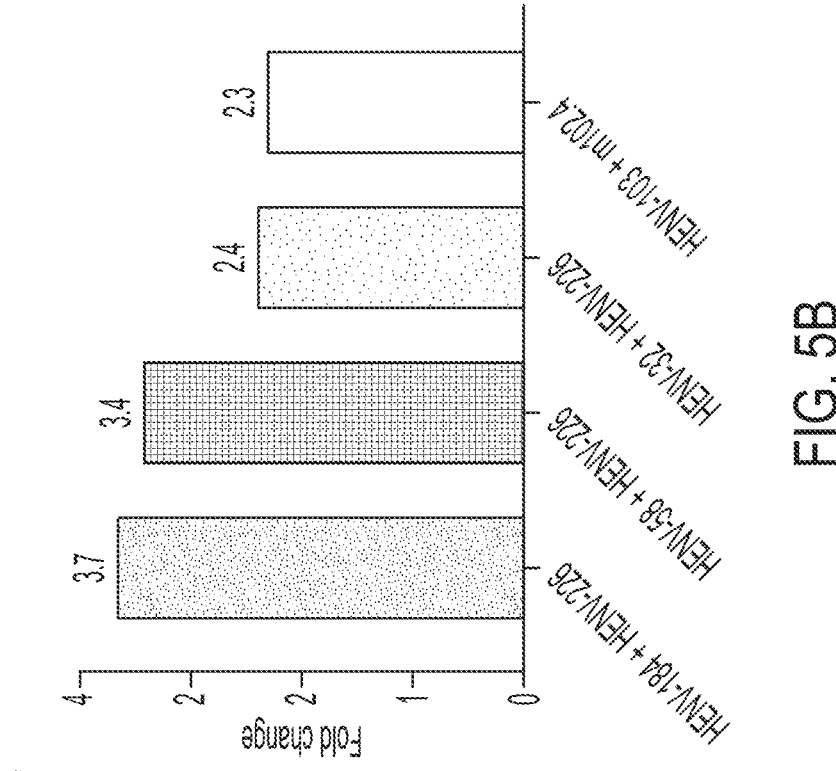

As mentioned above, Nδ1, and Nε2 of HENV-32 CDRH3 residue H98 form 2 H-bonds with the Y205 hydroxyl group (D–A distance=2.6 Å) and P263 mainchain oxygen (D–A distance=2.7 Å), and its sidechain also interacts extensively with surrounding residues from HeV-RBP via van der Waals force, e.g., a small pocket formed by I203, Y205, T206, V262, P263, and S264 (FIG. 4B, FIG. 4D, and FIG. 5B). Thus, CDRH3 residue H98 is the most important residue for the Ab-Ag interaction. Consistent with the highly hydrophilic interface of the HENV-32/HeV-RBP complex, there is a total of 34 visible water molecules, 15 of which are screened from bulk water, at the interface forming an H-bond network and mediating the Ab-Ag interaction (FIG. 15B). Given the tight binding of HENV-32 to HeV-RBP (Table A and FIGS. 12A-B, FIGS. 13A-B) and relatively small buried area of the complex, the number of interface water molecules of the complex is unusual because there is, on average, about one interface water per 100 Å² of interface area (Lo Conte et al., 1999). Taken together, water-mediated Ab-Ag interactions likely are a major factor in the high binding affinity of HENV-32 to RBPs. In sum, the binding of HENV-32 to HeV-RBP appears to be highly driven by enthalpy in a process involving extensive charge-charge interactions and water-mediated hydrogen bonding.

HENV-32 binding causes conformational changes of the HeV-RBP head domain. When the inventor superimposed all five available HeV-RBP crystal structures (FIG. 5A), he observed extensive conformational variations at the epitope recognized by HENV-32 among these structures (note: residues Y205-R212 of β6S4/β1S1 loop are missing in the crystal structure of the ephrinB2/HeV-RBP complex). RMSD values (Å) between Cα atoms of HeV-RBP structures in the different binding states are shown in Table S3. There are 4 major regions of the epitope showing large structural variations: the β5S4/β6S1 loop, β6S4/β1S1 loop, β6S2/β6S3 loop, and β1S3/β1S4 j-turn. From the discussion above, one knows that the β5S4/β6S1 loop might not contribute significantly to binding energy. In addition, in the second copy of the HENV-32/HeV-RBP complex, the conformation of the β5S4/β6S1 loop is similar to that in the HENV-26/HeV-RBP complex, suggesting that the structural variations at this loop do not affect the binding or function of HENV-32 and only reflect the innate structural flexibility of the loop and/or represent a crystallization artifact. Conformational changes in the β6S2/β6S3 loop can be seen in both copies of the ASU in the HENV-32/HeV-RBP complex. However, as above, this region also may not be critical for binding either. Therefore, these conformational changes may be secondary conformational adjustments induced by the conformational changes of the adjacent β6S4/β1S1 loop, which is one major region of the interface of the complex. From the structure overlay, it is clear that β6S4/β1S1 loop is the most flexible region of HeV-RBP (FIG. 5A). HENV-32 binding stabilizes this region in certain conformations (there are still subtle conformational differences between the two copies in one ASU of the crystal structure). The conformation of this loop in the HENV-32 bound form is similar to, but different from, those in the HENV-26-bound or m102.3-bound forms (FIG. 5A and FIG. 16A), suggesting that the conformational changes result from a combination of conformation selection and induced fit. The β1S3/β1S4 β-turn also shows large conformational variations among the HeV-RBP structures (FIGS. 5A-C). The β1S3/β1S4 β-turn and β6S2/β6S3 loop, especially residues R201-N210, constitute the major epitope region interacting with mainly with the heavy chain CDRs. Their conformational changes are essential in order for HENV-32 to bind. The small pocket of HeV-RBP between the β1S3/β1S4 β-turn and the β6S2/β6S3 loop is recognized by HENV-32 CDRH3 residue H98 (FIG. 4B, FIG. 15B, and FIG. 5B), as discussed above. In all other HeV-RBP crystal structures, this pocket is covered by a salt bridge pair from the β1S3/β1S4 loop, R258 and D260 (FIG. 5B, FIGS. 17A-F), although the mainchain conformation varies among these structures (FIG. 5A). When HENV-32 binds, the sidechain of residue R258 moves away from the pocket, accompanying opening movement of the mainchain of the loop. Meanwhile, residue R96 of the HENV-32

CDRH3, replacing HeV-RBP residue R258, forms a new salt bridge with residue D260 of the loop (FIG. 5B). The positively-charged residues R94 and R96 of CDRH3 may provide a repulsive force for the opening movement of β1S3/β1S4 loop and stabilize the position of D260. The CDRH3 residue H98 probably also participates in remodeling the pocket by interacting with HeV-RBP residue P263 and I203 (by H-bonding and van der Waals force). These features support the case for an induced fit mechanism of protein-protein interaction. On the other hand, a conformation selection mechanism also may contribute to the conformational changes, due to the flexibility of the β1S3/β1S4 β-turn seen in the structure overlay (FIG. 5A). A mixed mechanism could be used to explain the conformational changes of HeV-RBP when HENV-32 binds. The inventor suggests that HENV-32 may bind to highly flexible regions of RBP head domains via a "mixed mechanism", suggesting that its heavy chain CDRs should be rigid to minimize entropy cost to the binding reaction. The inventor tested whether or not HENV-32 could disrupt soluble HeV-RBP oligomers, but it did not (data not shown).

As above, HENV-32 cross-reacts with both HeV-RBP and NiV-RBP (Table A). Mapping the HeV-RBP epitope recognized by HENV-32 onto the amino acid sequences of HeV-RBP and NiV-RBP (FIGS. 15D-G) shows that 26 of the 30 interface residues are conserved in NiV-RBP and HeV-RBP. There is a H-bond between residue T197 side chain in HeV-RBP and HENV-32 light chain G29 carbonyl oxygen in one copy of HENV-32/HeV-RBP complex, but it is missing in the other. Thus, this H-bond is not critical for binding. The substitution of the position with Q197 in NiV-RBP could make van der Waals contacts with HENV-32 CDRL1 as T197 does, causing minimal effect on binding. Residue R201 of HeV-RBP is neutralized by D50 of HENV-32 CDRL2, and forms 2 H-bonds with S32 of CDRL1 and the G97 mainchain oxygen of CDRH3. The substitution with K201 in NiV-RBP would preserve the salt bridge and most probably one H-bond with G97 of CDRH3 or S32 of CDRL1. HeV-RBP residue N210 makes van der Waals contacts with HENV-32 residue V56. Sequence variation from asparagine to valine at this position in NiV-RBP would maintain the van der Waals contacts in addition to improving the hydrophobic effect between NiV-RBP V210 and HENV-32 V54/V56. Residues E553 and E602 of HeV-RBP form ionic interactions with HENV-32 CDRL1 K31 and CDRL2 R52, respectively, in one copy in an ASU of the complex, but the interactions are missing in the other, suggesting that they likely are dispensable for Ab-Ag binding. To summarize, HENV-32 can recognize both HeV-RBP and NiV-RBP (including both Bangladesh and Malaysia strains) because of the conservation of the sequences and structures of the epitope in these strains. The epitope recognized by HENV-32 is located in the putative dimeric interface of RBP head domains, especially the site bound by the heavy chain CDRs. If RBP dimerization is functionally important for henipaviruses, it may be difficult for HeV or NiV to generate mutant viruses that escape neutralization from HENV-32 mAb.

Lack of cross-reactivity with RBPs from Cedar virus or Ghanaian bat henipavirus. The inventor also examined whether or not HENV-26 of HENV-32 could recognize more distantly related henipaviruses including Cedar virus (CedV) and Ghanaian bat henipavirus (GhV). The RBP of the more distantly related henipavirus Mòjiāng virus was not tested as it is more divergent in sequence, is antigenically distinct, and lacks an ephrinB2/B3 binding domain (Rissanen et al., 2017). The HENV mAbs did not bind to recombinant forms of RBPs from CedV or GhV in ELISA, whereas CedV- or GhV- -specific control antibodies did bind (FIG. 15C). There are numerous differences in the epitopes when RBP sequence alignments between HeV/NiV and CedV or GhV are compared that suggest why the antibodies do not recognize CedV or GhV (FIGS. 15D-G), and these differences can be understood in the context of the RBP structures. Superimposition of the CedV-RBP or GhV-RBP crystal structure onto that of HeV-RBP in the HENV-26/ HeV-RBP complex explains the absence of binding of HENV-26 to CedV-RBP or GhV-RBP (data not shown). Sequence variations of CedV-RBP and GhV-RBP at several key positions from those of HeV-RBP or NiV-RBP cause loss of several interactions including H-bonds. The side chains of residues N497, S491, T531, and N529 in HeV-RBP form H-bonds with residues of HENV-26, while the residue variations at the structurally corresponding positions in CedV-RBP (residues H518, G512, L552, and D550) would abolish these H-bonds. Furthermore, L552 in CedV-RBP would make steric clashes with residue S93 of HENV-26 light chain in the superimposed structures, disrupting potential H-bond between S93 of HENV-26 light chain and residue S549 of CedV-RBP. Similarly, residue variations at V541, G500, E539, and T511 in GhV-RBP (corresponding to residues T531, Q490, N529, and E501 respectively in HeV-RBP) disrupt 5 potential H-bonds between GhV-RBP and HENV-26. Additionally, residue V468 in GhV-RBP (Y458 in HeV-RBP) could significantly weaken hydrophobic/van der Waals interaction between this position and residue L100B of CDRH3 of HENV-26. Due to significant sequence differences of CedV-RBP (residues P219-Q233) or GhV-RBP (residues P212-T226) from HeV-RBP (residues T196-N210) or NiV-RBP (residues Q196-V210) in one major epitope region recognized by HENV-32, the backbone conformations of CedV-RBP and GhV-RBP deviate significantly from those of HeV-RBP and NiV-RBP at this region. This finding indicates that the energy barrier is prohibitively high for CedV-RBP or GhV-RBP to adopt a similar backbone conformation to that of HeV-RBP in the Ab-Ag complex at the region, explaining the inability of binding of CedV-RBP and GhV-RBP by HENV-32.

Post-exposure efficacy of human mAbs in a ferret model of henipavirus infection. To determine the therapeutic activity of these cross-neutralizing Abs, the tested two antibodies in ferrets. He focused on potent cross-reactive antibodies for challenge with NiV_B. He selected the two mAbs HENV-26 and HENV-32, because they bound non-overlapping antigenic regions in the competition-binding experiments and structural studies. Female ferrets (~3-5 months old) received 15 mg/kg of antibody by the intraperitoneal route on days 3 and 5 (for a total of 30 mg/kg cumulative dose) after intranasal inoculation with 5,000 PFU of NiV_B. The serum 50% virus neutralizing titers for NiV_B for ferrets treated with HENV-26 were 1:369 (day 5) and 1:765 (day 7), while the titers for ferrets treated with HENV-32 were 1: 135 (day 5) and 1:132 (day 7). HENV-26 and HENV-32 each reduced disease and protected ferrets from death when delivered 3 and 5 days after virus challenge (FIGS. 6A-B). All untreated control animals exhibited a clinical course and pathology consistent with previous reports of henipavirus infection in ferrets including: pulmonary complications, lymphopenia, neutrophilia, thrombocytopenia, and hypoalbuminemia (Mire et al., 2013). Circulating viral genomes were detected beginning on day 5, with a mean value of 5.64 (+/−0.26 SD) $\log_{10}$ genomes/mL (FIG. 6C). Viral genomes were detected in all tissues tested (FIG. 6D), and infectious virus was detected at low levels in spleen, kidney, adrenal glands, lung (data not shown). All control animals displayed gross and histologic lesions consistent with NiV infection (FIGS. 18A-L/top and bottom). Significant lesions included necrohemorrhagic hepatitis, splenitis, and pneumonia. Positive immunolabeling for specific anti-NiV N protein was noted in the hepatic sinusoidal lining cells, endothelium of small caliber vessels and rarely mononuclear cells and/or hepatocytes, endothelium and mononuclear cells of the spleen, endothelium of small caliber vessels within the neural parenchyma, and the endothelium of the pulmonary alveolar septa, endothelium of small caliber vessels, mononuclear cells within alveolar septa, alveolar macrophages and rarely the lower airway epithelium. None of the HENV-32 treated subjects exhibited overt signs of clinical disease, although evidence of infection was detected through the presence of transient hematological changes. In HENV-26 treated subjects, 4 of 5 exhibited observable clinical signs that included depression and mild respiratory signs (Table S4). Circulating viral genomes were not detected from any animal from the HENV32 treated group; however, in the HENV-26 treated group between 4 and 5 $\log_{10}$ of viral genome/mL was detected on day 5 (in 3 of 5 subjects) and on day 14 (in 1 of 5 subjects) (FIG. 6C). The significance of this observation of late viremia is uncertain. It is possible that viral RNA had been cleared temporarily from circulation but had otherwise already become established in the tissues to some degree, whereby on day 14 it was then detected, likely harbored by scavenging antigen presenting cells in circulation. Another factor that cannot be ruled out is rapid clearance of the therapeutic human antibody allowing for a secondary phase of viremia, which may have been brought under control by the emerging host immune responses.

All ten treated ferrets in the study were euthanized at the study end point on day 28 after challenge. Gross inspection at necropsy revealed that all ten animals failed to display significant lesions associated with NiV infection. Two ferrets from the group treated with HENV-26 (designated HENV-26_B & HENV-26_E) and one ferret from the group treated with HENV-32 (designated HENV-32_B) had minimal lymphocytic aggregates within the liver and in at least one lung lobe (data not shown); however, no other significant lesions or significant immunolabeling were noted. One of the HENV-26 treated animals (HENV-26A) had minimal lymphocytic aggregates within the liver, in at least one lung lobe, and in the brainstem; however, no other significant lesions or significant immunolabeling were present in this animal (data not shown). A different ferret from the same treatment group (HENV-26_D) had minimal lymphocytic aggregates within the liver, in at least one lung lobe, and in the brainstem and had significant immunolabeling of neurons in the brainstem (FIGS. 18A-L/top and bottom). Every animal was sampled for the presence of virus once from brain, spleen, and liver. Lung lobes from the left upper and lower lobes were also sampled, so each lung was sampled in two different regions of the lung. Sampled areas from any tissue were largely representative of the entire organ in terms of severity of gross pathology since the pathology revealed appeared to be uniform throughout the organs. Viral genomes were detected in the brain of two HENV-26-treated subjects (HENV-26_A & HENV-26_D) and in the upper quadrant of the lung of one HENV-32-treated subject (HENV-32_E) (FIG. 6D). The inventor tested both the spleen and liver tissue of each of the 10 animals in the two treatment groups (five animals per group), and infectious virus was not detected in any organ sampled from any animal.

Example 4—Discussion

The inventor obtained the first panel of naturally occurring human mAbs from a human individual immune to HeV and found mAbs that were potently neutralizing, including 4 that exhibited breadth of recognition for the major strains of NiV. The two most potent, cross-reactive mAbs, HENV-26 and HENV-32, afforded post-exposure protection against the notably more pathogenic Bangladesh strain of NiV in an animal model (Clayton et al., 2012; Lo et al., 2012; Mire et al., 2016). There is no FDA-approved HeV or NiV vaccine or effective treatment for these viruses, and NiV can be transmitted person to person. These two mAbs could be considered lead candidates for prophylaxis or therapy of HeV or NiV infections. HENV-26 directly competes with ephrinB2 for RBP binding, while HENV-32 does not, and crystal structures revealed very distinct antigenic sites. The two mAbs do not compete with each other for HeV/NiV binding, and they neutralize the viruses by very different mechanisms. Therefore, a combination prevention or treatment formulation combining these two mAbs could be considered. MAb combinations may be desirable for treatment of RNA virus infections to prevent virus escape and may produce cooperative effects.

The cross-reactivity of the antibodies isolated for recognition and neutralization of HeV, $NiV_M$ and $NiV_B$, and protection against those viruses, is desirable since it is plausible that a single regimen of monotherapy or a cocktail of these antibodies could prevent or treat each of the three viruses. The inventor tested for breadth of binding for other more distantly related henipaviruses but did not detect cross-reactivity to other viruses. This finding was not surprising, since the RBPs of NiV and HeV have been reported to elicit only a limited cross-reactive antibody response, and cross-protection between Mòjiāng virus or Ghana virus, and the highly pathogenic henipaviruses was not detected (Li et al., 2020).

To explore structural mechanisms of binding and neutralization of the two mAbs, the inventor solved the crystal structures of the mAbs in complex with HeV-RBP and/or NiV-RBP head domains. HENV-26 targets the central cavity and top loops of mainly blade 4, 5, and 6 of the propeller-fold of HeV-RBP and NiV-RBP head domains, overlapping the ephrinB2/B3 binding sites, thus directly competing with ephrinB2/B3 for RBP binding. Therefore, HENV-26 neutralizes HeV or NiV by blocking the receptor binding site of the viruses, thus protecting animals against viral infection by inhibition of viral entry. The major interacting residues of RBPs are conserved between HeV-RBP and NiV-RBP (FIGS. 15D-G), making the mAb cross reactive to both viruses. All of the HENV-26 CDRs participate in the formation of the Ab-Ag interface, in contrast to the interaction mode of the previously described phage display library derived antibody m102.3 (Xu et al., 2013).

Figure 16C:
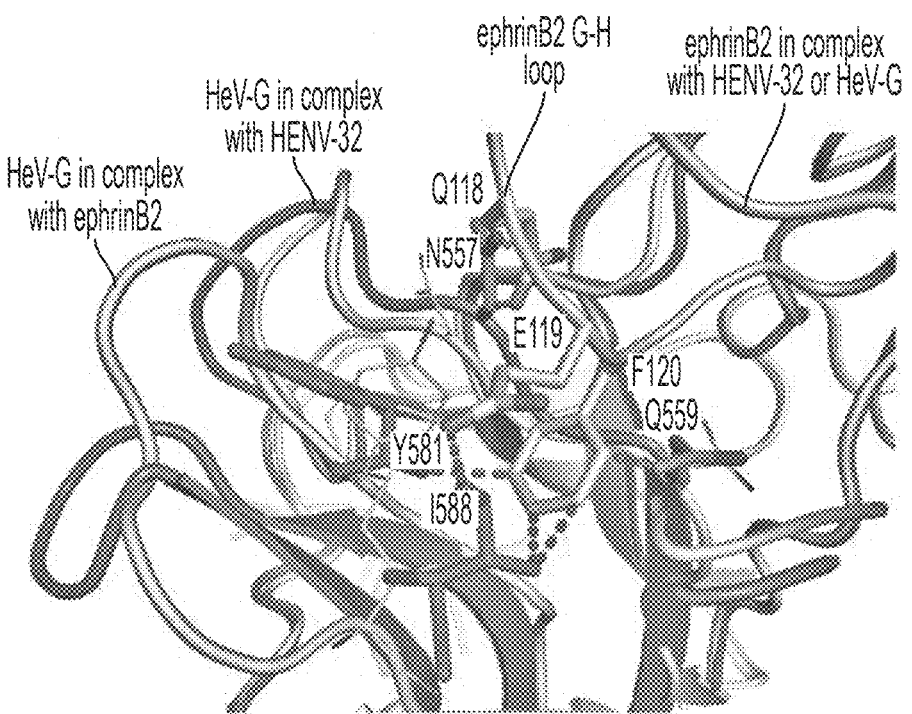

In contrast, HENV-32 binding causes conformational changes at the β5S4/β6S1 loop and β6S4/β1S1 loops. If HENV-32 bound HeV-RBP is superimposed onto ephrinB2-bound HeV-RBP, the conformational changes at these two loops result in steric clashes between the ephrinB2 G-H loop and residues in these loops of HeV-RBP (FIG. 16C). The inventor considered whether HENV-32 could compete with the binding of ephrinB2 via an allosteric effect. However, he did not observe competition between HENV-32 and ephrinB2 for HeV-RBP binding in a BLI assay (FIG. 14A). Therefore, the binding of HENV-32 to the putative dimeric interface of RBP head domains likely neutralizes HeV or NiV by altering dynamic features of the surface protein on virions. There is extensive literature defining the dimeric architecture of the RBP (Bowden et al., 2010), which forms a functional tetrameric unit when two disulfide-linked dimers associate (Bossart et al., 2005; Bowden et al., 2008; Negrete et al., 2007), and a disulfide bond in the stalk stabilizes the tetramer (Maar et al., 2012). The henipavirus RBP interacts with host cellular B class ephrins, triggering conformational alterations in RBP that lead to the activation of the F glycoprotein, which facilitates the membrane fusion process (Bradel-Tretheway et al., 2019; Navaratnarajah et al., 2020; Steffen et al., 2012).

Possibly, HENV-32 binding causes rearrangement of the quaternary structure of the RBPs in the head domains in such a way that the orientation of the receptor-binding sites of the RBPs are no longer suitable for receptor binding, preventing viral attachment to cells. However, the inventor found that a soluble recombinant form of ephrinB2 can bind in the presence of HENV-32. Another possibility is that HENV-32 interferes with the activation of HeV/NiV fusion proteins by RBPs, in a mechanism suggest by previous studies of a rabbit antibody with inhibitory activity that likely binds near the epitope recognized by the human mAb HENV-32 (Aguilar et al., 2009). The rearrangement of quaternary structure caused by HENV-32 binding also might make the activation residues in the stem regions of the RBPs inaccessible to the fusion proteins, thus inhibiting viral entry to cells. Further studies are needed to clarify these possibilities.

The solved crystal structures of these Ab-Ag complexes also inform opportunities for future rational antibody engineering efforts to improve binding affinities of the mAbs. HENV-26 CDRH1 residue R31 makes only loose van der Waals interactions with HeV-RBP V502 or NiV-RBP residues I502 and P403. Insertions and mutations at R31 position might enhance binding. As mentioned above, there are significant rearrangements of polar interactions between the HENV-26/HeV-RBP and HENV-26/NiV-RBP complexes at the interface between CDRL1 and RBP region D555-Q559. This finding suggests that CDRL1 may be a malleable region for improvement of binding. HENV-32 CDRL3 residue N93 interacts with a hydrophobic patch on HeV-RBP (comprising residues P200, L202, and F593) and with the mainchain carbonyl oxygen atom of residue P200 via an H-bond. It could be interesting to examine the effects of mutations of CDRL3 residue N93 to aliphatic residues (valine, leucine, or isoleucine) on binding affinity, because the mutation might improve the hydrophobic effect between N93 and the hydrophobic patch but lose a H-bond between Ab and Ag.

Vaccine development for NiV is a high priority for many recommending bodies. The epitopes recognized by these broad and potent antibodies could be used in structure-based reverse vaccinology design programs to design new vaccine candidates. Thus, the studies provide important new conceptual data on henipavirus immunity, but there are significant limitations of these studies. First, the mAbs in this study were isolated from a single human immune individual, and it is uncertain how generalizable these findings would be in a population. Second, the studies focus on antibodies to RBP, since the individual studied had exposure to a vaccine RBP and the inventor screened for antibodies reacting to the RBP head domain; from these studies he cannot determine the role for antibodies to the RBP stem, potential complex quaternary epitopes at the head/stem interface, or fusion protein in immunity to henipaviruses and more antigenic sites are possible. Third, there may be a role for non-neutralizing antibodies to henipaviruses, but the inventor did not explore that mode of immunity here. These limitations point to the need for additional in-depth studies of this type for immunity to henipaviruses.

TABLE A

| Binding and neutralizing activity of human monoclonal antibodies | | | | | | | | | | |
|---|---|---|---|---|---|---|---|---|---|---|
| | | Binding to RBP head domain from indicated virus in ELISA | | | Neutralization of indicated virus | | | | | |
| Competition-binding | | $EC_{50}$ values[b] in µg/mL (Area under the curve) | | | $IC_{50}$ values[d] in µg/mL (Area under the curve) | | | $IC_{80}$ values[d] in µg/mL (Max % Inhibition) | | |
| group[a] | Clone | HeV | $NiV_B$ | $NiV_M$ | HeV | $NiV_B$ | $NiV_M$ | HeV | $NiV_B$ | $NiV_M$ |
| A | HENV-1 | 0.19 (3.27) | >[c] (0.61) | > (0.67) | 0.63 (187) | > (7.98) | > (22.6) | 1.70 (100) | > (32.7) | > (34.9) |
| B | HENV-32 | 0.36 (3.71) | 0.96 (6.6) | 0.42 (8.0) | 0.27 (198) | 0.38 (194) | 0.31 (201) | 1.26 (100) | 1.14 (100) | 2.15 (100) |
| | HENV-21 | 0.42 (3.30) | 2.44 (5.5) | 0.87 (7.2) | 1.94 (133) | 1.91 (140) | 2.01 (129) | 5.54 (100) | 4.09 (100) | 8.44 (92.4) |
| | HENV-10 | 0.21 (5.49) | > (0.63) | > (0.76) | 0.62 (181) | 1.07 (140) | 0.22 (152) | 1.71 (100) | 9.42 (96.3) | 1.44 (84.2) |
| B/C | HENV-2 | 0.13 (5.81) | 0.51 (6.4) | 0.28 (9.0) | 0.78 (166) | 1.39 (143) | 0.75 (186) | 2.57 (100) | 4.88 (95.8) | 2.67 (100) |
| C | HENV-9 | 0.60 (3.19) | > (0.57) | 0.75 (4.2) | 0.37 (195) | > (11.9) | 8.93 (69.2) | 1.88 (100) | > (35.2) | > (61.5) |
| | HENV-43 | 0.86 (6.87) | > (0.59) | 1.49 (1.4) | 0.61 (178) | > (9.2) | > (45.2) | 2.39 (100) | > (40.0) | > (51.9) |
| D | HENV-18[e] | 0.21 (5.80) | > (0.56) | > (0.60) | 0.38 (211) | > (5.7) | > (51.1) | 1.16 (100) | > (31.4) | > (50.8) |
| | HENV-19[e] | 0.25 (3.69) | > (0.52) | > (0.61) | 0.35 (209) | > (7.2) | 8.08 (43.1) | 0.89 (100) | > (33.9) | > (49.2) |
| E | HENV-26 | 0.14 (5.39) | 0.09 (10.5) | 0.07 (11.0) | 0.07 (281) | 0.03 (289) | 0.040 (293) | 0.19 (100) | 0.12 (100) | 0.11 (100) |

Experiments were conducted with 2 or 3 biological replicates, each with 2 technical replicates, with consistent results. Binding data from one representative experiment are shown, with neutralization data combined from 3 independent experiments.
[a]Competition-binding group, as determined by data in FIG. 1.
[b]50% maximal effective concentration.
[c]The ">" symbol indicates half maximal binding or neutralization is not achieved below the highest concentration tested: 20 µg/mL for HeV RBP binding, 50 µg/mL for $NiV_M$ or $NiV_B$ binding, or 50 µg/mL for neutralization of each of the three viruses.
[d]50% maximal inhibitory concentration.
[e]After all functional studies were completed, antibody variable gene sequencing later revealed the independently-derived clones HENV-18 and -19 shared identical antibody variable gene sequences (Table S1).

TABLE S1

Related to FIG. 2. Sequence features of HENV antibodies
Heavy chain

| mAb | Isotype | IGHV | IGHD | IGHJ | HCDR3 amino acids | HCDR3 length | GenBank ID | % AA germline identity |
|-----|---------|------|------|------|-------------------|--------------|------------|------------------------|
| HENV-1 | IgG1 | VGHV4-34*01 | IGHD5-12*01 | IGHJ6*02 | ARLKWLLSRGLRGHYYG MDV (SEQ ID NO: 244) | 20 | MW039654 | 94.8 |
| HENV-2 | IgG1 | IGHV1-69*01, IGHV1-69D*01 | IGHD3-3*01/02 | IGHJ3*02 | ARRGAWSGYRNWFDF (SEQ ID NO: 245) | 15 | MW039656 | 94.9 |
| HENV-9 | IgG1 | IGHV3-30*18 IGHV3-30-5*01 | IGHD3-3*01, IGHD3-3*02 | IGHJ4*02 | AKDGQSLEWLVY (SEQ ID NO: 246) | 12 | MW039658 | 90.8 |
| HENV-10 | IgG1 | IGHV1-18*01 | IGHD3-16*01 | IGHJ4*02 | AGSYGEYVSFGH (SEQ ID NO: 247) | 12 | MW039660 | 89.7 |
| HENV-18/19 | IgG1 | IGHV1-18*01 | IGHD6-19*01 | IGHJ4*02 | AREPPQYSSGWRQSLYY FDY (SEQ ID NO: 248) | 20 | MW039662 | 91.8 |
| HENV-21 | IgG1 | IGHV1-69*18 | IGHD1-26*01 | IGHJ4*02 | ARANSGSFLDY (SEQ ID NO: 249) | 11 | MW039664 | 88.8 |
| HENV-26 | IgG1 | IGHV3-23*01, IGHV3-23D*01 | IGHD6-13*01 | IGHJ5*02 | AKDGFVGQQLMRRGPWW FDP (SEQ ID NO: 250) | 20 | MW039666 | 90.8 |
| HENV-32 | IgG1 | IGHV1-69*02, IGHV1-69*04 | IGHD3-10*01, IGHD3-10*02 | IGHJ5*02 | ARFRGHNYFDP (SEQ ID NO: 99) | 11 | MW039668 | 80.6 |
| HENV-43 | IgG1 | IGHV4-61*02 | IGHD2-2*01/ *02/*03 | IGHJ6*02 | ARDPPYCSGNICYLYHY ALDV (SEQ ID NO: 251) | 21 | MW039670 | 97.0 |

TABLE S2

Related to FIG. 2. Data collection and refinement statistics for the crystals
of HENV-26/HeV-RBP, HENV-26/NiV-RBP, and HENV-32/HeV-RBP complexes Data collection

| Crystal | HENV-26/HeV-RBP | HENV-26/NiV-RBP | HENV-32/HeV-RBP |
|---------|-----------------|-----------------|-----------------|
| PDB ID | 6OM9 | 6OMD | 6OLW |
| Wave length (Å) | 0.97856 | 0.97856 | 0.97856 |
| Space group | $P22_12_1$ | $P3_22$ | C2 |
| Unit cell dimensions | | | |
| a, b, c (Å) | 70.8, 79.8, 177.1 | 186.7, 186.7, 81.3 | 195.9, 84.5, 122.8 |
| α, β, γ | 90, 90, 90 | 90.0, 90.0, 120.0 | 90.0, 95.9, 90.0 |
| Resolution (Å) | 47.46 – 2.60 | 48.85 – 3.40 | 49.51 – 2.00 |
| Unique reflections | 31674 (4550) | 22696 (3283) | 134705 (19582) |
| Redundancy | 14.8 (15.0) | 3.5 (3.6) | 7.7 (7.6) |
| Completeness (%) | 99.9 (99.8) | 100.0 (100.0) | 100.0 (100.0) |
| $R_{merge}$ (%) | 11.8 (75.7) | 14.1 (51.4) | 8.8 (69.3) |
| I/σ(I) | 16.8 (4.0) | 7.2 (2.1) | 11.7 (2.8) |
| Refinement statistics | | | |
| $R_{factor}$ (%) | 19.7 | 20.8 | 18.3 |
| $R_{free}$ (%) | 24.7 | 25.0 | 22.6 |
| R.m.s.d. (bond) (Å) | 0.0031 | 0.0020 | 0.0086 |
| R.m.s.d. (angle) (deg) | 0.663 | 0.527 | 0.897 |

TABLE S2-continued

Related to FIG. 2. Data collection and refinement statistics for the crystals
of HENV-26/HeV-RBP, HENV-26/NiV-RBP, and HENV-32/HeV-RBP complexes Ramachandran plot

| | | | |
|---|---|---|---|
| Favored (%) | 96.56 | 92.59 | 97.03 |
| Allowed (%) | 3.44 | 7.41 | 3.97 |
| Outliers (%) | 0.00 | 0.00 | 0.00 |

$R_{merger} = \Sigma \Sigma |I_{hkl} - I_{hkl(j)}|/\Sigma I_{hkl}$, where $I_{hkl(j)}$ is the observed intensity and $I_{hkl}$ is the final average intensity.
$R_{work} = \Sigma ||Fobs| - |Fcalc||/\Sigma |Fobs|$ and $R_{free} = \Sigma ||Fobs| - |Fcalc||/\Sigma |Fobs|$, where $R_{free}$ and $R_{work}$ are calculated using a randomly selected test set of 5% of the data and all reflections excluding the 5% test set, respectively. Numbers in parentheses are for the highest resolution shell.

TABLE S3

RMSD values (Å) between Cα atoms of HeV-RBP structures in different binding states. Related to FIG. 5.

| | apo HeV-RBP | HENV-32 + HeV-RBP | ephrinB2 + HeV-RBP | HENV-26 + HeV-RBP | M102.3 + HeV-RBP |
|---|---|---|---|---|---|
| apo HeV-RBP | — | 1.194 (2.925) | 0.649 (1.214) | 0.962 (2.316) | 1.061 (2.676) |
| HENV-32 + HeV-RBP | — | — | 0.982 (2.274) | 0.803 (1.851) | 0.787 (1.555) |
| ephrinB2 + HeV-RBP | — | — | — | 0.656 (1.254) | 0.806 (1.930) |
| HENV-26 + HeV-RBP | — | — | — | — | 0.676 (1.413) |

Note:
RMSD values were calculated with PyMOL (align) for all Cα atoms of corresponding structure pairs.
Values in parenthesis are RMSD values in regions with large structural variations among the structures (aa 191-215, 237-244, 256-264, 580-591).

TABLE S4

Illness and clinical pathology findings in ferret challenge study

| Group | Subject ID | Clinical Illness | Clinical Pathology |
|---|---|---|---|
| Control | C1 | Nasal and ocular discharge (d 6-8); sneezing (d 6); depression (d 7-8); loss of appetite (d 7-8); labor breathing (d 7-8); Hypothermia (d 8); Animal euthanized on day 8 | [b]Lymphopenia (d 5, 7); monocytopenia (d 5, 7), neutrophilia (d 5, 7), thrombocytopenia (d 3-8); hypoalbuminemia (d 7-8); hypoamylasemia (d 7); ALT >2-fold ↑ (d 8); AST >2-fold ↑ (d 8) |
| | C2 | Nasal and ocular discharge (d 6-7); sneezing (d 6-7); depression (d 6-7); loss of appetite (d 6-7); labor breathing (d 7); Hypothermia (d 7); Animal euthanized on day 7 | Lymphopenia (d 5, 7); monocytopenia (d 5, 7), neutrophilia (d 5, 7), thrombocytopenia (d 3-7); hypoalbuminemia (d-7); hypoamylasemia (d 7); AST >2-fold ↑ (d 7). |
| | C3 | Nasal and ocular discharge (d 6-8); depression (d 6-8); loss of appetite (d 6-8); labor breathing (d 7-8); Animal euthanized on day 8 | Lymphopenia (d 5, 7); monocytopenia (d 5, 7), neutrophilia (d 5, 7), thrombocytopenia (d 3-8); hypoalbuminemia (d 7-8); hypoamylasemia (d 7); AST >2-fold ↑ (d 8). |
| HENV-26-treated | HENV-26_A | Fever (d 3, 7); sneezing (d 8); depression (d 7-9) | Monocytosis (d 3, 10); neutrophilia (d 3-28); thrombocytopenia (d 5); BUN >2-fold ↑ (d l0, 14, 21); AST >2-fold ↑ (d 28). |
| | HENV-26 B | Fever (d 3, 7); sneezing (d 8); depression (d 7-9) | Thrombocytopenia (d 3-10); hypoalbuminemia (d 7-10). |
| | HENV-26_C | Fever (d 3, 21); sneezing (d 8); depression (d 9). | Lymphopenia (d 5-7); monocytosis (d 3); neutrophilia (d 5-28); thrombocytopenia (d 3-10); BUN >2-fold ↑ (d l0-28); hypoamylasemia (d 7, 21); AST >2-fold ↑ (d 28). |
| | HENV-26_D | Sneezing (d 8); depression (8, 9). | Lymphopenia (d 3-7); monocytosis (d 5-28); neutrophilia (d 5-28); >2-fold ↑ (d l0-28): ALT >2-fold ↑ (d 7, 21, 28). |
| | HENV-26_E | Fever (d 5); depression (d 9). | Monocytosis (d 5-28); neutrophilia (d 3-28); thrombocytopenia (d 3); BUN >2-fold ↑ (d 7-28); hypoamylasemia (d 7, 14, 21). |
| HENV-32-treated | HENV-32_A | None | Lymphopenia (d 3-7); monocytosis (d 3, 5, 21); neutrophilia (d 5-28); thrombocytopenia (d 3-5); AST >2-fold ↑ (d 28). |
| | HENV-32_B | None | Lymphocytosis (d 3); lymphopenia (d 5 ); neutrophilia (d 5-28); thrombocytopenia (d 3, 5, 14, 21); BUN >2-fold ↑ (d l0); hypoamylasemia (D 10, 28); AST >2-fold ↑ (d 28). |
| | HENV-32_C | None | Monocytosis (d 3-10); neutrophilia (d 3-28); thrombocytopenia (d 3-14); BUN >2-fold ↑ (d l0); hypoamylasemia (d 21); AST >2-fold ↑ (d 28). |
| | HENV-32_D | None | Lymphopenia (d 3, 5); monocytosis (d 3); neutrophilia (d 5-28); thrombocytopenia (d 3, 5); BUN >2-fold ↑ (d 21); hypoamylasemia (d 5, 14, 28); AST >2-fold ↑ (d 28). |
| | HENV-32_E | None | Lymphocytosis (d 14); lymphopenia (d 3-5); monocytosis (d 3-28); neutrophilia (d 3, 7, 10); thrombocytopenia (d 5, 10)); AST >2-fold ↑ (d 28). |

Abbreviations: ALT, alanine aminotransferase; AST, aspartate aminotransferase; BUN, blood urea nitrogen
[a]Fever was defined as a temperature more than 10° C. over baseline or at least 1.5° C. over baseline and ≥40° C.
[b]Days after NiV challenge are in parentheses. Lymphopenia and thrombocytopenia are defined by a ≥35% drop in numbers of lymphocytes and platelets, respectively. Leukocytosis, monocytosis, and neutrophilia are defined by a 2-fold or greater increase in numbers of white blood cells over base line. Hypoalbuminemia is defined by a ≥25% decrease in levels of albumin. Hypoamylasemia is defined by a ≥25% decrease in levels of serum amylase.

TABLE 1

NUCLEOTIDE SEQUENCES FOR ANTIBODY VARIABLE REGIONS

| Clone | SEQ ID NO: | Chain | Variable Sequence Region |
|-------|-----------|-------|--------------------------|
| HENV-32 | 1 | heavy | CCAGGTCCAGCTGGTGCAGTCTGGGGCTGAGGTGAAGAAGCCTGGGTCCTCGGTGAAGGTCTCCTGCAAAGTTTCTG<br>GAGGCATCTTCAACAGGGAGACCATCAACTGGGTGCGACAGGCCCCTGGACAAGGGCTTGAGTGGATGGGAAGGAT<br>CACCCCTATTGTTGACGTCCCAAATTACCCTCGGAAGTTCCGAGGCAGAGTCACCATTACCGCGGACAAATCCACGAGT<br>ACAGTTTACATGGAGCTGAGCGGCCTGAGATTTGAGGACACGGCCATCTATTTCTGTGCGCGTTTTCGGGGACACAAC<br>TACTTCGACCCCTGGGGCCAGGGAACCCTGGTCACCGTCTCCTCAG |
| | 2 | light | TCCTATGTGCTGACTCAGCCACCCTCGGTGTCAGTGGCCCCAGGACAGACGGCCAGGATTACCTGTGGGGGAAACAAC<br>ATTGGGGGTAAAAGTGTGCACTGGTACCAGCAGAAGCCAGGCCAGGCCCCTGTCTTGGTCGTCTATGATGACCGCGA<br>CCGGCCCTCAGGGATCCCTGAGCGATTCTCTGGCTCCAACTCTGGGGACACGGCGTCCCTGACGATCAGCAGGGTCGA<br>TGCCGGGGATGAGGCCGACTATTTCTGTCAGGTGTGGGATAATGCTAGTGATGAAGCGGTATTCGGCGGAGGGACGA<br>AGCTGACCGTCCTGG |
| HENV-58 | 3 | heavy | CAGGTCCAGCTGGTGCAGTCTGGGGCTGAGGTGAAGAAGCCTGGGTCCTCGGTGAAGGTCTCCTGTAAGGCTTCTGG<br>AGGCACCTTCAGCAACTATGTCATCAGCTGGGTGCGACAGGCCCCTGGACAAGGGTTTGAGTGGATGGGAAGGATCA<br>TCCCTATGATTGGAATCTCAAACTACGCACAGAAGTTCCAGGACAGAGTCACGATTACCGCGGACAAGGACGAGTCCA<br>CGACCACAGCCTACATGGAGTTGCGCGGCCTGAGATCTGAGGACACGGCCATGTATTATTGTGCGAGTAGTACGGTG<br>ACTGAGGTAGGGGCCTGGGGCCAGGGAACCCTGGTCACCGTCTCCTCA |
| | 4 | light | GCCATCCAGTTGACCCAGTCCCCATCCTCCCTGTCTGCATCTATAGGAGACAGAGTCACCATCACTTGCCGGGCAAGTC<br>AGGGCATTAGCAGTGCTTTAGCCTGGTTTCAGCAGAAACCAGGGAAACCTCCTATCCTCCTGATCTATGATGCCTCCAG<br>TCTGGAAAGTGGGGTCCCAGCAAGGTTCAGCGGCAGTGGATCTGGGACAGATTTCACTCTCACCATCAGCAGCCTGCA<br>GCCTGAAGATTTTGCAACTTACTACTGTCAACAATTTTATAATCACCCTCTCACTTTCGGCCCTGGGACCAAAGTGGATA<br>TCAAA |
| HENV-72 | 5 | heavy | GAGGTGCAGCTGGTGGAGTCTGGGGGAGGCCTGGTCAAGCCTGGGGGGTCCCTGAGACTCTCCTGTGCAGCCTCTGG<br>ATTCACAATCATTAACTATAGTTTGAGCTGGGTCCGCCAGGCTCCAGGGAAGGGGCTGGAGTGGGTCTCATCCATTAG<br>TGGCAGTAGTGATTACATATACTACGGAGACTCAGTGAAGGGCCGATTCACCATCTCCAGAGACAACGCCAAGAACTC<br>ACTGTATCTGCAAATGAACAGCCTGAGAGCCGAGGACGCGGCTGTATATTACTGTGCGAGAGAAAGAACTGGTTTTTT<br>CAGCCCACCCTCATACTTAATGGACGTCTGGGGCCAAGGGACCACGGTCACCGTCTCCTCA |
| | 6 | light | GCCATCCAGATGACCCAGTCTCCATCCTCCCTGTCTGCATCTGTAGGAGACAGAGTCACCATCACTTGCCGGGCAAGTC<br>AGGGCATTAGAAATGATTTAGGCTGGTATCAACAGAAACCAGGGAAAGCCCCTAAGCTCCTGATCTATGCTGCTTCCA<br>CTTTACAAAGTGGGGTCCCATCAAGGTTCAGCGGCAGTGGATCTGGCACAGATTTCACTCTCACCATCAGCAGCCTGC<br>AGCCTGAAGATTTTGCAACTTATTACTGTCTACAAGATTACAATTACCCTCGGACGTTCGGCCAGGGGACCAAGGTGG<br>AAATCAAA |
| HENV-78 | 7 | heavy | CAGGTTCAGCTGCTACAGTCTGGAGGTGAGGTGAAGAAGCCTGGGGCCTCAGTGAAGGTCTCCTGCAAGGCTACTGA<br>TAACACCTTAACCACCTATGGTCTCAGTTGGGTGCGACAGGCCCCTGGACAAGGGCTTGAGTGGATGGGGATGGGTCA<br>GCGCTTACAATGGTCACCCAAACTATGCACAGAAGTTCCAGGGCAGAGTCACCATGACCACAGACACGTCCACGAGCA<br>CAGCCTACATGGAGCTGCGGAGCCTGACTTCTGACGACACGGCCGTCTATTTCTGTGCGAGAGGTAGCAGTGCCTGGA<br>ATCCCTGGGGCCAAGGGACACTGGTCACCGTCTCTTCA |
| | 8 | light | GACATCCAGATGACCCAGTCTCCTTCCACCCTGTCTGCATCTGTAGGAGACAGAGTCACCATCACTTGCCGGGCCAGTC<br>AGAGTATTACTAGCTGGTTGGCCTGGTATCAGCAGAAACCAGGGAAAGCCCCTAAGCTCCTGATCTATAAGGCGTCTA<br>GTTTAGAAGGTGGGGTCCCATCAAGGTTCAGCGGCAGTGGATCTGGGACAGAATTCACTCTCACCATCAGCAGCCTGC<br>AGCCTGATGATCTTGCAACTTATTACTGCCAACAGTATAGCAGTTATCCGGTCACTTTCGGCGGAGGGACCAAGGTGG<br>AGATCAGA |
| HENV-83 | 9 | heavy | CAGGTGCAATTGGTGGAGTCGGGGGGAGGCGTGGTCCAGCCTGGGGGGTCCCTGAGACTCTCCTGTGCAGCCTCTGG<br>ATTCACCTTCCGTAGCTATTCTATGAACTGGGTCCGCCAGGCTCCAGGCAAGGGGCCGGAGTGGATGGCAGTTATATC<br>CTATGATGGAAGTAATAAATACTACACAGACTCCGTGAAGGGCCGATTCACCATCTCCAGAGACAACTCCAAGAACAC<br>GCTGAATCTCCAAATGAACAGCCTGACATCTGAGGACACGGCTATATATTACTGCGCGAGATTCCGGGGGGGGGGTC<br>GAATAGCAGCTCGTCCGGACGACTACGGTATGGACGTCTGGGGCCAGGGGACCACGGTCACCGTCTCCACA |
| | 10 | light | GACATCCAGATGACCCAGTCTCCATCCTCCCTGTCTGCATCTGTAGGAGACAGAGTCACCATCACTTGCCGGGCAAGTG<br>AGAGCGTCATTACGTATTTAAATTGGTATCAGCAGAAACCAGGGAAAGCCCCTAAGCTCCTGATCTATGGGCATCCA<br>CTTTGGAAAGTGGGGTCCCATCGAGGTTCAGTGGCAGTGGATCTGGGACAGTCTTCACTCTAACCATCAGCAGTCTGC<br>AACCTGAAGACATTGCAACTTACTACTGTCAACAGAGTTACAATATGTCCCCGTACACTTTTGGCCAGGGGACCAAGCT<br>GGAGATCAAA |
| HENV-93 | 11 | heavy | CAGGTGCTTCTGGTGCAGTCTGGGGCTGAGGTGAGGAAGCCTGGGGCCTCAGTGAAGGTCTCCTGCAGGGCTTCTGG<br>ATACACCTTCACCGACTACTATATGCACTGGGTGCGACAGGCCCCTGGACAAGGGCTTGAGTGGATGGGGATGGATCA<br>ACCCTAACAGTGGTGCCACAAAGTACGCACAGAAGTTTCAGGGCAGGGTCACCTTGACCAGGGACACGTCCATCAACA<br>CAGCCTACATGGAGCTCAGCGGGCTGCGATCTGTCGACACGGCCGTGTTTTACTGTGCGAGTGTTCCCCCTAGTGGTTT<br>TTTCTATTGGGGCTCTGACTACTGGGGCCAGGGAACCCTGGTCACCGTCTCGTCA |
| | | light | Not Available |
| HENV-98 | 12 | heavy | GCGGTCCAGCTGGTGGAGTCTGGGGGAGGCCTGGTCCAGCCTGGGGGGTCCCTGAGACTCTCCTGTGAAGCCTCTGG<br>ATTCACCTTTAGTGGCTATTGGATGAGCTGGGTCCGCCAGGCTCCAGGGAAGGGGCTGGAGTGGGTGGCCAACATAA<br>AGGGGAGATGGAAGTGAAAAATACTATGTGGACTCTGTGAAGGGCCGATTCACCATCTTCAGAGACAACGCCAAGACC<br>TCACTGTATCTGCAAGTGAACAGCCTGAGAGCCGAGGACACGGCTGTCTATTACTGTGCGAGAGAGAGGCACTTCTTA<br>GCAGCTCGTCCTGGTTACTACATCTACAGCGGTCTGGACGTCTGGGGCCAGGGAACCACCGTCACCGTCTCCTCA |
| | 13 | light | GACATCCAGATGACCCAGTCTCCATCCTCCCTGTCTGCATCTGTAGGAGACAGAGTCACCATCACTTGCCGGGCAAGTC<br>AGAGCATTGACAACTATTTAAATTGGTATCAGCAGAAACAGGGAAGGTCCCTAAACTCCTGATCTATGCTGCATCCAA<br>TTTGCAAAGTGGGGTCCCATCAAGGTTCAGTGGCGGTGGATCTGGGACAGATTTCACTCTCACCATCAGCAGTCTGCA<br>ACCTGACGATTTTGCAACCTACTACTGTCAACAGAGTTTCGGTACCCCTCGAACGTTCGGCCAGGGGACCAGGGTGGA<br>AATCAAA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| HENV-99 | 14 | heavy | CAGGTGCTTCTGGTGCAGTCTGGGGCTGAGGTGAGGAAGCCTGGGGCCTCAGTGAAGGTCTCCTGCAGGGCTTCTGG<br>ATACACCTTCACCGACTACTATATGCACTGGGTGCGACAGGCCCCTGGACAAGGGCTTGAGTGGATGGGATGGATCA<br>ACCCTAACAGTGGTGCCACAAAGTACGCACAGAAGTTTCAGGGCAGGGTCACCTTGACCAGGGACACGTCCATCAACA<br>CAGCCTACATGGAGCTCAGCGGGCTGCGATCTGTCGACACGGCCGTGTTTTACTGTGCGAGTGTTCCCCCTAGTGGTTT<br>TTTCTATTGGGGCTCTGACTACTGGGGCCAGGGAACCCTGGTCACCGTCTCGTCA |
|  | 15 | light | GATGTTGTGTTGACTCAGTCTCCGCTCTCCCTGCCCGTCACCCTTGGACAGCCGGCCTCCATCTCCTGTAGGTCTAGTCA<br>AAGCCTCGTATACAGTGATGGGACCACCTACTTGAATTGGTTTCAGCAGAGGCCAGGCCAATCTCCAAGGCGCCTAAT<br>TTATAAGGTTTCTTATCGGGACTCTGGGGTCCCAGACAGATTCAGTGGCAGTGGGTCAGGCACTGATTTCACACTGGA<br>AATCAGCAGGGTGGAGGCTGAGGATGTTGGGATTTATTACTGCATGCACGGTACACACTGGGAAACGTGGACGTTCG<br>GCCAAGGGACCAAGGTGGAAATCAAA |
| HENV-100 | 16 | heavy | CAGGTGCAGCTGGTGCAGTCTGGGGCTGAGGTTAAGAAGCCTGGGGCCTCAGTGAAGGTTTCCTGCAAGGCATCAGG<br>ATACACCTTCACGAGCTACTATATTAACTGGGTTCGACAGGCCCCTGGACAAGGGCTTGAGTGGGTAGGAACAATCAA<br>CCCTAGTGGAGGTAGCACAACCTACGCACAGAAGTTCCAGGGCAGAGTCACCGTGACCAGGGACACGTCCACGAGCA<br>CAGTCTACATGGACCTGAGCGGCCTGAGATCGGGGGACACGGCCGTGTATTACTGTGCGAGAGATCGTAAGGGGTTA<br>GCTGCTACTCCCGTATATTCCGACTACTACTACGGTATGGACGTCTGGGGCCAGGGGACCACGGTCACCGTCTCCTCA |
|  | 17 | light | GAAATTGTGTTGACACAGTCTCCAGCCACCCTGTCTTTGTCTCCAGGGGAAAGAGCCACCCTCTCCTGCAGGGCCAGTC<br>AGAGTGTTAGTAGCTTCTTAGCCTGGTACCAACAGAAACCTGGCCAGGCTCCCAGGCTCCTCATCTCTGATGCATCCAA<br>AAGGGCCACTGGCATCCCAGCCAGGTTCAGTGGCAGTGGGTCTGGGACGGACTTCTCTCTCACCATCAGCAGCCTAGA<br>GGCTGAAGATTTTGCAGTTTATTACTGTCAGCAGAGTACCAACTGGCGGATCACCTTCGGCCAAGGGACACGACTGGA<br>GCTTAAA |
| HENV-103 | 18 | heavy | CAGGTGCAGCTGCAGGGGTCGGGCCCAGGACTGGTGAAGCCTTCACAGACCCTGTCCCTCACCTGCTCTGTCTCTGGT<br>GGCTCCGTCAGCAGAAGTGGCTACTACTGGGGCTGGATCCGGCAGCACCCAGGGAAGGGCCTGGAGTGTATTGGGT<br>ACATCTATTACAGTGGGATCACCTACTACAACCCGTCCCTCAGCGGTCGACTTACCATCTCAGTAGACACGTCTAAGAA<br>CCAGTTCTCCCTGGAGCTGAGCTCTGTGACTGCCGCGGACACGGCCGTGTATTACTGCGCGAGAGTTTGGTTGGGGG<br>GTGGTGTCTTTGACTTCTGGGGCCAGGGATCCCTGGTCACCGTCTCCTCA |
|  | 19 | light | GAAATAGTGATGACGCAGTCTCCAGCCACCCTGTCTGTGTCTCCAGGGGAAAGAGCCACCCTCTCCTGCAGGGCCAGT<br>CAGAGTGTTAGCAGCAACTTAGCCTGGTATCAGCAGAAACCTGGCCAGGCTCCCAGGCTCCTCATCTATGATGCATCC<br>ACCAGGGCCACTGGTATCCCAGCCAGGTTCAGTGGCAGTGGGTCTGGGACAGAGTTCACTCTCACCATCAGCAGCCTG<br>CAGTCTGAAGATTTTGCAGTTTATTACTGTCAGCAGTATAATGACTGGCGGACGTTCGGCCGAGGGACCAAGGTGGAA<br>ATGAGA |
| HENV-107 |  | heavy<br>light | Not Available<br>Not Available |
| HENV-113 | 20 | heavy | CAGGTGCAGCTGATGGAGTCTGGGGGAGGCGTGGTCCAGCCTGGGAGGTCCCTGAGACTCTCCTGTTCAGCCTCTGG<br>ATTCACCTTCAGTAACTATGCTTTGCACTGGGTCCGCCAGGCTCCAGGCAAGGGGCTGGAGTGGCTTGCATTTATTTCA<br>TATGATGGAAGTTTTAAATATTACGCAGACTCTGTGAAGGGCCGATTCACCGTCTCCCGAGACGATTCTAGGAATACTC<br>TATATCTCCAAATGAGCAGCCTGAGACCTGAGGACACGGCTGTCTATTACTGTACGAGAGATGATGATCCCCCCGTTG<br>AAAACTTCCAGATCTGGGGCCAGGGTACCCTGGTCACCGTCTCCTCA |
|  |  | light |  |
| HENV-114 | 21 | heavy | CAGGTGCAGCTGCAGGAGTCGGGCCCAGGACTGGTGAAGCCTTCACAGACCCTGTCCCTCACCTGTTCTGTCTCTGGT<br>GACTCCATCAGCAGTGGTACTCACTACTGGAGCTGGATCCGGCAGCCCGCCGGGAAGGGACTGGAGTGGATTGGGCG<br>TATCTATGCCACTGGGAACAGCAACTACAACCCCTCCTTCAGGAGTCGAGTCACCATATCAGTCGACACGTCCAAGAAC<br>CAATTCTCCCTGAAGCTGAGCTCTGTGACCGCCGCAGACACGGCCGTCTATTACTGTGTGAGAGATGAAGCAGTGGCT<br>GATATGGCTGTCGAAAACTATTACGGTATGGACGTCTGGGGCCAAGGGACCTCGGTCACCGTCTCCGCA |
|  | 22 | light | GAAATTGTGTTGACACAGTCTCCAGCCACCCTGTCTTTGTCTCCAGGGGAAAGAGCCACCCTCTCCTGCAGGGCCAGTC<br>AGACGATTAGCAGCTACTTAGTCTGGTACCAACAGAAGCCTGGCCAGGCTCCCAGGCCCCTCATCTATGATGCATCCAT<br>CAGGGCCACTGGCATCCCAGCCAGGTTCAGTGGCAGTGGGTCTGGGACAGACTTCACTCTCACCATCAGCAGCCTAGA<br>GCCTGAAGATTTTGCAGTTTATTACTGTCAGCAGCGTTACAACTGGCCTCGGACGTTCGGCCAAGGGACCAAGGTGGA<br>AATCAAA |
| HENV-117 | 23 | heavy | CAGGTGCAGCTACAGCAGTGGGGCGCAGGACTGTTGAAGCCTTCGGAGACCCTGTCCCTCACCTGCGATTGTCTGGT<br>GGGTCCTTCACTAATTACTACTGGACCTGGATACGCCACCTCCCAGGGAAGGGGCTGGAGTGGCTTGGAGAAATCAAT<br>CATAGTGGAAGAACCAACTACAGCCCGTCCCTCAAGAGTCGAGTCACCATATCAGTAGACACGTCCAAGAACCAGTTC<br>TCCCTGAGGCTGAGTTCTGTGACCGCCGCGGACACGGCTGTATATTATTGTGCGAGAGACATCCGTAAGTTGGCCCCA<br>AAACCTCATTCTTACGACCTCTATTACGGTATGGACGTCTGGGGCCAAGGGACCACGGTCACCGTCTCCTCA |
|  | 24 | light | GAAATTGTGTTGACGCAGTCTCCAGGCACCCTGTCTTTGTCTCCAGGGGAAAGAGCCACCCTCTCCTGCAGGGCCAGT<br>CAGAGTGTTGGTAGCAACTATTTAACCTGGTATCAGCAAAAACCTGGCCAGCCTCCCAGGCTCCTCATCTATGGTGCAT<br>CCAACCGGGCCGCTGGCATCCCAGCAGGTTCAGTGGCAGTGGGTCTGGGACAGACTTCACTCTCACCATCAGCAGAC<br>TGGAGCCTGAAGATTTTGCTGTTTATTACTGTCAGCAATATGAGACCTCATCCCGGACGTTCGGCCAAGGGACCAAGG<br>TGGACATCAGA |
| HENV-122 | 25 | heavy | GAGGTGCAGCTGTTGGAGTCTGGGGGAGGCCTGGTACAGCCTGGGGGGTCCCTGAGACTCTCCTGTGCAGCCTCTGG<br>ATTCACCTTTAGCACCAATGCCATGAGCTGGGTCCGCCAGGCTCCAGGGAAGGGGCTGGAGTGGGTCTCTACTGTTAG<br>TGGTAGTGGGTGCACACCCAAATTATGGAGACTCCGTGAAGGGCCGGTTCACCATCTCCAGAGTCAATTCCAAGAACAC<br>GCTATTTCTACAAATGAGCAGCCTGAGAGCCGAGGACACGGCCATATATTACTGTGCGAGAGTTTCCACGGTTACAGT<br>TGGGGGACACATACCCCGGGGCTACTACTTTGACTACTGGGGCCAGGGAACCCTGGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 26 | light | GAAATTCTGTTGACGCAGTCTCCAGGCACCCTGTCTTTGTCTCCAGGGGAAAGAGCCACCCTCTCCTGCAGGGCCAGTC AGAGTGCTAGCAGCAGCTACTTAGCCTGGTACCAACAGAAACCTGGCCAGGCTCCCAGGCTCCTCATCTATGGTGCAT CCACCAGGGCCACTGGCATCCCAGACAGGTTCAGTGGCAGTGGGTCTGGGACAGAGTTCACTCTCACAATCAGCAGA CTGGAGTCTGAAGATTTTGCAGTGTATTACTGTCATCATTATGGTAGTTCACGGACGTTCGGCCAAGGGACCAAGGTG GAGGTCAAA |
| HENV-137 | 27 | heavy | GAGGTGCAGCTGGTGGAGTCTGGGGGAGGCTTGGTCCAGCCTCGGGGGTCCCTGAGACTCTCCTGTGCAGCCTCTGG ATTCACCTTTAGTGGCTATTGGATGAGCTGGGTCCGCCAGGCTCCAGGGAAGGGGCTGGAGTGGGTGGCCAAGATAA AGAAAGATGGAAGTGAGAAAACCTATGTGGACTCTGTGAAGGGCCGATTCACCATCTCCAGAGACAACGCCAAGGAC TCATTGTATCTGCAAATGAACAGCCTGAGAGCCGAGGACACGGCTGTCTATTACTGTGCGAGAGAGCGGTTGTTAGTA CCAGCTGCTATAGTTGGATTGGACTACTACACGCTATGGTCTGGGGCCAAGGGACCACGGTCACCGTCTCCTCA |
| | 28 | light | GACATCCAGATGACCCAGTCTCCATCCTCCCTGTCTGCATCTGTAGGAGACAGAGTCACCATCACTTGCCGGGCAAGTC AGAACATGAGCACCTATTTAAATTGGTATCAGCAGAAACCAGGGAAAGCCCCTAAGTTCCTGATCTATGGAGCATCCA GATTACAGAATGGGGTCCCATCAAGGTTCAGTGGCGGTGGATCTGGGACAGATTTCACTCTCACCATCAGCAGTCTGC AACCTGAAGATTTTGCAACTTACTACTGTCAACAGAGTTACAATATCCCGATCACCTTCGGCCAAGGGACACGACTGGA GATTAAA |
| HENV-141 | 29 | heavy | CAGGTCCAACTGGTGCAATCTGGGGCTGAGGTGAAGAAGCCTGGGTCCTCGGTGAAGGTCTCCTGTAAGGCTTCTGG AGGCACCTTCAGCAGCTATACTATCTATCAGCTGGGTACGGCAGGCCCCTGGACAAGGGCTTGAGTGGATGGGAAGGATCA TCCCTATTTCTGGTATAACAAACTACGCACAGAAGTTCCAGGGCAGAGTCACGATTACCGCGGACAAATCCACGAGCA CAGCCTACATGGAGCTGAGCAGCCTGAGATCTGAGGACACGGCCGTGTATTACTGTGCGAAAGATTGTTACTATGGTT CAGGGACTTATTATGGTTGCCGTGCGGATTACCAGTGGCACCACACTATGGACGTCTGGGGCCAGGGGACCACGGTC ACCGTCTCCTCA |
| | 30 | light | GACATCCAGATGACCCAGTCTCCATCCTCCCTGTCTGCATCTGTAGGAGACAGAGTCACCATCACTTGCCGGGCAAGTC AGGGCATTAGAAATGATTTAGGCTGGTTTCAGCAGAAACAGGGGAAAGCCCCTAAGCGCCTGATCTATGCTGCTTCCA GTTTGCAAAGTGGGGTCCCATCAAGGTTCAGCGGCAGTGGATCTGGGACAGAATTCACTCTCACAATCAGCAGCCTGC AGCCTGAAGATTTTGCAACTTATTTCTGTCTACAGCATAATACTTACCCTCTGACGTTCGGCCAAGGGACCAAGGTGGA AATCAAA |
| HENV-142 | 31 | heavy | CAGGTGCGGCTGCAGGAGTCGGGCCCAAGACTGGTGAAGCCTTCACAGACCCTGTCCCTCACCTGCACTGTCTCTGGT GGCTCCATCAGCAGTCGGGACTACTACTGGAGCTGGATCCGCCAGCACCCAGGGAAGGGCCTGGAGTGGATTGGCTA CATCTATTACAGTGGGGACCACCTACTACAACCCGTCCCTCGAGAGTCGAGTTACCCTCTCTCTCGACACGTCTAAGAAC CAGTTCTCCCTGGACCTGACCTCTGTGACTGCCGCGGACACGGCCGTCTATCACTGCGCGAGAGTTTGGTTGGGGGGT GGTGTCTTTGACTTCTGGGGCCAGGGAACCCTGGTCACCGTCTCCGCA |
| | 32 | light | GAAATAGTGATGACGCAGTCTCCAGACACCCTGTCTGTGTCTCCAGGGGAAAGAGCCACCCTCTCCTGCAGGGCCAGT CACAGTGTTACCACCAACTTAGCCTGGTACCAGCAGAGACCTGGCCAGGCTCCCAGGCTCCTCATTTTTGATGCATCCA CCAGGGCCACTGGTATCCCAGCCAGGTTCAGTGGCAGTGGGTCTGGGACAGAGTTCACTCTCACCATCGGCAGCCTAC AGTCTGAAGATTTTGCAGTTTATTACTGTCAACAATACAATGACGGGCGACGTTCGGCCAAGGGACCAAGGTGGAA ATCAAA |
| HENV-150 | 33 | heavy | GAGGTGCAGCTGTTGGAGTCTGGGGGAGGCTTGGTACAGCCTGGGGGGTCCCTGAGACTCTCCTGTGCAGCCTCTGG ATTCACCTTTAGCAGTAGTGCCATGAGCTGGGTCCGCCAGACTCCAGGGAAGGGGCTGGAGTGGGTCTCAACTATTAG TGGTAGTGGTGCTAACACATACTACGCAGCCTCCGTGAAGGGCCGGTTCCCCATCTCCAGAGACAATTCCAAGAACAC ACTCTTTCTGCAAATGAACAGCCTGAGAGCCGAGGACACGGCCGTATATTACTGTGCGAAAGTTTCCACGGTTACATTT GGGGGACACGTACCCCGGGGCTCCTACTTTGACTACTGGGGCCAGGGAACCCAGGTCACCGTCTCCTCA |
| | 34 | light | TCCTATGTGCTGACTCAGCCACCCTCGGTGTCAGTGGCCCCAGGACAGACGGCCAGGATTCCCTGTGGGGGAAACAAC ATTGGAAGTAAAAGTGTGCACTGGTACCAGCAGAAGCCAGGCCAGGCCCCTGTGCTGGTCGTCTATGATGAGAACGA CCGGCCCTCAGGGATCCCTGAGCGATTCTCTGCTTCCAAATCTGGGAACACGGCCACCCTGACCATCAGCAGGGTCGA AGCCGGGGATGAGGCCGACTATTACTGTCAGGTGTGGGATAGTCGTAGTGATCATTATGTCTTCGGAACTGGGACCA AGGTCACCGTCCTC |
| HENV-170 | 35 | heavy | GAGGTGCAGCTGTTGGAGTCTGGGGGAGGCTTGGTACAGCCTGGGGGGTCCCTGAGACTCTCCTGTGCAGCCTCTGG ATTCACCTTTAGCAGCTATACCATGAGCTGGGTCCGCCAGGCTCCAGGGAAGGGGCTGGAGTGGGTCTCCGGTATTAG TGGTAGTGGTGGTAACACATACTACGCAGGCTCCGTGAAGGGCCGGTTCACCATCTCCAGAGACAATTCCAAGAACAC GCTGTATCTGCAAATGAACAGCCTGAGAGCCGAGGACACGGCCGTATATTACTGTGCGAAAGTGGGTATACAGGTC AACAGCTTATGCGTCGAGGACCCTGGTGGTTCGACCCCTGGGGCCAGGGAACCCTGGTCACCGTCTCCTCA |
| | 36 | light | TCCTATGTGCTGACTCAGCCACCCTCGGTGTCAGTGGCCCCAGGACAGACGGCCAGGATTACCTGTGGGGGAAACAAC ATTGGAAGTAAAAGTGTGCACTGGTACCAGCAGAAGCCAGGCCAGGCCCCTGTGCTGGTCGTCTATGATGATAGCGA CCGGCCCTCAGGGATCCCTGAGCGATTCTCTGGCTCCAAGTCTGGGAACACGGCCACCCTGACCATCAGCAGGGTCGA AGCCGGGGATGAGGCCGATTATTACTGTCAGGTGTGGGATAGTAGTAGTGATCATGTAGTATTCGGCGGAGGGACCA AGCTGACCGTCCTA |
| HENV-184 | 37 | heavy | CAGGTGCAGCTGGTACAATCTGGGACTGAGGTGAAGAACCCTGGGTCCTCGGTGAAGGTCTCCTGCAAGGCTTCTGG AGGCACTTTCAGCGGCTTTGGTATCAGCTGGGTGCGACAGGCCCCTGGACAAGGCCTTGAGTGGATGGGAGGGGTCC TCCCTATTTTTGGTTCACCAAACTACGCACAGAAGTTCCAGGGCAGAGTCACGATTACCGCGGACGAATCCACGGGCA CAGCCTACATGGATCTGAGCAGCCTGAGATCTGACGACACGGCCATGTATTACTGTGCGAGAGATCAGTCAGGAGGC TTCTTTGACTACTGGGGCCAGGGAACCCTGGTCATCGTCTCCTCC |
| | 38 | light | GAAATTGTGTTGACACAGTCTCCAGCCACCCTGTCTTTGTCTCCAGGGGAAAGAGCCACCCTCTCCTGCAGGGCCAGTC AGAGTGTTAGCAGCAACTTGGCCTGGTACCAACAAAAACCTGGCCAGGCTCCCAGGCTCCTCATCTATGATGCATCCG ACAGGGCCACTGGCGTCCCAGCCAGGTTCAGTGGCAGTGGGTCTGGGACAGACTTCACTCTCACCATCAGCAGCCTAG AGCCTGAGGATTTTGCACTTTATTACTGTCAGCAGCGTTACAACTGGCGGGTCACCTTCGGCCAGGGGACACGACTGG AGATTAAA |

TABLE 1-continued

NUCLEOTIDE SEQUENCES FOR ANTIBODY VARIABLE REGIONS

| Clone | SEQ ID NO: | Chain | Variable Sequence Region |
|-------|------------|-------|--------------------------|
| HENV-188 | 39 | heavy | CAGGTGCAGGTGGTGGAGTCTGGGGGAGGCGTGGTCCACCCTGGGCGGTCCCTGCGACTCTCCTGTGCAGGCTCTGG<br>ATTCATCTTCAATAACTATGCTTTTCACTGGGTCCGCCAGGCTCCAGGCGGGGGGCTGGAGTGGATGGCCTATATTTCA<br>TATGATGGGAGGTATAAATACTACGCAGCCTCCGTGAGGGGCCGGTTCACCATCTCCAGAGACGATTCCAAGAACACC<br>CTGTATCTGCAAATGTCCAGCCTGAGAACTGAGGACACGGCTCTGTATTACTGTGCGATCTCGGACTACGCTGAACCCC<br>TTGACAACTGGGGCCAAGGAACCCTGGTCACCGTCTCCTCA |
| | 40 | light | CAAATTGTGTTGACACAGTCTCCAGCCACCCTGTCTTTGTCTCCAGGGGACAGAGCCACCCTCTCCTGCGGGCCAGTC<br>AGAGTGTTAGCAGCAACGTAGCCTGGTACCAACAGAAACCTGGCCAGGCTCCCAGGCTCCTCATCTATAATGTATCCA<br>ACAGGGCCACTGGCATCCCAGCCAGGTTCAGTGGCAGTGGGTCTGGGACAGACTTCACTCTCACCATCAGCAGCCTAG<br>AGCCTGAAGATTTTGCAGTTTATTACTGTCACCAGCGTACCAACTGGCCCCTCACTTTCGGCGGAGGGACCAAGGTGG<br>AGATCAAA |
| HENV-202 | 41 | heavy | CAGGGGCAGCTACAGCAGTGGGGCGCAGGACTGTTGAAGCCTTCGGAGACCCTGTCCCTCACCTGCGGTGTCTATAG<br>TGGGTCCTTCAGTGGTTACTACTGGAGCTGGATCCGCCAGCCCCCAGGGAAGGGGCTGGAGTGGATCGGGGAAATCA<br>ATCATAGTGGAAGAACAGACTACAACCCGTCCCTCAAGAGTCGAGTCACCATGTCAGTGGACACGTCCAAGAACCAGT<br>TCTCCCTGAGGCTGAGCTCTGTGACCGCCGCAGACACGGCTGTATATTTCTGTGCGAGAGCGACCCCCCCGACACTAT<br>GGGTCAGGGACTTCTTATGGGGCTACTTTGACTCCTGGGGCCAGGGAACCCTGGTCTCCGTCTCCTCA |
| | 42 | light | GACATCGTGATGACCCAGTCTCCTGACTCCCTGGCTGTGTCTCTGGGCGAGAGGGCCACCATCAACTGCAAGTCCAGC<br>CAGAGTGTCTTATACACCTCCAACAATAAGAACTACTTAGCTTGGTACCAGCAGAAACCAGGACAGCCTCCTAAACTAC<br>TCATTTTCTGGGCATCTACCCGGGAATCCGGGGTCCCTGACCGATTCAGTGGCAGCGGGTCTGGGACAGATTTCACTC<br>TCACCATCAGCAGCCTGCAGGCTGAAGATGTGGCAGTTTATTACTGTCAGCAATATTATACTACTCCTAAGACTTTCGG<br>CCCTGGGACCAAAGTGGATCTCAAA |
| HENV-222 | 43 | heavy | CAGGTGCAGCTGCAGGAGTCGGGCCCAGGACTGGTGAAGCCTTCGGAGACCCTGTCCCTCACCTGCACTGTCTCTGGT<br>GGCTCCATCGATAGTTACTACTGGAGTTGGATCCGGCAGCCCGCCGGGAAGGGACTGGAGTGGATTGGGCGTATCTA<br>TCCCAGTGGGACCACCAACTACAACCCTCCCTCAAGAGTCGAGTCACCATGTCAGTAGACACGTCCAAGAACCAGTTC<br>TCCCTGAAGGTGACCTCTGTGACCGCCGCGGACACGGCCGTGTATTACTGTGCGAGGATGCAAACCGGATTTGGCAGC<br>AGCTTGTTCTTCGTTCCATACTTTGACAACTGGGGCCAGGGAACCCTGGTCACCGTCTCCTCA |
| | 44 | light | GAAATTGTGTTGACGCAGTCTCCAGCCACCCTGTCTTTGTCTCCAGGGGAAAGAGCCACCCTCTCCTGCAGGGCCAGTC<br>AGAGTGTTAGCAGCTACTTAGCCTGGTACCAACAGAAACCTGGCCAGGCTCCCAGGCTCCTCATCTATGATGCATCCAA<br>CAGGGCCACTGGCATCCCAGCCAGGTTCAGTGGCAGTGGGTCTGGGACAGACTTCACTCTCACCATCAGCAGCCTAGA<br>GCCTGAAGATTTTGCAGTTTATTACTGTCAGCAGCGTGGCAACTGGCCGCTCACTTTCGGCGGAGGGACCAAGGTGGA<br>GATCAAA |
| HENV-226 | 45 | heavy | GAAGAGCGACTGGTGCAGTCTGGGGGAGGCTTGGCACAGCCTGGACAGTCTCTGAGACTCTCCTGTGCAGGCTTTGG<br>ATTCACCTTCACTAGATACGAAATGAATTGGGTCCGCCAGGCTCCAGGGAAGGGGCTGGAGTGGATTGCGCACATAA<br>GTACTAGGGGCGATACCATTAGCTACGCGGACTCTGTGAAGGGCCGAGCCACCATCTCCAGAGATGACACCAACAACT<br>CACTGGATCTGCAGATGGACAGCCTGAGAGCCGAGGACACGGCCATTTATTTTTGTGCGAGAGATAGGGGGTCTCTTT<br>CAACTCGACCTCCAGACTCATATCACTACTACTATCACGGTATGGACGTCTGGGGCCAAGGGACCACGGTCATCGTCTC<br>GTCA |
| | 46 | light | GAAATTGTGTTGACACAGTCTCCTGCCACCCTGTCTTTGTCTCCAGGGGAAAGAGCCACCCTCTCCTGCAGGGCCAGTC<br>AGAGCATTGACACCTACTTAGCCTGGTACCAACAAAAACCTGGCCAGGCTCCCAGGCTCCTCATCTATGATGCATCCAA<br>CAGGGCCACTGGCATCCCAGCCAGGTTCAGTGGCAGTGGGTCTGGGACAGACTTCTCTCTCACCATCAGCAGCCTCGA<br>GCCTGATGACTTTGCAGTTTATTACTGTCAGCAGCGTTCCAATAGGCCTCCTAGGTACACTTTTGGCCTGGGGACGAGG<br>CTGGAGATCAAA |
| HENV-242 | 47 | heavy | CAGGTCCAGCTGGTGCAGTCTGGGGCTGAGGTGAAGAAGCCTGGGTCCTCGGTGACAGTCTCCTGCAAGACTTCTGG<br>GGGCACCTTCAGCGGCTATGCTGTCAGTTGGGTGCGACAGGCCCCTGGACAAGGGCTTGAGTGGATGGGGAGGATC<br>GTCCCTCAGTTTAATATTCCAAACTACGCACAGAAGTTCCAGGACAGAGTCACGATTACCGCGGACGAGTCCACGGGC<br>ACATCCTACATGGAGCTGAGCAGCCTGAGATCCGACGACACGGCCGTCTTCTACTGTGCGAGAGAAAACATCCAAACG<br>ATTTTTGGAGTGGTTGCGATGATGGGCGGGGGAGGCTACTTTGACTCCTGGGGCCAGGGAACCCTGGTCACCGTCTCC<br>CTCA |
| | 48 | light | GACATCCAGATGACCCAGTCGCCATCCTCCCTGTCTGCATCTGTAGGAGACAGAGTCACCATCACTTGCCAGGCGAATC<br>AGGACATTAACACCTATTTAAATTGGTATCTGCAGAAACCAGGGAAAGCCCCTCAGCTCCTGGTCTTCGATGCATCCAA<br>TTTGGTGACAGGGGTCCCATCAAGGTTCAGTGGAGGTGGATCTAGGACAGATTTTACTTTGACCATCGACAGCCTGCA<br>GCCCGAAGATATTGGAACATATTACTGTCAACAGTATGATCATCTCCCGAGGCTACATTCACTTTCGGCCCTGGGACC<br>AAGGTGGATCTCAAG |

TABLE 2

PROTEIN SEQUENCES FOR ANTIBODY VARIABLE REGIONS

| Clone | SEQ ID NO: | Chain | Variable Sequence |
|-------|------------|-------|-------------------|
| HENV-32 | 49 | heavy | QVQLVQSGAEVKKPGSSVKVSCKVSGGIFNRETINWVRQAPGQGLEWM<br>GRITPIVDVPNYPRKFRGRVTITADKSTSTVYMELSGLRFEDTAIYFCARFR<br>GHNYFDPWGQGTLVTVSS |
| | 50 | light | SYVLTQPPSVSVAPGQTARITCGGNNIGGKSVHWYQQKPGQAPVLVVYD<br>DRDRPSGIPERFSGSNSGDTASLTISRVDAGDEADYFCQVWDNASDEAVF<br>GGGTKLTVL |

TABLE 2-continued

PROTEIN SEQUENCES FOR ANTIBODY VARIABLE REGIONS

| Clone | SEQ ID NO: | Chain | Variable Sequence |
|-------|-----------|-------|-------------------|
| HENV-58 | 51 | heavy | QVQLVQSGAEVKKPGSSVKVSCKASGGTFSNYVISWVRQAPGQGFEWM GRIIPMIGISNYAQKFQDRVTITADKDESTTTAYMELRGLRSEDTAMYYCA SSTVTEVGAWGQGTLVTVSS |
| | 52 | light | AIQLTQSPSSLSASIGDRVTITCRASQGISSALAWFQQKPGKPPILLIYDASSL ESGVPARFSGSGSGTDFTLTISSLQPEDFATYYCQQFYNHPLTFGPGTKVDI K |
| HENV-72 | 53 | heavy | EVQLVESGGGLVKPGGSLRLSCAASGFTIINYSLSWVRQAPGKGLEWVSSI SGSSDYIYYGDSVKGRFTISRDNAKNSLYLQMNSLRAEDAAVYYCARERTG FFSPPSYLMDVWGQGTTVTVSS |
| | 54 | light | AIQMTQSPSSLSASVGDRVTITCRASQGIRNDLGWYQQKPGKAPKLLIYA ASTLQSGVPSRFSGSGSGTDFTLTISSLQPEDFATYYCLQDYNYPRTFGQGT KVEIK |
| HENV-78 | 55 | heavy | QVQLLQSGGEVKKPGASVKVSCKATDNTLTTYGLSWVRQAPGQGLEWM GWVSAYNGHPNYAQKFQGRVTMTTDTSTSTAYMELRSLTSDDTAVYFC ARGSSAWNPWGQGTLVTVSS |
| | 56 | light | DIQMTQSPSTLSASVGDRVTITCRASQSITSWLAWYQQKPGKAPNLLIYKA SSLEGGVPSRFSGSGSGTEFTLTISSLQPDDLATYYCQQYSSYPVTFGGGTK VEIR |
| HENV-83 | 57 | heavy | QVQLVESGGGVVQPGGSLRLSCAASGFTFRSYSMNWVRQAPGKGPEW MAVISYDGSNKYYTDSVKGRFTISRDNSKNTLNLQMNSLTSEDTAIYYCAR FRGGGRIAARPDDYGMDVWGQGTTVTVST |
| | 58 | light | DIQMTQSPSSLSASVGDRVTITCRASESVITYLNWYQQKPGKAPKLLIYGAS TLESGVPSRFSGSGSGTVFTLTISSLQPEDIATYYCQQSYNMSPYTFGQGTK LEIK |
| HENV-93 | 59 | heavy | QVLLVQSGAEVRKPGASVKVSCRASGYTFTDYYMHWVRQAPGQGLEW MGWINPNSGATKYAQKFQGRVTLTRDTSINTAYMELSGLRSVDTAVFYC ASVPPSGFFYWGSDYWGQGTLVTVSS |
| | | light | Not Available |
| HENV-98 | 60 | heavy | AVQLVESGGGLVQPGGSLRLSCEASGFTFSGYWMSWVRQAPGKGLEWV ANIKGDGSEKYYVDSVKGRFTIFRDNAKTSLYLQVNSLRAEDTAVYYCARE RHFLAARPGYYIYSGLDVWGPGTTVTVSS |
| | 61 | light | DIQMTQSPSSLSASVGDRVTITCRASQSIDNYLNWYQQKPGKVPKLLIYAA SNLQSGVPSKFSGGGSGTDFTLTISSLQPDDFATYYCQQSFGTPRTFGQGT RVEIK |
| HENV-99 | 62 | heavy | QVLLVQSGAEVRKPGASVKVSCRASGYTFTDYYMHWVRQAPGQGLEW MGWINPNSGATKYAQKFQGRVTLTRDTSINTAYMELSGLRSVDTAVFYC ASVPPSGFFYWGSDYWGQGTLVTVSS |
| | 63 | light | DVVLTQSPLSLPVTLGQPASISCRSSQSLVYSDGTTYLNWFQQRPGQSPRR LIYKVSYRDSGVPDRFSGSGSGTDFTLEISRVEAEDVGIYYCMHGTHWET WTFGQGTKVEIK |
| HENV-100 | 64 | heavy | QVQLVQSGAEVKKPGASVKVSCKASGYTFTSYYINWVRQAPGQGLEWV GTINPSGGSTTYAQKFQGRVTVTRDTSTSTVYMDLSGLRSGDTAVYYCAR DRKGLAATPVYSDYYYGMDVWGQGTTVTVSS |
| | 65 | light | EIVLTQSPATLSLSPGERATLSCRASQSVSSFLAWYQQKPGQAPRLLISDAS KRATGIPARFSGSGSGTDFSLTISSLEAEDFAVYYCQQSTNWRITFGQGTRL ELK |
| HENV-103 | 66 | heavy | QVQLQGSGPGLVKPSQTLSLTCSVSGGSVSRSGYYWGWIRQHPGKGLECI GYIYYSGITYYNPSLSGRLTISVDTSKNQFSLELSSVTAADTAVYYCARVWLG GGVFDFWGQGSLVTVSS |
| | 67 | light | EIVMTQSPATLSVSPGEGATLSCRASQSVSSNLAWYQQKPGQAPRLLIYD ASTRATGIPARFSGSGSGTEFTLTISSLQSEDFAVYYCQQYNDWRTFGRGT KVEMR |
| HENV-113 | 68 | heavy | QVQLMESGGGVVQPGRSLRLSCSASGFTFSNYALHWVRQAPGKGLEWL AFISYDGSFKYYADSVKGRFTVSRDDSRNTLYLQMSSLRPEDTAVYYCTRD DDPPVENFQIWGQGTLVTVSS |
| | | light | Not Available |
| HENV-114 | 69 | heavy | QVQLQESGPGLVKPSQTLSLTCSVSGDSISSGTHYWSWIRQPAGKGLEWI GRIYATGNSNYNPSFRSRVTISVDTSKNQFSLKLSSVTAADTAVYYCVRDEA VADMAVENYYGMDVWGQGTSVTVSA |
| | 70 | light | EIVLTQSPATLSLSPGERATLSCRASQTISSYLVWYQQKPGQAPRPLIYDASI RATGIPARFSGSGSGTDFTLTISSLEPEDFAVYYCQQRYNWPRTFGQGTKV EIK |

TABLE 2-continued

PROTEIN SEQUENCES FOR ANTIBODY VARIABLE REGIONS

| Clone | SEQ ID NO: | Chain | Variable Sequence |
|-------|------------|-------|-------------------|
| HENV-117 | 71 | heavy | QVQLQQWGAGLLKPSETLSLTCDLSGGSFTNYYWTWIRHLPGKGLEWLG EINHSGRTNYSPSLKSRVTISVDTSKNQFSLRLSSVTAADTAVYYCARDIRKL APKPHSYDLYYGMDVWGQGTTVTVSS |
| | 72 | light | EIVLTQSPGTLSLSPGERATLSCRASQSVGSNYLTWYQQKPGQPPRLLIYG ASNRAAGIPDRFSGSGSGTDFTLTISRLEPEDFAVYYCQQYETSSRTFGQGT KVDIR |
| HENV-122 | 73 | heavy | EVQLLESGGGLVQPGGSLRLSCAASGFTFSTNAMSWVRQAPGKGLEWVS TVSGSGAHPNYGDSVKGRFTISRVNSKNTLFLQMSSLRAEDTAIYYCARVS TVTVGGHIPRGYYFDYWGQGTLVTVSS |
| | 74 | light | EILLTQSPGTLSLSPGERATLSCRASQSASSSYLAWYQQKPGQAPRLLIYGA STRATGIPDRFSGSGSGTEFTLTISRLESEDFAVYYCHHYGSSRTFGQGTKV EVK |
| HENV-137 | 75 | heavy | EVQLVESGGGLVQPRGSLRLSCAASGFTFSGYWMSWVRQAPGKGLEWV AKIKKDGSEKTYVDSVKGRFTISRDNAKDSLYLQMNSLRAEDTAVYYCARE RLLVPAAIVGLDYYYAMDVWGQGTTVTVSS |
| | 76 | light | DIQMTQSPSSLSASVGDRVTITCRASQNMSTYLNWYQQKPGKAPKFLIYG ASRLQNGVPSRFSGGGSGTDFTLTISSLQPEDFATYYCQQSYNIPITFGQGT RLEIK |
| HENV-141 | 77 | heavy | QVQLVQSGAEVKKPGSSVKVSCKASGGTFSSYTISWVRQAPGQGLEWM GRIIPISGITNYAQKFQGRVTITADKSTSTAYMELSSLRSEDTAVYYCAKDCY YGSGTYYGCRADYQWHHTMDVWGQGTTVTVSS |
| | 78 | light | DIQMTQSPSSLSASVGDRVTITCRASQGIRNDLGWFQQKPGKAPKRLIYA ASSLQSGVPSRFSGSGSGTEFTLTISSLQPEDFATYFCLQHNTYPLTFGQGT KVEIK |
| HENV-142 | 79 | heavy | QVRLQESGPRLVKPSQTLSLTCTVSGGSISSRDYYWSWIRQHPGKGLEWI GYIYYSGTTYYNPSLESRVTLSLDTSKNQFSLDLTSVTAADTAVYHCARVWL GGGVFDFWGQGTLVTVSA |
| | 80 | light | EIVMTQSPDTLSVSPGERATLSCRASHSVTTNLAWYQQRPGQAPRLLIFD ASTRATGIPARFSGSGSGTEFTLTIGSLQSEDFAVYYCQQYNDGRTFGQGT KVEIK |
| HENV-150 | 81 | heavy | EVQLLESGGGLVQPGGSLRLSCAASGFTFSSSAMSWVRQTPGKGLEWVS TISGSGANTYYAASVKGRFPISRDNSKNTLFLQMNSLRAEDTAVYYCAKVS TVTFGGHVPRGSYFDYWGQGTQVTVSS |
| | 82 | light | SYVLTQPPSVSVAPGQTARIPCGGNNIGSKSVHWYQQKPGQAPVLVVYD ENDRPSGIPERFSASKSGNTATLTISRVEAGDEADYYCQVWDSRSDHYVF GTGTKVTVL |
| HENV-170 | 83 | heavy | EVQLLESGGGLVQPGGSLRLSCAASGFTFSSYTMSWVRQAPGKGLEWVS GISGSGGNTYYAGSVKGRFTISRDNSKNTLYLQMNSLRAEDTAVYYCAKD GYTGQQLMRRGPWWFDPWGQGTLVTVSS |
| | 84 | light | SYVLTQPPSVSVAPGQTARITCGGNNIGSKSVHWYQQKPGQAPVLVVYD DSDRPSGIPERFSGSKSGNTATLTISRVEAGDEADYYCQVWDSSSDHVVF GGGTKLTVL |
| HENV-184 | 85 | heavy | QVQLVQSGTEVKNPGSSVKVSCKASGGTFSGFGISWVRQAPGQGLEWM GGVLPIFGSPNYAQKFQGRVTITADESTGTAYMDLSSLRSDDTAMYYCAR DQSGGFFDYWGQGTLVIVSS |
| | 86 | light | EIVLTQSPATLSLSPGERATLSCRASQSVSSNLAWYQQKPGQAPRLLIYDAS DRATGVPARFSGSGSGTDFTLTISSLEPEDFALYYCQQRYNWRVTFGQGT RLEIK |
| HENV-188 | 87 | heavy | QVQVVESGGGVVHPGRSLRLSCAGSGFIFNNYAFHWVRQAPGGGLEW MAYISYDGRYKYYAASVRGRFTISRDDSKNTLYLQMSSLRTEDTALYYCAIS DYAEPLDNWGQGTLVTVSS |
| | 88 | light | QIVLTQSPATLSLSPGDRATLSCRASQSVSSNVAWYQQKPGQAPRLLIYNV SNRATGIPARFSGSGSGTDFTLTISSLEPEDFAVYYCHQRTNWPLTFGGGT KVEIK |
| HENV-202 | 89 | heavy | QGQLQQWGAGLLKPSETLSLTCGVYSGSFSGYYWSWIRQPPGKGLEWIG EINHSGRTDYNPSLKSRVTMSVDTSKNQFSLRLSSVTAADTAVYFCARATP PTLWVRDFLWGYFDSWGQGTLVSVSS |
| | 90 | light | DIVMTQSPDSLAVSLGERATINCKSSQSVLYTSNNKNYLAWYQQKPGQPP KLLIFWASTRESGVPDRFSGSGSGTDFTLTISSLQAEDVAVYYCQQYYTTPK TFGPGTKVDLK |
| HENV-222 | 91 | heavy | QVQLQESGPGLVKPSETLSLTCTVSGGSIDSYYWSWIRQPAGKGLEWIGRI YPSGTTNYNPSLKSRVTMSVDTSKNQFSLKVTSVTAADTAVYYCARMQTG FGSSLFFVPYFDNWGQGTLVTVSS |

TABLE 2-continued

PROTEIN SEQUENCES FOR ANTIBODY VARIABLE REGIONS

| Clone | SEQ ID NO: | Chain | Variable Sequence |
|---|---|---|---|
| | 92 | light | EIVLTQSPATLSLSPGERATLSCRASQSVSSYLAWYQQKPGQAPRLLIYDAS NRATGIPARFSGSGSGTDFTLTISSLEPEDFAVYYCQQRGNWPLTFGGGTK VEIK |
| HENV-226 | 93 | heavy | EERLVQSGGGLAQPGQSLRLSCAGFGFTFTRYEMNWVRQAPGKGLEWI AHISTRGDTISYADSVKGRATISRDDTNNSLDLQMDSLRAEDTAIYFCARD RGSLSTRPPDSYHYYYHGMDVWGQGTTVIVSS |
| | 94 | light | EIVLTQSPATLSLSPGERATLSCRASQSIDTYLAWYQQKPGQAPRLLIYDAS NRATGIPARFSGSGSGTDFSLTISSLEPDDFAVYYCQQRSNRPPRYTFGLGT RLEIK |
| HENV-242 | 95 | heavy | QVQLVQSGAEVKKPGSSVTVSCKTSGGTFSGYAVSWVRQAPGQGLEW MGRIVPQFNIPNYAQKFQDRVTITADESTGTSYMELSSLRSDDTAVFYCAR ENIQTIFGVVAMMGGGGYFDSWGQGTLVTVSS |
| | 96 | light | DIQMTQSPSSLSASVGDRVTITCQANQDINTYLNWYLQKPGKAPQLLVFD ASNLVTGVPSRFSGGGSRTDFTLTIDSLQPEDIGTYYCQQYDHLPRRTFTFG PGTKVDLK |

TABLE 3

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| HENV-32 | GGIFNRET 97 | ITPIVDVP 98 | ARFRGHNYFDP 99 |
| HENV-58 | GGTFSNYV 100 | IIPMIGIS 101 | ASSTVTEVGA 102 |
| HENV-72 | GFTIINYS 103 | ISGSSDYI 104 | ARERTGFFSPPS YLMDV 105 |
| HENV-78 | DNTLTTYG 106 | VSAYNGHP 107 | ARGSSAWNP 108 |
| HENV-83 | GFTFRSYS 109 | ISYDGSNK 110 | ARFRGGGRIAAR PDDYGMDV 111 |
| HENV-93 | GYTFTDYY 112 | INPNSGAT 113 | ASVPPSGFFYWG SDY 114 |
| HENV-98 | GFTFSGYW 115 | IKGDGSEK 116 | ARERHFLAARPG YYIYSGLDV 117 |
| HENV-99 | GYTFTDYY 118 | INPNSGAT 119 | ASVPPSGFFYWG SDY 120 |
| HENV-100 | GYTFTSYY 121 | INPSGGST 122 | ARDRKGLAATPV YSDYYYGMDV 123 |
| HENV-103 | GGSVSRSGYY 124 | IYYSGIT 125 | ARVWLGGGVFDF 126 |
| HENV-113 | GFTFSNYA 127 | ISYDGSFK 128 | TRDDDPPVENFQ I 129 |
| HENV-114 | GDSISSGTHY 130 | IYATGNS 131 | VRDEAVADMAVE NYYGMDV 132 |
| HENV-117 | GGSFTNYY 133 | INHSGRT 134 | ARDIRKLAPKPH SYDLYYGMDV 135 |

TABLE 3-continued

CDR HEAVY CHAIN SEQUENCES

| Clone | CDRH1 (SEQ ID NO:) | CDRH2 (SEQ ID NO:) | CDRH3 (SEQ ID NO:) |
|---|---|---|---|
| HENV-122 | GFTFSTNA 136 | VSGSGAHP 137 | ARVSTVTVGGHI PRGYYFDY 138 |
| HENV-137 | GFTFSGYW 139 | IKKDGSEK 140 | ARERLLVPAAIV GLDYYYAMDV 141 |
| HENV-141 | GGTFSSYT 142 | IIPISGIT 143 | AKDCYYGSGTYY GCRADYQWHHTM DV 144 |
| HENV-142 | GGSISSRDYY 145 | IYYSGTT 146 | ARVWLGGGVFDF 147 |
| HENV-150 | GFTFSSSA 148 | ISGSGANT 149 | AKVSTVTFGGHV PRGSYFDY 150 |
| HENV-170 | GFTFSSYT 151 | ISGSGGNT 152 | AKDGYTGQQLMR RGPWWFDP 153 |
| HENV-184 | GGTFSGFG 154 | VLPIFGSP 155 | ARDQSGGFFDY 156 |
| HENV-188 | GFIFNNYA 157 | ISYDGRYK 158 | AISDYAEPLDN 159 |
| HENV-202 | SGSFSGYY 160 | INHSGRT 161 | ARATPPTLWVRD FLWGYFDS 162 |
| HENV-222 | GGSIDSYY 163 | IYPSGTT 164 | ARMQTGFGSSLF FVPYFDN 165 |
| HENV-226 | GFTFTRYE 166 | ISTRGDTI 167 | ARDRGSLSTRPP DSYHYYYHGMDV 168 |
| HENV-242 | GGTFSGYA 169 | IVPQFNIP 170 | ARENIQTIFGVV AMMGGGGYFDS 171 |

TABLE 4

| Clone | CDRL1 (SEQ ID NO:) | CDRL2 (SEQ ID NO:) | CDRL3 (SEQ ID NO:) |
|---|---|---|---|
| HENV-32 | NIGGKS 172 | DDR 173 | QVWDNASDEAV 174 |
| HENV-58 | QGISSA 175 | DAS 176 | QQFYNHPLT 177 |
| HENV-72 | QGIRND 178 | AAS 179 | LQDYNYPRT 180 |
| HENV-78 | QSITSW 181 | KAS 182 | QQYSSYPVT 183 |
| HENV-83 | ESVITY 184 | GAS 185 | QQSYNMSPYT 186 |
| HENV-98 | QSIDNY 187 | AAS 188 | QQSFGTPRT 189 |
| HENV-99 | QSLVYSDGTTY 190 | KVS 191 | MHGTHWETWT 192 |
| HENV-100 | QSVSSF 193 | DAS 194 | QQSTNWRIT 195 |
| HENV-103 | QSVSSN 196 | DAS 197 | QQYNDWRT 198 |
| HENV-114 | QTISSY 199 | DAS 200 | QQRYNWPRT 201 |
| HENV-117 | QSVGSNY 202 | GAS 203 | QQYETSSRT 204 |
| HENV-122 | QSASSSY 205 | GAS 206 | HHYGSSRT 207 |
| HENV-137 | QNMSTY 208 | GAS 209 | QQSYNIPIT 210 |
| HENV-141 | QGIRND 211 | AAS 212 | LQHNTYPLT 213 |
| HENV-142 | HSVTTN 214 | DAS 215 | QQYNDGRT 216 |
| HENV-150 | NIGSKS 217 | DEN 218 | QVWDSRSDHYV 219 |
| HENV-170 | NIGSKS 220 | DDS 221 | QVWDSSSDHVV 222 |
| HENV-184 | QSVSSN 223 | DAS 224 | QQRYNWRVT 225 |
| HENV-188 | QSVSSN 226 | NVS 227 | HQRTNWPLT 228 |
| HENV-202 | QSVLYTSNNKNY 229 | WAS 230 | QQYYTTPKT 231 |
| HENV-222 | QSVSSY 232 | DAS 233 | QQRGNWPLT 234 |
| HENV-226 | QSIDTY 235 | DAS 236 | QQRSNRPPRYT 237 |
| HENV-242 | QDINTY 238 | DAS 239 | QQYDHLPRRTFT 240 |

* * * * * * * * * * * * * * * * *

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., Am. J. Pediatr. Hematol. Oncol., 12(4), 480-489, 1990.
Allred et al., Arch. Surg., 125(1), 107-113, 1990.
Atherton et al., Biol. of Reproduction, 32, 155-171, 1985.
Barzon et al., Euro Surveill. 2016 Aug. 11; 21(32).
Beltramello et al., Cell Host Microbe 8, 271-283, 2010.
Brown et al., J. Immunol. Meth., 12; 130(1):111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
De Jager et al., Semin. Nucl. Med. 23(2), 165-179, 1993.
Dholakia et al., J. Biol. Chem., 264, 20638-20642, 1989.
Diamond et al., J Virol 77, 2578-2586, 2003.
Doolittle and Ben-Zeev, Methods Mol. Biol., 109:215-237, 1999.
Duffy et al., N. Engl. J. Med. 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., Somatic Cell Genet., 3:231-236, 1977.

Gornet et al., *Semin Reprod Med.* 2016 September; 34(5): 285-292. Epub 2016 Sep. 14.

Gulbis and Galand, *Hum. Pathol.* 24(12), 1271-1285, 1993.

Halfon et al., *PLoS ONE* 2010; 5 (5) e10569

Hessell et al., *Nature* 449, 101-4, 2007.

Khatoon et al., *Ann. of Neurology,* 26, 210-219, 1989.

King et al., *J. Biol. Chem.,* 269, 10210-10218, 1989.

Kohler and Milstein, *Eur. J. Immunol.,* 6, 511-519, 1976.

Kohler and Milstein, *Nature,* 256, 495-497, 1975.

Kyte and Doolittle, *J. Mol. Biol.,* 157(1):105-132, 1982.

Mansuy et al., *Lancet Infect Dis.* 2016 October; 16(10): 1106-7.

Nakamura et al., In: *Enzyme Immunoassays: Heterogeneous and Homogeneous Systems*, Chapter 27, 1987.

O'Shannessy et al., *J. Immun. Meth.,* 99, 153-161, 1987.

Persic et al., *Gene* 187:1, 1997

Potter and Haley, *Meth. Enzymol.,* 91, 613-633, 1983.

Purpura et al., *Lancet Infect Dis.* 2016 October; 16(10): 1107-8. Epub 2016 Sep. 19.

Remington's Pharmaceutical Sciences, 15th Ed., 3:624-652, 1990.

Tang et al., *J. Biol. Chem.,* 271:28324-28330, 1996.

Wawrzynczak & Thorpe, In: *Immunoconjugates, Antibody Conjugates In Radioimaging And Therapy Of Cancer,* Vogel (Ed.), NY, Oxford University Press, 28, 1987.

Yu et al., *J Immunol Methods* 336, 142-151, doi:10.1016/j.jim.2008.04.008, 2008.

Adams et al. (2010). PHENIX: a comprehensive Python-based system for macromolecular structure solution. Acta Crystallogr D Biol Crystallogr 66, 213-221.

Aguilar et al. (2009). A novel receptor-induced activation site in the Nipah virus attachment glycoprotein (G) involved in triggering the fusion glycoprotein (F). J Biol Chem 284, 1628-1635.

Aguilar, H. C., and Iorio, R. M. (2012). Henipavirus membrane fusion and viral entry. Curr Top Microbiol Immunol 359, 79-94.

Bonaparte et al. (2005). Ephrin-B2 ligand is a functional receptor for Hendra virus and Nipah virus. Proc Natl Acad Sci USA 102, 10652-10657.

Bose et al. (2015). Timing is everything: Fine-tuned molecular machines orchestrate paramyxovirus entry. Virology 479-480, 518-531.

Bose et al. (2011). Structure and mutagenesis of the parainfluenza virus 5 hemagglutinin-neuraminidase stalk domain reveals a four-helix bundle and the role of the stalk in fusion promotion. J Virol 85, 12855-12866.

Bossart et al. (2005). Receptor binding, fusion inhibition, and induction of cross-reactive neutralizing antibodies by a soluble G glycoprotein of Hendra virus. J Virol 79, 6690-6702.

Bossart et al. (2013). Paramyxovirus entry. Adv Exp Med Biol 790, 95-127.

Bossart et al. (2011). A neutralizing human monoclonal antibody protects african green monkeys from hendra virus challenge. Sci Transl Med 3, 105ra103.

Bossart et al. (2009). A neutralizing human monoclonal antibody protects against lethal disease in a new ferret model of acute nipah virus infection. PLoS Pathog 5, e1000642.

Bowden et al. (2008). Structural basis of Nipah and Hendra virus attachment to their cell-surface receptor ephrin-B2. Nat Struct Mol Biol 15, 567-572.

Bowden et al. (2010). Dimeric architecture of the Hendra virus attachment glycoprotein: evidence for a conserved mode of assembly. J Virol 84, 6208-6217.

Bradel-Tretheway et al. (2019). Nipah and Hendra virus glycoproteins induce comparable homologous but distinct heterologous fusion phenotypes. J Virol 93, e00577-19.

Brochet et al. (2008). IMGT/V-QUEST: the highly customized and integrated system for IG and TR standardized V-J and V-D-J sequence analysis. Nucleic Acids Res 36, W503-508.

Broder et al. (2013). A treatment for and vaccine against the deadly Hendra and Nipah viruses. Antiviral Res 100, 8-13.

Burkovitz, A., and Ofran, Y. (2016). Understanding differences between synthetic and natural antibodies can help improve antibody engineering. MAbs 8, 278-287.

Chadha et al. (2006). Nipah virus-associated encephalitis outbreak, Siliguri, India. Emerg Infect Dis 12, 235-240.

Clayton et al. (2012). Transmission routes for Nipah virus from Malaysia and Bangladesh. Emerg Infect Dis 18, 1983-1993.

Crennell et al. (2000). Crystal structure of the multifunctional paramyxovirus hemagglutinin-neuraminidase. Nat Struct Biol 7, 1068-1074.

Drexler et al. (2012). Bats host major mammalian paramyxoviruses. Nat Commun 3, 796.

Emsley, P., and Cowtan, K. (2004). Coot: model-building tools for molecular graphics. Acta Crystallogr D Biol Crystallogr 60, 2126-2132.

Ferrara, F., and Temperton, N. (2018). Pseudotype neutralization assays: From laboratory bench to data analysis. Methods Protoc 1, 8.

Field, H. E. (2016). Hendra virus ecology and transmission. Curr Opin Virol 16, 120-125.

Flyak et al. (2015). Mechanism of human antibody-mediated neutralization of Marburg virus. Cell 160, 893-903.

Geisbert et al. (2014). Therapeutic treatment of Nipah virus infection in nonhuman primates with a neutralizing human monoclonal antibody. Sci Transl Med 6, 242ra282.

Giudicelli, V., and Lefranc, M. P. (2011). IMGT/junctionanalysis: IMGT standardized analysis of the V-J and V-D-J junctions of the rearranged immunoglobulins (IG) and T cell receptors (TR). Cold Spring Harb Protoc 2011, 716-725.

Gurley et al. (2007). Person-to-person transmission of Nipah virus in a Bangladeshi community. Emerg Infect Dis 13, 1031-1037.

Halpin et al. (2011). Pteropid bats are confirmed as the reservoir hosts of henipaviruses: a comprehensive experimental study of virus transmission. Am J Trop Med Hyg 85, 946-951.

Homaira et al. (2010). Nipah virus outbreak with person-to-person transmission in a district of Bangladesh, 2007. Epidemiol Infect 138, 1630-1636.

Jardetzky, T. S., and Lamb, R. A. (2014). Activation of paramyxovirus membrane fusion and virus entry. Curr Opin Virol 5, 24-33.

Kabsch, W. (2010). Xds. Acta Crystallogr D Biol Crystallogr 66, 125-132.

Kessler et al. (2018). Changing resource landscapes and spillover of henipaviruses. Ann N Y Acad Sci 1429, 78-99.

Lawrence et al. (2004). Structure of the haemagglutinin-neuraminidase from human parainfluenza virus type III. *J Mol Biol* 335, 1343-1357.

Li et al. (2020). Fc-based recombinant henipavirus vaccines elicit broad neutralizing antibody responses in mice. Viruses 12, 480.

Lo Conte et al. (1999). The atomic structure of protein-protein recognition sites. J Mol Biol 285, 2177-2198.

Lo et al. (2012). Characterization of Nipah virus from outbreaks in Bangladesh, 2008-2010. Emerg Infect Dis 18, 248-255.

Luby, S. P. (2013). The pandemic potential of Nipah virus. Antiviral Res 100, 38-43.

Maar et al. (2012). Cysteines in the stalk of the nipah virus G glycoprotein are located in a distinct subdomain critical for fusion activation. J Virol 86, 6632-6642.

Marsh et al. (2012). Cedar virus: a novel Henipavirus isolated from Australian bats. PLoS Pathog 8, e1002836.

Martin et al. (2018). Climate change could increase the geographic extent of hendra virus spillover risk. Eco-health 15, 509-525.

McCoy et al. (2007). Phaser crystallographic software. J Appl Crystallogr 40, 658-674.

Mire et al. (2019). A cross-reactive humanized monoclonal antibody targeting fusion glycoprotein function protects ferrets against lethal Nipah virus and Hendra virus infection. J Infect Dis 221, (Supplement 4):5471-5479.

Mire et al. (2016). Pathogenic differences between Nipah virus Bangladesh and Malaysia strains in primates: Implications for antibody therapy. Sci Rep 6, 30916.

Mire et al. (2013). Single injection recombinant vesicular stomatitis virus vaccines protect ferrets against lethal Nipah virus disease. Virol J 10, 353.

Murray et al. (1995). A morbillivirus that caused fatal disease in horses and humans. Science 268, 94-97.

Navaratnarajah et al. (2020). Receptor-mediated cell entry of paramyxoviruses: Mechanisms, and consequences for tropism and pathogenesis. J Biol Chem 295, 2771-2786.

Negrete et al. (2007). Single amino acid changes in the Nipah and Hendra virus attachment glycoproteins distinguish ephrinB2 from ephrinB3 usage. J Virol 81, 10804-10814.

Negrete et al. (2005). EphrinB2 is the entry receptor for Nipah virus, an emergent deadly paramyxovirus. Nature 436, 401-405.

Negrete et al. (2006). Two key residues in ephrinB3 are critical for its use as an alternative receptor for Nipah virus. PLoS Pathog 2, e7.

Playford et al. (2020). Safety, tolerability, pharmacokinetics, and immunogenicity of a human monoclonal antibody targeting the G glycoprotein of henipaviruses in healthy adults: a first-in-human, randomised, controlled, phase 1 study. Lancet Infect Dis 20, 445-454.

Plowright et al. (2015). Ecological dynamics of emerging bat virus spillover. Proc Biol Sci 282, 20142124.

Rissanen et al. (2017). Idiosyncratic Mojiang virus attachment glycoprotein directs a host-cell entry pathway distinct from genetically related henipaviruses. Nat Commun 8, 16060.

Rockx et al. (2010). A novel model of lethal Hendra virus infection in African green monkeys and the effectiveness of ribavirin treatment. J Virol 84, 9831-9839.

Santiago et al. (2010). Structure of the measles virus hemagglutinin bound to the CD46 receptor. Nat Struct Mol Biol 17, 124-129.

Schrodinger, LLC (2015). The PyMOL Molecular Graphics System, Version 1.8.

Selvey et al. (1995). Infection of humans and horses by a newly described morbillivirus. Med J Aust 162, 642-645.

Smith, I., and Wang, L. F. (2013). Bats and their virome: an important source of emerging viruses capable of infecting humans. Curr Opin Virol 3, 84-91.

Smith et al. (2012). Persistence of circulating memory B cell clones with potential for dengue virus disease enhancement for decades following infection. J Virol 86, 2665-2675.

Steffen et al. (2012). Henipavirus mediated membrane fusion, virus entry and targeted therapeutics. Viruses 4, 280-308.

Thornburg et al. (2016). H7N9 influenza virus neutralizing antibodies that possess few somatic mutations. J Clin Invest 126, 11482-94.

Vidgen et al. (2015). Novel paramyxoviruses in Australian flying-fox populations support host-virus co-evolution. J Gen Virol 96, 1619-1625.

Walsh et al. (2017). The impact of human population pressure on flying fox niches and the potential consequences for Hendra virus spillover. Sci Rep 7, 8226.

Weatherman et al. (2018). Transmission of henipaviruses. Curr Opin Virol 28, 7-11.

Welch et al. (2013). Structure of the parainfluenza virus 5 (PIV5) hemagglutinin-neuraminidase (HN) ectodomain. PLoS Pathog 9, e1003534.

Winn et al. (2011). Overview of the CCP4 suite and current developments. Acta Crystallogr D Biol Crystallogr 67, 235-242.

Wong et al. (2017). Monomeric ephrinB2 binding induces allosteric changes in Nipah virus G that precede its full activation. Nat Commun 8, 781.

Wu et al. (2014). Novel Henipa-like virus, Mojiang Paramyxovirus, in rats, China, 2012. Emerg Infect Dis 20, 1064-1066.

Xu et al. (2013). Crystal structure of the Hendra virus attachment G glycoprotein bound to a potent cross-reactive neutralizing human monoclonal antibody. PLoS Pathog 9, e1003684.

Yu et al. (2008). An optimized electrofusion-based protocol for generating virus-specific human monoclonal antibodies. J Immunol Methods 336, 142-151.

Yuan et al. (2008). Domain architecture and oligomerization properties of the paramyxovirus PIV 5 hemagglutinin-neuraminidase (HN) protein. Virology 378, 282-291.

Yuan et al. (2011). Structure of the Newcastle disease virus hemagglutinin-neuraminidase (HN) ectodomain reveals a four-helix bundle stalk. Proc Natl Acad Sci USA 108, 14920-14925.

Yuan et al. (2005). Structural studies of the parainfluenza virus 5 hemagglutinin-neuraminidase tetramer in complex with its receptor, sialyllactose. Structure 13, 803-815.

Zhu et al. (2008). Exceptionally potent cross-reactive neutralization of Nipah and Hendra viruses by a human monoclonal antibody. J Infect Dis 197, 846-853.

Zhu et al. (2006). Potent neutralization of Hendra and Nipah viruses by human monoclonal antibodies. J Virol 80, 891-899.

The invention claimed is:

1. A method of treating a subject infected with henipavirus, or reducing the likelihood of infection of a subject at risk of contracting henipavirus, comprising delivering to said subject an antibody or antibody fragment comprising heavy and light chain Complementarity Determining Regions 1-3, respectively, selected from: SEQ ID NOS: 97-99 and 172-174, respectively; SEQ ID NOS: 100-102 and 175-177, respectively; SEQ ID NOS: 103-105 and 178-180, respectively; SEQ ID NOS: 106-108 and 181-183, respectively; SEQ ID NOS: 109-111 and 184-186, respectively; SEQ ID NOS: 115-117 and 187-189, respectively; SEQ ID NOS: 118-120 and 190-192, respectively; SEQ ID NOS: 121-123 and 193-195, respectively; SEQ ID NOS: 124-126 and 196-198, respectively; SEQ ID NOS: 130-132 and 199-201, respectively; SEQ ID NOS: 133-135 and 202-204, respectively; SEQ ID NOS: 136-138 and 205-207, respectively; SEQ ID NOS: 139-141 and 208-210, respectively; SEQ ID NOS: 142-144 and 211-213, respectively; SEQ ID NOS: 145-147 and 214-216, respectively; SEQ ID NOS: 148-150 and 217-219, respectively; SEQ ID NOS: 151-153 and 220-222, respectively; SEQ ID NOS: 154-156 and 223-225, respectively; SEQ ID NOS: 157-159 and 226-228, respectively; SEQ ID NOS: 160-162 and 229-231, respectively; SEQ ID NOS: 163-165 and 232-234, respectively; SEQ ID NOS: 166-168 and 235-237, respectively; or SEQ ID NOS: 169-171 and 238-240, respectively.

2. The method of claim 1, wherein the antibody or antibody fragment is encoded by clone-paired heavy and light chain variable sequences comprising SEQ ID NOS: 1 and 2, respectively; SEQ ID NOS: 3 and 4, respectively; SEQ ID NOS: 5 and 6, respectively; SEQ ID NOS: 7 and 8, respectively; SEQ ID NOS: 9 and 10, respectively; SEQ ID NOS: 12 and 13, respectively; SEQ ID NOS: 14 and 15, respectively; SEQ ID NOS: 16 and 17, respectively; SEQ ID NOS: 18 and 19, respectively; SEQ ID NOS: 21 and 22, respectively; SEQ ID NOS: 23 and 24, respectively; SEQ ID NOS: 25 and 26, respectively; SEQ ID NOS: 27 and 28, respectively; SEQ ID NOS: 29 and 30, respectively; SEQ ID NOS: 31 and 32, respectively; SEQ ID NOS: 33 and 34, respectively; SEQ ID NOS: 35 and 36, respectively; SEQ ID NOS: 37 and 38, respectively; SEQ ID NOS: 39 and 40, respectively; SEQ ID NOS: 41 and 42, respectively; SEQ ID NOS: 43 and 44, respectively; SEQ ID NOS: 45 and 46, respectively; or SEQ ID NOS: 47 and 48, respectively.

3. The method of claim 1, wherein the antibody or antibody fragment is encoded by clone-paired heavy and light chain variable sequences having 95% identity to SEQ ID NOS: 1 and 2, respectively; SEQ ID NOS: 3 and 4, respectively; SEQ ID NOS: 5 and 6, respectively; SEQ ID NOS: 7 and 8, respectively; SEQ ID NOS: 9 and 10, respectively; SEQ ID NOS: 12 and 13, respectively; SEQ ID NOS: 14 and 15, respectively; SEQ ID NOS: 16 and 17, respectively; SEQ ID NOS: 18 and 19, respectively; SEQ ID NOS: 21 and 22, respectively; SEQ ID NOS: 23 and 24, respectively; SEQ ID NOS: 25 and 26, respectively; SEQ ID NOS: 27 and 28, respectively; SEQ ID NOS: 29 and 30, respectively; SEQ ID NOS: 31 and 32, respectively; SEQ ID NOS: 33 and 34, respectively; SEQ ID NOS: 35 and 36, respectively; SEQ ID NOS: 37 and 38, respectively; SEQ ID NOS: 39 and 40, respectively; SEQ ID NOS: 41 and 42, respectively; SEQ ID NOS: 43 and 44, respectively; SEQ ID NOS: 45 and 46, respectively; or SEQ ID NOS: 47 and 48, respectively.

4. The method of claim 1, wherein said antibody or antibody fragment is encoded by heavy and light chain variable sequences having 70%, 80%, or 90% identity to SEQ ID NOS: 1 and 2, respectively; SEQ ID NOS: 3 and 4, respectively; SEQ ID NOS: 5 and 6, respectively; SEQ ID NOS: 7 and 8, respectively; SEQ ID NOS: 9 and 10, respectively; SEQ ID NOS: 12 and 13, respectively; SEQ ID NOS: 14 and 15, respectively; SEQ ID NOS: 16 and 17, respectively; SEQ ID NOS: 18 and 19, respectively; SEQ ID NOS: 21 and 22, respectively; SEQ ID NOS: 23 and 24, respectively; SEQ ID NOS: 25 and 26, respectively; SEQ ID NOS: 27 and 28, respectively; SEQ ID NOS: 29 and 30, respectively; SEQ ID NOS: 31 and 32, respectively; SEQ ID NOS: 33 and 34, respectively; SEQ ID NOS: 35 and 36, respectively; SEQ ID NOS: 37 and 38, respectively; SEQ ID NOS: 39 and 40, respectively; SEQ ID NOS: 41 and 42, respectively; SEQ ID NOS: 43 and 44, respectively; SEQ ID NOS: 45 and 46, respectively; or SEQ ID NOS: 47 and 48, respectively.

5. The method of claim 1, wherein said antibody or antibody fragment comprises heavy and light chain variable sequences of SEQ ID NOS: 40 and 50, respectively; SEQ ID NOS: 51 and 52, respectively; SEQ ID NOS: 53 and 54, respectively; SEQ ID NOS: 55 and 56, respectively; SEQ ID NOS: 57 and 58, respectively; SEQ ID NOS: 60 and 61, respectively; SEQ ID NOS: 62 and 63, respectively; SEQ ID NOS: 64 and 65, respectively; SEQ ID NOS: 66 and 67, respectively; SEQ ID NOS: 69 and 70, respectively; SEQ ID NOS: 71 and 72, respectively; SEQ ID NOS: 73 and 74, respectively; SEQ ID NOS: 75 and 76, respectively; SEQ ID NOS: 77 and 78, respectively; SEQ ID NOS: 79 and 80, respectively; SEQ ID NOS: 81 and 82, respectively; SEQ ID NOS: 83 and 84, respectively; SEQ ID NOS: 85 and 86, respectively; SEQ ID NOS: 87 and 88, respectively; SEQ ID NOS: 89 and 90, respectively; SEQ ID NOS: 91 and 92, respectively; SEQ ID NOS: 93 and 94, respectively; or SEQ ID NOS: 95 and 96, respectively.

6. The method of claim 1, wherein said antibody or antibody fragment comprises heavy and light chain variable sequences having 70%, 80% or 90% identity to SEQ ID NOS: 40 and 50, respectively; SEQ ID NOS: 51 and 52, respectively; SEQ ID NOS: 53 and 54, respectively; SEQ ID NOS: 55 and 56, respectively; SEQ ID NOS: 57 and 58, respectively; SEQ ID NOS: 60 and 61, respectively; SEQ ID NOS: 62 and 63, respectively; SEQ ID NOS: 64 and 65, respectively; SEQ ID NOS: 66 and 67, respectively; SEQ ID NOS: 69 and 70, respectively; SEQ ID NOS: 71 and 72, respectively; SEQ ID NOS: 73 and 74, respectively; SEQ ID NOS: 75 and 76, respectively; SEQ ID NOS: 77 and 78, respectively; SEQ ID NOS: 79 and 80, respectively; SEQ ID NOS: 81 and 82, respectively; SEQ ID NOS: 83 and 84, respectively; SEQ ID NOS: 85 and 86, respectively; SEQ ID NOS: 87 and 88, respectively; SEQ ID NOS: 89 and 90, respectively; SEQ ID NOS: 91 and 92, respectively; SEQ ID NOS: 93 and 94, respectively; or SEQ ID NOS: 95 and 96, respectively.

7. The method of claim 1, wherein said antibody or antibody fragment comprises heavy and light chain variable sequences having 95% identity to SEQ ID NOS: 40 and 50, respectively; SEQ ID NOS: 51 and 52, respectively; SEQ ID NOS: 53 and 54, respectively; SEQ ID NOS: 55 and 56, respectively; SEQ ID NOS: 57 and 58, respectively; SEQ ID NOS: 60 and 61, respectively; SEQ ID NOS: 62 and 63, respectively; SEQ ID NOS: 64 and 65, respectively; SEQ ID NOS: 66 and 67, respectively; SEQ ID NOS: 69 and 70, respectively; SEQ ID NOS: 71 and 72, respectively; SEQ ID NOS: 73 and 74, respectively; SEQ ID NOS: 75 and 76, respectively; SEQ ID NOS: 77 and 78, respectively; SEQ ID NOS: 79 and 80, respectively; SEQ ID NOS: 81 and 82, respectively; SEQ ID NOS: 83 and 84, respectively; SEQ ID NOS: 85 and 86, respectively; SEQ ID NOS: 87 and 88, respectively; SEQ ID NOS: 89 and 90, respectively; SEQ ID NOS: 91 and 92, respectively; SEQ ID NOS: 93 and 94, respectively; or SEQ ID NOS: 95 and 96, respectively.

8. The method of claim 1, wherein the antibody fragment is a recombinant scFv (single chain fragment variable) antibody, Fab fragment, F(ab')$_2$ fragment, or Fv fragment.

9. The method of claim 1, wherein said antibody is an IgG, or a recombinant IgG antibody or antibody fragment comprising an Fc portion mutated to reduce, eliminate or enhance FcR interactions, to increase half-life and/or increase therapeutic efficacy, or glycan modified to reduce, eliminate or enhance FcR interactions.

10. The method of claim 9, wherein the Fc portion is mutated by LALA, N297, GASD/ALIE, YTE or LS mutation or is glycan modified by enzymatic or chemical addition or removal of glycans or expression in a cell line engineered with a defined glycosylating pattern.

11. The method of claim 1, wherein said antibody is a chimeric antibody or a bispecific antibody.

12. The method of claim 1, wherein said antibody or antibody fragment is administered prior to infection or after infection.

13. The method of claim 1, wherein said subject is a pregnant female, a sexually active female, or a female undergoing fertility treatments.

14. The method of claim 1, wherein delivering comprises antibody or antibody fragment administration, or genetic delivery with an RNA or DNA sequence or vector encoding the antibody or antibody fragment.

15. A monoclonal antibody or antibody fragment comprising heavy and light chain Complementarity Determining Regions 1-3, respectively, selected from: SEQ ID NOS: 97-99 and 172-174, respectively; SEQ ID NOS: 100-102 and 175-177, respectively; SEQ ID NOS: 103-105 and 178-180, respectively; SEQ ID NOS: 106-108 and 181-183, respectively; SEQ ID NOS: 109-111 and 184-186, respectively; SEQ ID NOS: 115-117 and 187-189, respectively; SEQ ID NOS: 118-120 and 190-192, respectively; SEQ ID NOS: 121-123 and 193-195, respectively; SEQ ID NOS: 124-126 and 196-198, respectively; SEQ ID NOS: 130-132 and 199-201, respectively; SEQ ID NOS: 133-135 and 202-204, respectively; SEQ ID NOS: 136-138 and 205-207, respectively; SEQ ID NOS: 139-141 and 208-210, respectively; SEQ ID NOS: 142-144 and 211-213, respectively; SEQ ID NOS: 145-147 and 214-216, respectively; SEQ ID NOS: 148-150 and 217-219, respectively; SEQ ID NOS: 151-153 and 220-222, respectively; SEQ ID NOS: 154-156 and 223-225, respectively; SEQ ID NOS: 157-159 and 226-228, respectively; SEQ ID NOS: 160-162 and 229-231, respectively; SEQ ID NOS: 163-165 and 232-234, respectively; SEQ ID NOS: 166-168 and 235-237, respectively; or SEQ ID NOS: 169-171 and 238-240, respectively, wherein said antibody is an IgG, or a recombinant IgG antibody or antibody fragment comprising an Fc portion mutated to eliminate or enhance FcR interactions, to increase half-life and/or increase therapeutic efficacy, or glycan modified to eliminate or enhance FcR interactions.

16. The monoclonal antibody or antibody fragment of claim 15, wherein the Fc portion is mutated by LALA, N297, GASD/ALIE, YTE or LS mutation or is glycan modified by enzymatic or chemical addition or removal of glycans or expression in a cell line engineered with a defined glycosylating pattern.

17. A hybridoma or engineered cell expressing an antibody or antibody fragment comprising heavy and light chain Complementarity Determining Regions 1-3, respectively, selected from: SEQ ID NOS: 97-99 and 172-174, respectively; SEQ ID NOS: 100-102 and 175-177, respectively; SEQ ID NOS: 103-105 and 178-180, respectively; SEQ ID NOS: 106-108 and 181-183, respectively; SEQ ID NOS: 109-111 and 184-186, respectively; SEQ ID NOS: 115-117 and 187-189, respectively; SEQ ID NOS: 118-120 and 190-192, respectively; SEQ ID NOS: 121-123 and 193-195, respectively; SEQ ID NOS: 124-126 and 196-198, respectively; SEQ ID NOS: 130-132 and 199-201, respectively; SEQ ID NOS: 133-135 and 202-204, respectively; SEQ ID NOS: 136-138 and 205-207, respectively; SEQ ID NOS: 139-141 and 208-210, respectively; SEQ ID NOS: 142-144 and 211-213, respectively; SEQ ID NOS: 145-147 and 214-216, respectively; SEQ ID NOS: 148-150 and 217-219, respectively; SEQ ID NOS: 151-153 and 220-222, respectively; SEQ ID NOS: 154-156 and 223-225, respectively; SEQ ID NOS: 157-159 and 226-228, respectively; SEQ ID NOS: 160-162 and 229-231, respectively; SEQ ID NOS: 163-165 and 232-234, respectively; SEQ ID NOS: 166-168 and 235-237, respectively; or SEQ ID NOS: 169-171 and 238-240, respectively.

18. A vaccine formulation comprising one or more antibodies or antibody fragments comprising heavy and light chain Complementarity Determining Regions 1-3, respectively, of: SEQ ID NOS: 97-99 and 172-174, respectively; SEQ ID NOS: 100-102 and 175-177, respectively; SEQ ID NOS: 103-105 and 178-180, respectively; SEQ ID NOS: 106-108 and 181-183, respectively; SEQ ID NOS: 109-111 and 184-186, respectively; SEQ ID NOS: 115-117 and 187-189, respectively; SEQ ID NOS: 118-120 and 190-192, respectively; SEQ ID NOS: 121-123 and 193-195, respectively; SEQ ID NOS: 124-126 and 196-198, respectively; SEQ ID NOS: 130-132 and 199-201, respectively; SEQ ID NOS: 133-135 and 202-204, respectively; SEQ ID NOS: 136-138 and 205-207, respectively; SEQ ID NOS: 139-141 and 208-210, respectively; SEQ ID NOS: 142-144 and 211-213, respectively; SEQ ID NOS: 145-147 and 214-216, respectively; SEQ ID NOS: 148-150 and 217-219, respectively; SEQ ID NOS: 151-153 and 220-222, respectively; SEQ ID NOS: 154-156 and 223-225, respectively; SEQ ID NOS: 157-159 and 226-228, respectively; SEQ ID NOS: 160-162 and 229-231, respectively; SEQ ID NOS: 163-165 and 232-234, respectively; SEQ ID NOS: 166-168 and 235-237, respectively; or SEQ ID NOS: 169-171 and 238-240, respectively.

* * * * *